US010577344B2

(12) United States Patent
DeBrabander et al.

(10) Patent No.: US 10,577,344 B2
(45) Date of Patent: *Mar. 3, 2020

(54) THERAPEUTICS TARGETING TRUNCATED ADENOMATOUS POLYPOSIS COLI (APC) PROTEINS

(71) Applicant: Board of Regents of the University of Texas System, Austin, TX (US)

(72) Inventors: Jef DeBrabander, Flower Mound, TX (US); Jerry W. Shay, Dallas, TX (US); Wentian Wang, Irving, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/823,150

(22) Filed: Nov. 27, 2017

(65) Prior Publication Data

US 2019/0135776 A1    May 9, 2019

Related U.S. Application Data

(62) Division of application No. 14/482,659, filed on Sep. 10, 2014, now Pat. No. 9,856,233.

(60) Provisional application No. 61/930,754, filed on Jan. 23, 2014, provisional application No. 61/875,933, filed on Sep. 10, 2013.

(51) Int. Cl.
*C07D 401/04* (2006.01)
*C07D 401/14* (2006.01)
*C07D 405/14* (2006.01)
*C07D 413/14* (2006.01)
*C07D 413/04* (2006.01)
*C07D 417/14* (2006.01)
*C07D 453/02* (2006.01)
*C07D 211/96* (2006.01)
*C07D 471/08* (2006.01)
*C12N 5/071* (2010.01)

(52) U.S. Cl.
CPC .......... *C07D 401/04* (2013.01); *C07D 211/96* (2013.01); *C07D 401/14* (2013.01); *C07D 405/14* (2013.01); *C07D 413/04* (2013.01); *C07D 413/14* (2013.01); *C07D 417/14* (2013.01); *C07D 453/02* (2013.01); *C07D 471/08* (2013.01); *C12N 5/0679* (2013.01); *C12N 2510/04* (2013.01)

(58) Field of Classification Search
None
See application file for complete search history.

(56) References Cited

U.S. PATENT DOCUMENTS

| 4,105,027 | A | 8/1978 | Lundquist |
| 4,192,309 | A | 3/1980 | Poulsen |
| 4,227,522 | A | 10/1980 | Carris |
| 4,627,432 | A | 12/1986 | Newell et al. |
| 4,778,054 | A | 10/1988 | Newell et al. |
| 4,798,897 | A | 1/1989 | Hidaka et al. |
| 4,811,731 | A | 3/1989 | Newell et al. |
| 5,035,237 | A | 7/1991 | Newell et al. |
| 6,921,527 | B2 | 7/2005 | Platz et al. |
| 8,603,465 | B1 | 12/2013 | Yao |
| 8,642,660 | B2 | 2/2014 | Goldfarb |
| 2002/0077337 | A1 | 6/2002 | Rigby et al. |
| 2002/0103205 | A1 | 8/2002 | Lowe et al. |
| 2006/0035884 | A1 | 2/2006 | Neitzel et al. |
| 2006/0223829 | A1 | 10/2006 | Aertgeerts et al. |
| 2008/0132503 | A1 | 6/2008 | Moradei et al. |
| 2010/0068708 | A1 | 3/2010 | Hood et al. |
| 2010/0197693 | A1 | 8/2010 | Zhang et al. |
| 2011/0076282 | A1 | 3/2011 | Ben-Neriah et al. |
| 2013/0330761 | A1 | 12/2013 | Laing et al. |

FOREIGN PATENT DOCUMENTS

| DE | 101 55 684 A1 | 5/2003 |
| EP | 1213289 B1 | 11/2003 |
| RU | 2003127116 | 3/2005 |
| RU | 2011134052 | 2/2013 |
| WO | WO 1991/016038 A1 | 10/1991 |
| WO | WO 2004/069828 A1 | 8/2004 |
| WO | WO 2005/113542 A2 | 12/2005 |
| WO | WO 2006/134481 A1 | 12/2006 |
| WO | WO 2007/115805 A2 | 10/2007 |
| WO | WO 2009/032703 A1 | 3/2009 |
| WO | WO 2012/166617 A2 | 12/2012 |
| WO | WO 2013/119950 A2 | 8/2013 |
| WO | WO 2015/038644 A3 | 5/2015 |

OTHER PUBLICATIONS

Australian Examination Report dated Jan. 11, 2019, regarding AU 2018202898.

(Continued)

*Primary Examiner* — Heidi Reese
(74) *Attorney, Agent, or Firm* — DLA Piper LLP (US)

(57) ABSTRACT

The described invention provides small molecule anti-cancer compounds that selectively target and inhibit measurable biological activity of truncated APC proteins, an immortalized Human Colonic Epithelial Cell (HCEC) model, and pharmaceutical compositions comprising at least one of the small molecule anti-cancer compounds and a pharmaceutically acceptable carrier.

31 Claims, 98 Drawing Sheets

Specification includes a Sequence Listing.

(56) References Cited

OTHER PUBLICATIONS

Casañola-Martín, G.M. et al.: "Dragon method for finding novel tyrosinase inhibitors: Biosilico identification and experimental in vitro assays"; Eur J Med Chem., Nov.-Dec. 2007; 42(11-12):1370-81. Epub Feb. 23, 2007.
CAS Registry No. 431927-84-3; STN entry date: Jun. 18, 2002; Chemical name: 1,4'-Bipiperidine, 1'-[(4-fluorophenyl)sulfonyl]-3-methyl- [3].
CAS Registry No. 431994-93-3; STN entry date: Jun. 19, 2002; Chemical name: 1,4'-Bipiperidine, 3-methyl-1'-(phenylsulfonyl)- [3].
CAS Registry No. 675151-51-6; STN entry date: Apr. 14, 2004; Chemical name: Piperidine, 1-[(4-methoxyphenyl)sulfonyl]-4-(1-pyrrolidinyl)- [3].
CAS Registry No. 792927-02-7; STN entry date; Dec. 6, 2004; Chemical name: 1,4'-Bipiperidine, 4-methyl-1'-[(4-methylphenyl)sulfonyl]- [3].
CAS Registry No. 792927-06-1; STN entry date: Dec. 6, 2004; Chemical name: 1,4'-Bipiperidine, 1'-[(4-methoxyphenyl)sulfonyl]-4-methyl- [3].
CAS Registry No. 951601-74-4; STN entry date: Oct. 26, 2007; Chemical name: Morpholine, 4-[1-[(2,4,6-trimethylphenyl)sulfonyl]-4-piperidinyl]- [3].
CAS Registry No. 1023042-35-4; STN entry date: May 27, 2008; Chemical name: Piperidine, 4-(1-pyrrolidinyl)-1-[[2,4,6-tris(1-methylethyl)phenyl]sulfonyl]- [3].
CAS Registry No. 1023237-18-4; STN entry date: May 28, 2008; Chemical name: Piperidine, 1-(1-naphthalenylsulfonyl)-4-(1-pyrrolidinyl)- [3].
Lau,T. et al: "A Novel Tankyrase Small-Molecule Inhibitor Suppresses APC Mutation-Driven Colorectal Tumor Growth", Cancer Research, vol. 73, No. 10, Mar. 28, 2013 pp. 3132-3144, XP055390391.
Shahlaei, Mohsen et al.: "Application of PC-ANN and PC-LS-SVM in QSAR of CCR1 antagonist compounds: A comparative study"; European Journal of Medicinal Chemistry, vol. 45, Issue 4, Apr. 2010, pp. 1572-1582.
Aertgeerts et al.: "Aryl sulfonyl-piperidines . . . "; CA145:419173 (2006).
Aoki, K. et al.: "Adenomatous polyposis coil (APC): a multifunctional tumor suppressor gene", Journal of Cell Science, 2007, vol. 120, pp. 3327-3335.
Bach, T.J.: "Some new aspects of isoprenoid biosynthesis in plants—a review," Lipids 30: 191-202 (1995).
Bae, et al.: "Cholesterol biosynthesis from lanosterol: molecular cloning, chromosonal localization, functional expression and liver-specific gene regulation of rat sterol D8-isomerase, a cholesterogenic enzyme with mulitple Functions", Biochem.J.,2001, vol. 353, pp. 689-699.
Bakhoum, S. F. et al.: "Deviant kinetochore microtubule dynamics underlie chromosomal instability", Current Biology, 2009, vol. 19, pp. 1937-1942, Elsevier Ltd.
Banker et al.: "Modern Pharmaceutics"; 3rd edition, Marcel Dekker, New York, pp. 451 and 596 (1996).
Baranowski, M.: "Biological role of liver X receptors," J. Physiol. Pharmacology. 59 Suppl. 7: 31-55 (2008).
Berthois, Y. et al.: "SR31747A is a sigma receptor ligand exhibiting antitumoural activity both in vitro and in vivo," Br. J. Cancer 88: 438-46 (2003).
Bhatia, B. et al.: "Sonic hedgehog signaling and malignant transformation of the cerebellar granule neuron precursor cells," Oncogene 30(4): 410-22 (2011).
Bjorkhem, I.: "Do oxysterols control cholesterol homeostasis," J. Clin. Invest. 110: 725-30 (2002).
Brown, M. I. et al.: "A macrophage receptor for apolipoprotein B48: cloning, expression and atherosclerosis," Proc. Natl Acad. Sci. USA 97: 7488 (2000).
Brown, M. S. and Goldstein, J. L.: "A proteolytic pathway that controls the cholesterol content of membranes, cells and blood," Proc. Natl Acad. Sci. USA 96: 11041-48 (1999).
Brown, M.S. and Goldstein, J. L.: "The SREBP pathway: regulation of cholesterol metabolism by proteolysis of a membrane-bound transcription factor," Cell 89: 331-40 (1997).
Burg, J. S. and Espenshade, P. J.: "Regulation of HMG-CoA reductase in mammals and yeast," Prog. Lipid Res. 50: 403-410 (2011).
Cayuso, J. and Marti, E.: "Morphogens in motion: Growth control of the neural tube"; Journal of Neurobiology, 34:376-387 (2005).
Chen, W. et al.: "Preferential ATP-binding cassette transporter AI-mediated cholesterol efflux from late endosomes/ ysosomes," J. Biol. Chem. 276: 43564-69 (2001).
Chittur, et al.: "Histone deacetylase inhibitors: A new mode for inhibition of cholesterol metabolism", BMC Genomics, 2008, vol. 9, pp. 1-14.
Coburn et al.: "Preparation of . . . "; CA162:670779 (2015).
Cruz, P. M. R. et al.: "The role of cholesterol metabolism and cholesterol transport in carcinogenesis: a review of scientific findings, relevant to future cancer therapeutics," Frontiers in Pharmacol. 4(119): doi: 10.3389/ phar.2013.00119.
Daimiel, L. A. et al: "Promoter analysis of the DHCR24 (3β-hydroxysterol Δ24-reductase) gene: characterization of 3REBP (sterol-regulatory element-binding-protein)-mediated activation," Biosci. Rep. (2013)/art:e000/doi 10.1042/ BSR20120095.
Dang, H. et al.: "Suppression of 2,3-oxidosqualene cyclase by high fat diet contributes to liver X receptor-mediated improvement of hepatic lipid profile," J. Biol. Chem. 284: 6218-26 (2009).
De La Grange, P. et al.: "a new advance in alternative splicing databases from catalogue to detailed analysis of regulation of expression and function of human alternative splicing variants," BMC Bioinformatics 8: 180 (2007).
De La Llera-Moya, M. et al.: "Scavenger receptor B1 (SR-B1) mediates free cholesterol flux independently of HDL tethering to the cell surface," J. Lipid Res. 40: 575-80 (1999).
De Man, F. H. et al.: "Lipolysis of very low density lipoproteins by heparin sulfate proteoglycan-bound lipoprotein lipase," J. Lipid Res. 38: 2465 (1997).
De Medina, P. et al.: "Identification and pharmacological characterization of choleseterol-5,6-epoxide hydrolase as a target for tamoxifen and AEBS ligands," Proc. Natl. Acad. Sci. USA 107: 13520-5 (2010).
De Medina, P. et al.: "Synthesis of new alkylaminooxysterols with potent cell differentiating activities: identification pf leads for the treatment of cancer and neurodegenerative diseases," J. Med. Chem. 52: 7765-77 (2009).
De Medina, P. P. et al.: "Dendrogenin A arises from cholesterol and histamine metabolism and shows cell lifferenhation and anti-tumour properties," Nature Communic. 4: 1840 (2013).
Debose-Boyd, R. A.: "Feedback Regulation of Cholesterol Synthesis: Sterol-accelerated ubiquitination and degradation of HMG CoA Reductase," Cell Res. 18 (6): 609-21 (2008).
Denis, M. et al.: "ATP-binding cassette A-1-mediated lipidation of apolipoprotein A-1 occurs at the plasma membrane and not in the endocytic compartments," J. Biol. Chem. 283: 16178-186 (2008).
Dikovskaya, D. et al.: "Loss of APC induces polyploidy as a result of a combination of defects in mitosis and apoptosis", The Journal of Cell Biology, 2016, vol. 176, pp. 183-195.
Cui et al.: "Preparation of 5-aralkyl . . . "; CA138:14005 (2002).
Dunlop, M. G. et al.: "Common variation near CDKN1A, POLD3 and SHROOM2 influences colorectal cancer risk", Nature Genetics 44, 770-776 (2012).
Edwards, P. A. et al.: "Purification and properties of rat liver 3-hydroxy-3-methylglutaryl coenzyme A reductase,"; Biochim. Biophys. Acta 574: 123-35 (1979).
Ehrenreiter, K. et al.: "Raf-1 Addiction in Ras-Induced Skin Carcinogenesis", Cancer Cell 16, 149-160 (2009).
Ehrenreiter, K. et al.: "Raf-1 regulates Rho signaling and cell migration"; J. Cell Biology; vol. 168, 955-964 ;-2005).
Elson, C. E. and Quereshi, A. A.: "Coupling the choleseterol—and tumor-suppressive actions of palm oil to the mpact of its minor

(56) References Cited

OTHER PUBLICATIONS constituents on 3-hydroxy-3-methylglutaryl coenzyme A reductase activity," Prostaglandins Leukot. Essent. Fatty Acids 52: 205-207 (1995).

Endo, A.: "A historical perspective on the discovery of statins," Proc. Jpn Acad, Ser. B Phys. Biol. Sci 86(5): 484-93 ;2010).

Eskiocak, U. et al.: "Functional parsing of driver mutations in the colorectal cancer genome reveals number suppressors of anchorage-independent growth", Cancer Research, 2011, vol. 71, pp. 4359-4365, American association for Cancer Research.

Farber, M. J. et al.: "Shroom2 regulates contractility to control endothelial morphogenesis"; Molecular Biology of the Cell; vol. 22, 795-805 (2011).

Faulkner, L. E. et al.: "An analysis of the role of a retroendocytosis pathway in ABCA1-mediated cholesterol efflux rom macrophages," J. Lipid Res. 49: 1322-32 (2008).

Fearon, E. R. and Vogelstein, B.: "A genetic model for colorectal tumorigenesis". Cell 61, 759-767 (1990).

Fernandez-Hernando, et al.: "MicroRNAs in metabolic disease," Arterioscl. Thromb. Vasc. Biol. 33: 178-85 ;2013).

Ferretti, R. et al. "Morgana/chp-1, a ROCK Inhibitor Involved in Centrosome Duplication and Tumorigenesis"; Developmental Cell 18, 486-495 (2010).

Freed-Pastor, W. A. et al.: "Mutant p53 disrupts mammary tissue architecture via the mevalonate pathway," Cell 148: 244-58 (2012).

Garattini, S.: "Active Drug Metabolites", Clinical Pharmacokinetics, vol. 10, Issue 3, pp. 216-227 (1985).

Garcia-Mata, R. et al.: "The 'invisible hand': regulation of RHO GTPases by RHOGDIs." Nature Reviews Molecular Cell Biology. (2011) 12:493-504; at 494).

Gaylor, J. L.: "Membrane bound enzymes of cholesterol synthesis from lanosterol," Biochem. Biophys. Res. Sommunic., 292: 1139-46 (2002).

Golbfarb et al. "Method using . . . "; CA151:115083 (2009).

Golbfarb et al.: "Method using . . . "; CA151:92836 (2009).

Golbfarb et al.: "Method using . . . "; CA151:92839 (2009).

Green, R. A. and Kaplan, K. B.: "Chromosome instability in colorectal tumor cells is associated with defects in nicrotubule plus-end attachments caused by a dominant mutation in APC" Journal of Cell Biology, 163:949-961 (2003).

Greenwood, J. et al.: "Statin therapy and autoimmune disease: from protein prenylation to immunomodulation," Vat. Rev. Immunol. 6: 358-70 (2006).

Gruenbacher, G. et al.: "CD56+ human blood dendritic cells effectively promote TH1-type gammadelta T cell responses," Blood 114: 4422-31 (2009).

Gruenbacher, G. et al.: "IL-2 costimulation enables statin-mediated activation of human NK cells, preferentially through a mechanism involving CD56+ dendritic cells," Cancer Res. 70: 9611-20 (2010).

Gu, X. et al.: "Scavenger receptor class B, type 1-mediated [3H] cholesterol efflux to high and a low density lipoproteins is dependent on lipoprotein binding to the receptor," J. Biol. Chem. 275: 29993-30001 (2000).

Guo, D. et al.: "EGFR signaling through han Akt-SREBP-1-dependent, rapamycin-resistant pathway sensitizes glioblastomas to antilipogenic therapy," Science Signaling 2: ra82 (2009).

Guo, D. et al.: "Targeting SREBP-1 driven lipid metabolism to treat cancer," Curr. Pharm Des. 20(15): 2619-26 ;2014).

Hagiwara et al.: "Hepatic mTORC2 activates glycolysis and lipogenesis through Akt, glucokinase and SREBP1c," Sell Metab. 15: 725-38 (2012).

Half, E. et al.: "Familial adenomatous polyposis", Orphanet Journal of Rare Diseases, vol. 4, pp. 1-23, licensee BioMed Central Ltd. (2009).

Hartman, Iz et al.: "Sterol-inducd dislocation of 3-hydroxy-3-methylglutaryl coenzyme A reductase from andoplasmic reticulum membranes into the cytosol through a subcellular compartment resembling lipi droplets," J. Biol. Chem, 285: 19288-98 (2010).

He, M. et al: "Mutations in the human SC4MOL gene encoding a methyl sterol oxidase cause psoriasiform lermatitis, microcephaly, and developmental delay," J. Clin. Invest. 121:97 6-984 (2011).

Hidaka et al. "Preparation of isoquinolin . . . "; CA108:37665 (1988).

Hidaka, Y. et al.: "Regulation of squalene epoxidase in HepG2 cells," J. Lipid Res. 31: 2087-94 (1990).

Hiltunen, T. P. et al: "Expression of LDL receptor, VLDL receptor, LDL receptor-related protein, and scavenger receptor in rabbit atherosclerotic lesions: Marked induction of scavenger receptor and VLDL receptor expression luring lesion development," Circulation 97: 1079 (1998).

Hinoi, T. et al.: "Mouse model of colonic adenoma-carcinoma progression based on somatic Apc inactivation", Cancer Res, 2007, vol. 67, pp. 9721-9730.

Hirsch, H. A. et al.: "A transcriptional signature and common gene networks link cancer with lipid metabolism and diverse human diseases," Cancer Cell. 17(4): 348-61 (2010).

Horton, J. D. et al.: "SREBPs: activators of the complete program of cholesterol and fatty acid synthesis in the liver," J. Clin. Invest. 109: 1125-31 (2002).

Hosono, Y. et al.: "Abstract LB-360: MYBPH, a novel transcriptional target of TTF-1/NKX2-1, inhibits ROCK1 and actomyosin assembly, and reduces cell motility and tumor metastasis"; http://cancerres.aacrjoumals.org/ mntent/71/8_Supplement/LB-360; DOI: 10.1158/1538-7445.AM2011-LB-360 published Apr. 2011.

Hua, X. et al.: "Sterol resistance in CHO cells traced to point mutation in SREBP cleavage-activating protein," Cell 87: 415-26 (1996).

Hussein, D. and Mo, H.: "d-δ-tocotrienol-mediated suppression of the proliferation of human PANC-1, MIA PaCa2 and BxPC-3 pancreatic carcinoma cells," Pancreas 38: e124-e136 (2009).

Inoue, S. et al.: "Inhibition of degradation of 3-hydroxyl-3-methylglutaryl-coenzyme A reductase in vivo by cysteine protease inhibitors," J. Biol. Chem. 266: 13311-17 (1991).

International Preliminary Report on Patentability for PCT/US2016/040931 dated Jan. 16, 2018.

Ji, Y. et al.: "Scavenger receptor B1 promotes high density lipoprotein-mediated cellular cholesterol efflux," J. Biol. Them. 272: 20982-985 (1997).

Jian, B. et al.: "Scavenger receptor class B type 1 as a mediator of cellular cholesterol efflux to lipoproteins and phospholipid acceptors," J. Biol. Chem. 273: 5599-5606 (1998).

Jiang, W. and Song, B. L.: "Ubiquitin Ligases in Cholesterol Metabolism," Diabetes Metab. 38: 171-80 (2014).

Jo, Y. and Debose-Boyd, R. A.: "Control of cholesterol synthesis through regulated ER-associated degradation of HMG CoA reductase," Crit Rev Biochem Mol. Bio. 445: 185-198 (2010).

Jo, Y. et al.: "ancient ubiquitous protein 1 mediates sterol-induced ubiquitination of 3-hydroxy-3-methylglutaryl CoA reductase in lipid droplet-associated endoplasmic reticulum membranes," Mol Biol. Cell 24: 169-83 (2013).

Polakis, P.: "The many ways of Wnt in cancer", Current Opinion in Genetics & Development, 2007, vol. 17, pp. 45-51 ivww.sciencedirect_com.

Kaplan, K. B. et al.: "A role for the adenomatous polyposis coli protein in chromosome segregation", Nature Cell Biology, 2001, vol. 3, pp. 429-432, Macmillan Magazines Ltd.

Kastritis, E. et al.: "Somatic mutations of adenomatous polyposis coli gene and nuclear b-catenin accumulation have prognostic significance in invasive urothelial carcinomas: evidence for Wnt pathway implication", International Journal of Cancer, 124:103-108 (2009).

Kawabata, S. et al.: "Interaction of Rho-kinase with myosin II at stress fibres"; Genes to Cells, 9, 653-660 (2004).

Keldenich: "Subsituted bipiperi . . . "; CA163:145662 (2015).

Kennedy, M. A. et al.: "ABCG1 has a critical role in mediating cholesterol efflux to HDL and preventing cellular lipid accumulation," Cell Metab. 1: 121-31 (2005).

Khaidakov, M. et al: "Oxidized LDL receptor 1 (OLR1) as a possible link between obesity, dyslipidemia and cancer," PLoS One 6(5): e20277 (2011).

(56) References Cited

OTHER PUBLICATIONS

Kim, J. et al.: "Itraconazole, a commonly used antifungal that inhibits Hedgehog pathway activity and cancer growth," Cancer Cell. 17(4): 388-99 (2010).

Kimura, K. et al.: "Regulation of Myosin Phosphatase by Rho and Rho-Associated Kinase (Rho-Kinase)", Science, vol. 273, 245-248 (1996).

Kinzler, K. W. et al: "Identification of FAP locus genes from chromosome 5q21", Science, 1991, vol. 253, pp. 661-664.

Kinzler, K. W. et al: "Lessons from hereditary colorectal cancer", Cell, 1996, vol. 87, pp. 159-170.

Konstantinopoulos, P. A. et al.: "Post translational modifications and regulation of the RAS superfamily of 3TPases as anticancer targets," Nat. Rev. Drug Discov. 6: 541-55 (2007).

Krinbou, L. et al.: "Biogenesis and speciation of nascent apo A1-containing particles in various cell lines," J. Lipid Res. 46: 1668 (2005).

Kuwabara, P. E.: "The sterol-sensing domain: multiple families, a unique role," Trends Genet. 18: 193-201 (2002).

Labit-Le Bouteiller, C. et al.: "Antiproliferative effects of SR31747A in animal cell lines are mediated by inhibition of cholesterol biosynthesis at the sterol isomerase step," Eur. J. Biochem. 256: 342-49 (1998).

Landry, Y. D. et al.: "ATP-binding cassette transporter A1 expression disrupts raft membrane microdomains through its ATPase-related functions," J. Biol. Chem. 281: 36091-101 (2006).

Lange, Y. et al.: "Effectors of rapid homeostatic responses of endoplasmic reticulum cholesterol and 3-hydroxy-3-methylglutaryl-CoA reductase," J. Biol. Chem. 283: 1445-55 (2008).

Lee et al.: "Preparation of 5-amino . . . "; CA130:168237 (1999).

Lee, P. C. et al.: "Isolation of sterol-resistant Chinese hamster ovary cells with genetic deficiencies in both insig-1 and insig-2," J. Biol. Chem. 280: 25242-249 (2005).

Lehmann, J. M. et al.: "Activation of the nuclear receptor LXR by oxysterols defines a new hormone response pathway," J. Biol. Chem. 272: 3137-40 (1997).

Leichner, G. S. et al.: "Metabolically regulated endoplasmic reticulum-associated degradation of 3-hydroxy-3--methylglutaryl-CoA reductase. Evidence for requirement of a geranylgeranylated protein," J. Biol. Chem. 286: 32150-61 (2011).

Leung, T. et al.: "p80 ROKa binding protein is a novel splice variant of CRMP-1 which associates with CRMP-2 and modulates RhoA-induced neuronal morphology"; FEBS Letters 532, 445-449 (2002).

Liu, Y. and Tang, C.: "Regulation of ABCA1 functions by signaling pathways," Biochim. Biophys. Acta, 1821: 522-29 (2012).

Lo Sasso, G. et al.: "Liver X receptors inhibit proliferation of human colorectal cancer cells and growth of intestinal tumors in mice," Gastroenterology 144(7): 1497-507 (2013).

Loberg, R. D. et al.: "Enhanced glyocen sythase kinase-3b activity mediates hypoxia-induced apoptosis of vascular smooth cells and is prevented by glucose transport and metabolixm", The Journal of Biological Chemistry, 2002, vol. 277, pp. 41667-41673, The American Society for Biochemistry and Molecular Biology, Inc.

Longin, K. et al.: "Comparison of antifading agents used in fluorescence microscopy: Image analysis and laser=focal microscopy study", The Journal of Histochemistry and Cytochemistry, 1993, vol. 41, pp. 1833-1840, The Histochemical Society, Inc.

Ly, P. et al: "RNAi screening of the human colorectal cancer genome identifies multifunctional tumor suppressors regulating epithelia cell invasion", Cell Research, 2012, vol. 22, pp. 1605-1608.

Ma, Wei et al.: "RhoE is Frequently Down-regulated in Hepatocellular Carcinoma (HCC) and Suppresses HCC invasion Through Antagonizing the Rho/Rho-Kinase/Myosin Phosphatase Target Pathway" Hepatology, Jan. 2013, vol. 57, 152-161.

Ma, Z. et al.: "Interaction between ROCK II and Nucleophosmin/B23 in the Regulation of Centrosome Duplication", Molecular and Cellular Biology, 9016-9034 (2006).

Mahley, RW, JI, ZS, "Remnant lipoprotein metabolism: key pathways involving cell-surface heparin sulfate proteoglycans and apolipoprotein E," J. Lipid Res. 40: 1-16 (1999).

Maniar, A. et al.: "Human gammadelta T lymphocytes induce robust NK cell-mediated antitumor cytotoxicity through CD137 engagement," Blood 116: 1726-33 (2010).

Mashima, T. et al.: "De novo fatty-acid synthesis and related pathways as molecular targets for cancer therapy," Br. J. Cancer 100 (9): 1369-72 (2009).

Mazein, A. et al.: "A comprehensive machine-readable view of the mammalian cholesterol biosynthesis pathway," Biochemical Pharmacol. 86: 56-66 (2013).

McGee, T. P. et al.: "Degradation of 3-hydroxy-3-methylglutaryl-CoA reductase in endoplasmic reticulum membranes s accelerated as a result of increased susceptibility to proteolysis," J. Biol. Chem. 271: 25630-638 (1996).

Medina, M. W. et al.: "Coordinately regulated alternative splicing of genes involved in cholesterol biosynthesis and uptake," PLosONE 6: e19420 (2011).

Menendez, J. A. and Lupu, R.: "Fatty acid synthase and the lipogenic phenotype in cancer pathogenesis," Nat. Rev. 7,ancer 7(10): 763-77 (2007).

Meyer, J. M. et al.: "New developments in selective cholesteryl ester uptake," Curt Opin. Lipidol. 24: 386-92 (2013).

Minde, D. et al.: Messing up disorder: how do missense mutations in the tumor suppressor protein APC lead to cancer?, Molecular Cancer 10:101 (2011).

Mineo, C. and Shaul, P. W.: "Regulation of signal transduction by HDL," J. Lipid Res. 54:2315-24 (2013).

Mo, H. and Elfakhani, C. E.: Mevalonate-suppressive tocotrienols for cancer chemoprevention and adjuvant therapy, in Tocotrienols: Vitamin E beyond tocopherols, eds. RR. Wilson et al (Boca Raton: CRC Press), 135-149 (2013).

Mo, H. and Elson, C. E.: "Studies of the isopreoid-mediated inhibition of mevalonate synthesis applied to cancer chemotherapy and chemoprevention," Exp. Biol. Med. (Maywood) 229: 567-85 (2004).

Morgan-Fisher, M. et al.: "Regulation of ROCK Activity in Cancer", Journal of Histochemistry & Cytochemistry, 61:185-198 (2013).

Mueller, B. K. et al.: "Rho Kinase, a promising drug target for neurological disorders." Nat Rev Mal Cell Bio., I4(6): 387-398 (2005).

Munz, C. et al.: "Dendritic cell maturation by innate lymphocytes: coordinated stimulation of innate and adaptive immunity," J. Exptl Med. 202: 203-7 (2005).

Nagahashi, M. et al.: "Multivalent control of 3-hydroxy-3-methylglutaryl coenzyme A reductase. Mevalonate-derived product inhibits translation of mRNA and accelerates degradation of enzyme," J. Biol. Chem. 263: 8929-37 (1988).

Nagahashi, M. et al.: "Sphingosine-I-phosphate produced by sphingosine kinase 1 promotes breast cancer progression by stimulating angiogenesis and lymphangiogenesis," Cancer Res. 72(3): 726-35 (2012).

Neitzel et al.: "Preparation of N-cyclic . . . "; CA144:22719 (2005).

Nguyen, A. D. et al.: "Hypoxyia stimulates degradation of 3-hydroxy-3-methylglutaryl-coenzyme A reductase through accumulation of lanosterol and hypoxia-inducible factor-mediated induction of Insigs," J. Biol. Chem. 282: 27436-446 ;2007).

Nguyen-Vu, T. et al.: "Liver x receptor ligands disrupt breast cancer cell proliferation through an E2F-mediated mechanism," Breast Cancer Res. 15: R51 (2013).

Niault, T. et al.: "From autoinhibition to inhibition in trans: the Raf-1 regulatory domain inhibits Rok-a kinase activity", J. Cell Biol., vol. 187(3), 335-342 (2009).

Nimph, J, and Schneider, W. J.: "The VLDL receptor: an LDL receptor relative with eight ligand binding repeats, LR8". Atherosclerosis 141: 191-202 (1998).

Nishimura, T. et al.: "Shroom3-mediated recruitment of Rho kinases to the apical cell junctions regulates epithelial and neuroepithelial planar remodeling", Development, 135, 1493-1502 (2008).

Nohturfft, A. et al.: "A substitution in a single codon of SREBP cleavage-activating protein causes sterol resistance in three mutant Chinese hamster ovary cell lines,"; Proc. Natl Acad. Sci. USA 93: 13709-714 (1996).

(56) References Cited

OTHER PUBLICATIONS

Nohturfft, A. et al.: "Sterols regulate processing of carbohydrate chains of wild-type SREBP cleavage-activating protein (SCAP), but not sterol-resistant mutants Y298C o D443N," Proc. Natl Acad. Sci. USA 95: 12848-853 (1998).
Nohturfft, A. et al.: "Topology of SREBP cleavage-activating protein, a polytopic membrane protein with a sterol sensing domain," J. Biol. Chem. 273: 17243-250 (1998).
Oliverase, G. et al.: "Novel anti-fatty acid synthase compounds with anti-cancer activity in Her2+ breast cancer," Ann. N. Y. Acad. Sci. 1210: 86-92 (2010).
Olson, M. F:. "Applications for ROCK kinase inhibition" Cr Opin Cell Biol. 20(2): 242-248, at 242-243 (2008).
Paul, R. et al.: "Both the immunosuppressant SR31747 and the antiestrogen tamoxifen bind to an emopamil—insensative site of Mammalian D8-D7 sterol isomerase,"; J. Pharmacol. Exptl Thera. 285(3): 1296-1302 (1998).
Pehkonen, P. et al.: "Genome-wide landscape of liver X receptor chromatin binding and gene regulation in human macrophages," BMC Genomics 13: 50 (2012).
Peterson, T. R. et al.: "DEPTOR is an mTOR inhibitor frequently overexpressed in multiple myeloma cells and required for their survival," Cell 137: 873-86 (2009).
Peterson, T. R. et al.: "mTOR complex I regulates lipin 1 localization to control the SREBP pathway," Cell 146: 408-20 (2011).
Phelps, R. A. et al.: "New perspectives on APC control of cell fate and proliferation in colorectal cancer", Cell Cycle, 2009, vol. 8, pp. 2549-2556.
Phillips, M. C.: "Molecular Mechanisms of Cellular Cholesterol Efflux," J. Biol. Chem. 289 (35): 24020-29 (2014).
Phillips, M. C.: "New insights into the determination of HDL structure by apolipoproteins," J. Lipid Res. 54: 2034-48 ;2013).
Piazzolla, D. et al.: "Raf-1 sets the threshold of Fas sensitivity by modulating Rok-a signaling"; J. Cell Biol. 171, 1013-1022 (2005).
Pinner, S. and Sahai, E.: "PDK1 regulates cancer cell motility by antagonising inhibition of ROCK1 by RhoE"; Nature Cell Biology 10(2), (2008).
Quazi, F. and Molday, R. S.: "Differential phospholipid substrates and directional transport by ATP-binding cassette proteins ABCA, ABCA7, and ABCA4 and disease-causing mutants," J. Biol. Chem. 288: 34414-26 (2013).
Radhakrishnan, A. et al.: "Direct binding of cholesterol to the purified membrane region of SCAP: Mechanism for a sterol-sensing domain," Mol. Cell 15: 259-68 (2004).
Radhakrishnan, A. et al.: "From the Cover: Sterol-regulated transport of SREBPs from endoplasmic reticulum to Golgi: Oxysterols block transport by binding to Insig," Proc. Natl Acad. Sci. USA 104: 6511-18 (2007).
Rana, M. K. and Worthylake, R. A: "Novel Mechanism for Negatively Regulating Rho-Kinase (ROCK) Signaling through Coronin1B Protein in Neuregulin 1 (NRG-1)-induced Tumor Cell Motility", The Journal of Biological Chemistry, vol. 287, No. 26, 21836-21845, Jun. 22, 2012.
Ravid, T. et al.: "The ubiquitin proteasome pathway mediates the regulated degradation of mammalian 3-hydroxy-3-methylglutaryl-3enzyme A reductase," J. Biol. Chem. 275: 35840-47 (2000).
Ravid, T. et al.: "The ubiquitin proteasome pathway mediates the regulated degradation of mammalian 3-hydroxy-3-methylglutaryl-Coenzyme A reductase," J. Biol. Chem. 275: 35840-47 (2000).
Ren, Y. et al.: "Small molecule Wnt inhibitors enhance the efficiency of BMP-4-directed cardiac differentiation of human pluripotent stem cells", J Mol Cell Cardiol, 2011; vol. 51, pp. 280-287.
Riento, K. and Ridley, A. J.: "ROCKs: multifunction kinases in cell behavior." Nat Rev Mol Cell Biol. 4:446-456 2003).
Rodde, R. et al.: "Mutations in the APC tumour suppressor gene cause chromosomal instability", Nature Cell Biology, 2001, vol. 3, pp. 433-443.
Roig, A.I et al.: "Immortalized epithelial cells derived from human colon biopsies express stem cell markers and Differentiate in vitro", Gastroentology, 2010, vol. 138, pp. 1012-1021.

Roitelman, J. and Simoni, R. D.: "Distinct sterol and nonsterol signals for the regulated degradation of 3-hydroxy-3-methylglutaryl-CoA reductase," J. Biol. Chem. 267: 25264-273 (1992).
Rosenson, R. S. et al: "Cholesterol efflux and atheroprotection: advancing the concept of reverse cholesterol transport," Circulation 125: 1905-19 (2012).
Rothblat, G. H. and Phillips, M. C.: "High-density lipoprotein heterogeneity and function in reverse cholesterol transport," CLUT. Opin. Lipidol. 21: 229-38 (2010).
Rusan, N. M. et al.: "Original CIN: reviewing roles for APC in chromosome instability", The Journal of Cell Biology, 2008, vol. 181, pp. 719-726.
Russell, D. W.: "Oxsterol biosynthetic enzymes," Biochim. Biophys. Acta—Malec. Cell Biol. Lipids 1529: 126-135 2000).
Sabatini, D. M. "mTOR and cancer: insights into a complex relationship," Nat. Rev. Cancer 6: 729-34 (2006).
Sabitova, L. et al.: "Molecular Pathways: Sterols and receptor signaling in Cancer," Clin. Cancer Res. 19(23): 3344-50 (2013).
Sankaranarayanan, S. et al: Effects of acceptor composition and mechanism of ABCG1-mediated cellular free cholesterol efflux, J. Lipid Res. 50: 275-84 (2009).
Sato, M. et al.: "Multiple oncogenic changes (K-RAV v12, p53 knockdown, mutant EGFRs, p16 Bypass, Telomerase) are not sufficient to confer a full malignant phenotype on human bronchial epithelial cells", Cancer Res, 2006, vol. 66, pp. 2116-2128.
Sawamura, T. et al.: "an endothelial receptor for oxidized low-density lipoprotein," Nature 386: 73 (1997).
Sawhney, A. S. et al.: "Bioerodible hydrogels based on photopolymerized poly (ethylene glycol)-co-poly (a-hydroxy acid) diacrylate macromers", Macromolecus, 1993, vol. 26, vol. 581-587.
Schnekeirt, J. et al.: "Truncated APC regulates the transcriptional activity of B-catenin in a cell cycle dependent mannter", Human Molecular Genetics, 2007, vol. 16, pp. 199-209.
Scholl, F. A. et al.: "Mek1/2 MAPK inases are essential form mammalian development, homeostasis, and Raf-Induced hyperplasia", Development Cell, 2007, vol. 12, pp. 615-629.
Schroepfer, G. J., Jr.: "Oxysterols: modulators of cholesterol metabolism and other processes," Physiol. Rev. 80: 361-554 (2000).
Sever, N. et al.: "Accelerated degradation of HMG CoA reductase mediated by binding of insig-1 to its sterol-sensing domain," Mol. Cell 11: 25-33 (2003).
Sever, N. et al.: "Insig-dependent ubiquitination and degradation of mammalian 3-hydroxy-3-methylglutaryl CoA-eductase stimulated by sterols and geranylgeraniol," J. Biol. Chem. 278: 52479-90 (2003).
Sharpe, L. J. and Brown, A. J.: "Controlling cholesterol synthesis beyond 3-hydroxy-3-methylglutaryl CoA reductase HMGCR)," J. Biol. Chem_ 288 (26): 18707-715 (2013).
Shi, Q. et al.: "Chromosome nondisjunction yields tetraploid rather than aneuploid cells in human cell lines", Nature, 2005, vol. 437, pp. 1038-1043.
Sill, S. et al.: "Cholesterol-dependent degradation of squalene monooxygenase, a control point in cholesterol synthesis beyond HMG-CoA reductase, " Cell Metab. 13: 260-73 (2011).
Sillotte, K. L. et al.: "Removal of cellular cholesterol by pre-?-HDL involves plasma membrane microsolubilization," J. Lipid Res. 39: 1918-28 (1998).
Smith, J. D. et al.: "ABCA1 mediates concurrent cholesterol and phospholipid efflux to apolipoprotein A-1," J. Lipid Res. 45: 635-44 (2004).
Song, B. L. et al.: "Gp8, a membrane-anchored ubiquitin ligase, associates with Insig-1 and couples sterol-regulated ubiquitination to degradation of HMG CoA reductase," Mol. Cell 19: 829-40 (2005).
Song, B. L. et al: "Insig-mediated degradation of HMG-CoA reductase stimulated by lanosterol, an intermediate in the synthesis of choleseterol," Cell Meta. 1: 179-89 (2005).
Song, Y. et al.: "Sterol-regulated ubiquitination and degradation of Insig-1 creates a convergent mechanism for feedback control of cholesterol synthesis and uptake," Cell Metab. 3: 15-24 (2006).
Sonzalez, R. et al.: "Two major regulatory steps in cholesterol synthesis by human renal cancer cells," Arch. Biochem. Biophys. 196: 574-80 (1979).

(56) References Cited

OTHER PUBLICATIONS

Sorin, A. et al.: "Regulation of cholesterol biosynthesis and cancer signaling," Curr. Op. Pharmcol. 12(6) 710-16 2012).
Spann, N. J. et al.: "Regulated accumulation of desmosterol integrates macrophage lipid metabolism and Inflammatory responses," Cell 151: 138-52 (2012).
Spencer, T. A. et al.: "24(S),25-epoxyscholesterol. Evidence consistent with a role in the regulation of hepatic cholestrogenesis," J. Biol. Chem. 260: 13391-94 (1985).
Steinman, R. M. and Banchereau, J.: "Taking dendritic cells into medicine," Nature 449: 419-26 (2007).
Still, W. C. et al.: "Rapid chromatographic technique for preparative separations with moderate resolution", J. Org. Chem, 1978, vol. 43, pp. 2923-2925, American Chemical Society.
Street, C. A. and Bryan, B. A.: "Rho Kinase Proteins-Pleiotropic Modulators of Cell Survival and Apoptosis" Anticancer Res., 31(11): 3645-3657 (2011).
Sun, L.P. et al.: "From the Cover: Sterol-regulated transport of SREBPs from endoplasmic reticulum to Golgi: Insig renders sorting signal in Scap inaccessible to COPII proteins," Proc. Natl Acad. Sci. USA 104: 6519-26 (2007).
Szarnecka, H. and Yokoyama, S.: "Regulation of cellular cholesterol efflux by lecithin: cholesterol acyltransferase reaction through nonspecific lipid exchange," J. Biol. Chem. 271: 1023-27 (1996).
Tang, et al.: "Histone deacetylases as targets for treatment of multiple diseases", Clin. Sci, 2013, vol. 124, pp. 351-662.
Tapash, K. Ghosh et al.: "Transdermal and Topical Drug Delivery Systems", eds., 1997, pp. 249-297.
Thuahnai, S. T. et al.: "SR-B1-mediated cholesteryl ester selective uptake and efflux of unesterified cholesterol: Influence of HDL size and structure," J. Biol. Chem. 279: 12448-455 (2004).
Thumher, M. et al.: "Novel aspects of mevalonate pathway inhibitors as antitumor agents," Clin. Cancer Res. 18: 3524-31 (2012).
Ton, S. et al.: "Identification of scavenger receptor SR-B1 as a high density lipoprotein receptor," Science 271: 518 (1996).
Uddin, S. et al.: "High prevalence of fatty acid synthase expression in colorectal cancers in Middle Eastern patients and its potential role as a therapeutic target," Am. J. Gastroenterol 104(7): 1790-1801 (2009).
Vaughan, A.M. and Oram, J.F.: "ABCG1 redistributes cell cholesterol to domains removable by high density lipoprotein but not by lipid-depleted apolipoproteins," J. Biol. Chem. 280: 20150-57 (2005).
Wang, N. et al.: "ATP-binding cassette transporters G1 and G4 mediate cellular cholesterol efflux to high-density lipoproteins," Proc. Natl Acad. Sci. USA 101: 9774-79 (2004).
Wang, Y. et al.: "Regulation of cholesterologenesis by the oxysterol receptor, LXRalpha" J. Biol. Chem. 283: 26332-339 '2008).
Wang, Y. et al.: "ROCK Isoform Regulation of Myosin Phosphatase and Contractility in Vascular Smooth Muscle Cells", Circ. Res_ vol. 104, 531-540 (2009).
Ward, Y. et al.: "The GTP binding proteins Gem and Rad are negative regulators of the Rho-Rho kinase pathway" J. sell Biol. 157(2): 291-302 (2002).
Wheeler, A.P. and Ridley, A.J.: "Why three Rho proteins? RhoA, RhoB , RhoC and cell motility," Exp. Cell Res. 301 1): 43-49 (2004).
Williams, D.L. et al.: "Binding and cross-linking studies show that scavenger receptor B1 interacts with multiple sites In apolipoprotein A-1 and identify the class A amphipathic alpha-helix as a recognition motif," J. Biol. Chem. 275: 18897-18904 (2000).
Williams, D.L. et al.: "Scavenger receptor B1 and cholesterol trafficking," Curr. Opin. Lipidol. 10: 329-39 (1999).
Williams, M.T. et al.: "Investigation of the rate-determining microsomal reaction of cholesterol biosynthesis from lanosterol in Morris hepatomas and liver," Cancer Res. 37 : 1377-83 (1977).
Willner, E. et al.: "Deficiency of acyl CoA:cholesterol aceyltransferase 2 prevents atherosclerosis in apolipoprotein E-deficient mice.", Proc. Natl Acad. Sci. USA 100: 1262 (2003).
Wolf, M.E. "Burger's Medicinal Chemistry"; 5th edition, Part I, John Wiley & Sons, pp. 975-977 (1995).

Wong, J. et al.: "Endogenous 24(S),25-epoxycholesterol fine-tunes acute control of cellular cholesterol homeostasis," J. Biol. Chem, 283:700-707 (2008).
Wong, W. W. et al.: "HMG-CoA reductase inhibitors and the malignant cell: the statin family of drugs as triggers of Tumor-specific apoptosis," Leukemia 16: 508-19 (2002).
Xu, J. et al.: "Cholesterol trafficking is required for mTPOR activation in endothelial cells," Proc. Natl Acad. Sci. USA 107(10): 4764-69 (2010).
Yabe, D. et al.: "Insig-2, a second endoplasmic reticulum protein that binds SCAP and blocks export of sterol regulatory element-binding proteins," Proc. Natl. Acad. Sci. USA 99: 12753-758 (2002).
Yabe, D. et al.: "Three mutations in sterol-sensing domain of SCAP block interaction with insig and render SREBP 3leavage insensitive to sterols," Proc Natl Acad. Sci. USA 99: 16672-77 (2002).
Yancey, P.G. et al.: "High density lipoprotein phospholipid composition is a major determinant of the bi-directional lux and net movement of cellular free cholesterol mediated by scavenger receptor B1," J. Biol. Chem. 275: 36596-36604 (2000).
Yang, C. et al.: "Sterol intermediates from cholesterol biosynthetic pathway as liver X receptor ligands," J. Biol. Chem. 281: 27816-826 (2006).
Yang, T. et al.: "Crucial step in cholesterol homeostasis: sterols promote binding of SCAP to INSIG-1, a membrane protein that facilitates retention of SREBPs in ER," Cell 110: 489-500 (2002).
Yoneda, A. et al.: "A Collapsin Response Mediator Protein 2 Isoform Controls Myosin II-Mediated Cell Migration and Matrix Assembly by Trapping ROCK II"; Mol. Cell. Biol. 1788-1804 (2012).
Yoshioka, K. et al.: "Overexpression of Small GTP-binding protein RhoA promotes Invasion of Tumor Cells," J. cancer Res_ 59: 2004-2010 (1999).
Zannis, V. et al.: "Role of apoA-1, ABCA1, LCAT and SR-B1 in the biogenesis of HDL," J. Mol. Med. 84: 276-94 2006).
Zerenturk, E. J. et al.: "Sterols regulate 3β-hydroxysterol Δ24-reductase (DHCR24) via dual sterol regulatory elements: cooperative induction of key enzymes in lipid synthesis by sterol regulatory element binding proteins," Biochim. Et Biophys. Acta 1821 (10): 1350-60 (2012).
Zerenturk, E. J. et al.: "The endogenous regulator 24(S),25-epoxycholesterol inhibits cholesterol synthesis at D-HCR24 (Seladin-1)," Biochim. Biophys_ Acta 1821: 1269-77 (2012).
Zhang, L. et al.: "Identification of novel driver tumor suppressors through functional interrogataion of putative passenger mutations in colorectal cancer", International Journal of Cancer, 2012, vol. 132, pp. 732-737.
Zhu, J. et al.: "Effects of FoxO4 overexpression on cholesterol biosynthesis, triacylglycerol accumulation, and glucose uptake," J. Lipid Res. 51: 1312-24 (2010).
Zhuang, L. et al.: "Cholesterol targeting alters lipid raft composition and cell survival in prostate cancer cells and Zenografts," J. Clin. Invest. 115: 959-68 (2005).
Zumbrunn, J. et al.: "Binding of the adenomatous polyposis coli protein to microtubules increases microtubule—stability and is regulated by GSK3b phosphorylation"; Current Biology, 11:44-49, (2001).
Pubchem. Compound Summary for CID 22721249. Create Date: Dec. 5, 2007. [retrieval on Feb. 3, 2015]. Retrived 'rom the Internet. <URL: http://pubchem.ncbi.nim.nih.govicompound/22721249>. entire_document_.
Pubchem. Compound Summary for CID 2911561. Create Date: Jul. 29, 2005. [retrieval on Feb. 3, 2015]. Retrived 'rom the Internet. <URL: http://pubchem.ncbi.nim.nih.govicompound/2911561>. entire_document_.
Pubchem. Compound Summary for CID 46851969. Create Date: Aug. 30, 2010. [retrieval on Feb. 3, 2015]. Retrived 'rom the Internet. <URL: http://pubchem.ncbi.nim.nih.govicompound/46851969>. entire_document_.
Pubchem. Compound Summary for CID 47305059. Create Date: Nov. 26, 2010. [retrieval on Feb. 3, 2015]. Retrived 'rom the Internet.<URL:http://pubchem_ncbi_nim_nih_govicompound/47305059>_ entire_document.

(56) References Cited

OTHER PUBLICATIONS

Pubchem. Compound Summary for CID 57290202. Create Date: Jun. 15, 2012. [retrieval on Feb. 3, 2015]. Retrived 'rom the Internet. <URL: http://pubchem.ncbi.nim.nih.govicompound/57290202>. entire_document_.

Pubchem. Compound Summary for CID 61047227. Create Date: Oct. 19, 2012. [retrieval on Feb. 3, 2015]. Retrived 'rom the Internet. <URL: http://pubchem.ncbi.nim.nih.govicompound/61047227>. entire_document_.

Acton, S. et al.: "*Identification of scavenger receptor SR-B1 as a high density lipoprotein receptor*,"; Science, 271: 518 (1996).

Czarnecka, H. et. al.: "*Regulation of cellular cholesterol efflux by lecithin: cholesterol 3cyltransferase reaction through nonspecific lipid exchange*,"; J. Biol. Chem., 271: 1023-27 (1996).

Foode, R. et al.: "*Mutations in the APC tumour suppressor gene cause chromosomal instability*"; Nature Cell Biology, 2001, vol. 3, pp. 433-443.

Gabitova, L. et al.: "*Molecular Pathways: Sterols and receptor signaling in Cancer*,"; Clin. Cancer Res. 19(23): 3344-50 (2013).

Gill, S. et al.: "*Cholesterol-dependent degradation of squalene monooxygenase, a control point in cholesterol synthesis beyond HMG-CoA reductase*,"; Cell Metab., 13: 260-73, (2011).

Gillotte, K.L. et al,: "*Removal of cellular cholesterol by pre-HDL involves plasma membrane microsolubilization*,"; J. Lipid Res. 39: 1918-28 (1998).

Gong, Y. et al.: "*Sterol-regulated ubiquitination and degradation of Insig-1 creates a convergent mechanism for feedback control of cholesterol synthesis and uptake*"; Cell Metab. 3: 15-24 (2006).

Gonzalez, R. et al.: "*Two major regulatory steps in cholesterol synthesis by human renal cancer cells*,"; Arch. Biochem. Biophys., 196: 574-80. (1979).

Gorin, A. et al.: "*Regulation of cholesterol biosynthesis and cancer signaling*,"; Curr. Op. Pharmcol., 12(6), 710-16, 2012.

Polakis, P. et al.: "*The many ways of Wnt in cancer*"; Current Opinion in Genetics & Development, 2007, vol. 17, pp. 45-51, www.sciencedirect_com.

Berardi, Francesco et al.: "*Novel 4-(4-Aryl)cyclohexyl-1-(2-pyridyl)piperazines as [Delta] 8-[Delta] 7 Sterol Isomerase (Emopamil Binding Protein) Selective Ligands with Antiproliferative Activity*"; J. of Medicinal Chemistry, vol. 51, No. 23, Nov. 14, 2008, pp. 7523-7531, XP055552416.

Supplementary European Search Report dated Mar. 8, 2019, regarding EP 16 82 4891.

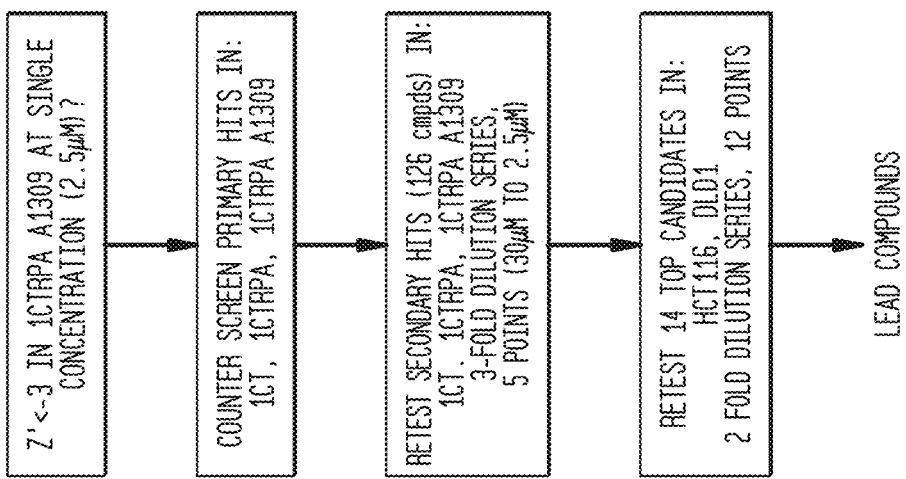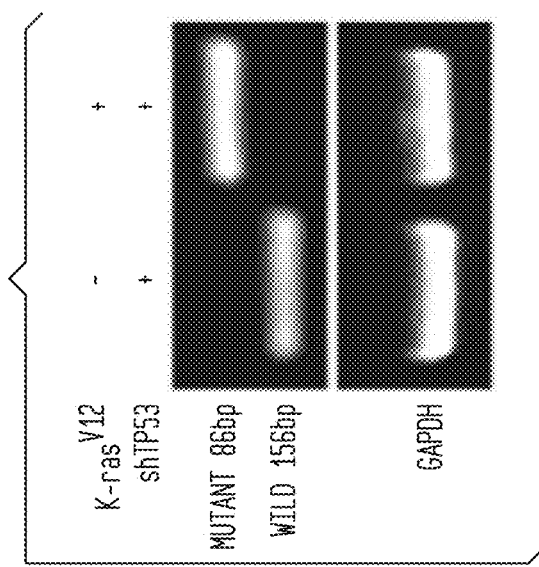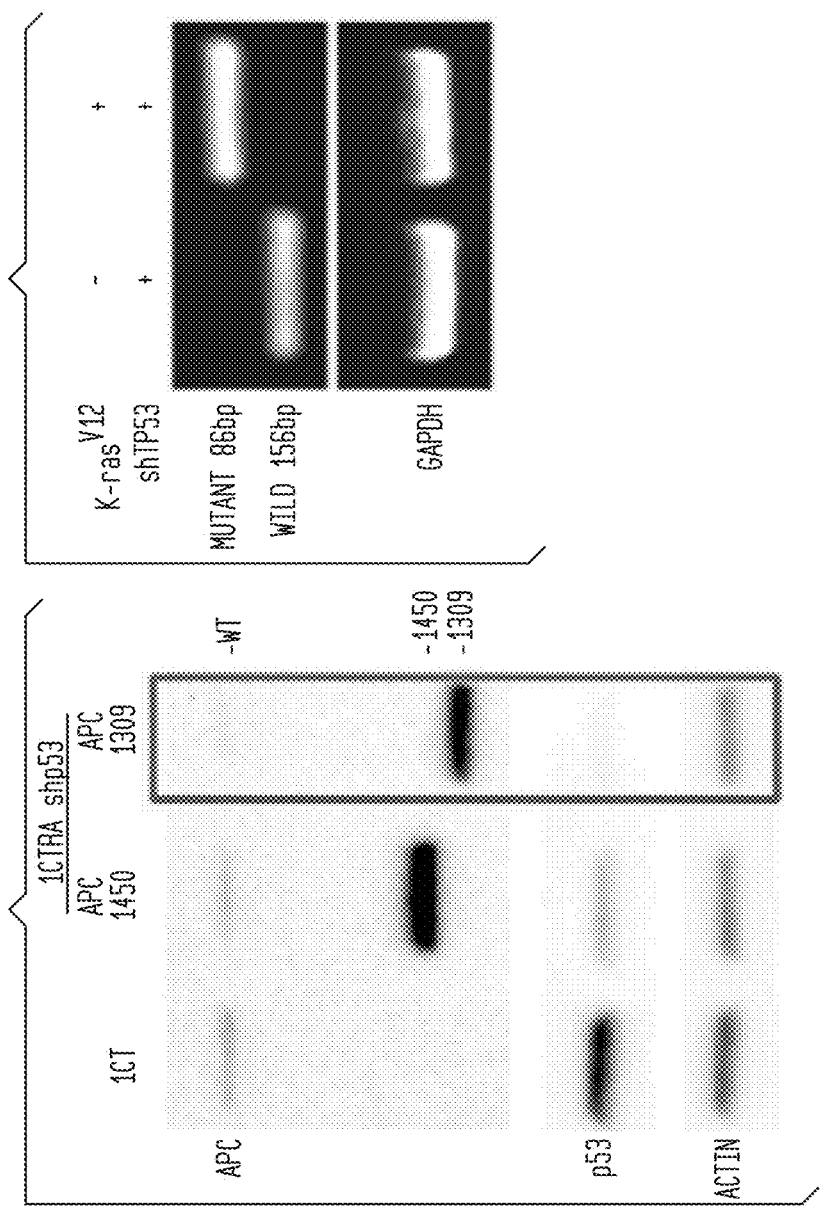

FIG. 7A
| CELL LINES | GENETIC ALTERATIONS |
|---|---|
| 1CT | HCECs IMMORTALIZED WITH CDK4 AND hTERT |
| 1CTRPA | $Kras^{V12}$, shTP53, shAPC |
| 1CTRPA A1309 | $Kras^{V12}$, shTP53, shAPC, APC TRUNCATION (aa1-1309) |
FIG. 7B
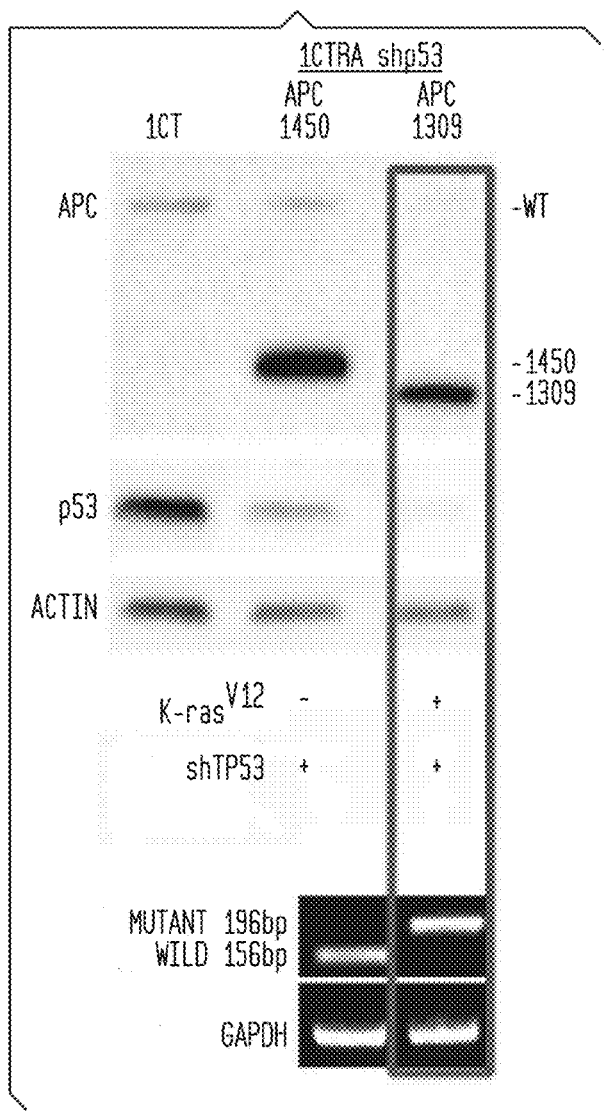
FIG. 7C
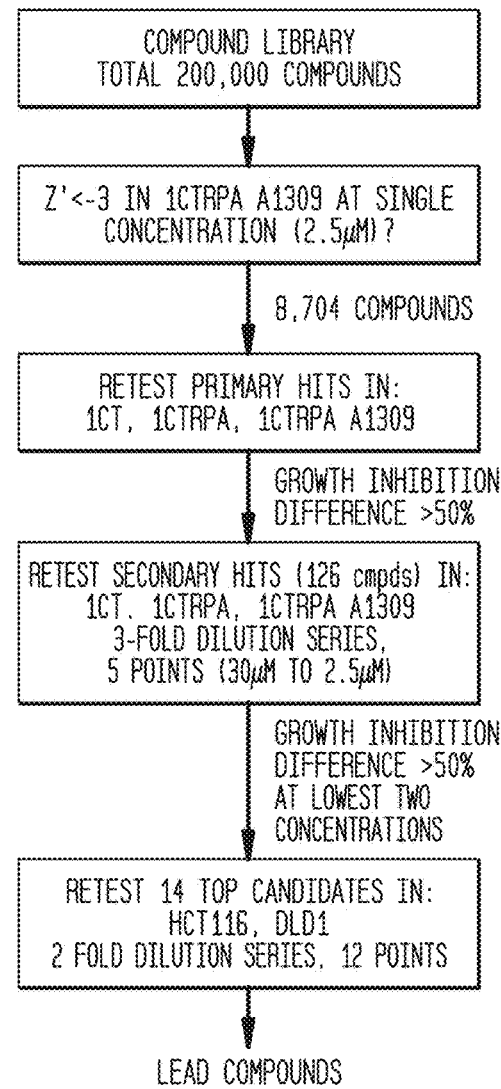

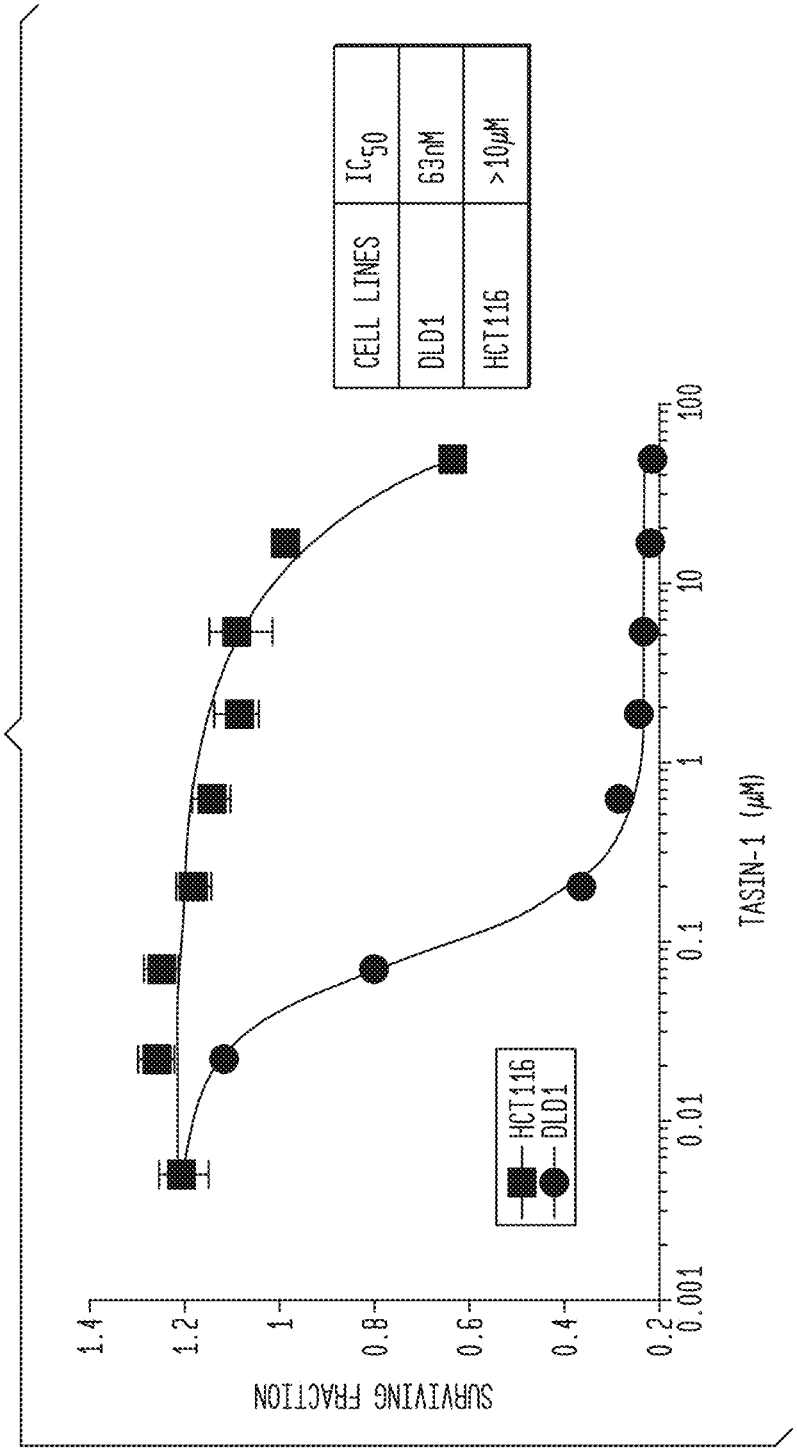
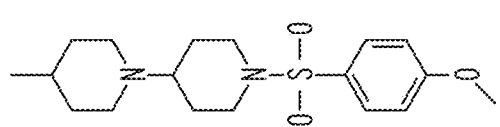
FIG. 7D
FIG. 7E

| CELL LINE | IC$_{50}$ (µM) | APC STATUS |
|---|---|---|
| HTC116 | 42 | WT |
| HTC116 p53-/- | 40.8 | WT |
| RKO | 37.2 | WT |
| Lovo | 7.5 | aa1430 |
| Caco-2 | 5.2 | aa1367 |
| SW480 | 3.6 | aa1338 |
| SW620 | 3.6 | aa1338 |
| HCT15 | 3.3 | aa1416 |
| HT29 | 0.075 | aa8358.1555 |
| DKD1 | 0.063 | aa1416 |

SW168427 PK (10mg/kg IP, FEMALE CD-Q MICE)

LIC: LARGE INTESTINE CONTENT

* p<0.05,  p<0.01, *p<0.001

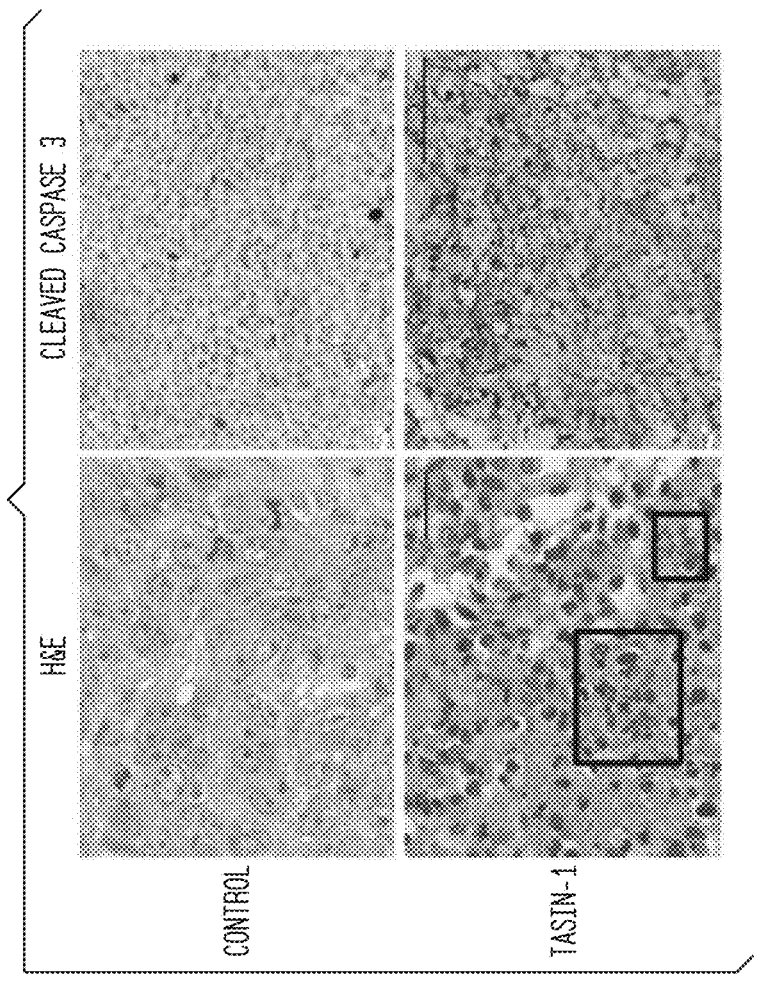
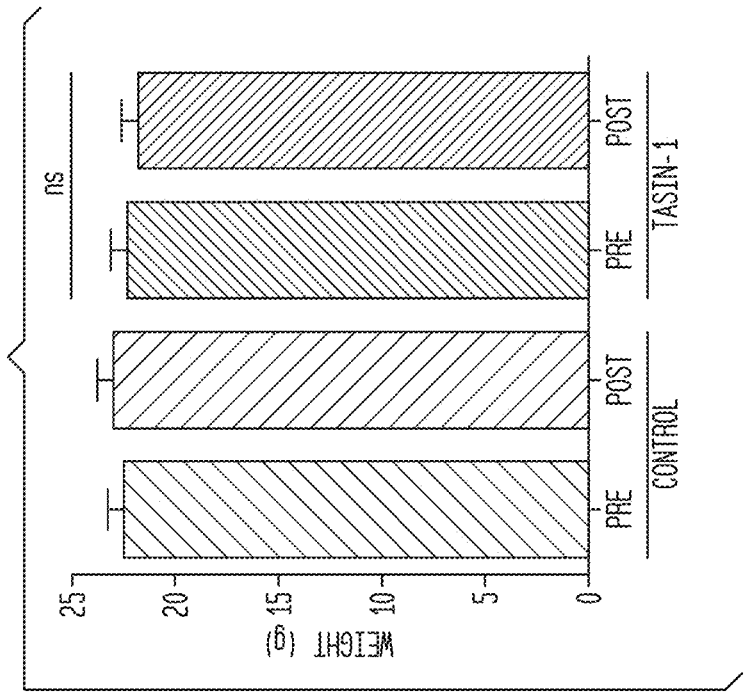
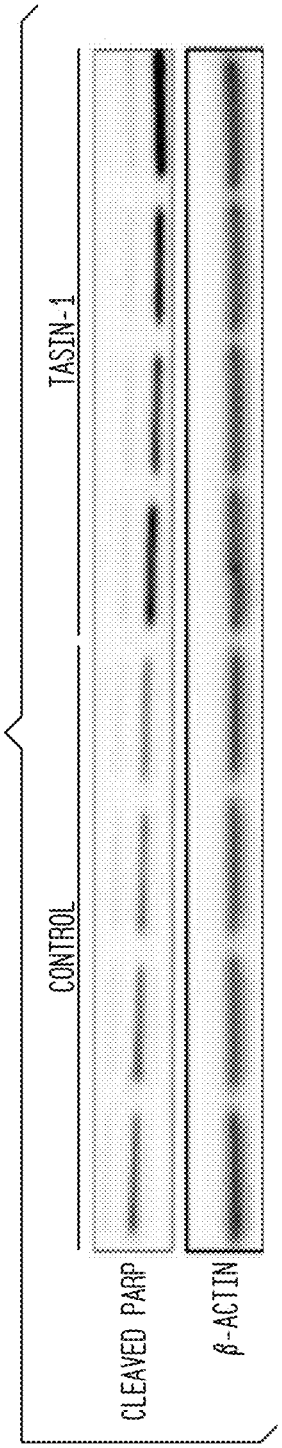

FIG. 30
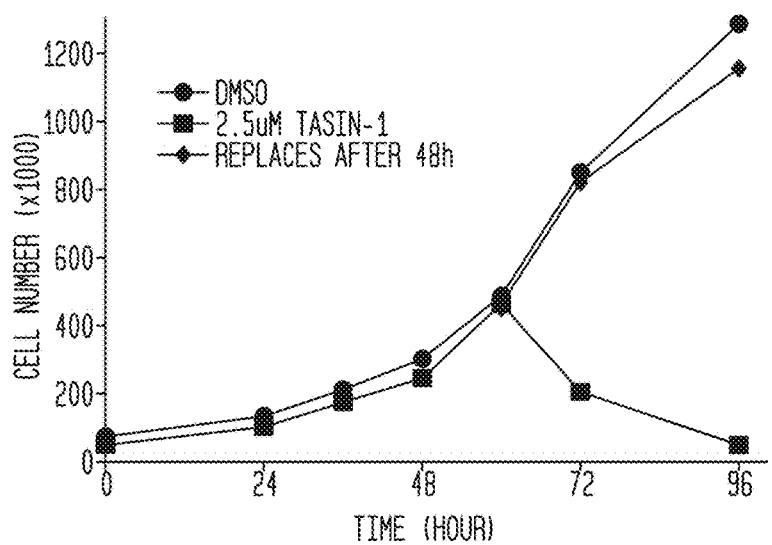
FIG. 31
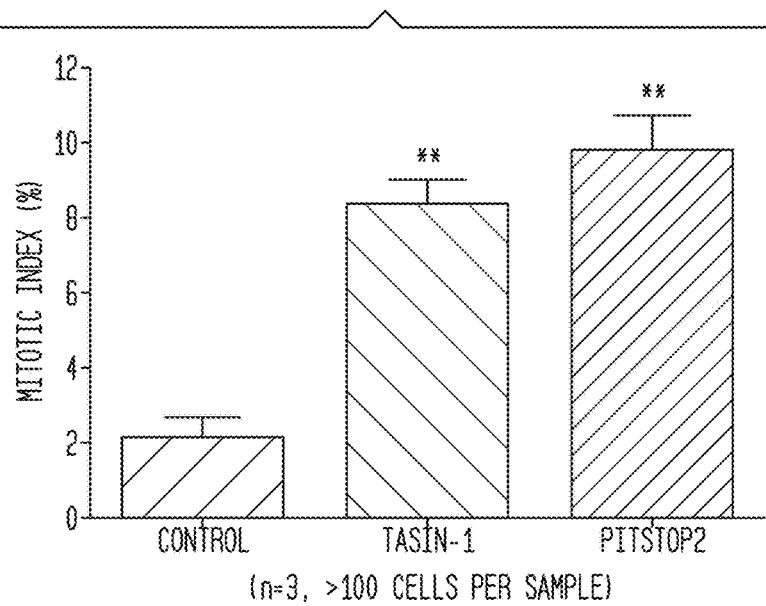
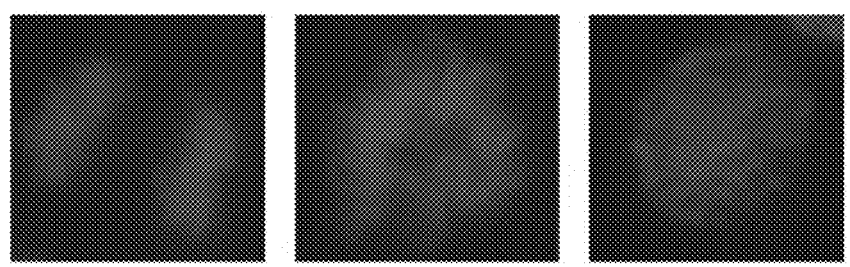

FIG. 32
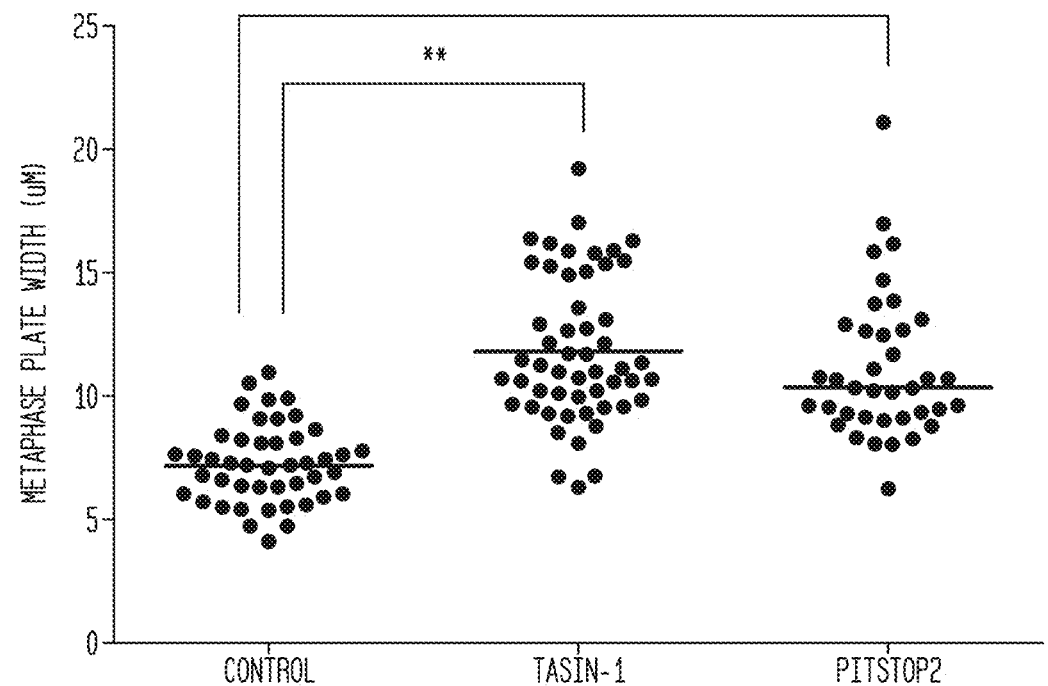
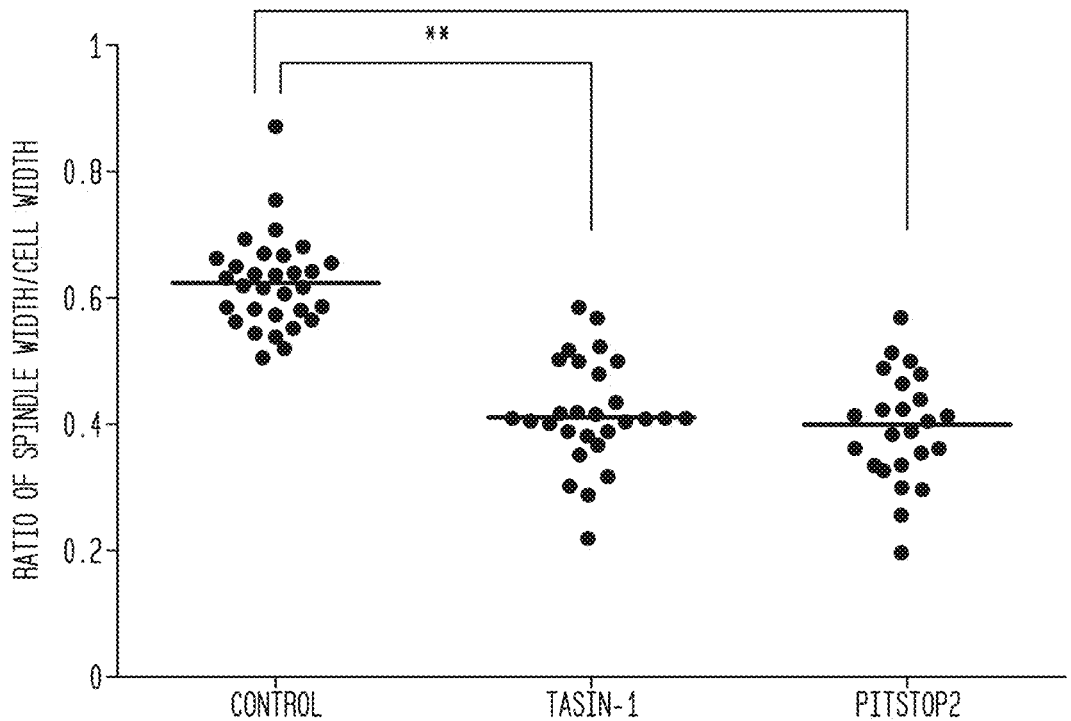

THERAPEUTICS TARGETING TRUNCATED ADENOMATOUS POLYPOSIS COLI (APC) PROTEINS

CROSS-REFERENCE TO RELATED APPLICATIONS

This application is a Divisional Application of U.S. patent application Ser. No. 14/482,659 filed on Sep. 10, 2014, which claims the benefit of priority to U.S. provisional application No. 61/875,933 (filed Sep. 10, 2013), and U.S. Provisional Application No. 61/930,754 (filed Jan. 23, 2014). The content of each of these applications is incorporated by reference herein in its entirety.

FIELD OF INVENTION

The described invention relates to colorectal cancer, the APC tumor suppressor gene, truncated APC gene products produced by mutation of the gene, and therapeutic agents targeting colon cancer cell lines and other human cancer cell lines with truncated APC gene products.

BACKGROUND OF THE INVENTION

Colorectal cancer (CRC) is the third most commonly diagnosed cancer and third leading cause of cancer-related mortality in the United States, with an estimated 141,000 cases of colon and rectal cancer diagnosed in 2011. Thus, 1 in 19 Americans will be diagnosed with CRC in their lifetime for an overall risk of 5.4%. Fortunately, surgical excision of early, noninvasive adenomas is essentially curative. However, there are few effective treatment options for patients suffering from advanced forms of CRC, and the prognosis is often poor. Despite a prolonged latency phase, too few lesions are identified at a stage where they can be surgically excised (See Phelps et al. Cell Cycle, 2009; 8:16, 2549-2556).

Mutations in the human APC tumor suppressor gene are linked to Familial Adenomatous Polyposis (FAP), an inherited cancer-prone condition in which numerous polyps are formed in the epithelium of the large intestine (See Kinzler et al., Science, 1991; 253:661-665; Kinzler and Vogelstein, Cell, 1996; 87:159-170; Half et al., Orphanet Journal of Rare Diseases, 2009; 4:22). The development of CRC is initiated by the aberrant outgrowth of adenomatous polyps from the colonic epithelium that ultimately evolve into aggressive carcinomas (See Kinzler and Vogelstein, Cell, 1996; 87: 159-170). About 85% of sporadic colorectal cancers have been reported to harbor APC truncating mutations (See Kinzler and Vogelstein, Cell, 1996; 87:159-170). The growth of the polyps is associated in most cases with alterations of both alleles of the Adenomatous Polyposis Coli (APC) gene. A first mutational hit occurs roughly in the middle of the open reading frame, generating a truncated APC molecule lacking the C-terminal half. Such truncation mutations are located in the so-called mutation cluster region (MCR) (See Schneikert et al., Human Molecular Genetics, 2006; 16: 199-209). The second mutational hit involves either deletion of the second allele or a mutation that leads to the synthesis of a truncated product, almost never occurring after the MCR (See Schneikert et al., Human Molecular Genetics, 2006; 16: 199-209). Thus, colon cancer cells express at least a truncated APC molecule whose length is defined by the position of the MCR and, occasionally, an additional but shorter fragment.

CRC treatment is primarily reliant upon chemotherapeutic agents that act with minimal specificity for the underlying genetic basis of disease. These chemotherapeutic agents frequently disrupt the function of normal cells while disrupting cancer cells due to shared reliance on the chemical target. Better, more precise therapeutic agents are needed to improve treatment of patients diagnosed with CRC.

Adenomatous Polyposis Coli (APC) Gene

APC, which does not act as a classical tumor suppressor, influences Wnt signaling thereby regulating gene transcription. Wnts are a family of secreted cysteine-rich glycoproteins that have been implicated in the regulation of stem cell maintenance, proliferation, and differentiation during embryonic development. Canonical Wnt signaling increases the stability of cytoplasmic β-catenin by receptor-mediated inactivation of GSK-3 kinase activity and promotes β-catenin translocation into the nucleus. The canonical Wnt signaling pathway also functions as a stem cell mitogen via the stabilization of intracellular β-catenin and activation of the β-catenin/TCF/LEF transcription complex, resulting in activated expression of cell cycle regulatory genes, such as Myc, cyclin D1, EPhrinB (EPhB) and Msx1, which promote cell proliferation (See Cayuso and Marti, Journal of Neurobiology, 2005; 64:376-387).

APC is the negative regulator of Wnt signaling. Without this negative regulation, the Wnt pathway is more active and is important in cancer (See Polakis, Current Opinion in Genetics & Development, 2007; 17: 45-51). Studies comparing tumor cells with mutations in both APC alleles to correlate levels of Wnt signaling and severity of disease in both humans and mice have aided in establishing a model in which gene dosage effects generate a defined window of enhanced Wnt signaling, leading to polyp formation in the intestine. Combinations of 'milder' APC mutations, associated with weaker enhancement of Wnt signaling, give rise to tumors in extra-intestinal tissues. According to this model, the nature of the germline mutation in APC determines the type of somatic mutation that occurs in the second allele. (See Minde et al. Molecular Cancer, 2011; 10:101).

APC Protein

The APC gene product is a 312 kDa protein consisting of multiple domains, which bind to various proteins, including beta-catenin, axin, C-terminal binding protein (CtBP), APC-stimulated guanine nucleotide exchange factors (Asefs), Ras GTPase-activating-like protein (IQGAP1), end binding-1 (EB1) and microtubules. Studies using mutant mice and cultured cells demonstrated that APC suppresses canonical Wnt signaling, which is essential for tumorigenesis, development and homeostasis of a variety of cell types, including epithelial and lymphoid cells. Further studies have suggested that the APC protein functions in several other fundamental cellular processes. These cellular processes include cell adhesion and migration, organization of actin and microtubule networks, spindle formation and chromosome segregation. Deregulation of these processes caused by mutations in APC is implicated in the initiation and expansion of colon cancer (See Aoki and Taketo, Journal of Cell Science, 2007; 120:3327-3335).

The APC protein functions as a signaling hub or scaffold, in that it physically interacts with a number of proteins relevant to carcinogenesis. Loss of APC influences cell adhesion, cell migration, the cytoskeleton, and chromosome segregation (See Aoki and Taketo, Journal of Cell Science, 2007; 120:3327-3335).

Most investigators believe that APC mutations cause a loss of function change in colon cancer. Missense mutations yield point mutations in APC, while truncation mutations cause the loss of large portions of the APC protein, including defined regulatory domains. A significant number of APC missense mutations have been reported in tumors originating from various tissues, and have been linked to worse disease outcome in invasive urothelial carcinomas (See Kastritis et al., International Journal of Cancer, 2009; 124:103-108), suggesting the functional relevance of point mutated APC protein in the development of extra-intestinal tumors. The molecular basis by which these mutations interfere with the function of APC remains unresolved.

APC mutation resulting in a change of function can influence chromosome instability in at least three manners: by diminishing kinetochore-microtubule interaction, by the loss of mitotic checkpoint function and by generating polyploid cells. For example, studies have shown that APC bound to microtubules increased microtubule stability in vivo and in vitro, suggesting a role of APC in microtubule stability (See Zumbrunn et al., Current Biology, 2001; 11:44-49). Truncated APC led to chromosomal instability in mouse embryonic stem cells (See Fodde et al., Nature Cell Biology, 2001; 3:433-438), interfered with microtubule plus-end attachments, and caused a dramatic increase in mitotic abnormalities (See Green and Kaplan, Journal of Cell Biology, 2003; 163:949-961). Studies have shown that cancer cells with APC mutations have a diminished capacity to correct erroneous kinetochore-microtubule attachments, which account for the wide-spread occurrence of chromosome instability in tumors (See Bakhoum et al., Current Biology, 2009; 19:1937-1942). In addition, abrogation of the spindle checkpoint function was reported with APC loss of function. Knockdown of APC with siRNA indicated that loss of APC causes loss of mitotic spindle checkpoint function by reducing the association between the kinetochore and checkpoint proteins Bub1 and BubR1. Thus, loss of APC reduces apoptosis and induces polyploidy (See Kaplan et al., Nature Cell Biology, 2001; 3:429-432; Dikovskaya et al., Journal of Cell Biology, 2007; 176:183-195; Rusan and Peifer, Journal of Cell Biology, 2008; 181:719-726). Polyploidy is a major source for aneuploidy since it can lead to multipolar mitosis (See Shi and King, Nature, 2005; 437:1038-1042).

While loss of function due to APC may be partially correct, there are reports showing that a large fraction of colon cancer patients have at least one APC gene product that is truncated, and that this has a gain of function. Thus truncated APC proteins may play an active role in colon cancer initiation and progression as opposed to being recessive; for example, truncated APC, but not full-length APC may activate Asef and promote cell migration.

Although defects in APC occur in a high fraction of colon cancer cases, there are currently no therapeutics targeting vulnerabilities resulting from these defects. The described invention provides small molecule inhibitor compounds that selectively target truncated APC in immortalized Human Colonic Epithelial Cells (HCECs) for treating colon cancer.

SUMMARY OF THE INVENTION

According to one aspect, the described invention provides a series of small molecule compounds that selectively inhibit the growth of human cancer cells that contain a truncated Adenomatous Polyposis *Coli* (APC) protein.

According to one embodiment, the small molecule anti-cancer compound is a compound of Formula I. According to another embodiment, the small molecule anti-cancer compound is a compound of Formula I-a. According to another embodiment, the small molecule anti-cancer compound is a compound of Formula I-b. According to another embodiment, the small molecule anti-cancer compound is a compound of Formula I-c. According to another embodiment, the small molecule anti-cancer compound is a compound of Formula I-d. According to another embodiment, the small molecule anti-cancer compound is a compound selected from the group consisting of the 43 structures disclosed in claim 3. According to another embodiment, the small molecule anti-cancer compound is a compound of the structural formula disclosed in claim 5. According to another embodiment, the small molecule anti-cancer compound is selected from the group consisting of the 5 structures disclosed in claim 7. According to another embodiment, the small molecule anti-cancer compound is a compound of the structural formula disclosed in claim 9. According to another embodiment, the $IC_{50}$ of the small molecule anti-cancer compound is from 0.01 nM to 5 µM. According to another embodiment, the small molecule anti-cancer compound is in the form of a pharmaceutical composition comprising a therapeutic amount of the compound and a pharmaceutically acceptable carrier. According to another embodiment, the therapeutic amount of the small molecule anti-cancer compound is effective to inhibit tumor growth, inhibit tumor proliferation, induce cell death or a combination thereof.

According to another aspect, the described invention provides a method of treating colorectal cancer in a subject whose colonic epithelial cells express at least one truncated APC protein, comprising administering to the subject a pharmaceutical composition comprising a therapeutic amount of at least one small molecule anti-cancer compound of any one of claims 1 through 19 and a pharmaceutically acceptable carrier, wherein the therapeutic amount is effective to inhibit tumor growth, inhibit tumor proliferation, induce cell death, or a combination thereof.

According to another aspect, the described invention provides an immortalized human colonic epithelial cell (HCEC) comprising a full length, wild type APC gene, wherein the cell comprises at least one of the following: an ectopically expressed vector containing Kirsten rat sarcoma viral oncogene homolog ($Krasv^{12}$), a small hairpin RNA against tumor protein p53 (shp53), and a small hairpin RNA against APC (shAPC). According to one embodiment, the APC gene contains a somatic mutation at codon 1450. According to another embodiment, the APC gene contains a somatic mutation at codon 1309. According to another embodiment, the cell expresses a LacZ protein. According to another embodiment, the cell expresses the Kirsten rat sarcoma viral oncogene homolog ($Krasv^{12}$) and the small hairpin RNA against APC (shAPC). According to another embodiment, the cell is transduced with retroviral cyclin-dependent kinase 4 (Cdk4) and a catalytic component of human telomerase (hTERT).

BRIEF DESCRIPTION OF THE DRAWINGS

FIG. 6A-6C show APC truncations and identification of APC inhibitor. (a) and (b) are gels showing APC truncations. (c) is a flow chart showing steps in the identification of TASIN-1 (Truncated APC Selective Inhibitor) through high-throughput screening.

FIG. 7A-7F shows that TASIN-1 is selectively toxic to Colorectal Cancer (CRC) lines with APC truncation. (a) shows genetic alterations. (b) Validation of ectopic expression of APC truncation, knockdown of WT APC, and p53 and expression of oncogenic Kras$^{v12}$ by Western Blot or a restriction digest assay. The cell line used in the primary screen is highlighted in the red box. (c) is a flow chart describing the process for identifying lead compounds. (d) shows the structure of a compound. (e) Dose response curve of TASIN-1 in HCT116 and DLD1 cells. The table (e) lists the $IC_{50}$ value for both cell lines. DLD1 expresses truncated APC, while HCT116 expresses wild type APC. Thus, TASIN-1 inhibits DLD1 cells expressing truncated APC from surviving and forming colonies but has little or no affect on HCT116 cells (f) Representative photographs and quantification of HCT116 and DLD1 cells grown in soft agar in the presence or absence of TASIN-1 for 7 days. Data represent mean±s.d., n=3. Student's t-test, ***P<0.001.

FIG. 25A-25C shows that TASIN-1 inhibits tumor in xenograft mouse model through induction of apoptosis without noticeable toxicity. (a) Body weights before and after treatment in control or TASIN-1-treated mice. (b) Representative H&E staining images and immunohistochemistry for cleaved caspase 3 in TASIN-1 or solvent treated DLD1 xenografts. Scale bar (left), 50 μM; (right), 200 μM. TASIN-1 treated tumors showed areas of apoptotic tumor cells (marked by box, lower left) and were positive staining for cleaved caspase 3 (lower right). (c) Cleaved PARP was detected in extracts of control or TASIN-1 treated tumor specimen by Western blot.

FIG. 30 shows that 2.5 μM TASIN-1 induces slow and reversible cell death.

FIG. 31 shows that TASIN-1 increases mitotic index 4-fold over control cells.

FIG. 32 shows that TASIN-1 disrupts chromosome congression similar to the positive control PITSTOP2.

TASIN-1 treatment induces lagging microsome and anaphase bridges as indicated by the red arrow. All scale bars: 1004.

Figure 34A:
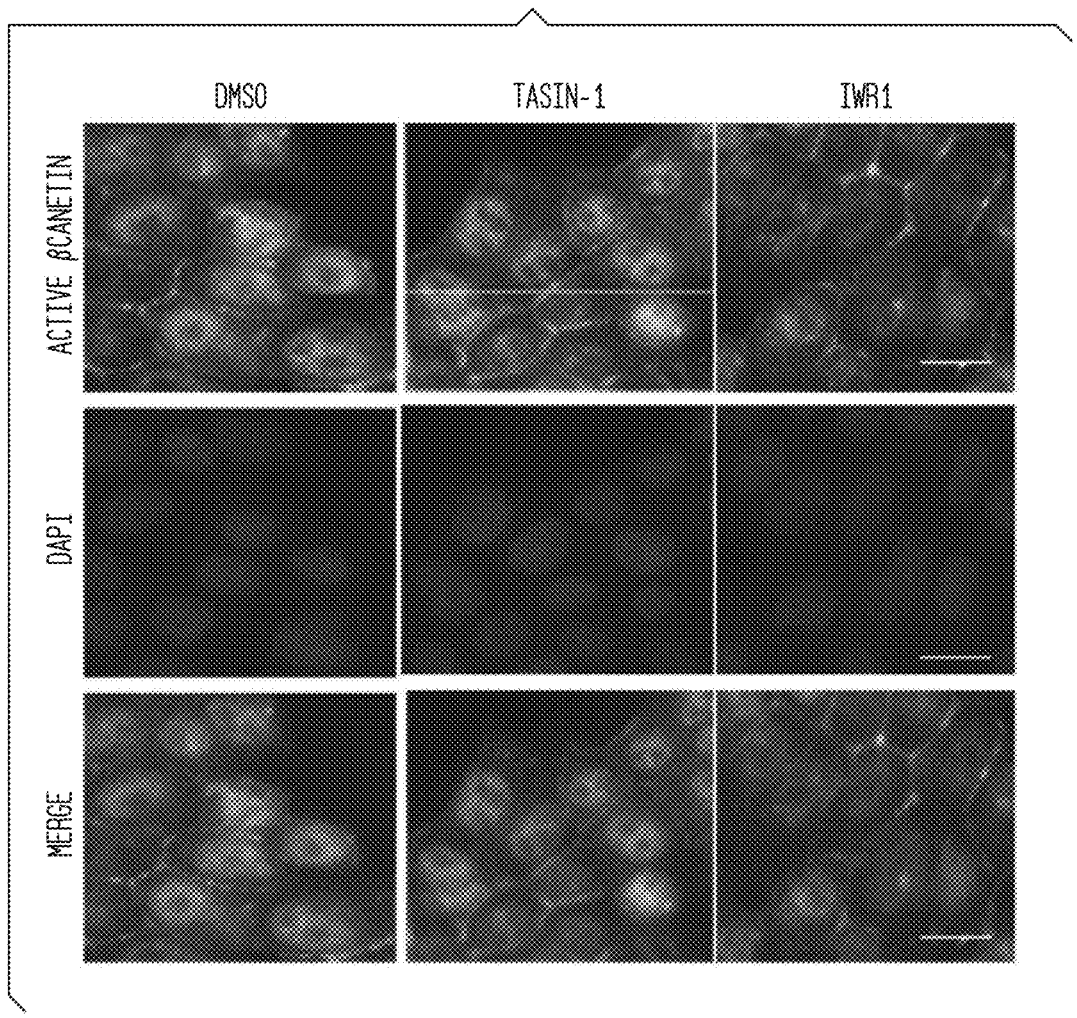
Figure 34B:
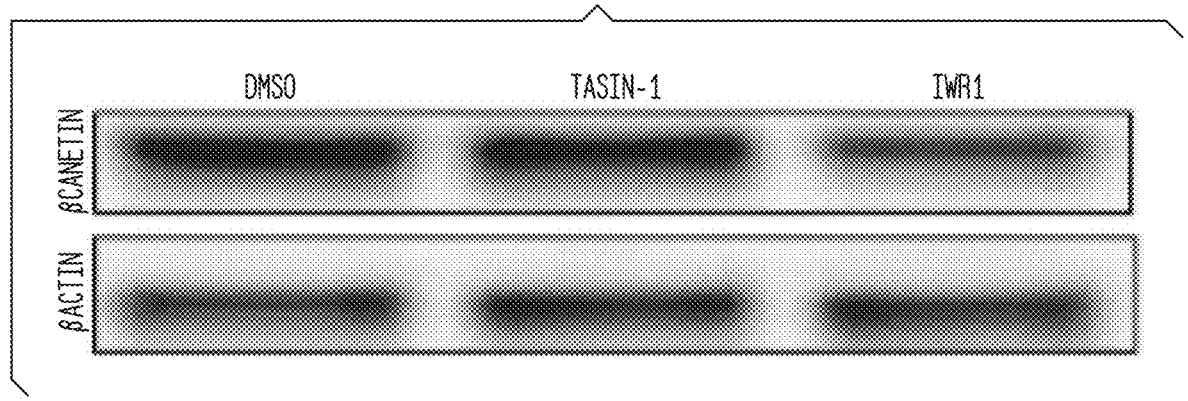
Figure 34C:
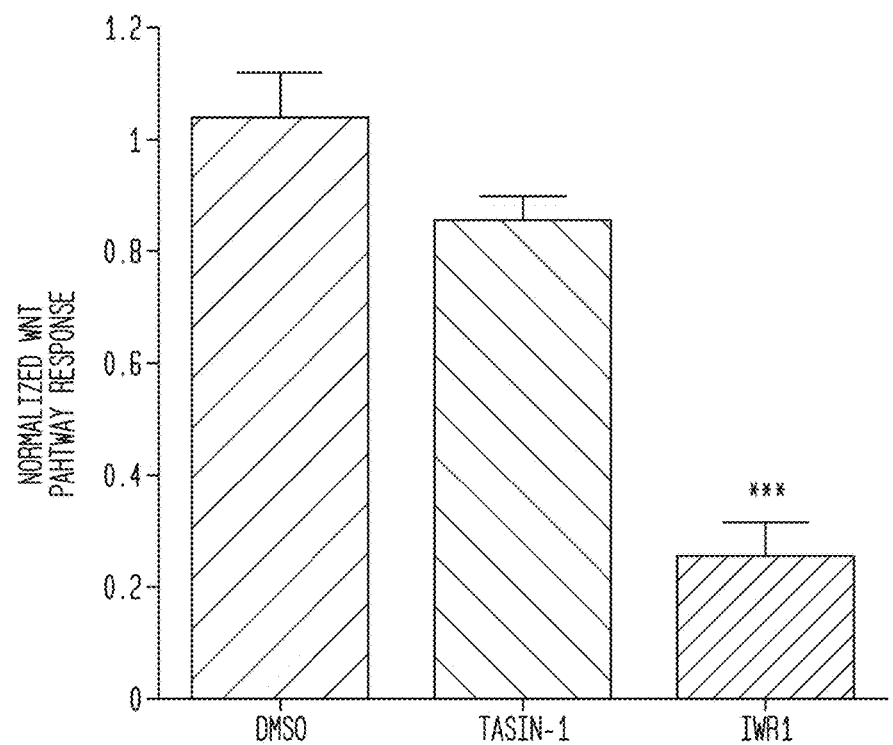

FIG. 34A-34C shows that TASIN-1 does not affect Wnt pathway activity in DLD1 cells. Immunostaining for active β-catenin (a) and Western blot for total β-catenin (b) in DLD1 cells treated with TASIN-1 for 24 hours. (c) TASIN-1 did not affect Wnt pathway activity using the STF reporter. IWR was used as a positive control (Chen, C. et al. Small molecule-mediated disruption of Wnt-dependent signaling in tissue regeneration and cancer. *Nature chemical biology* 5, 100-107 (2009)). Data represent mean±s.d., n=3. Student's t-test, P<0.01, *P<0.001. All scale bars: 10 μM.

Figure 35A:
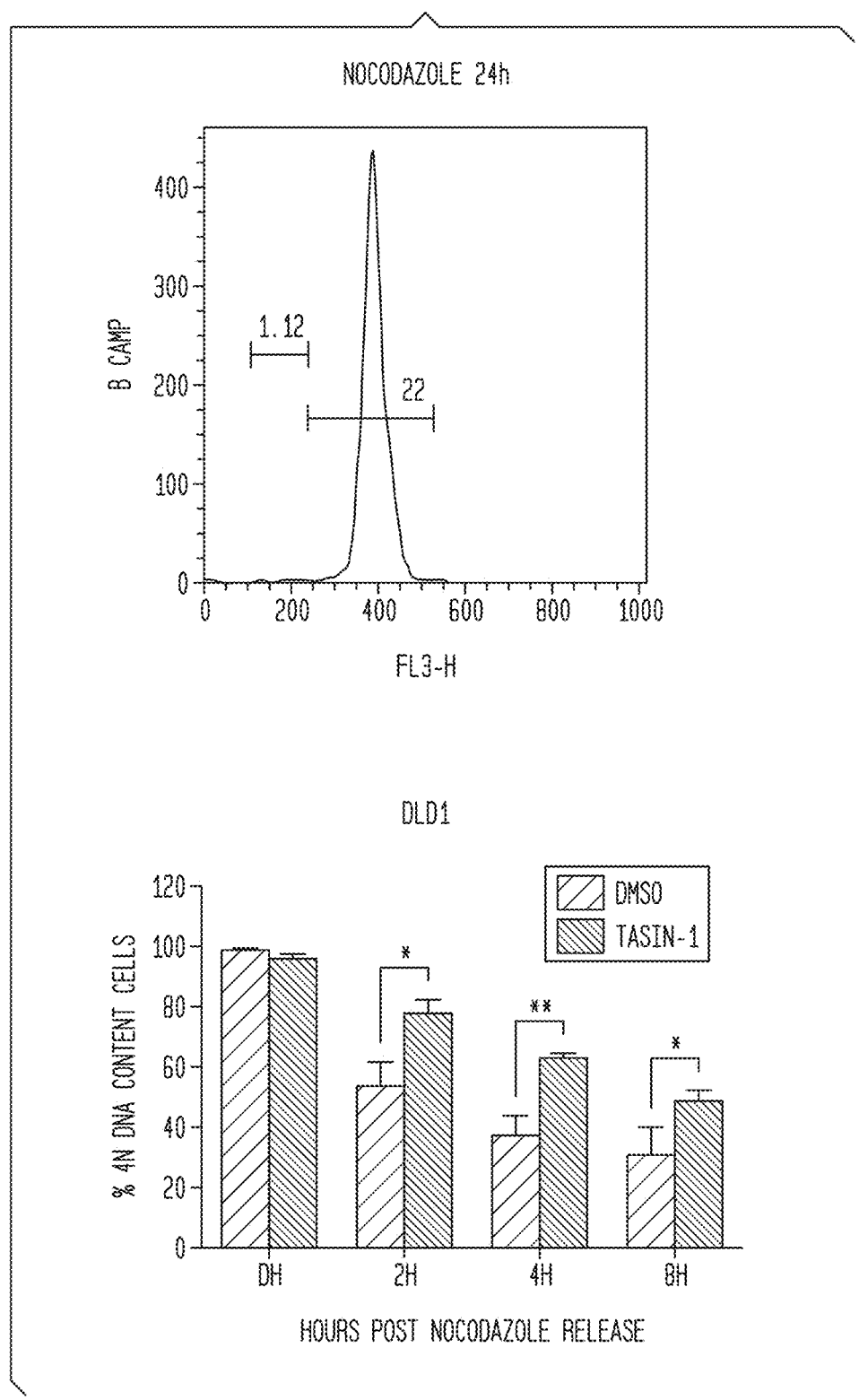
Figure 35B:
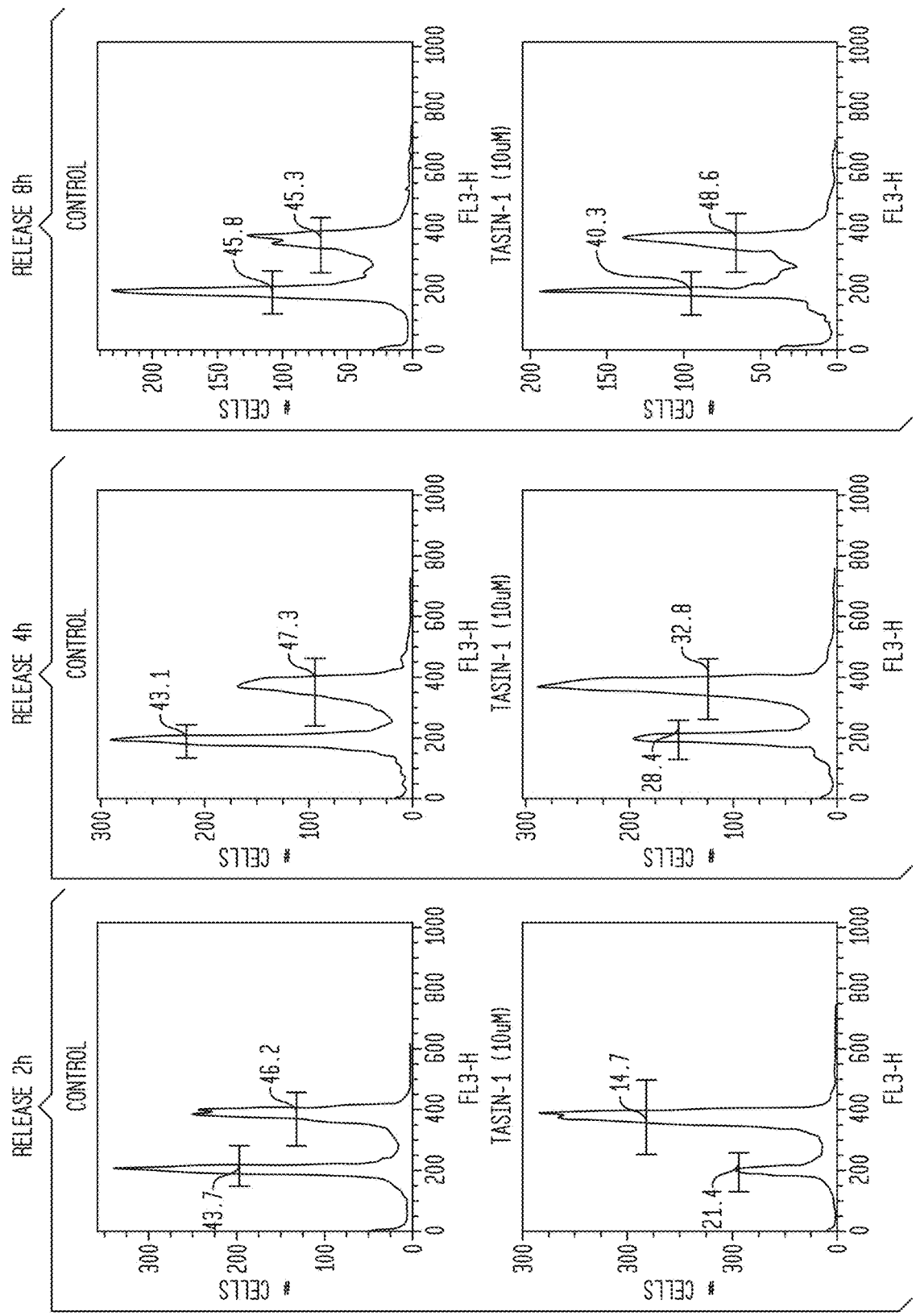

FIG. 35A-35B shows that TASIN-1 delays entry into G1 phase in DLD-1 cells after release from nocodazole synchronization (a-b).

Figure 36A:
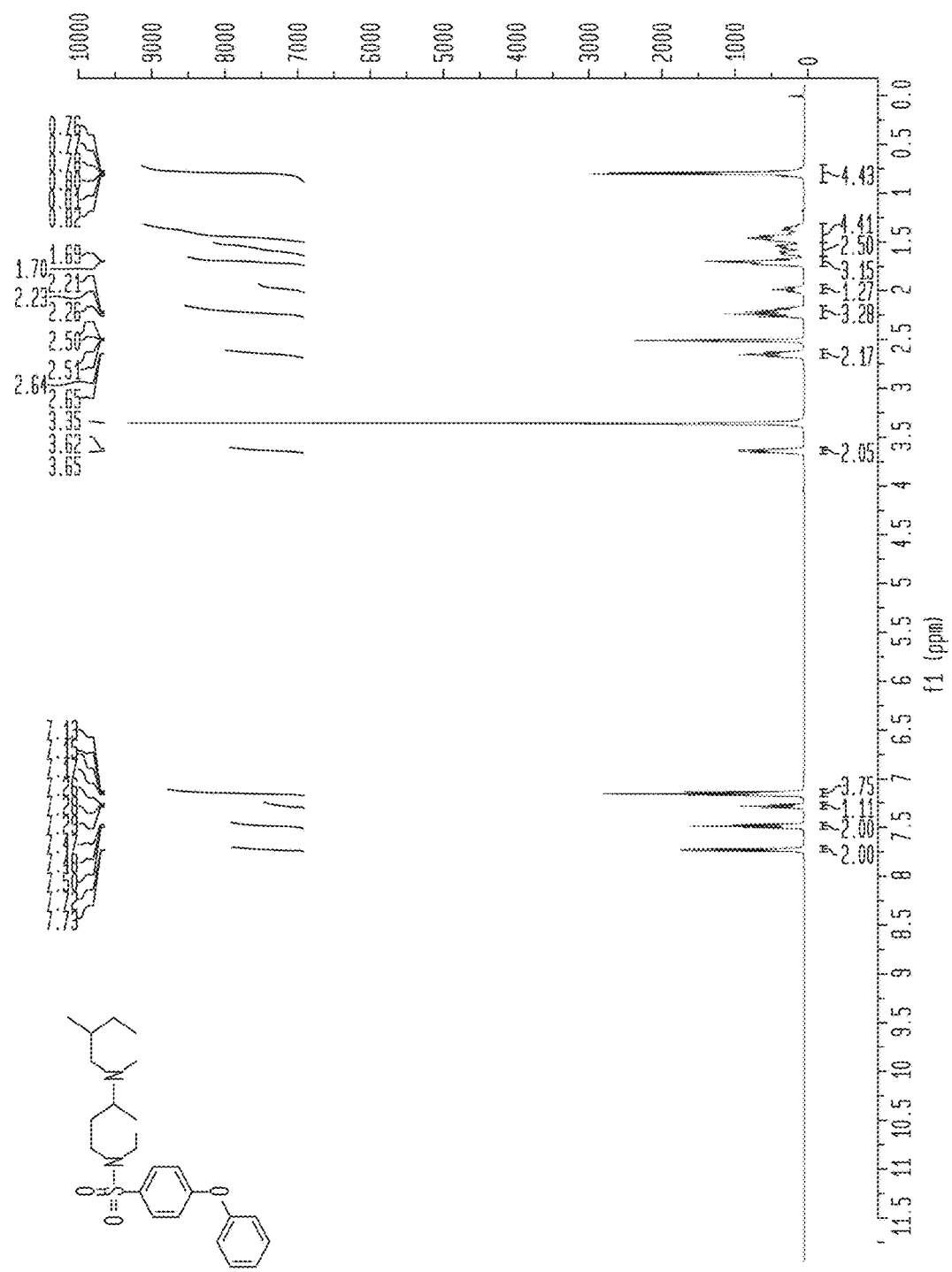
Figure 36B:
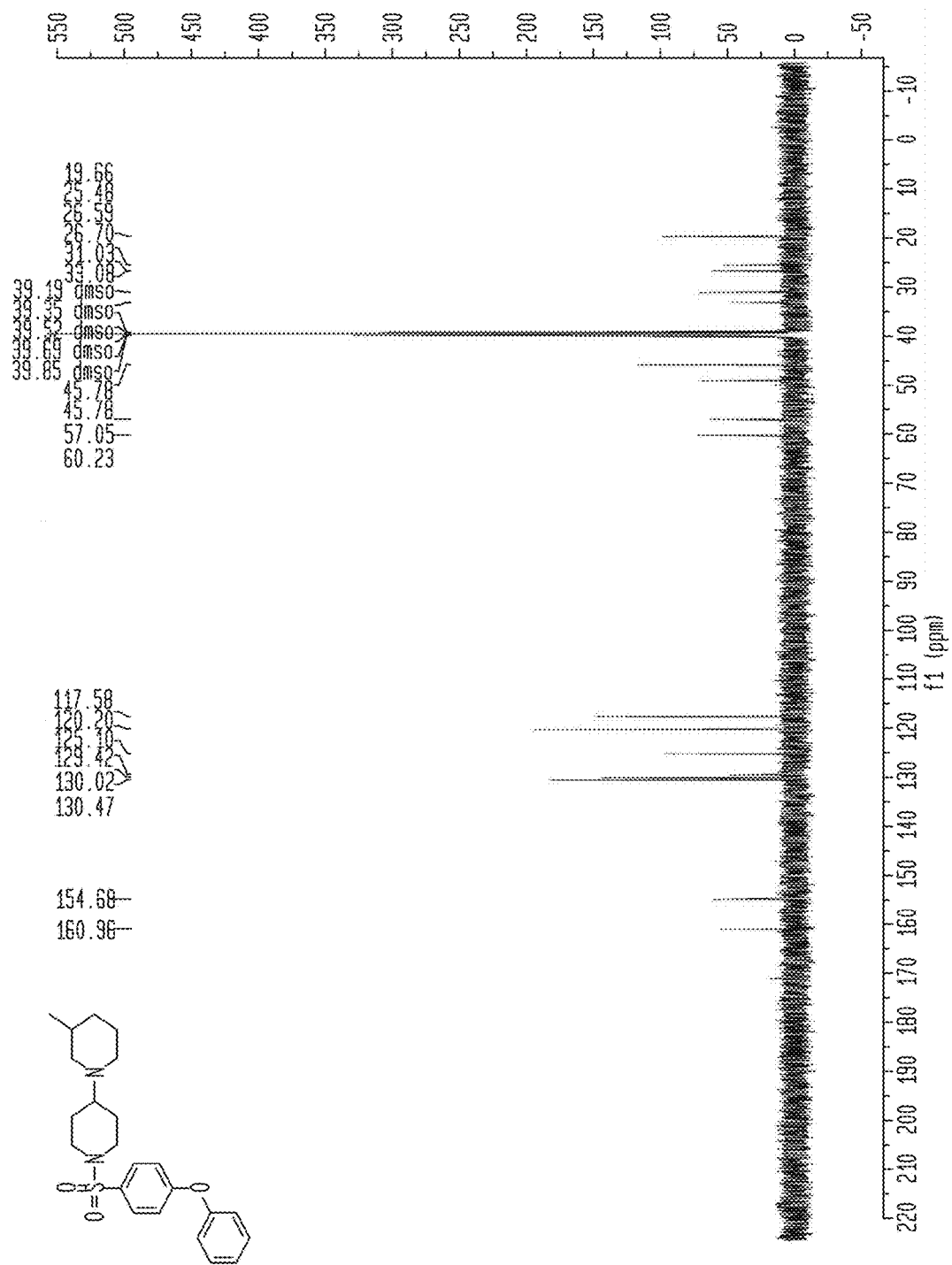
Figure 36C:
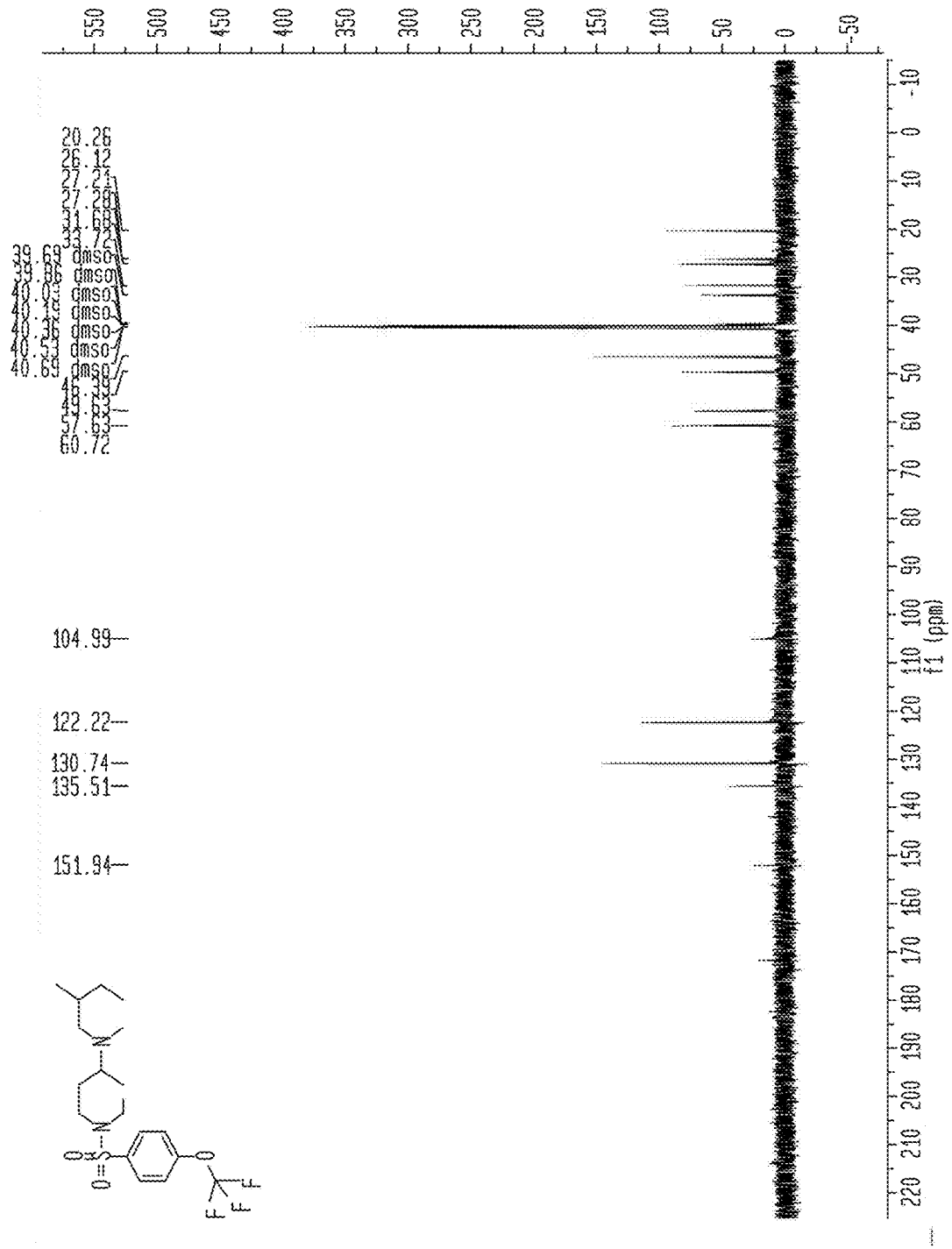
Figure 36D:
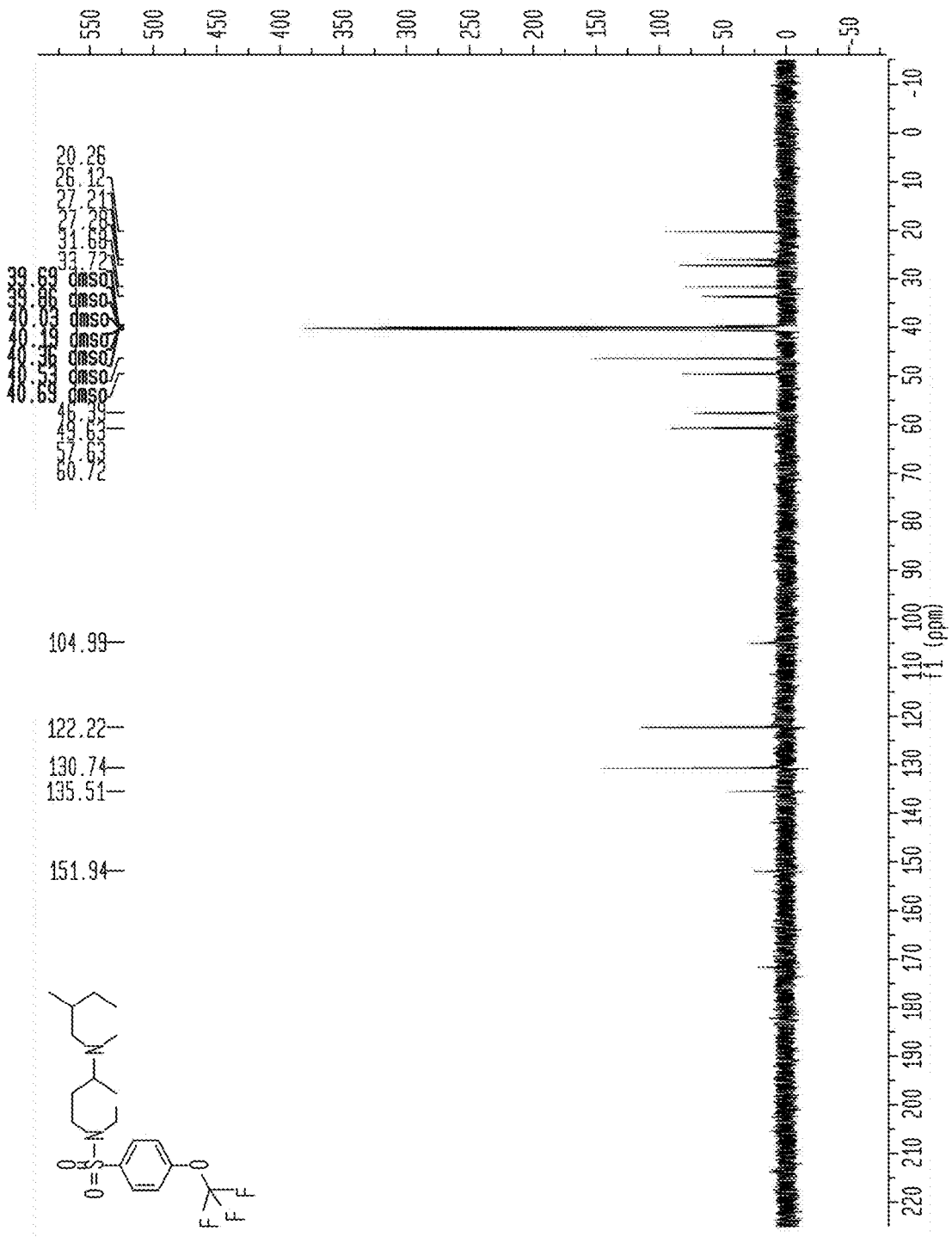
Figure 36E:
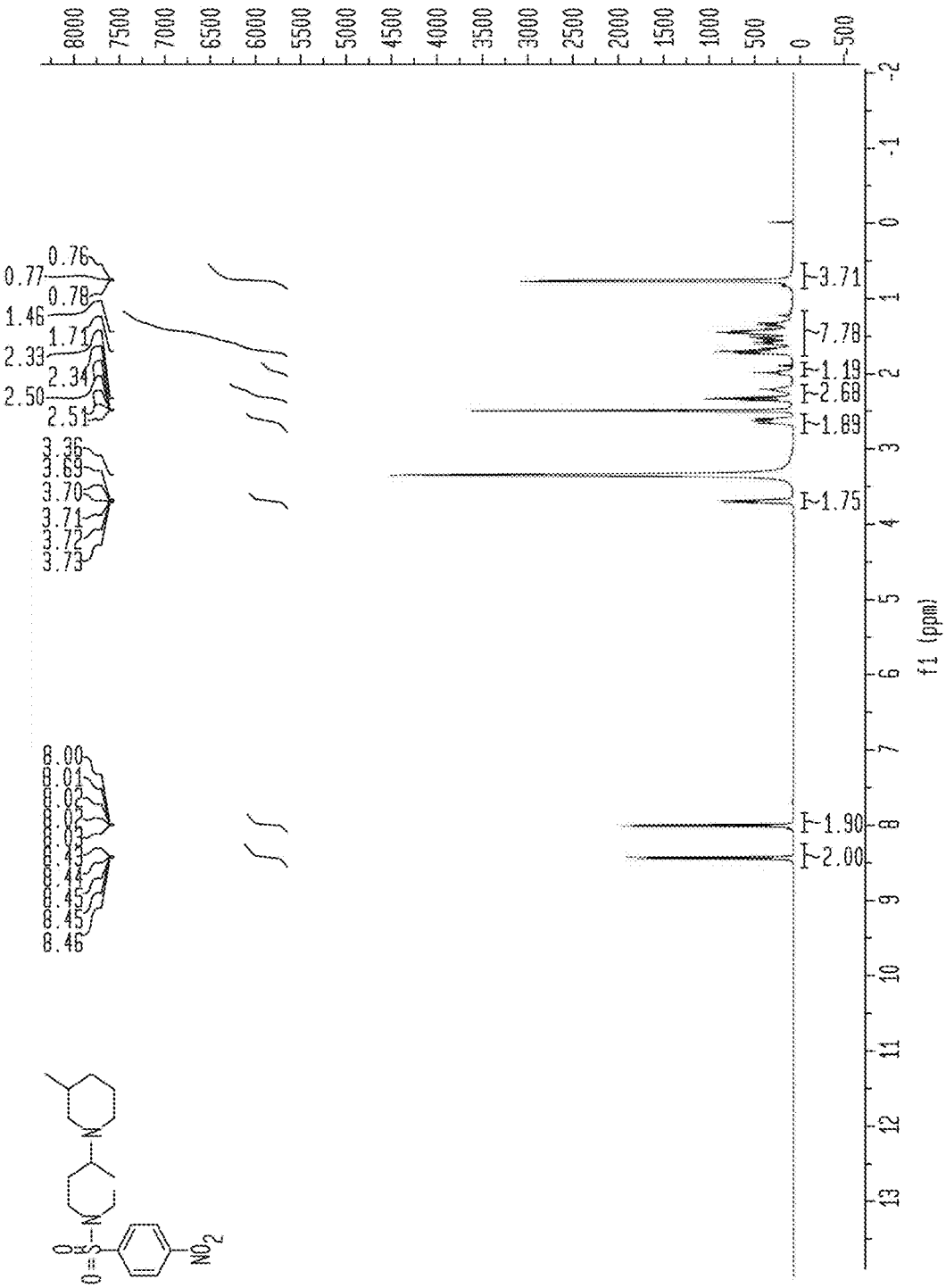
Figure 36F:
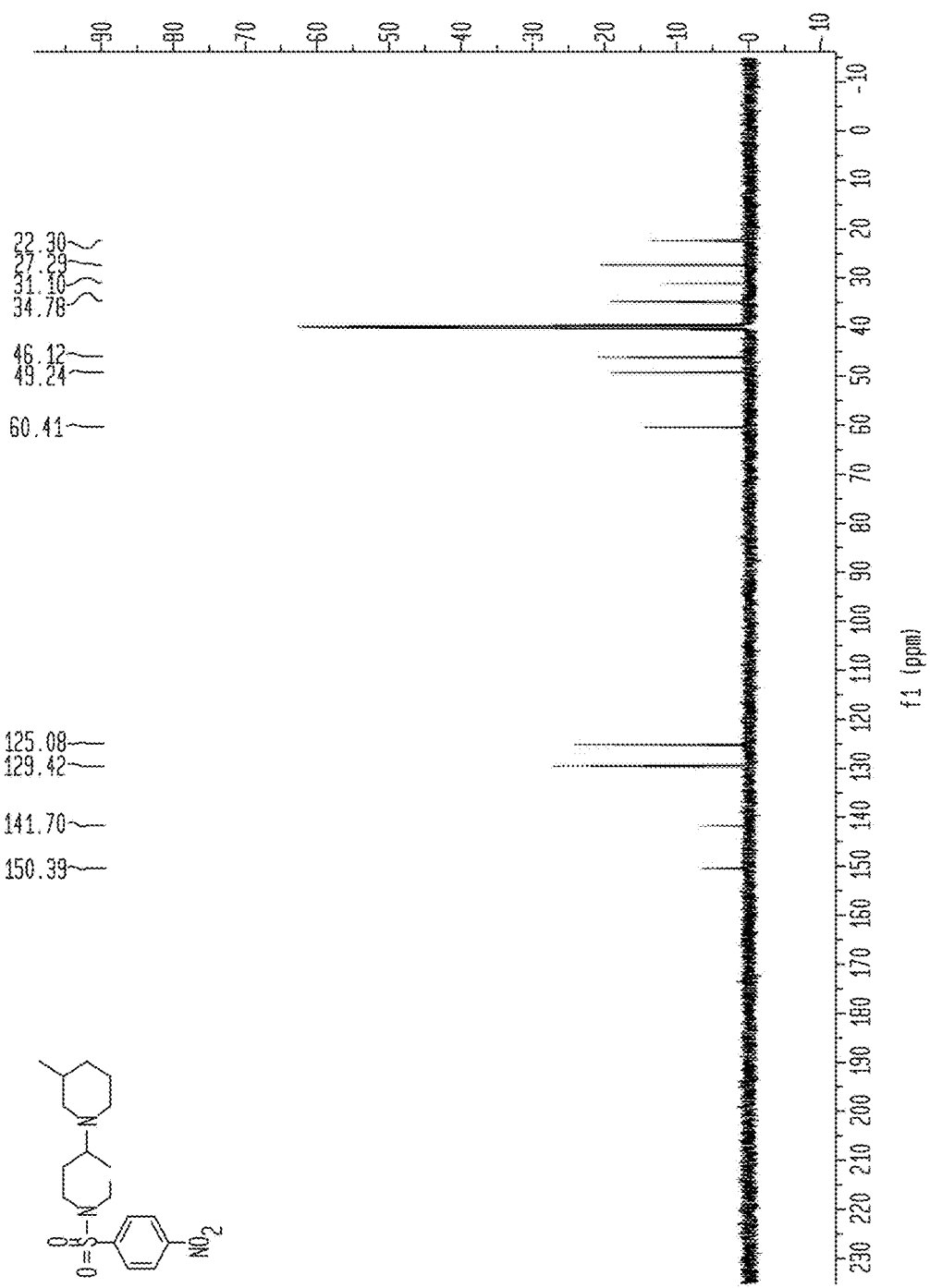
Figure 36G:
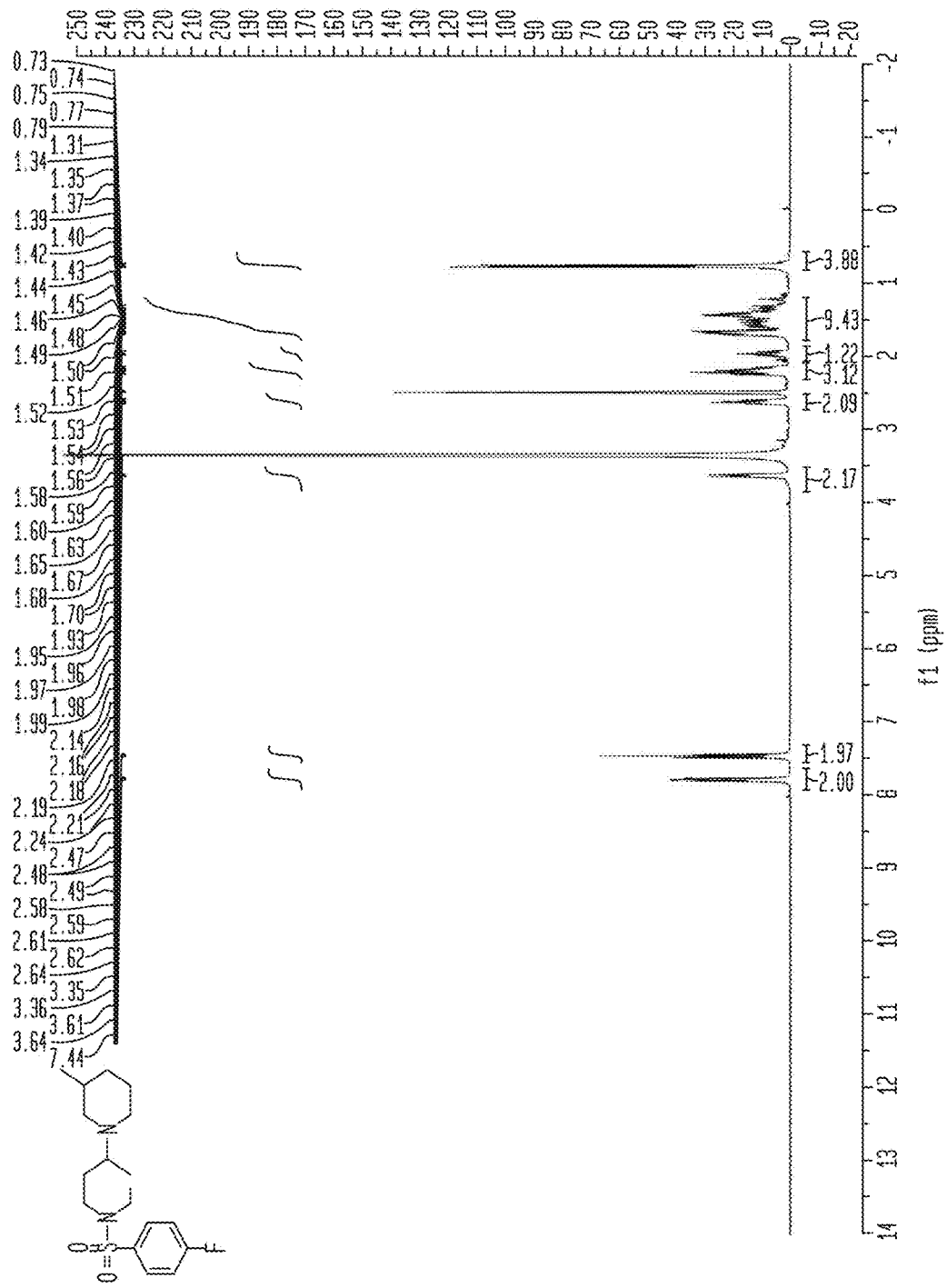
Figure 36H:
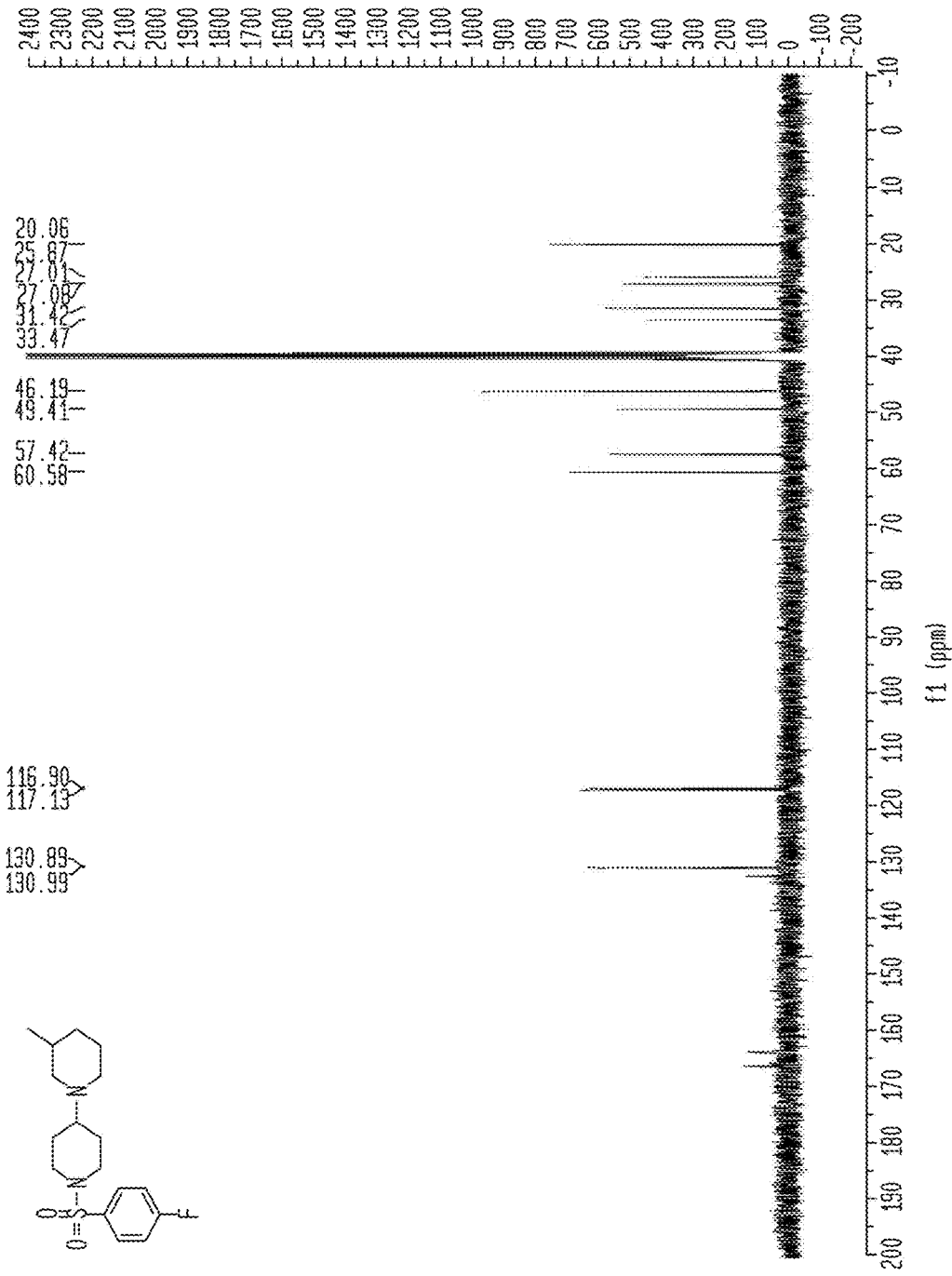
Figure 36I:
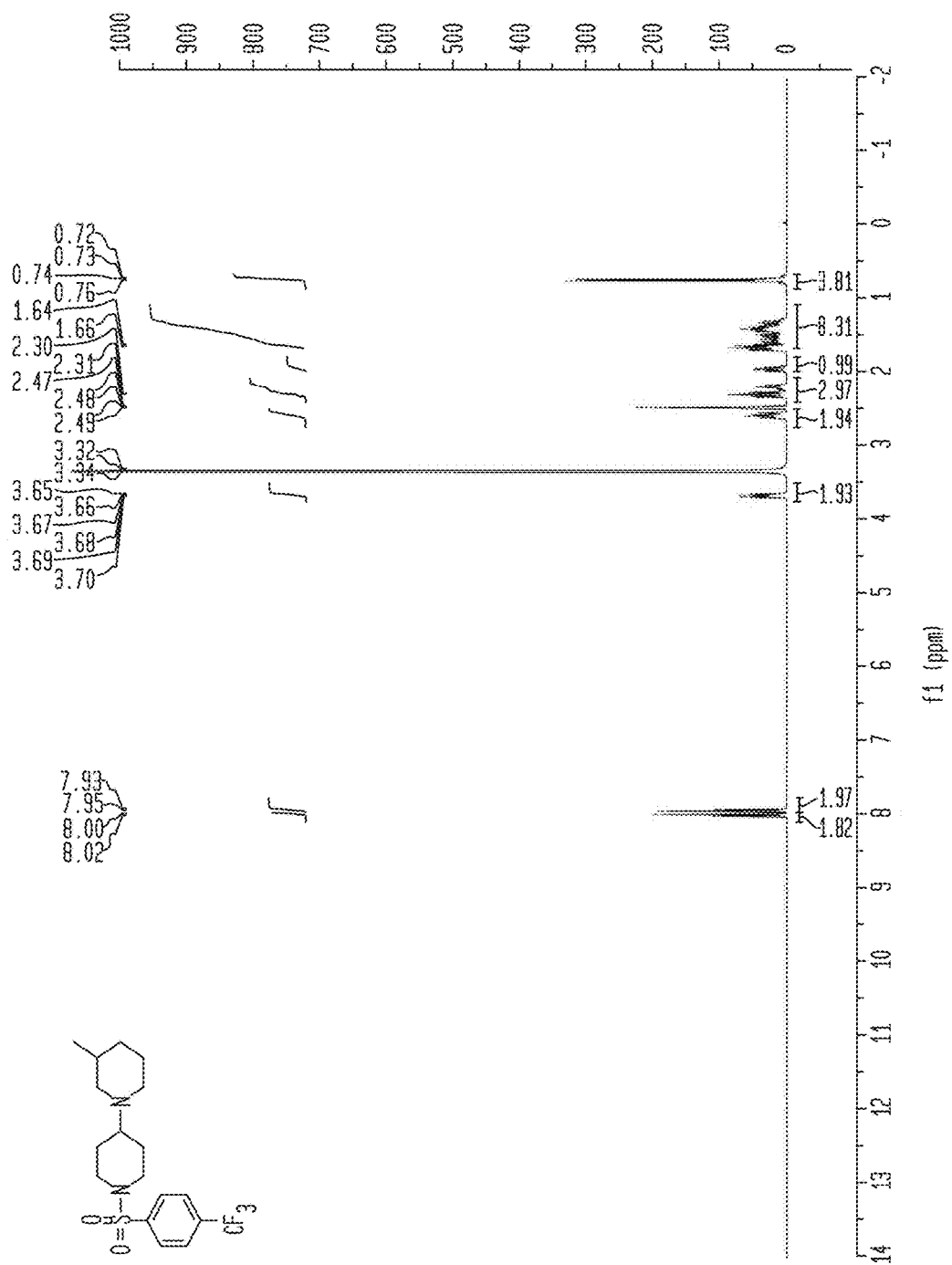
Figure 36J:
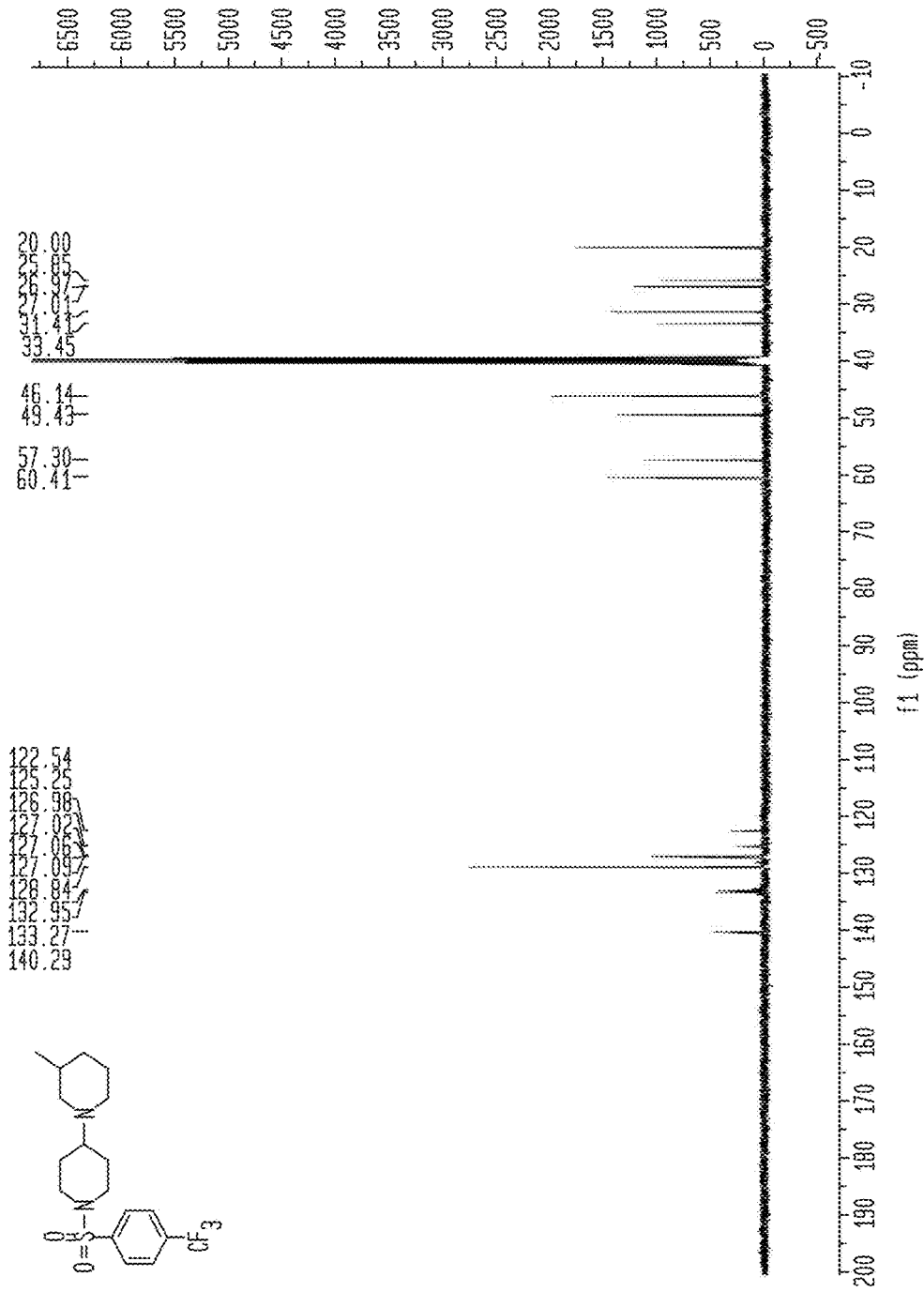
Figure 36K:
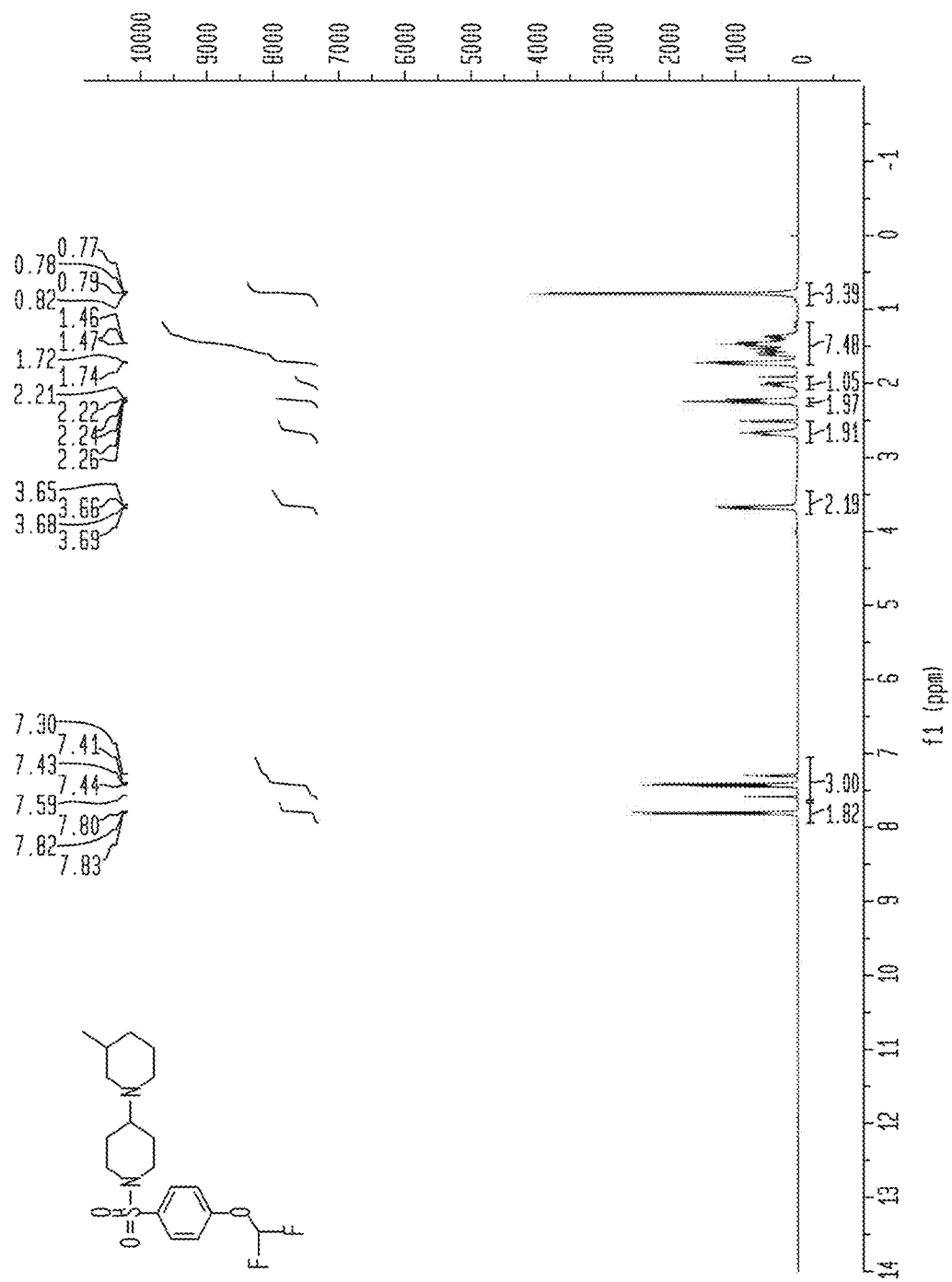
Figure 36L:
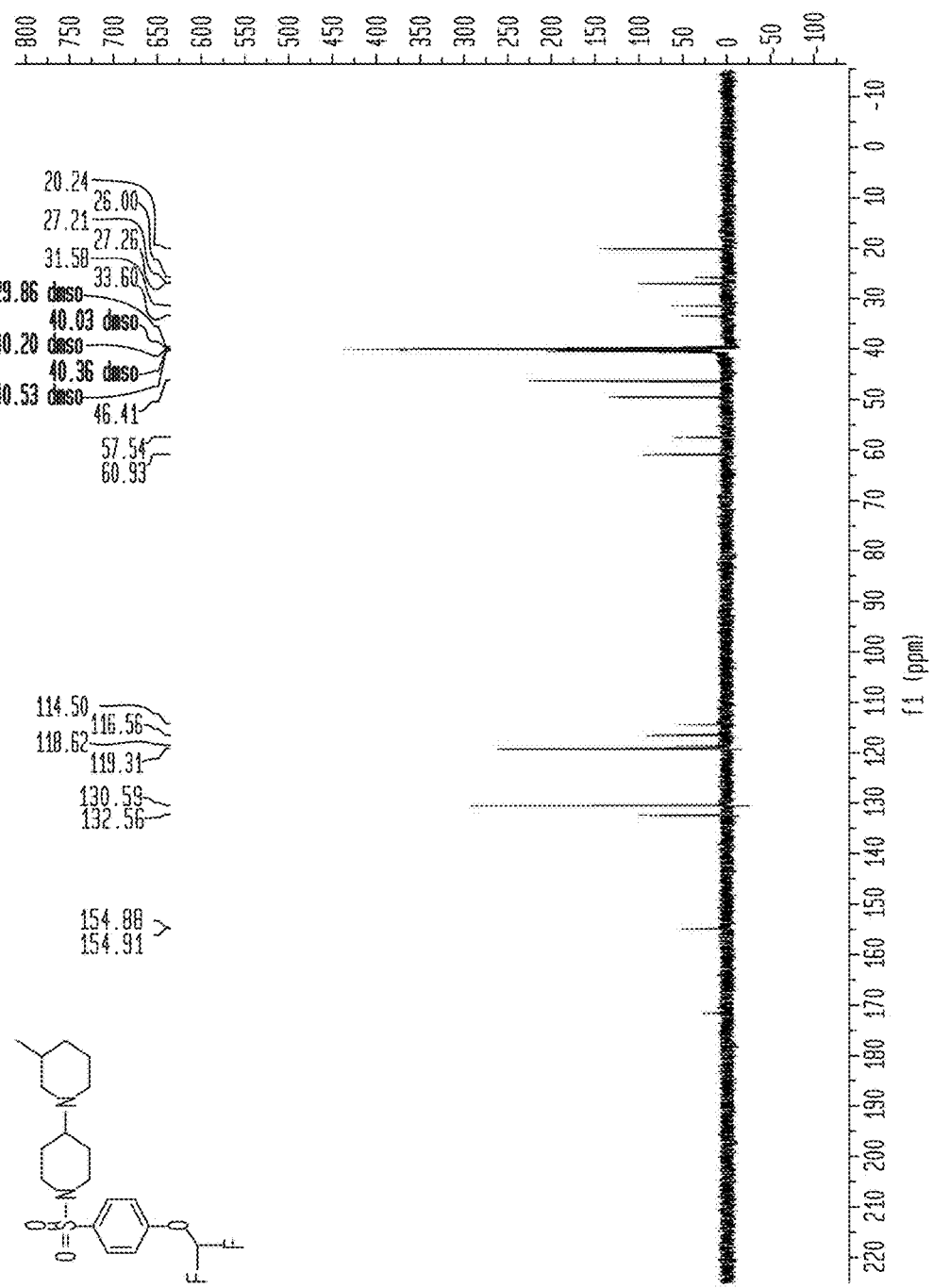
Figure 36M:
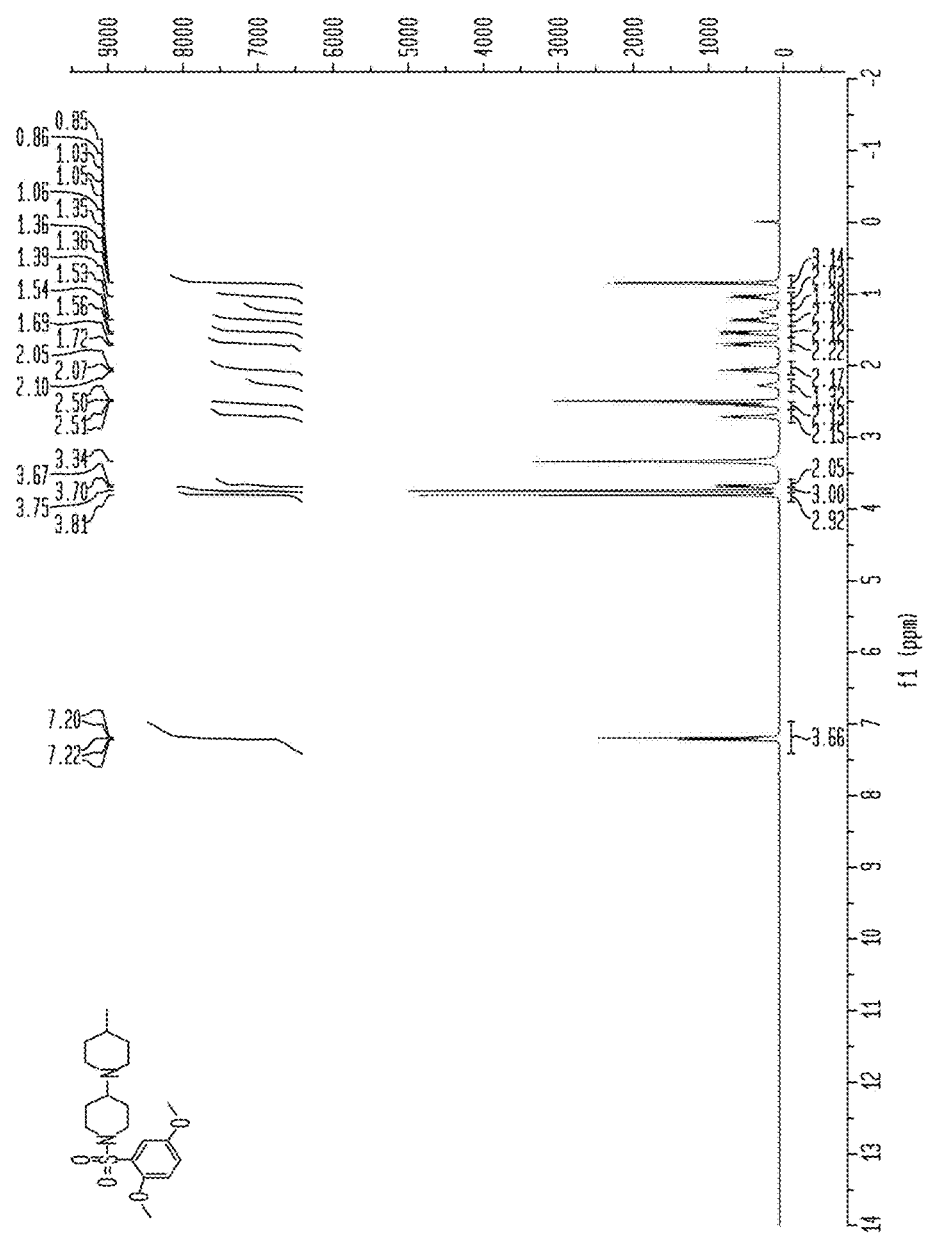
Figure 36N:
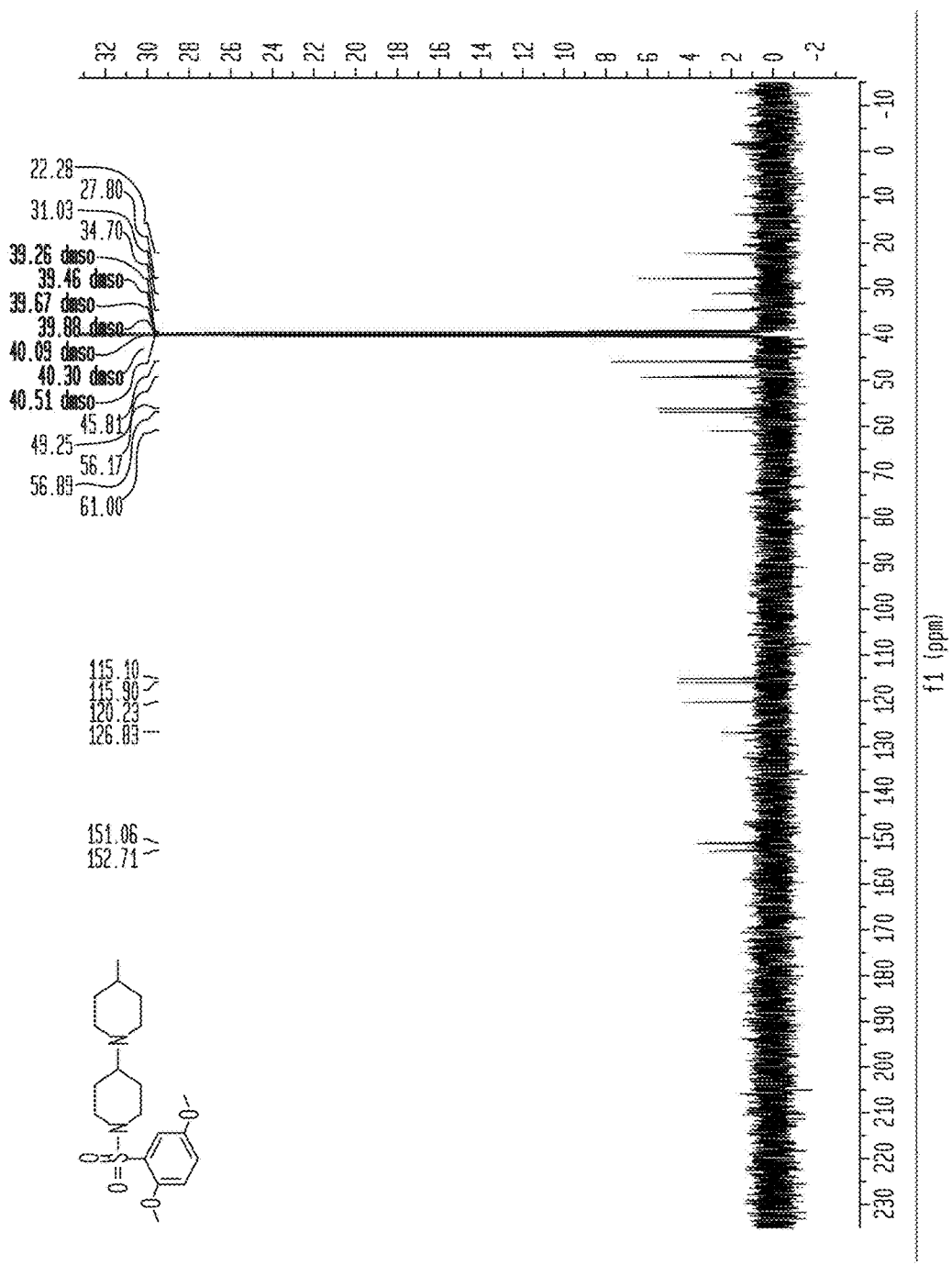
Figure 36O:
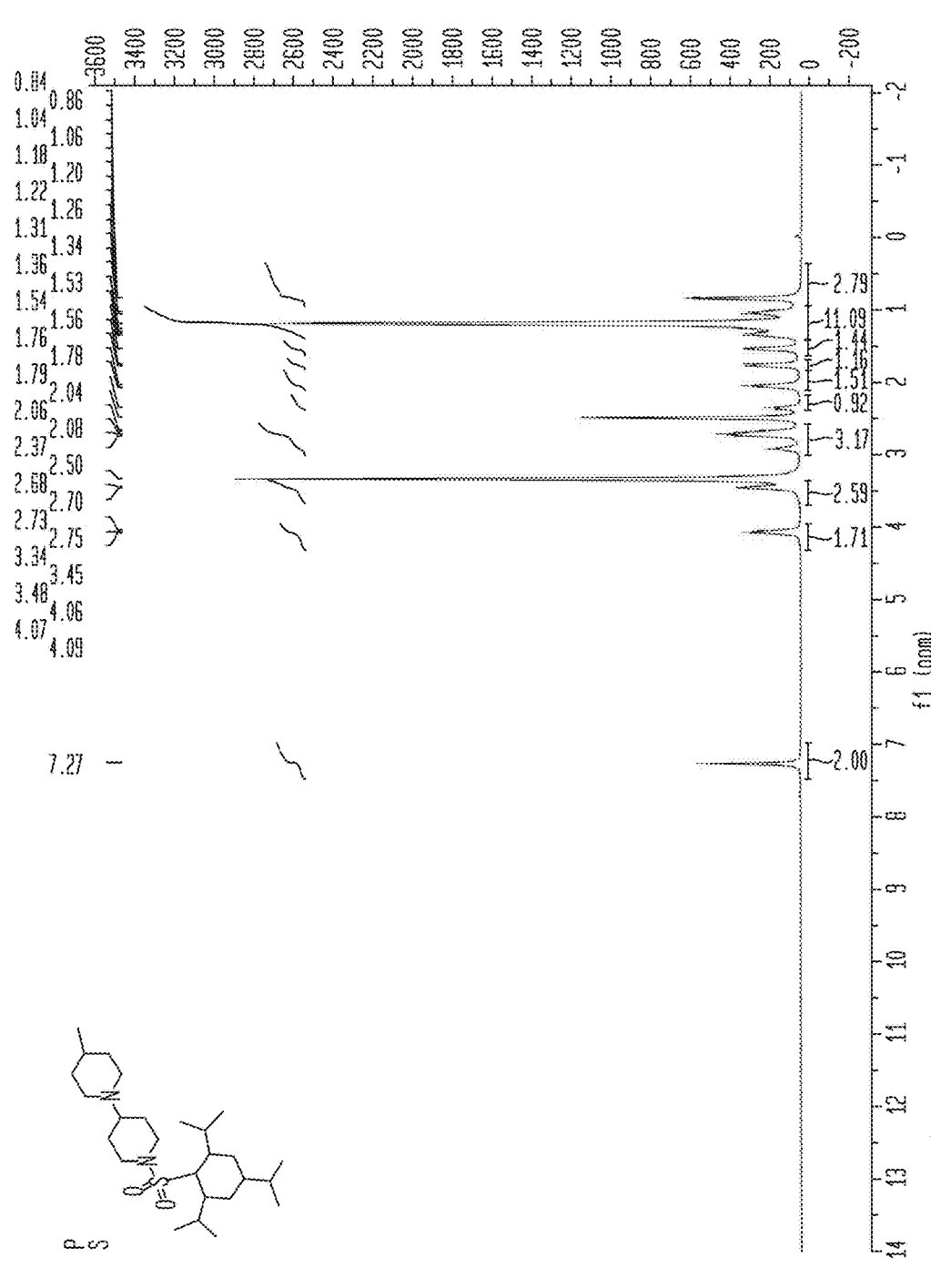
Figure 36P:
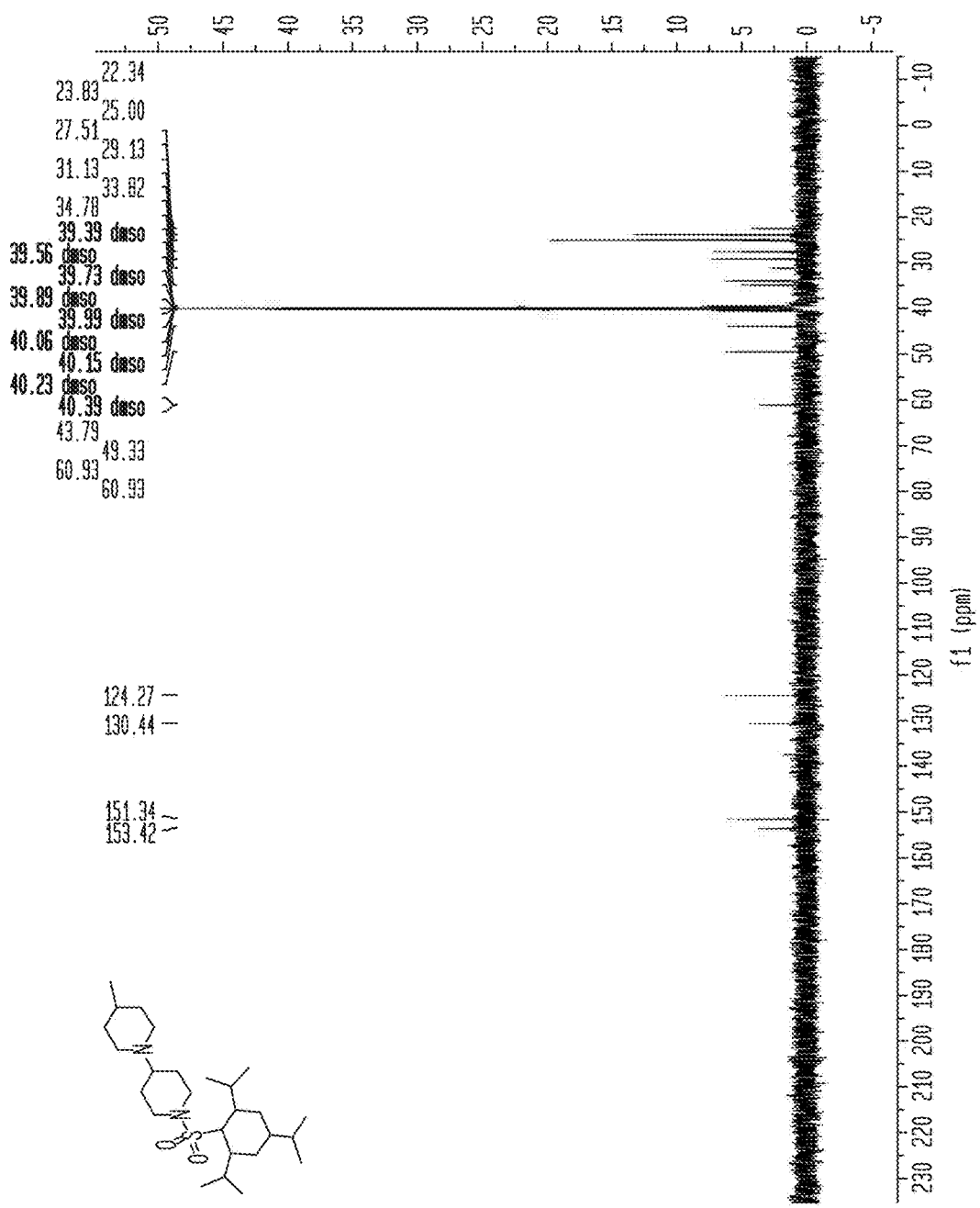
Figure 36Q:
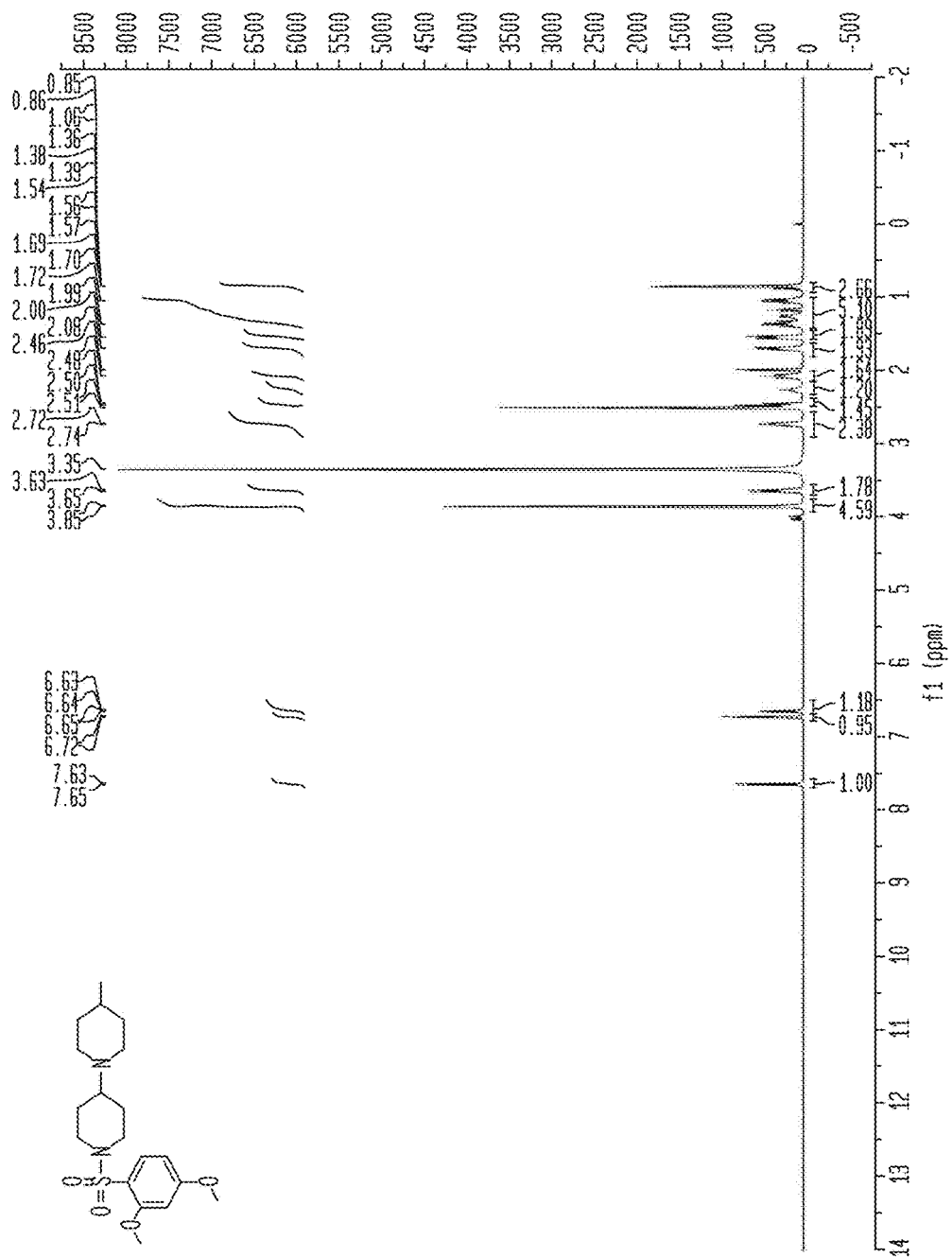
Figure 36R:
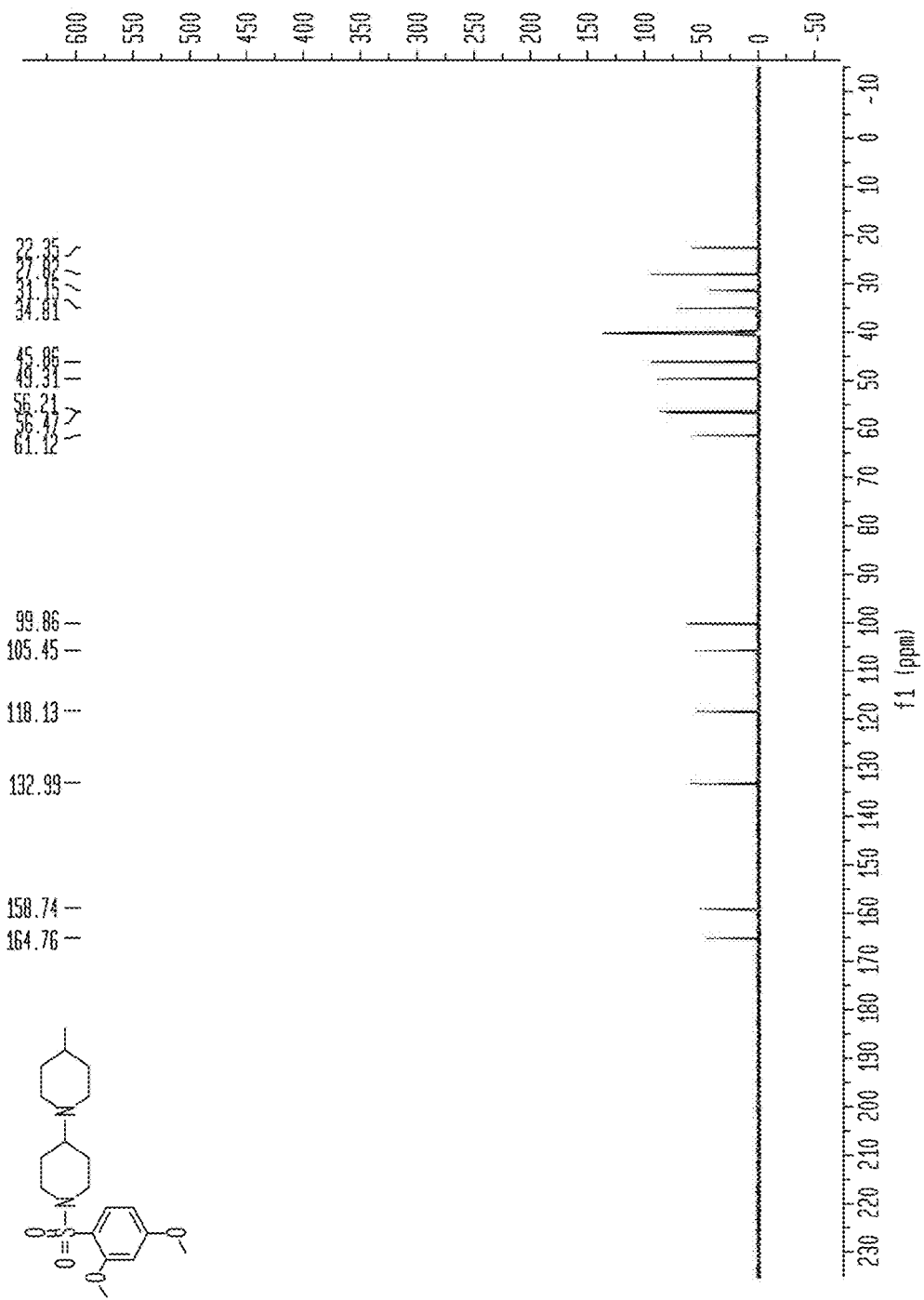
Figure 36S:
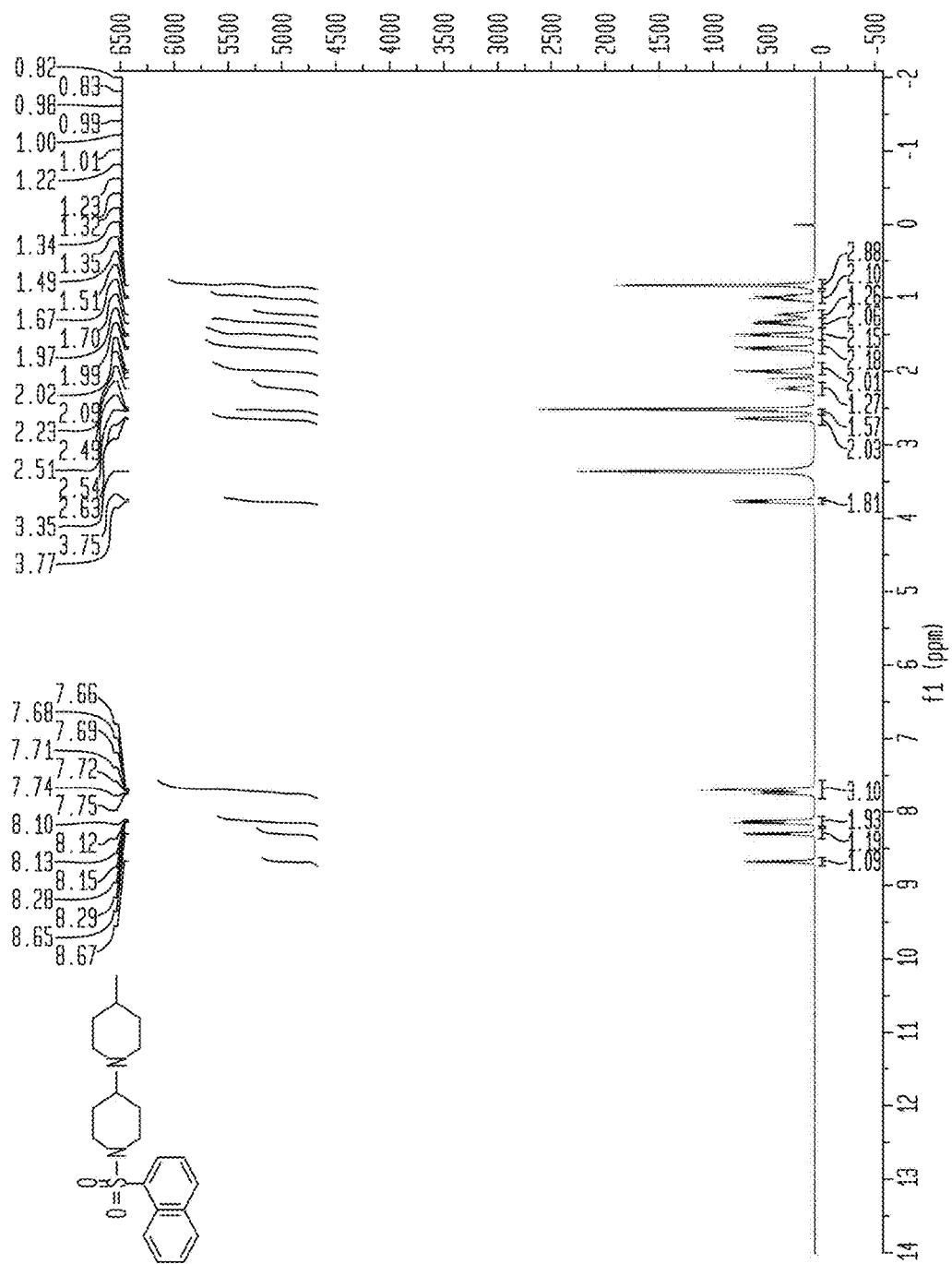
Figure 36T:
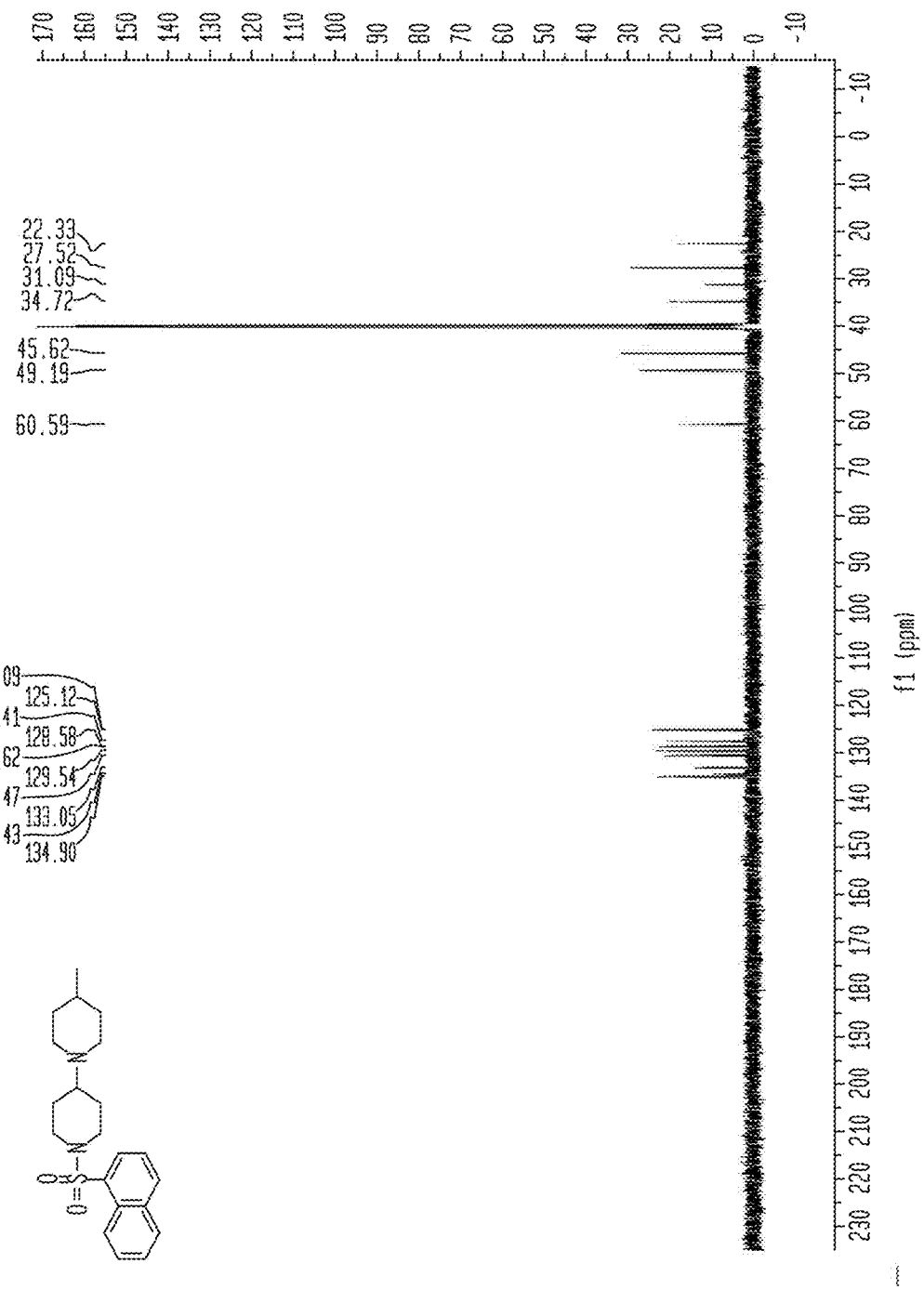
Figure 36U:
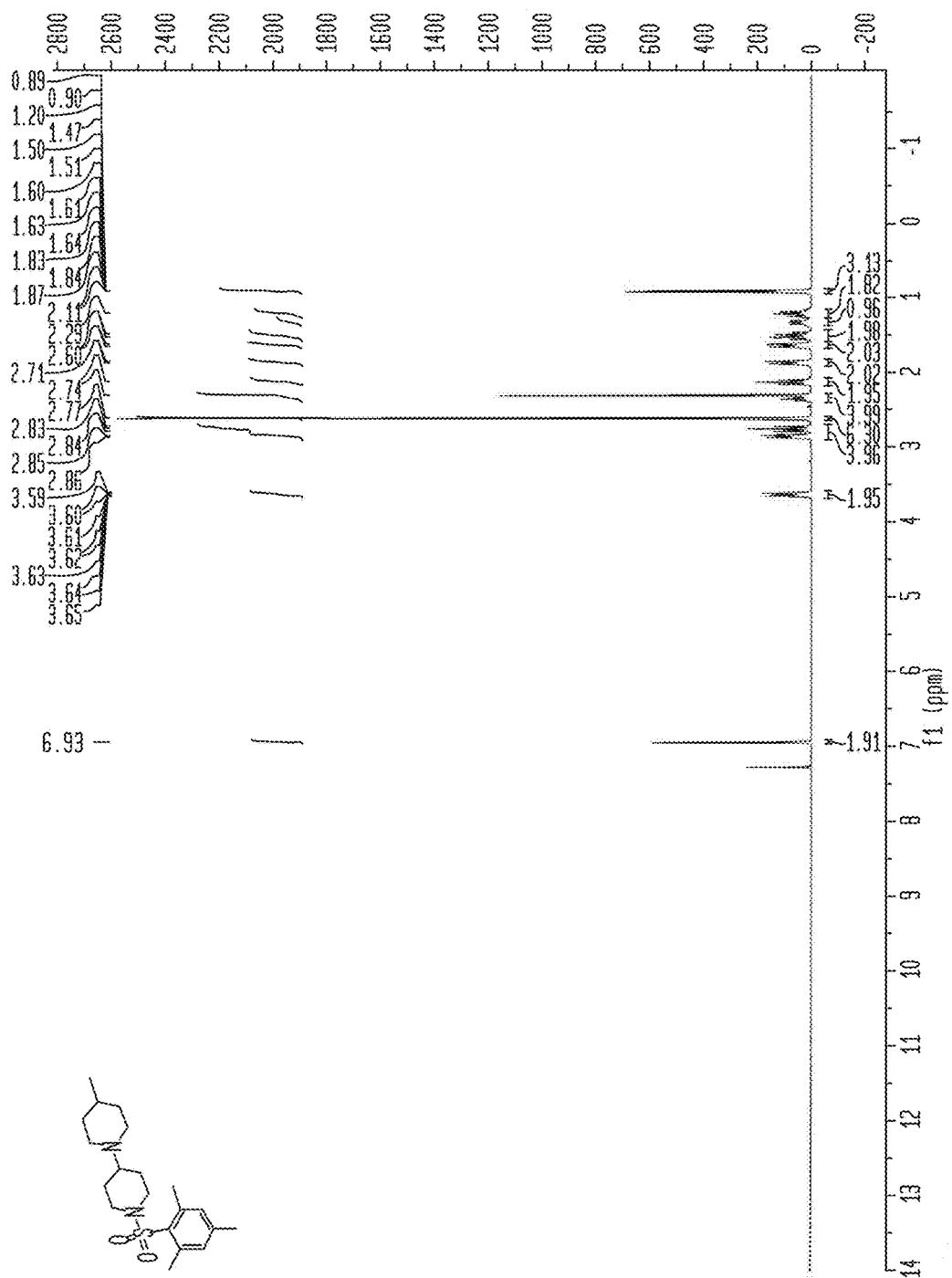
Figure 36V:
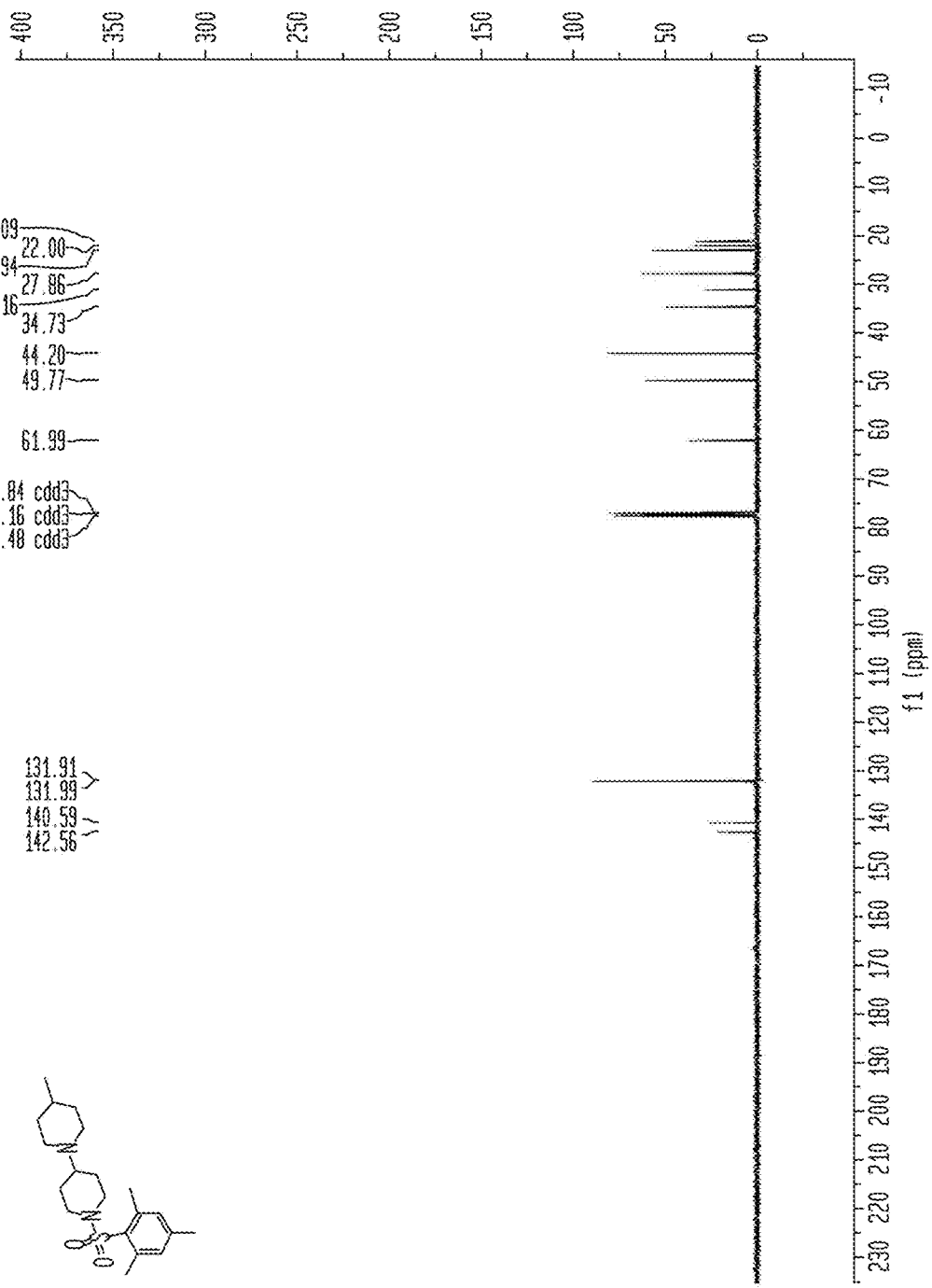
Figure 36W:
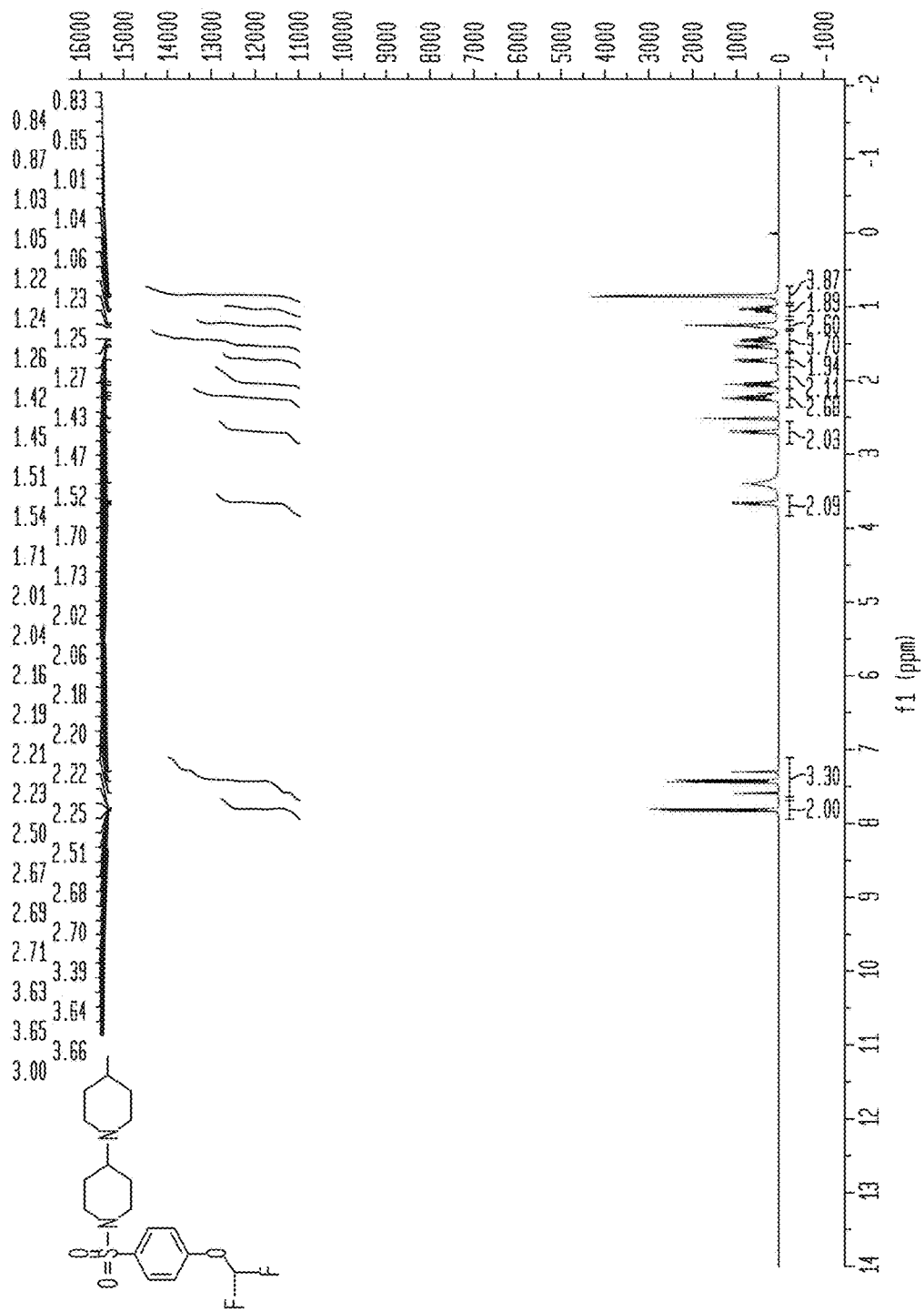
Figure 36X:
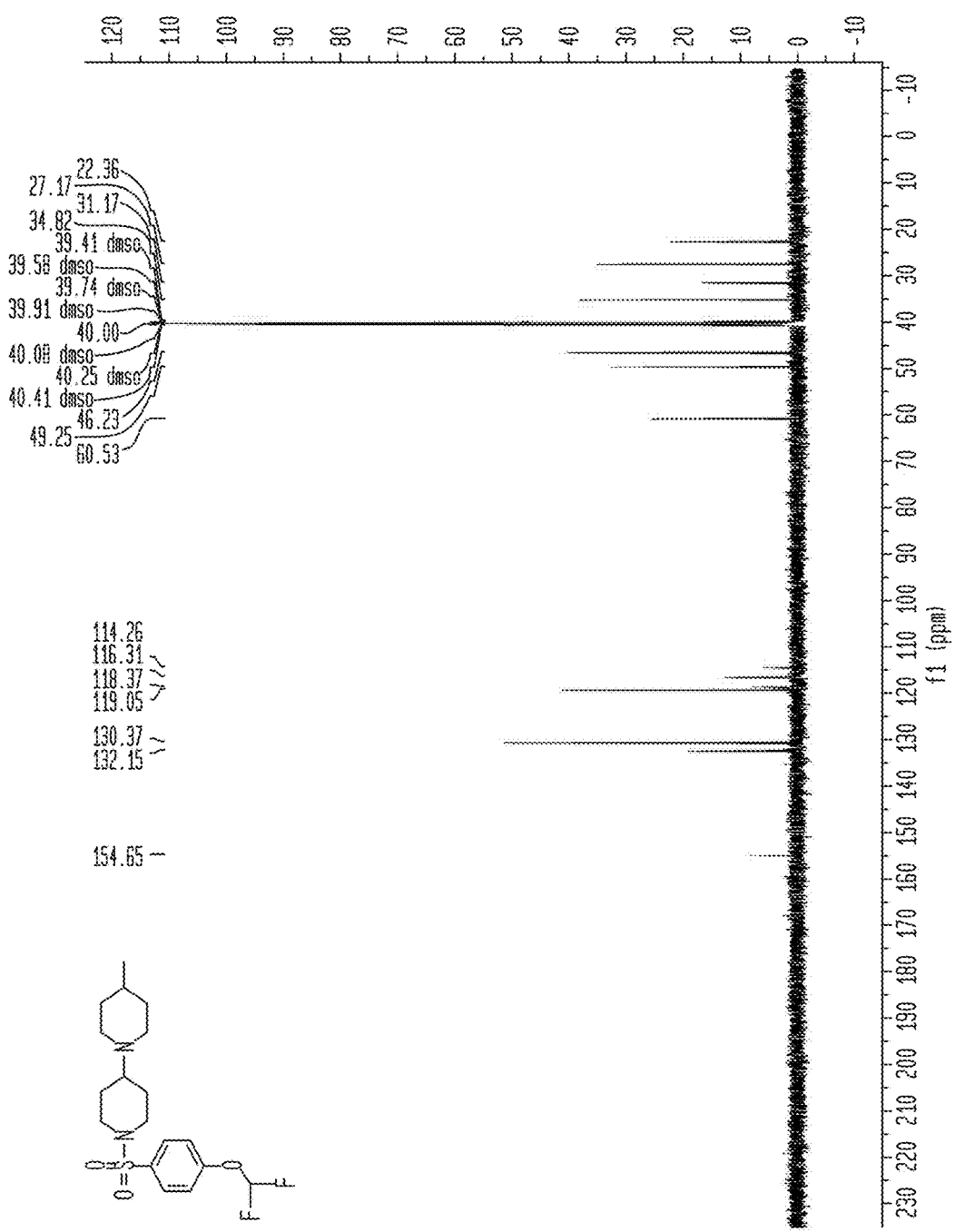
Figure 36Y:
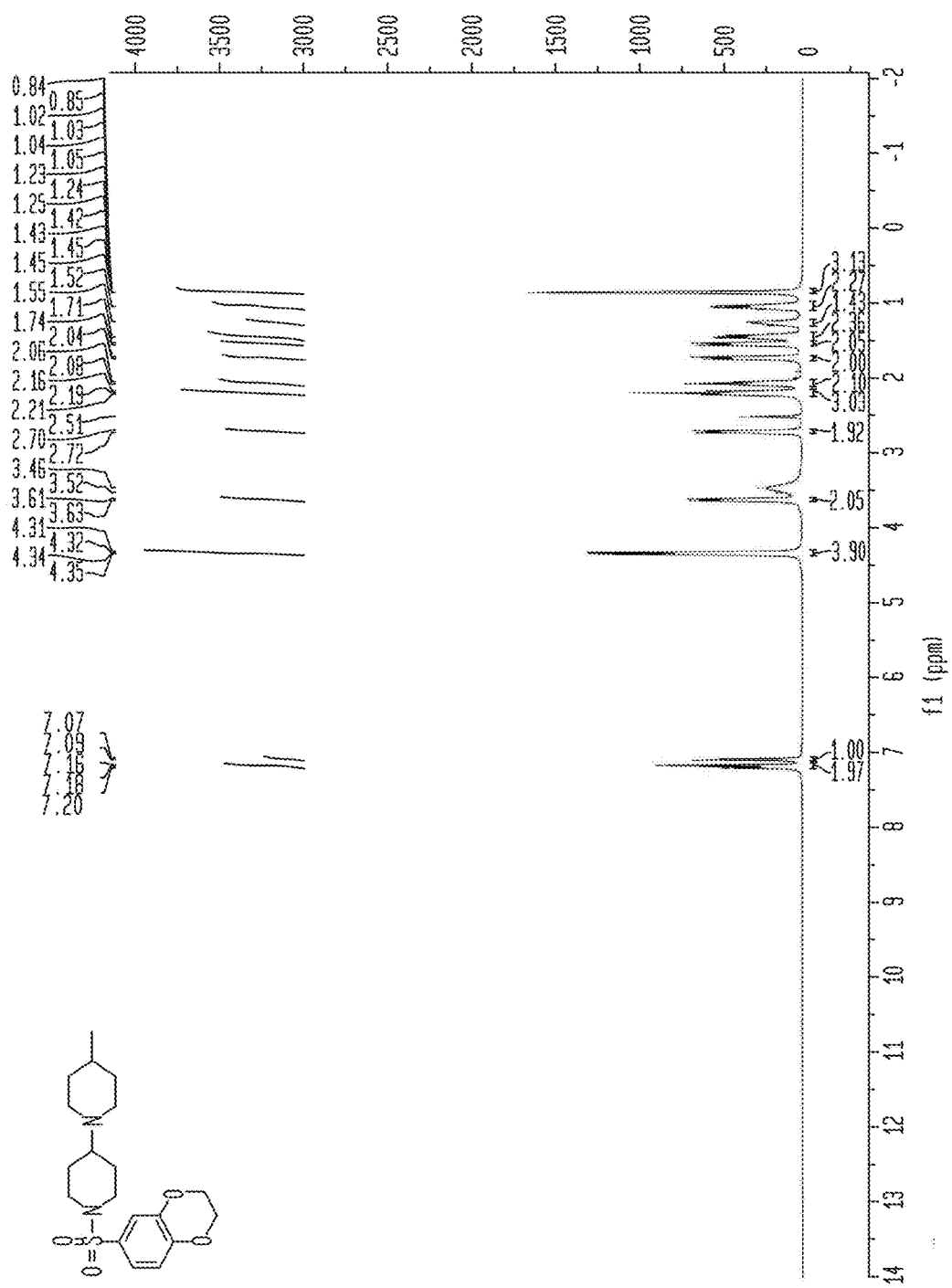
Figure 36Z:
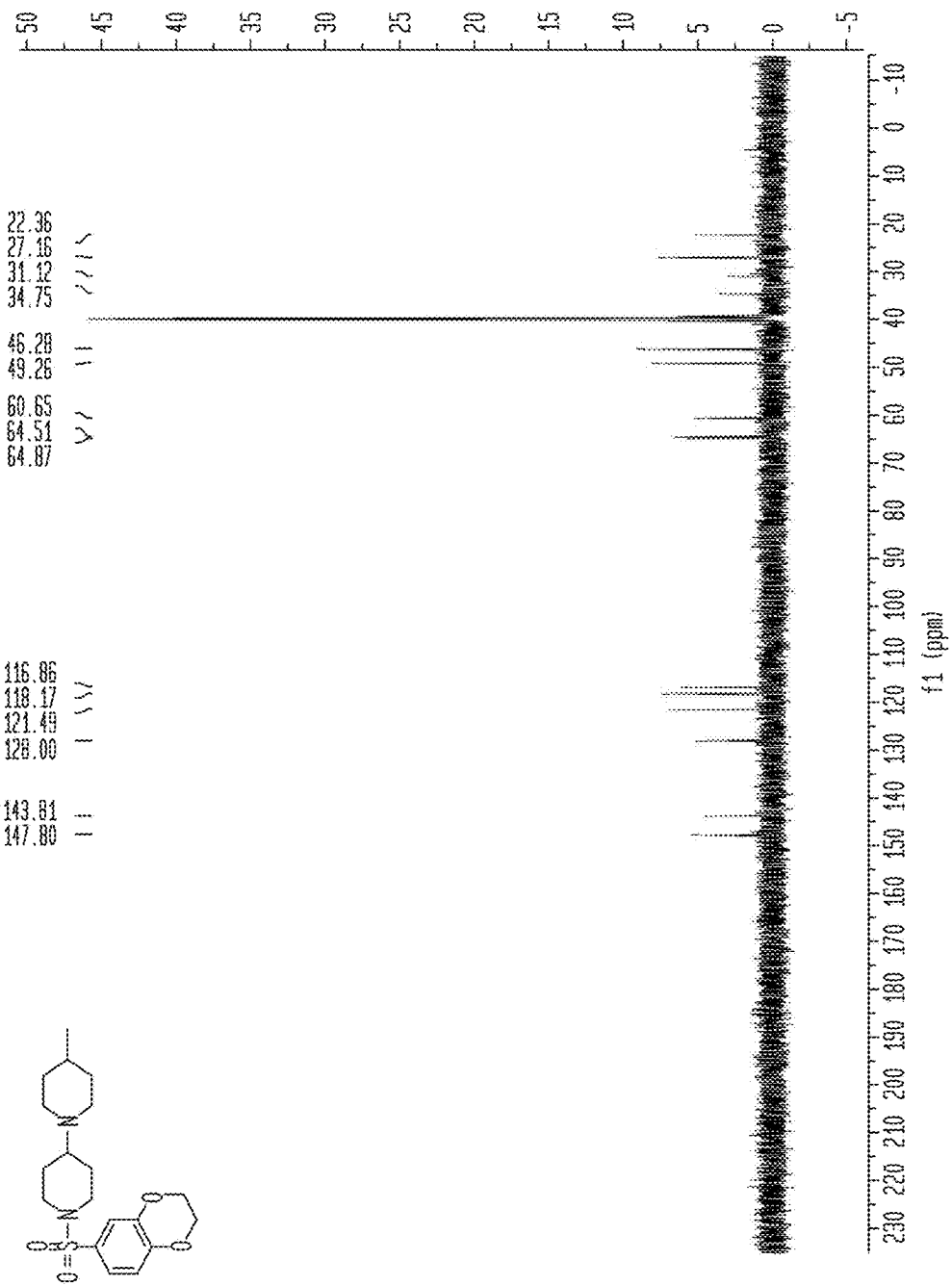
Figure 36A:
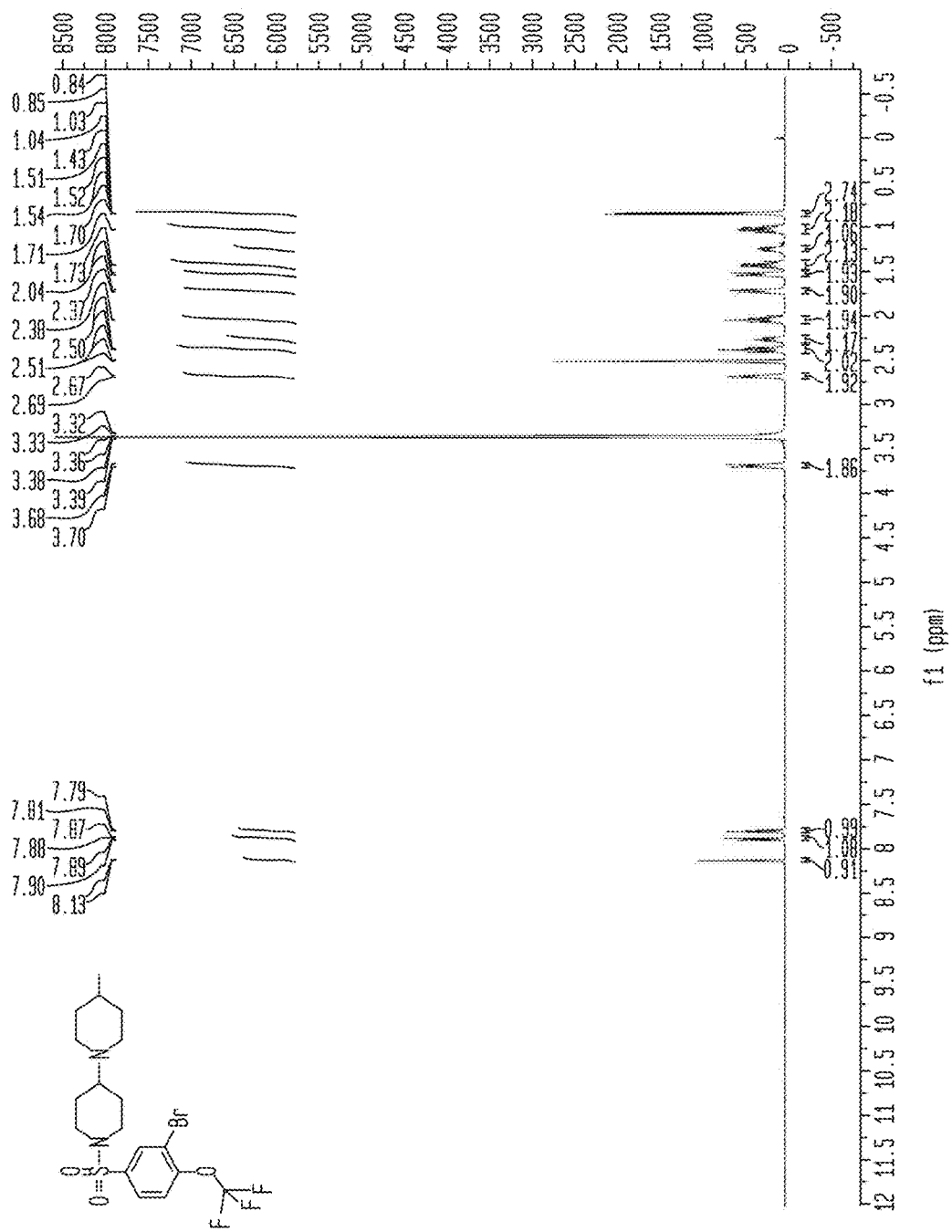
Figure 36A:
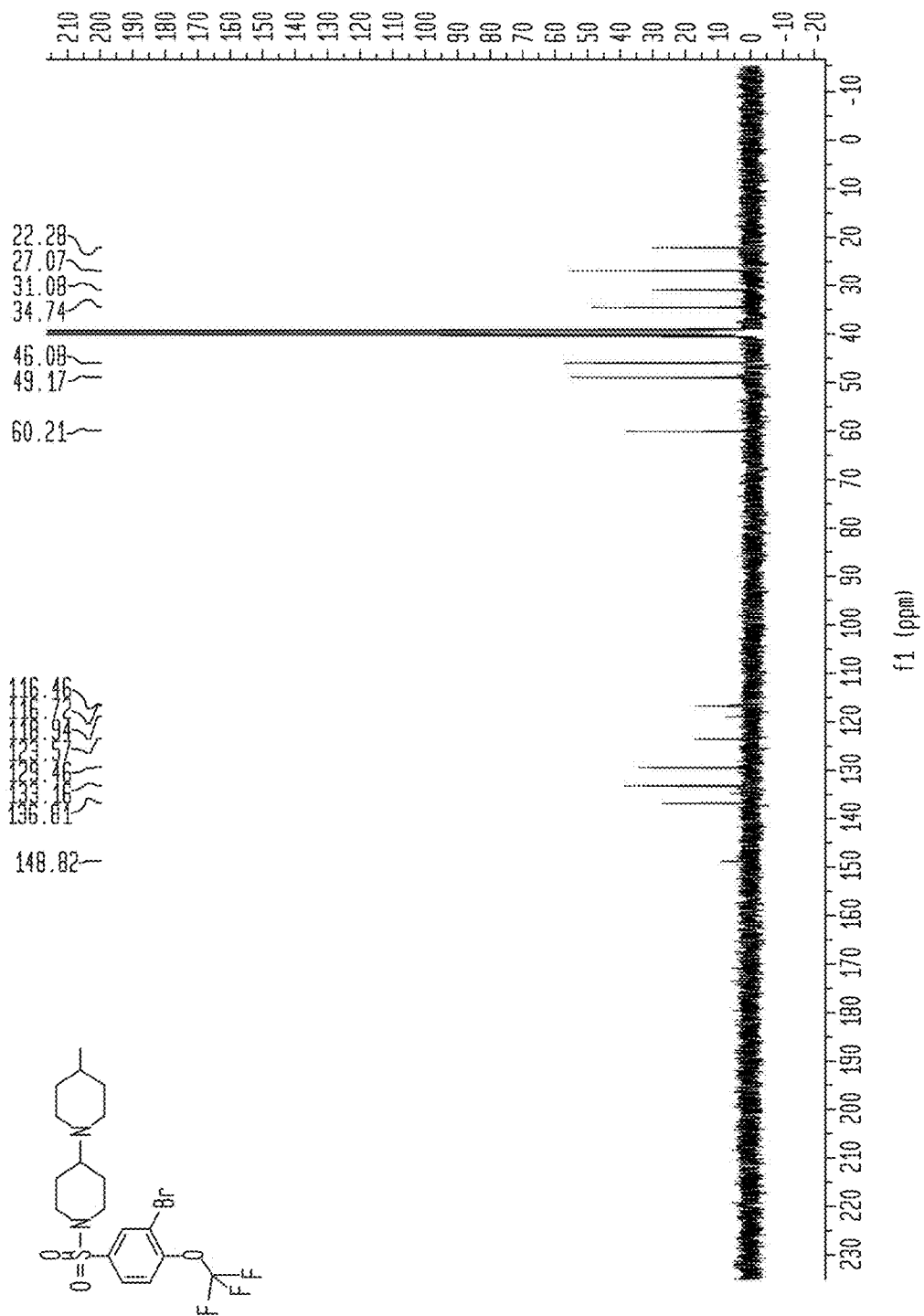
Figure 36A:
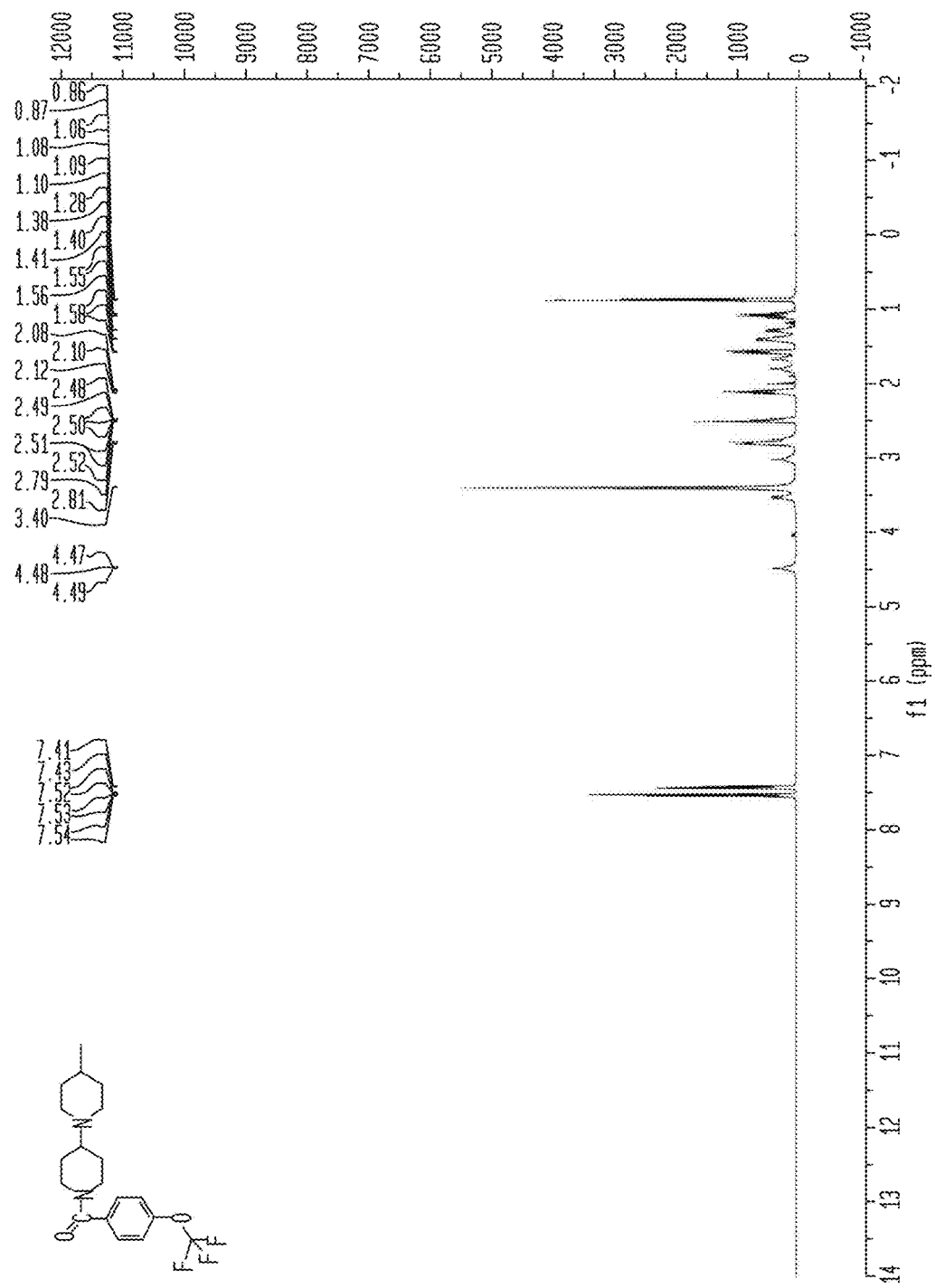
Figure 36A:
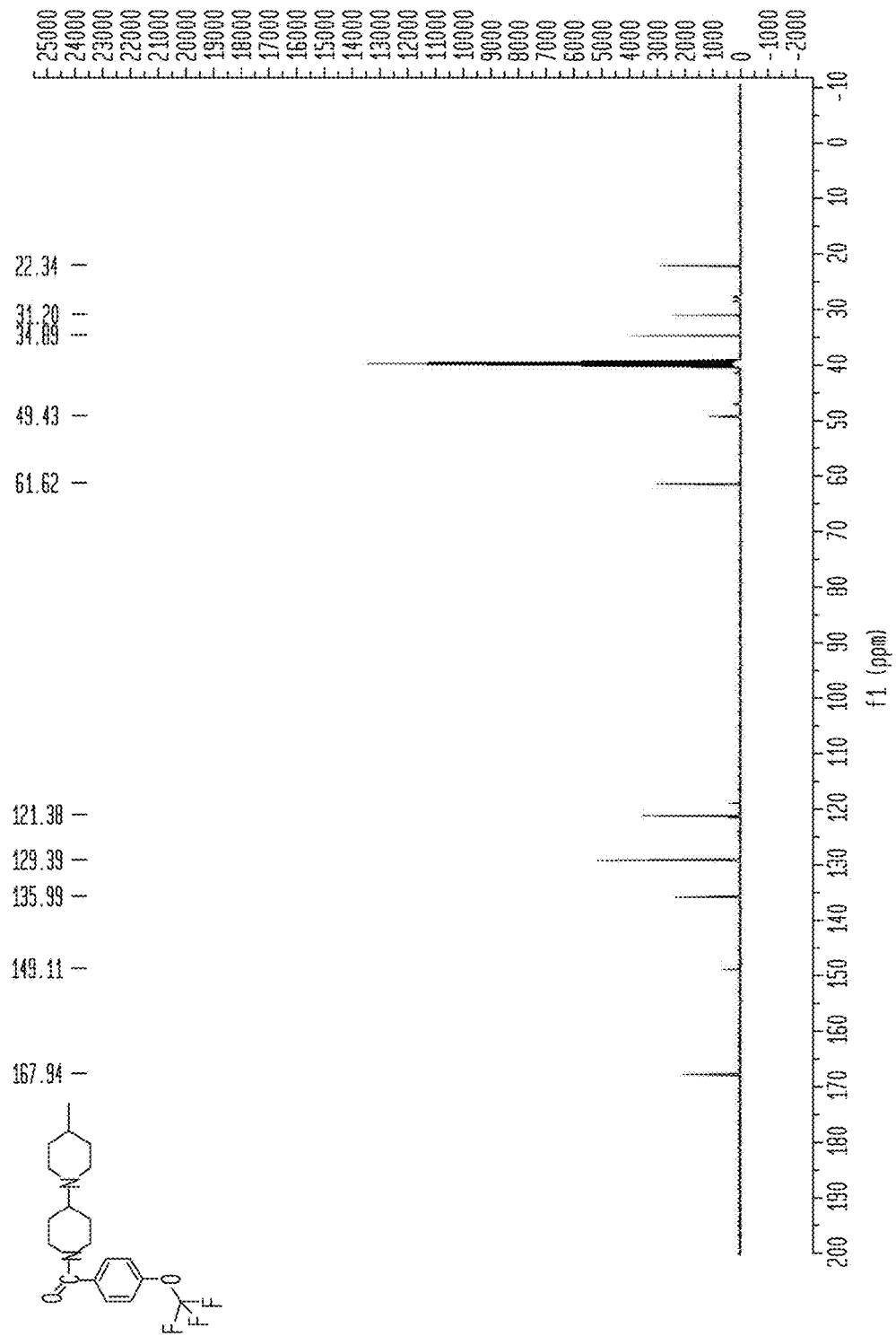
Figure 36A:
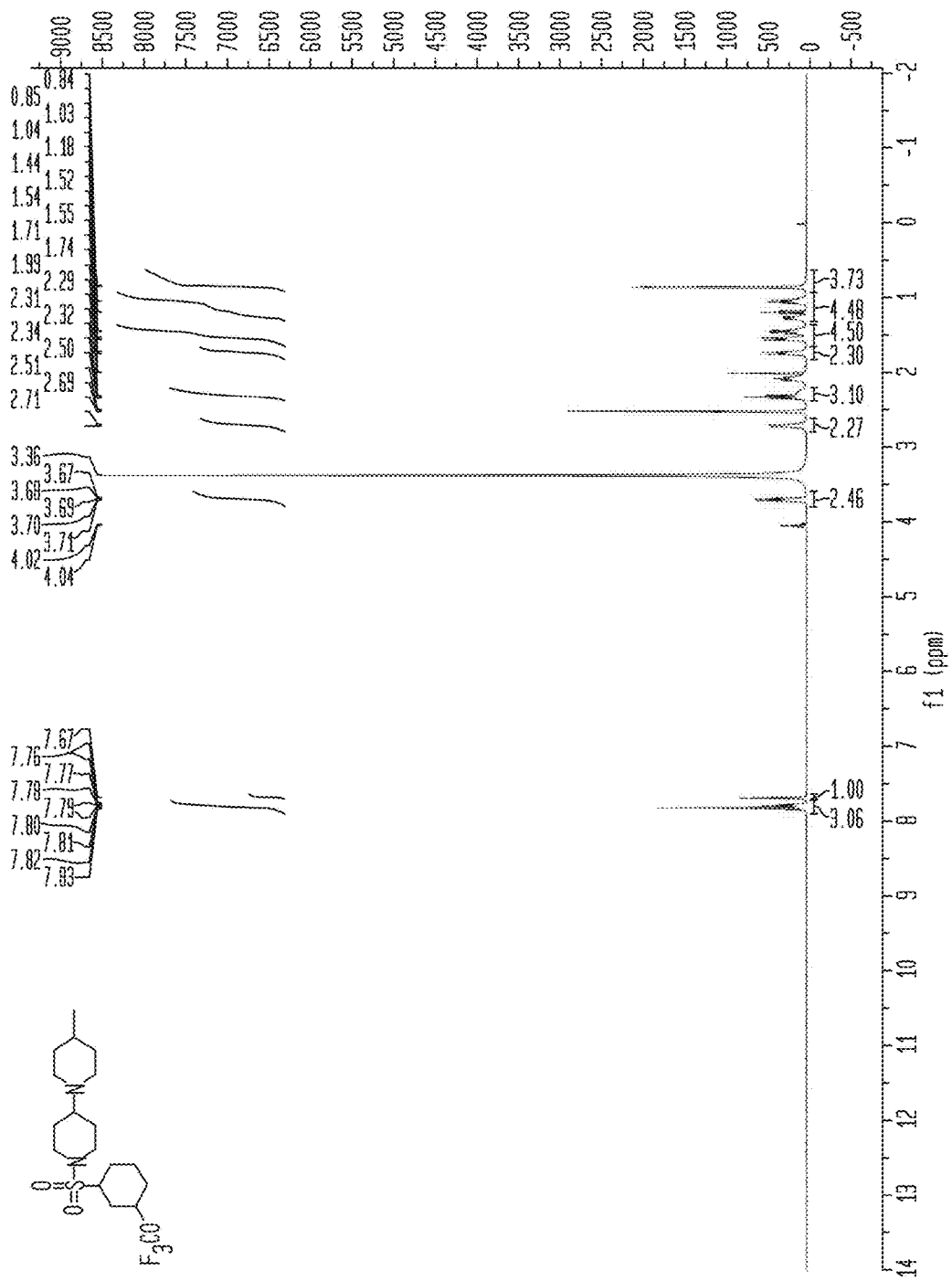
Figure 36A:
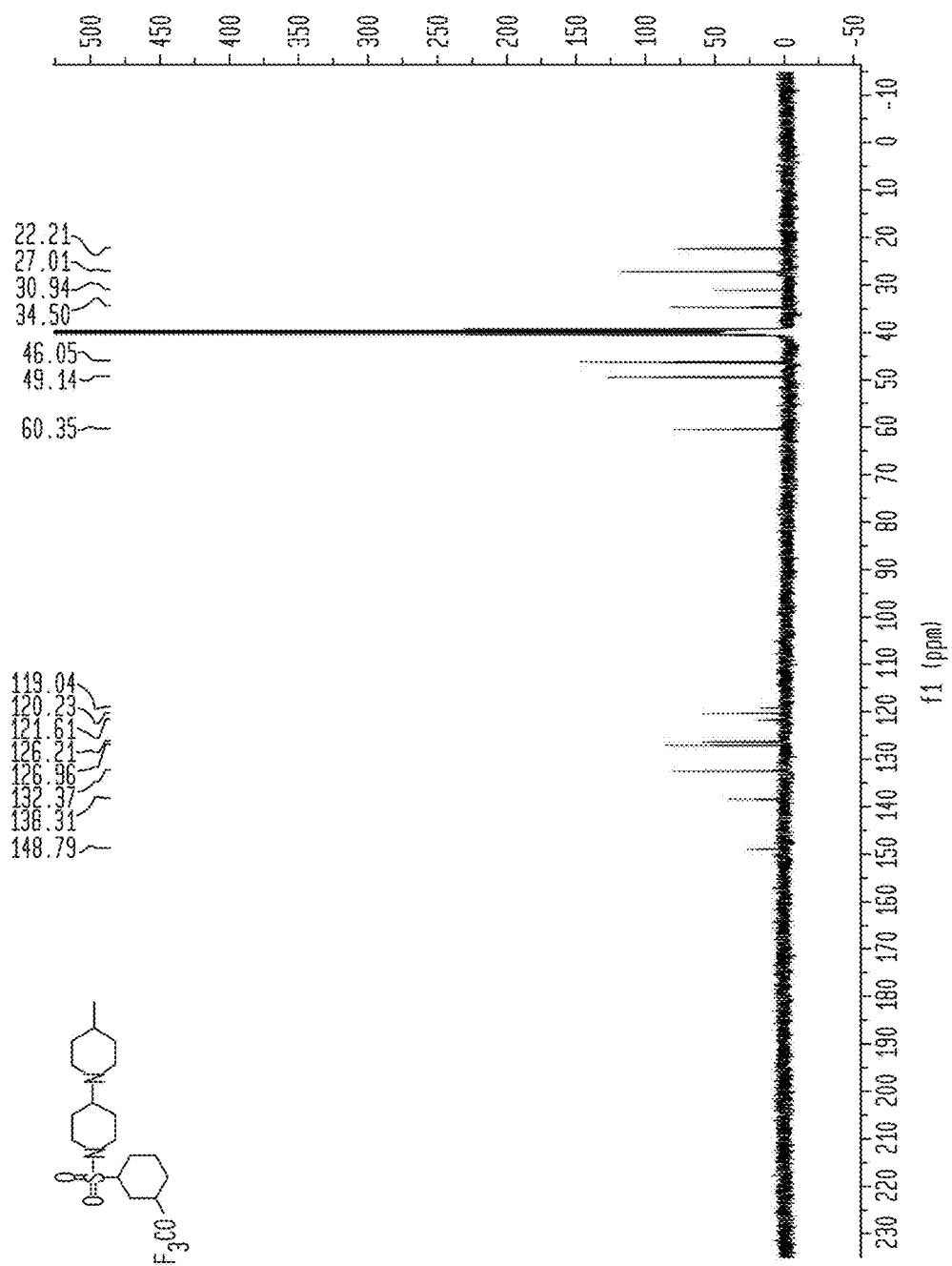
Figure 36A:
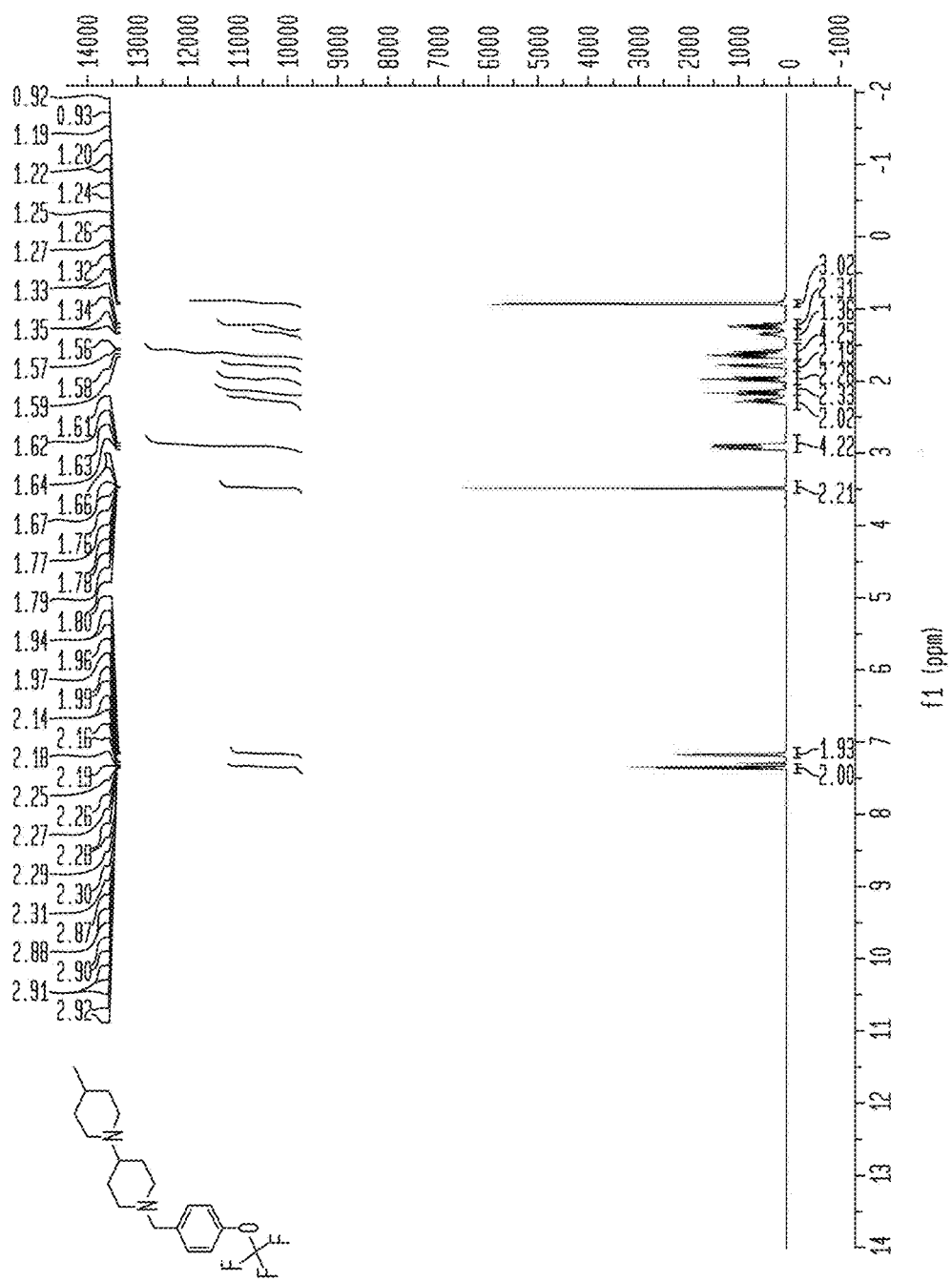
Figure 36A:
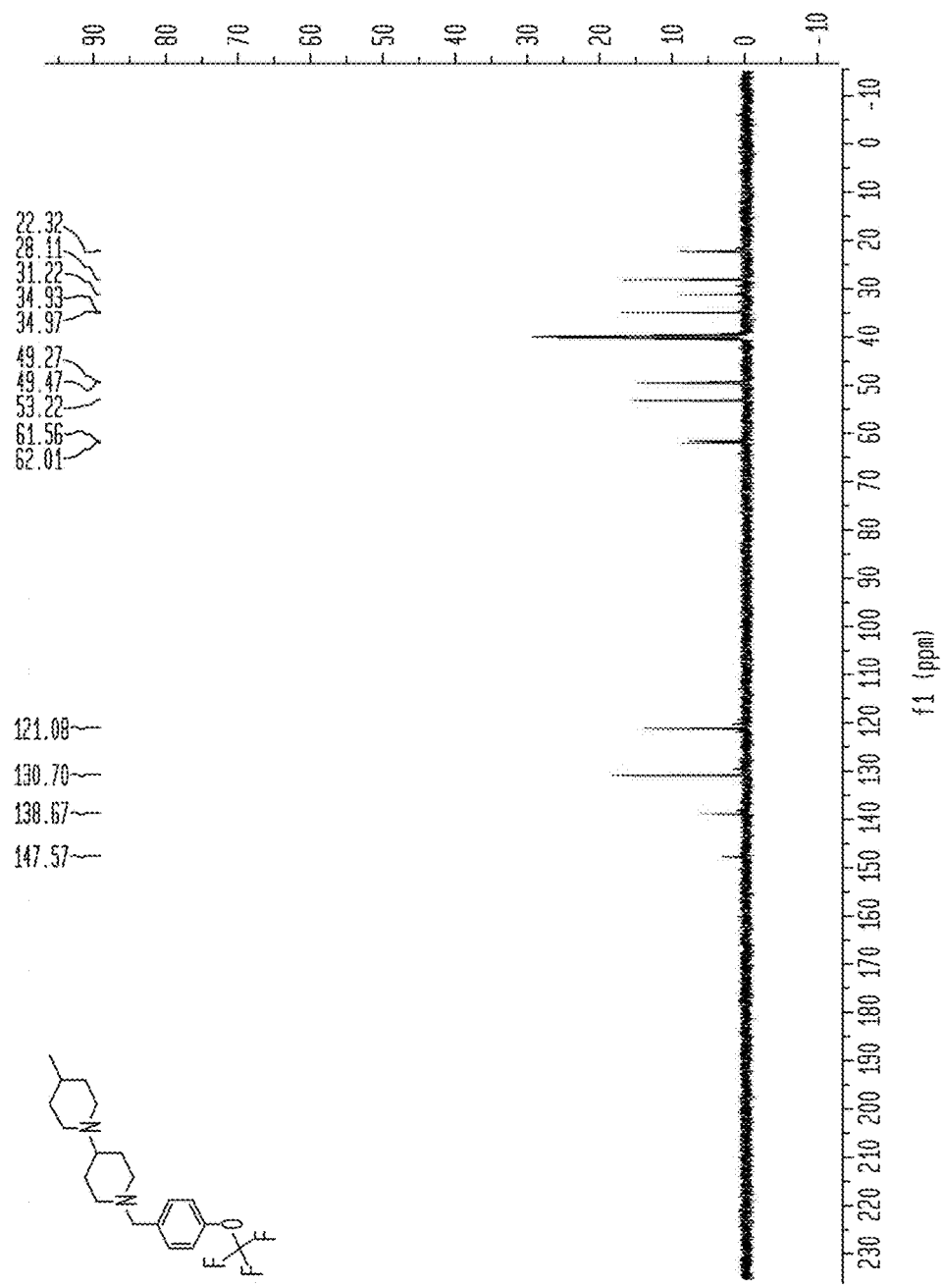
Figure 36A:
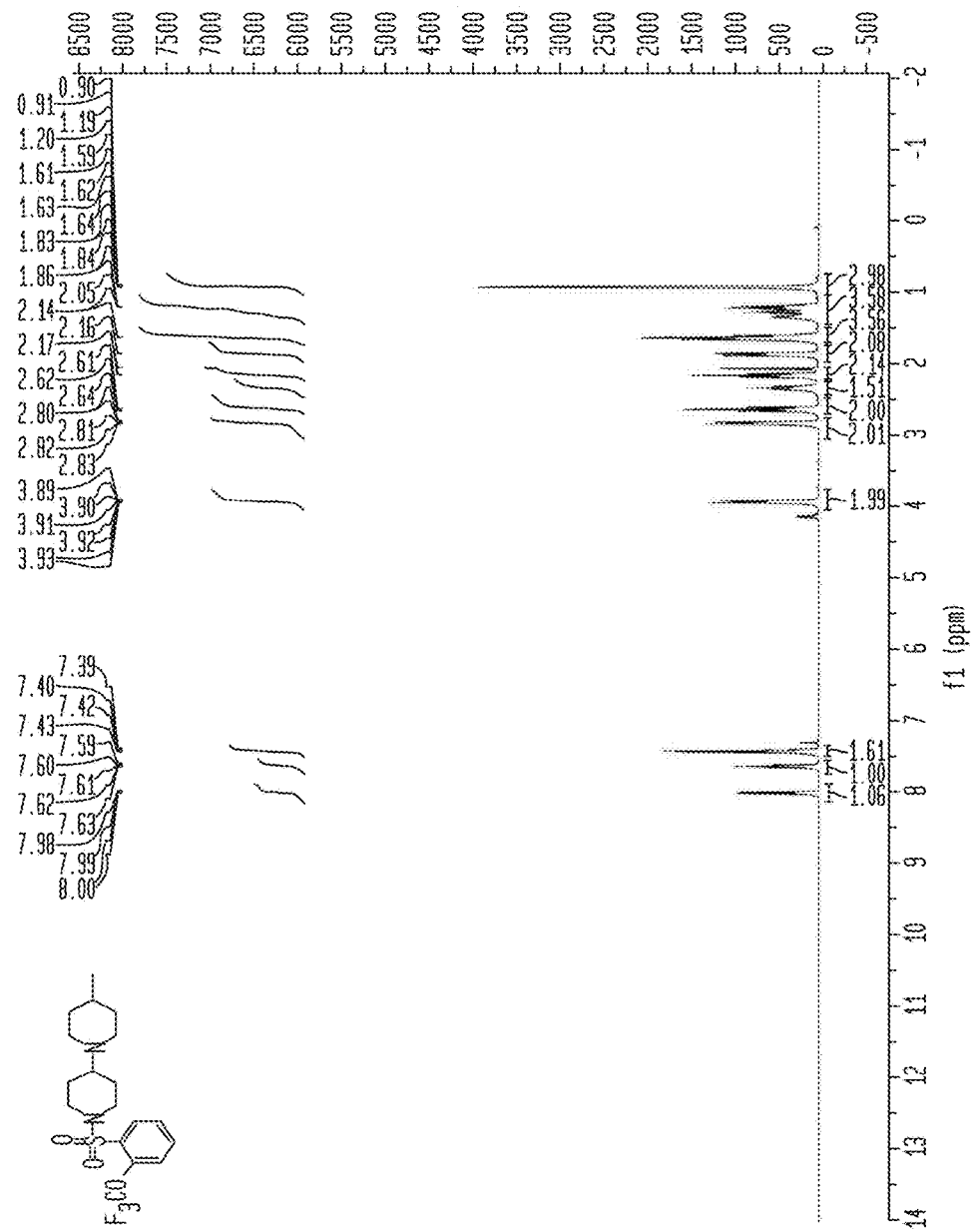
Figure 36A:
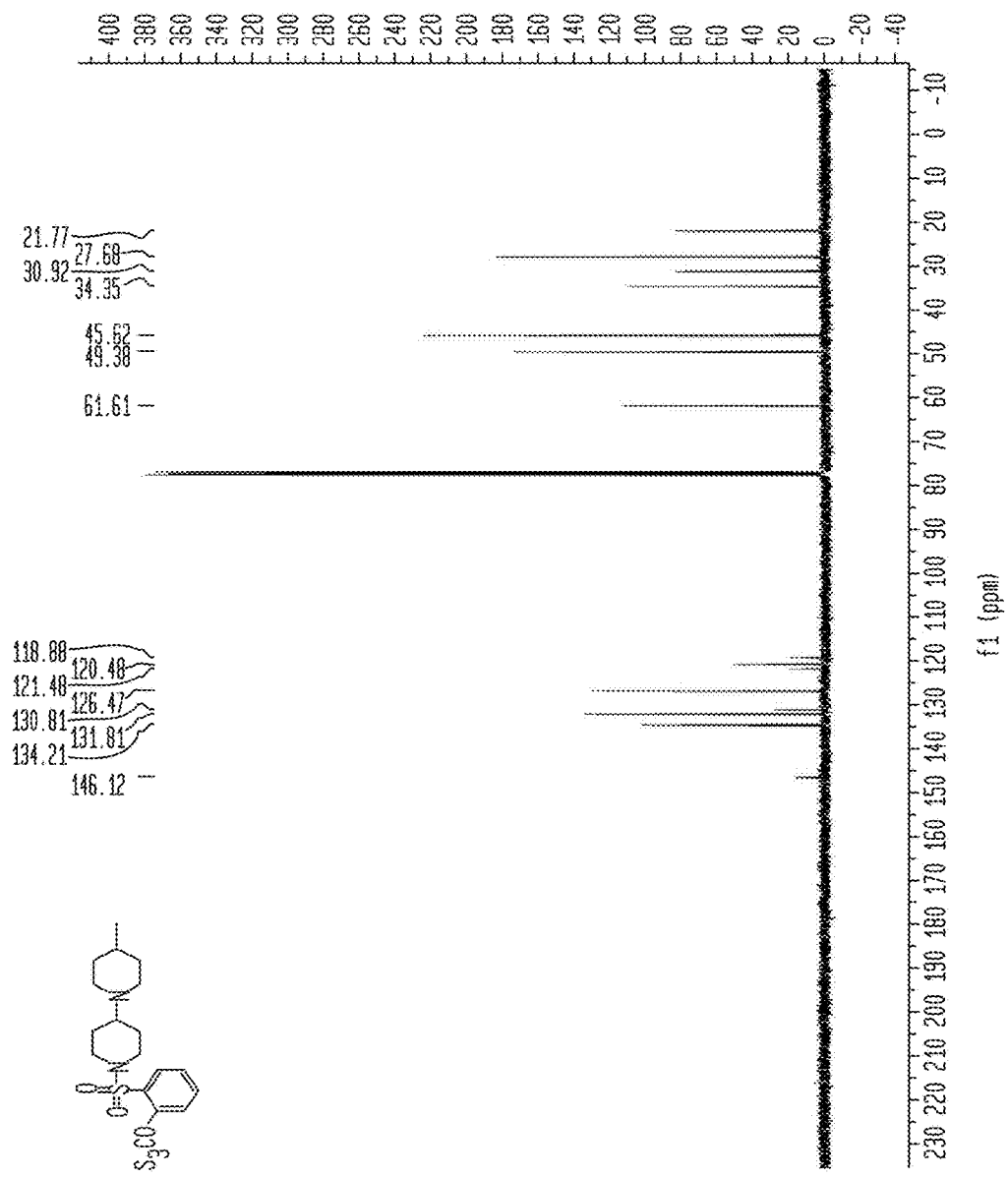
Figure 36A:
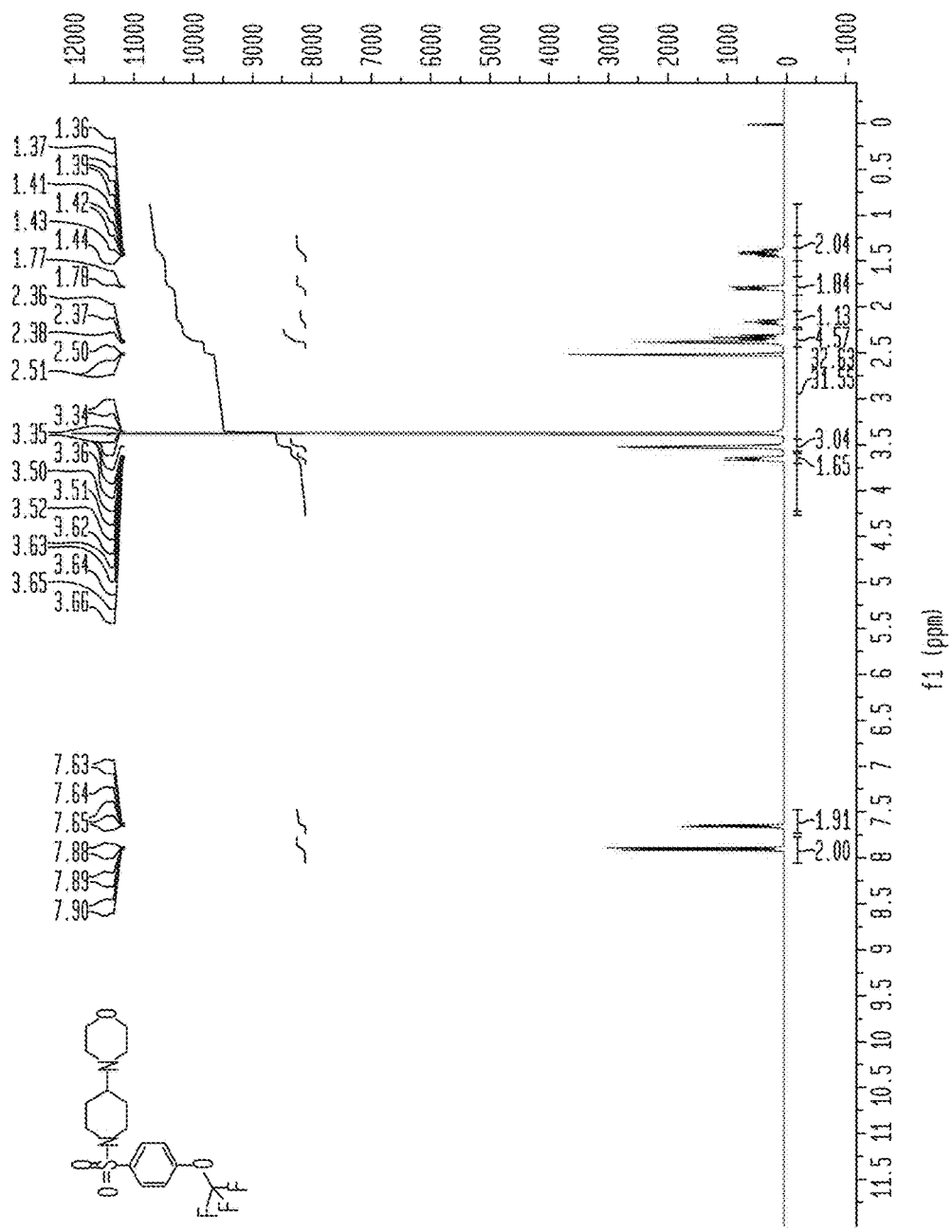
Figure 36A:
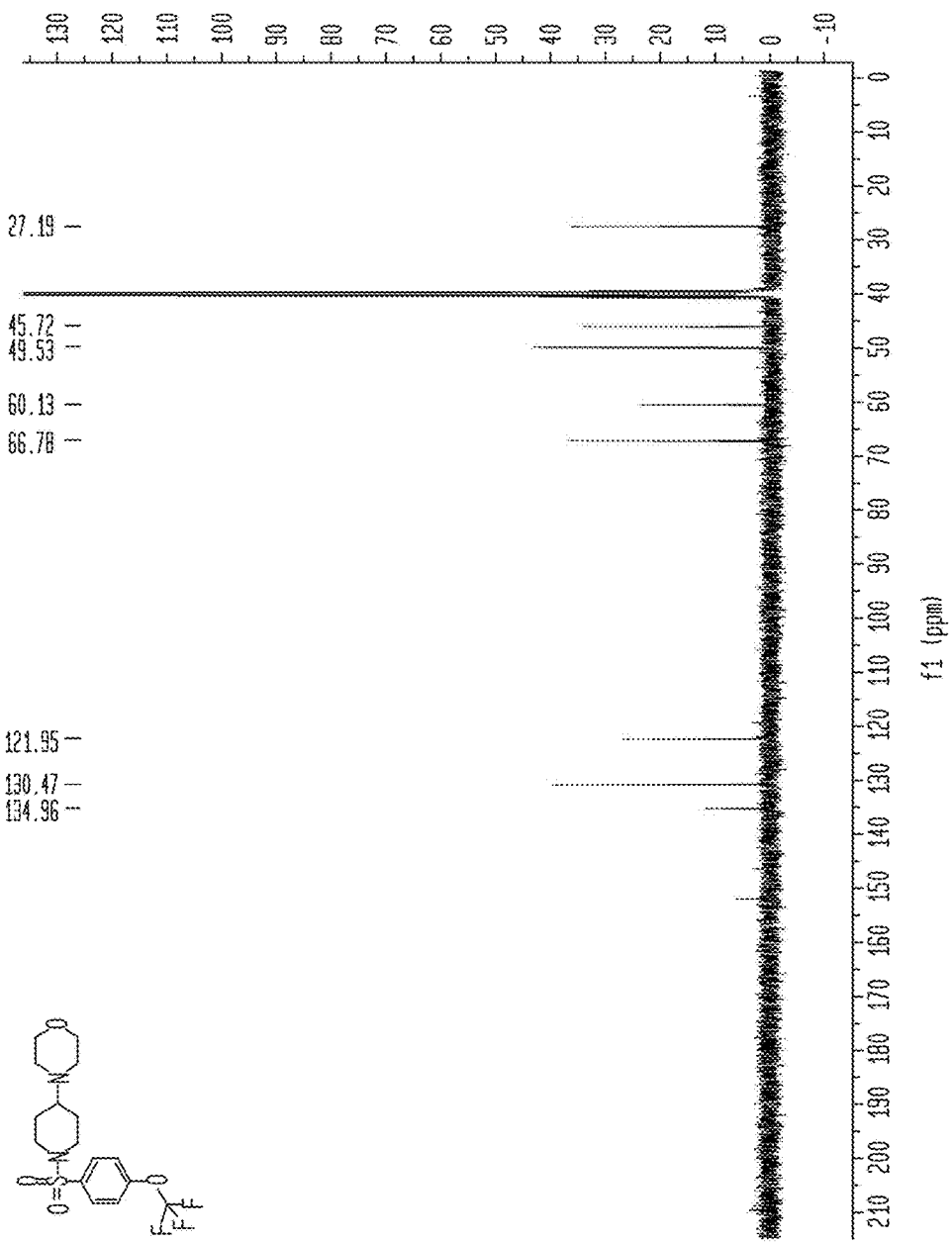
Figure 36A:
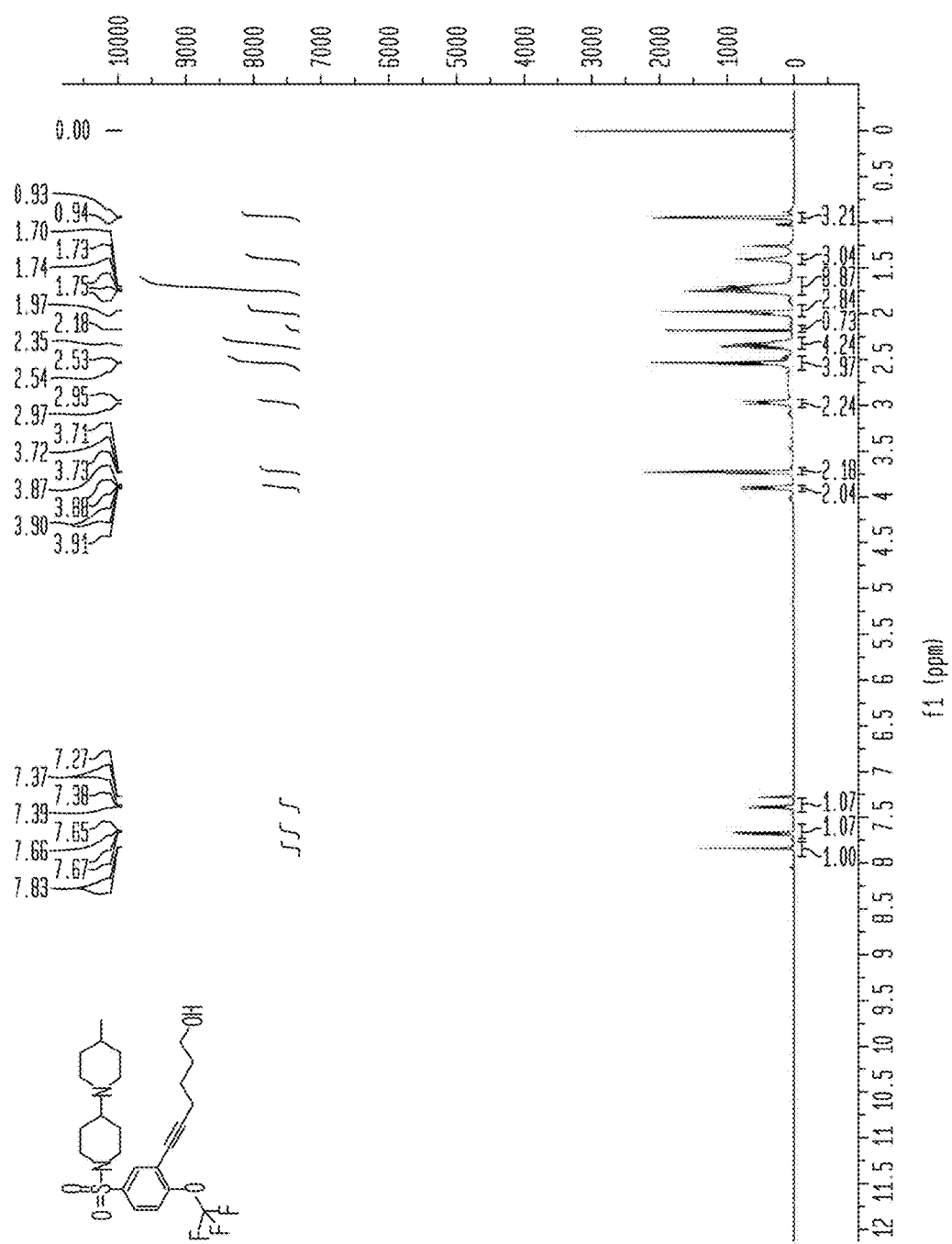
Figure 36A:
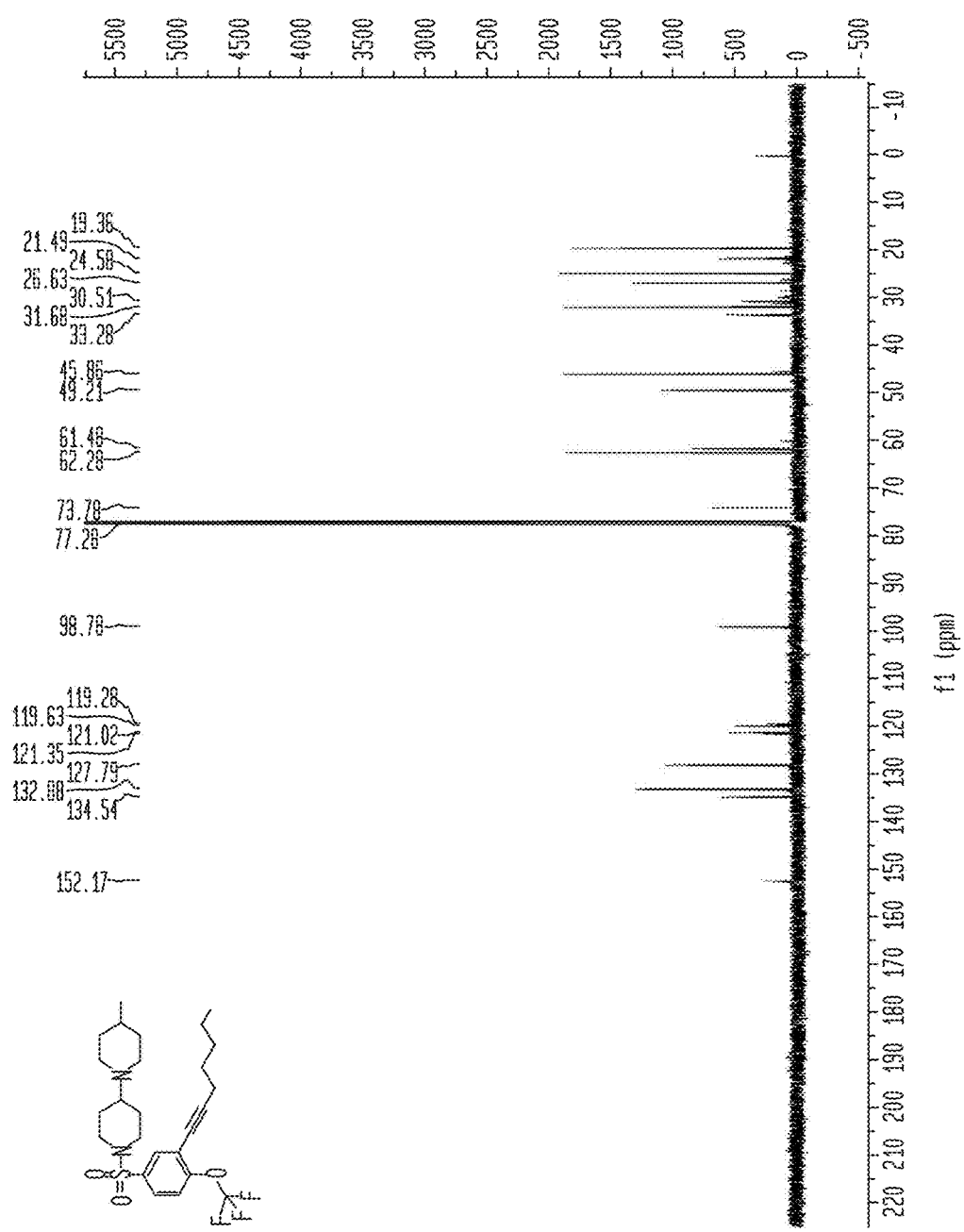
Figure 36A:
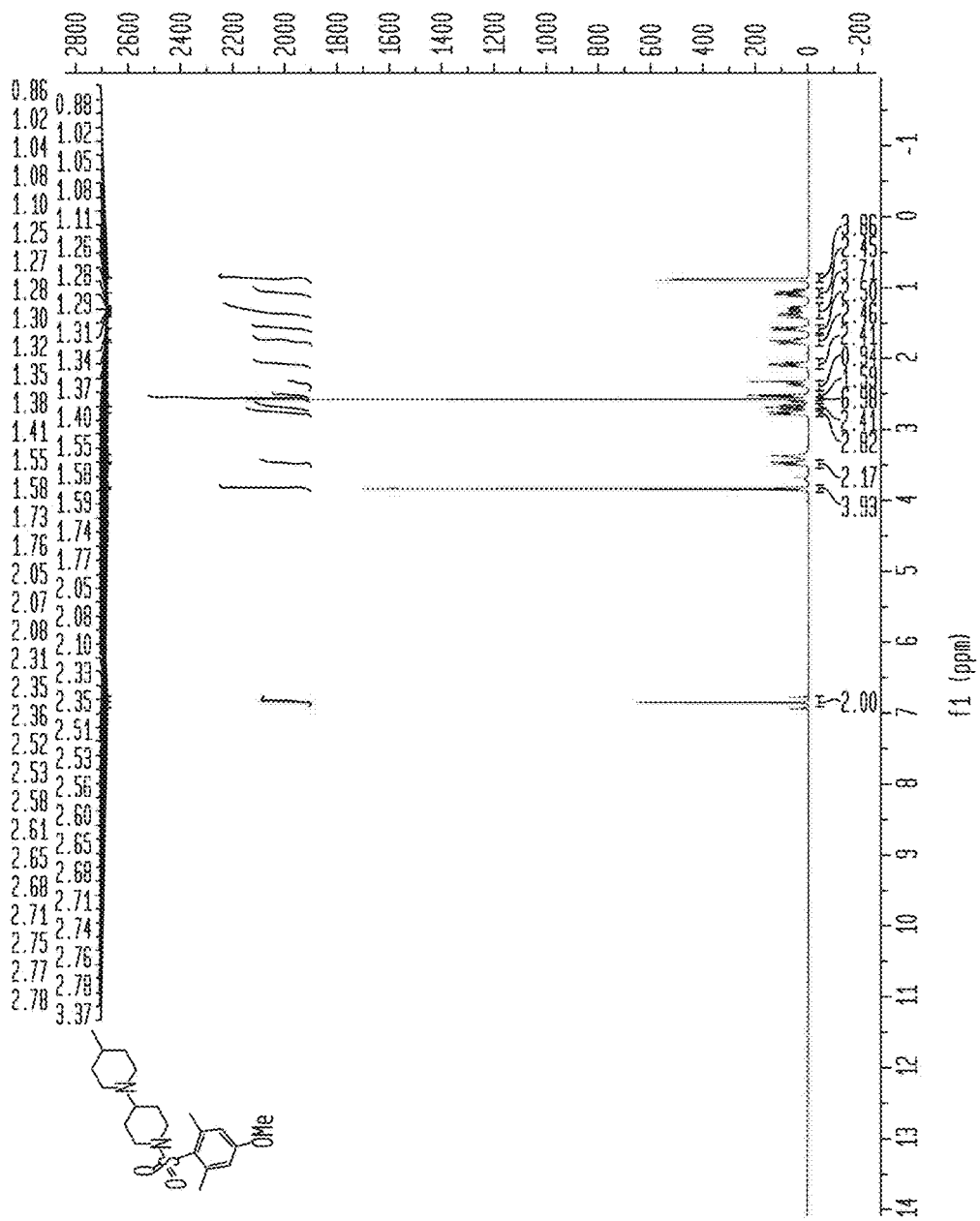
Figure 36A:
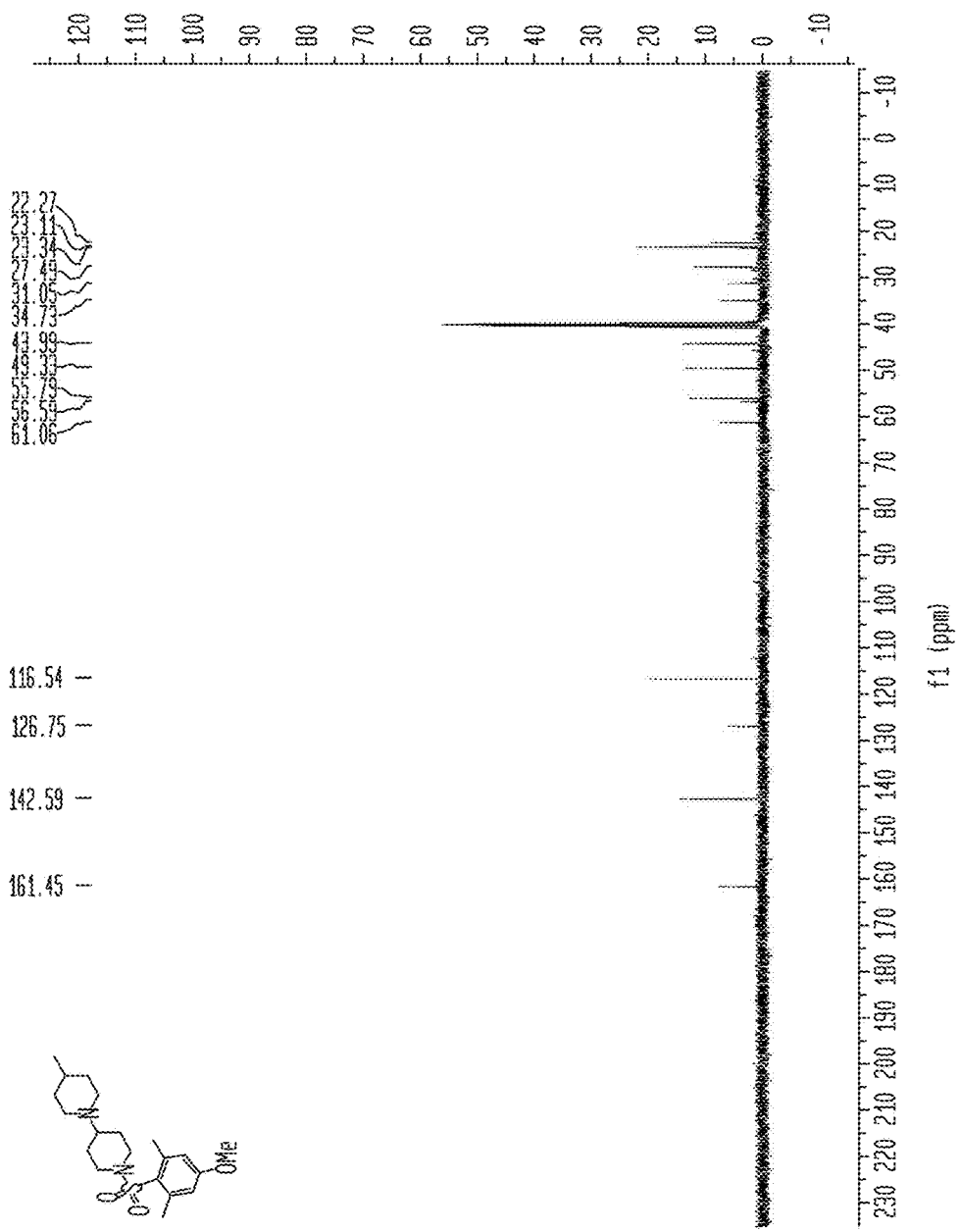
Figure 36A:
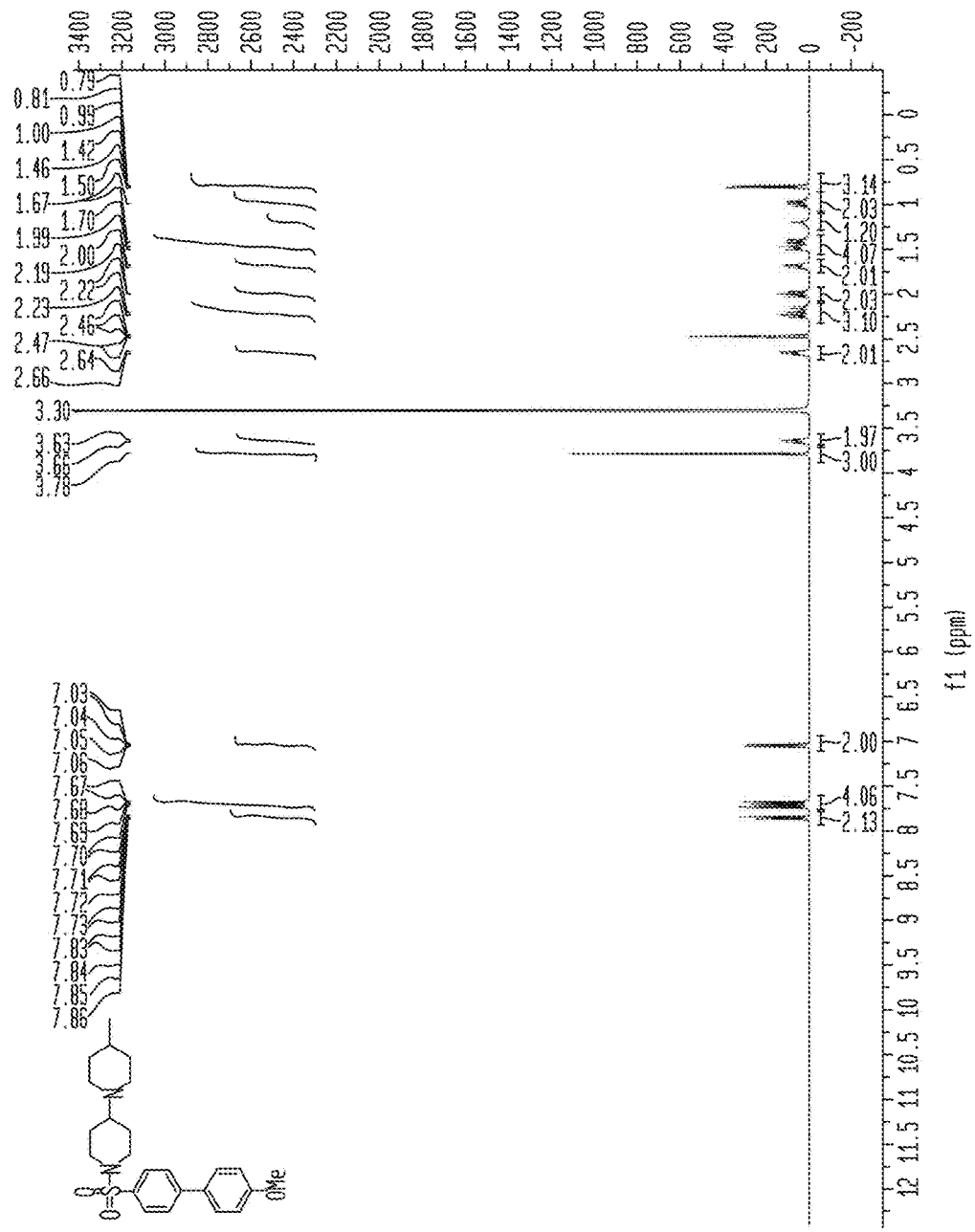
Figure 36A:
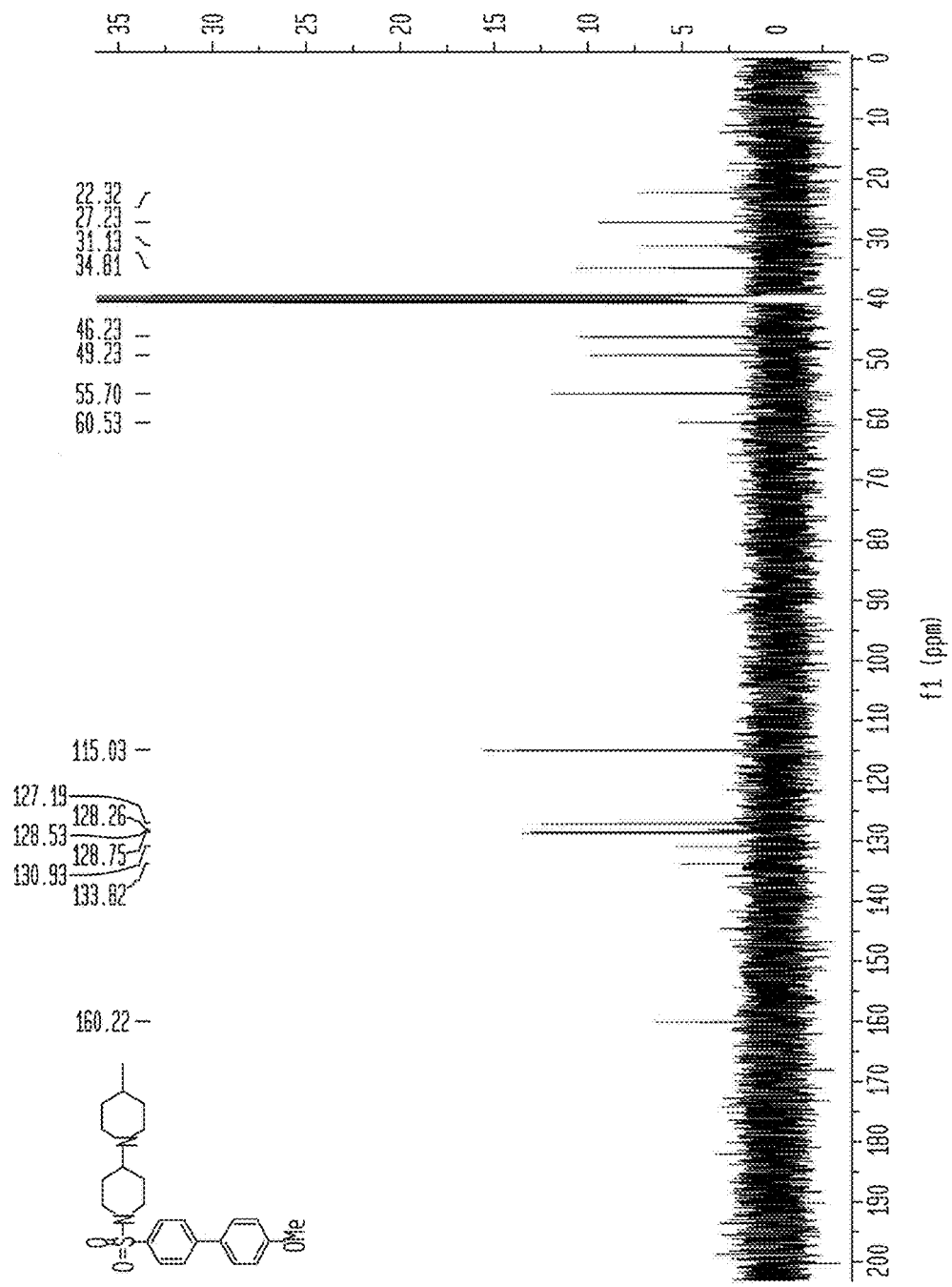
Figure 36A:
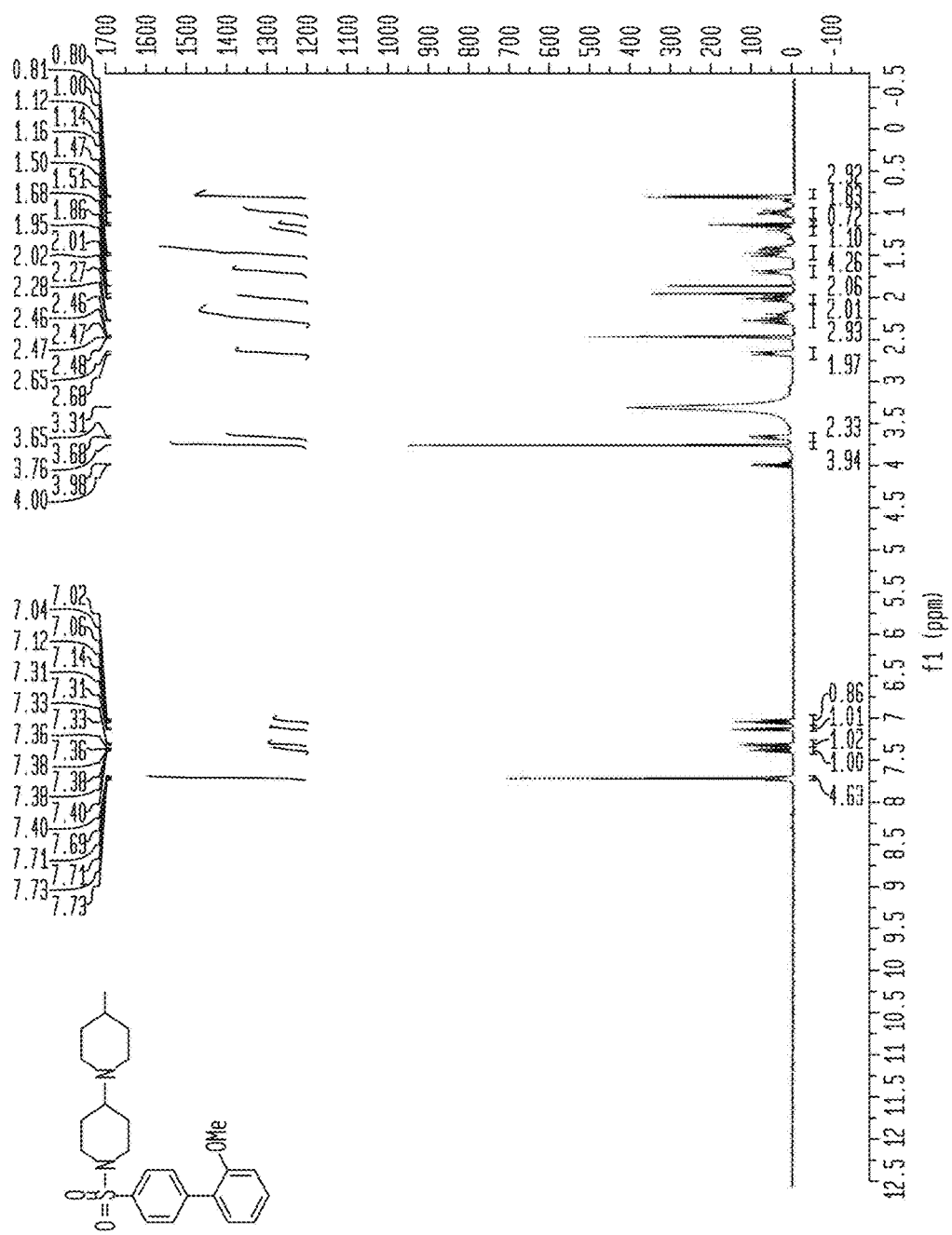
Figure 36A:
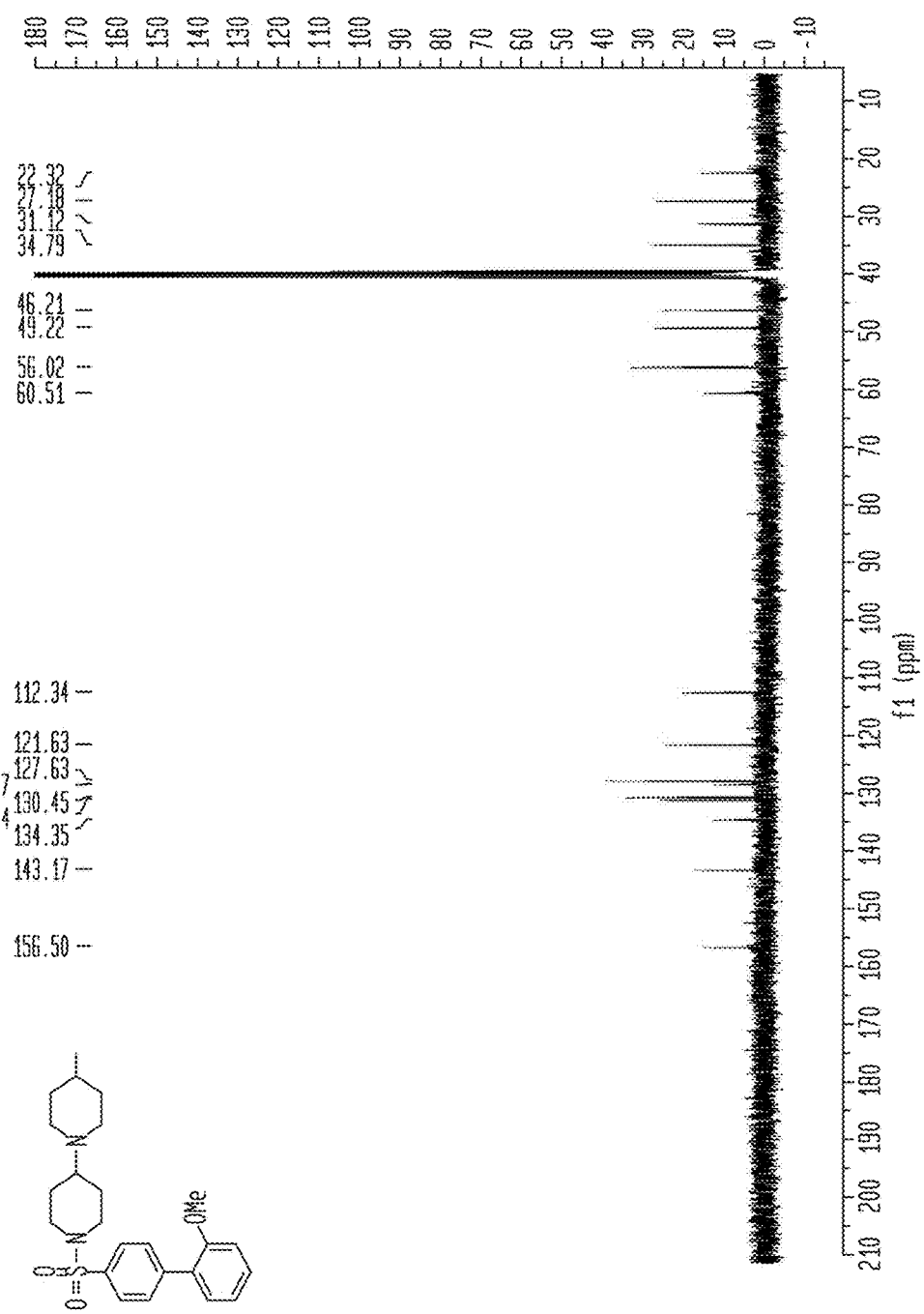
Figure 36A:
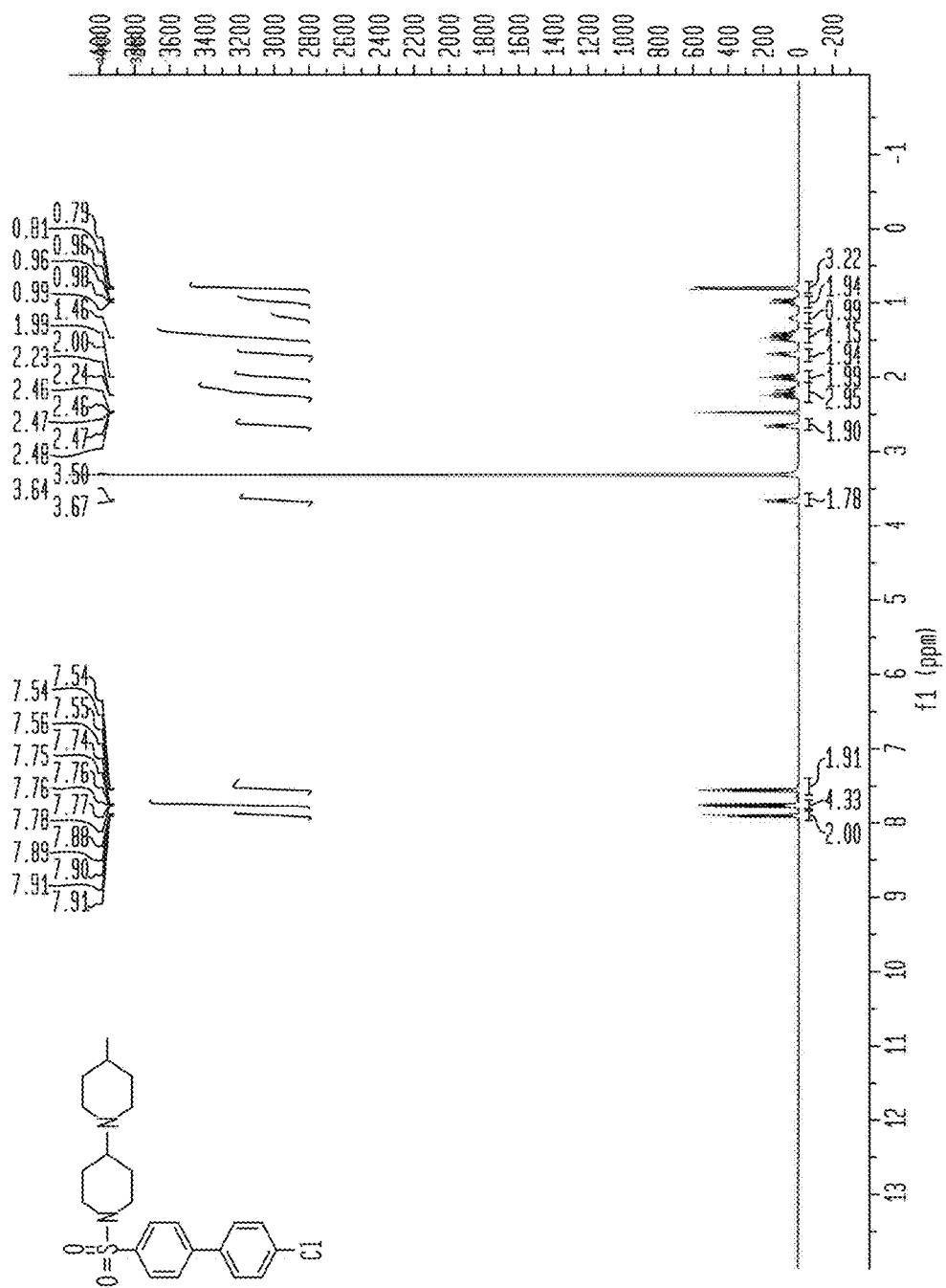
Figure 36A:
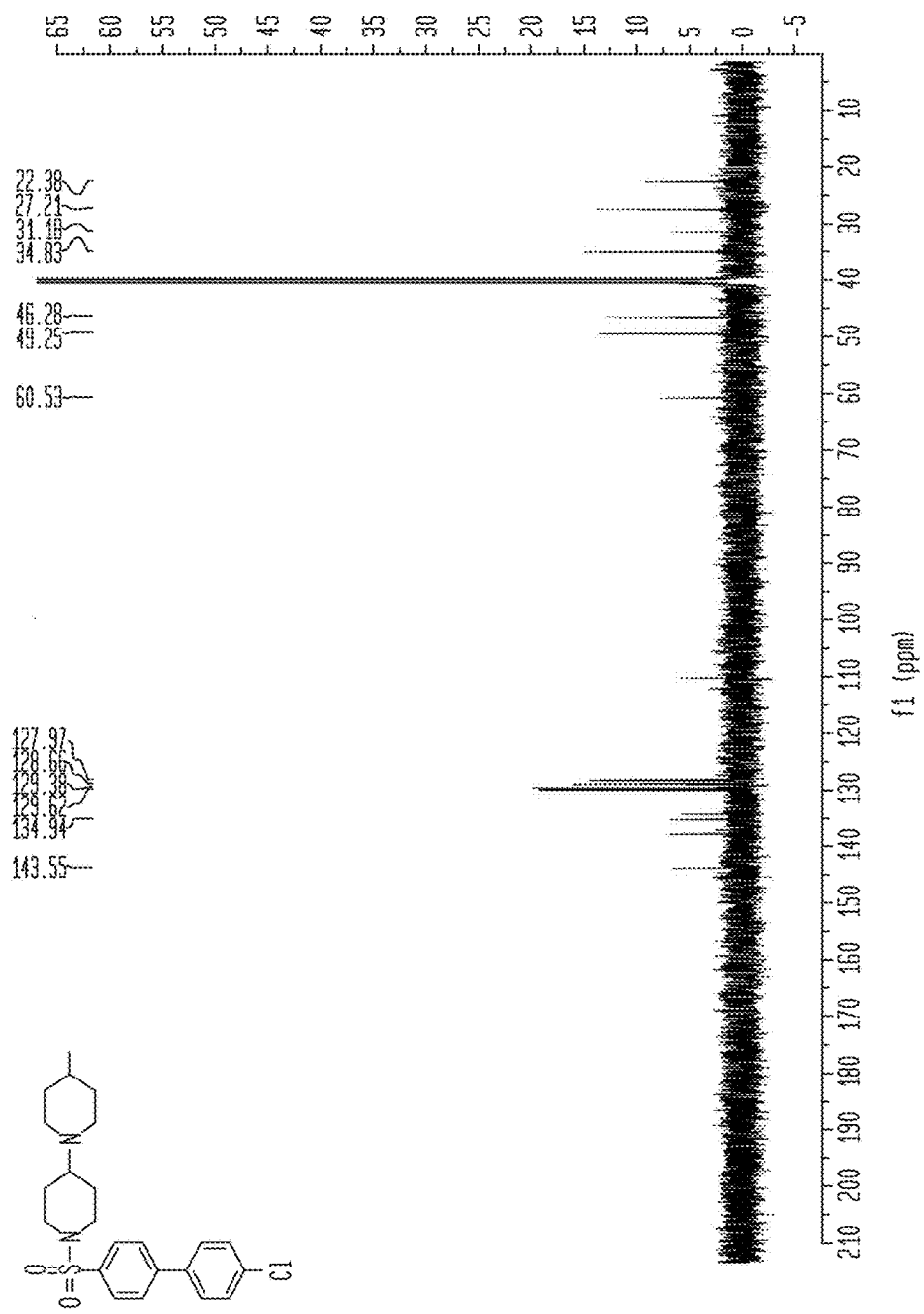
Figure 36A:
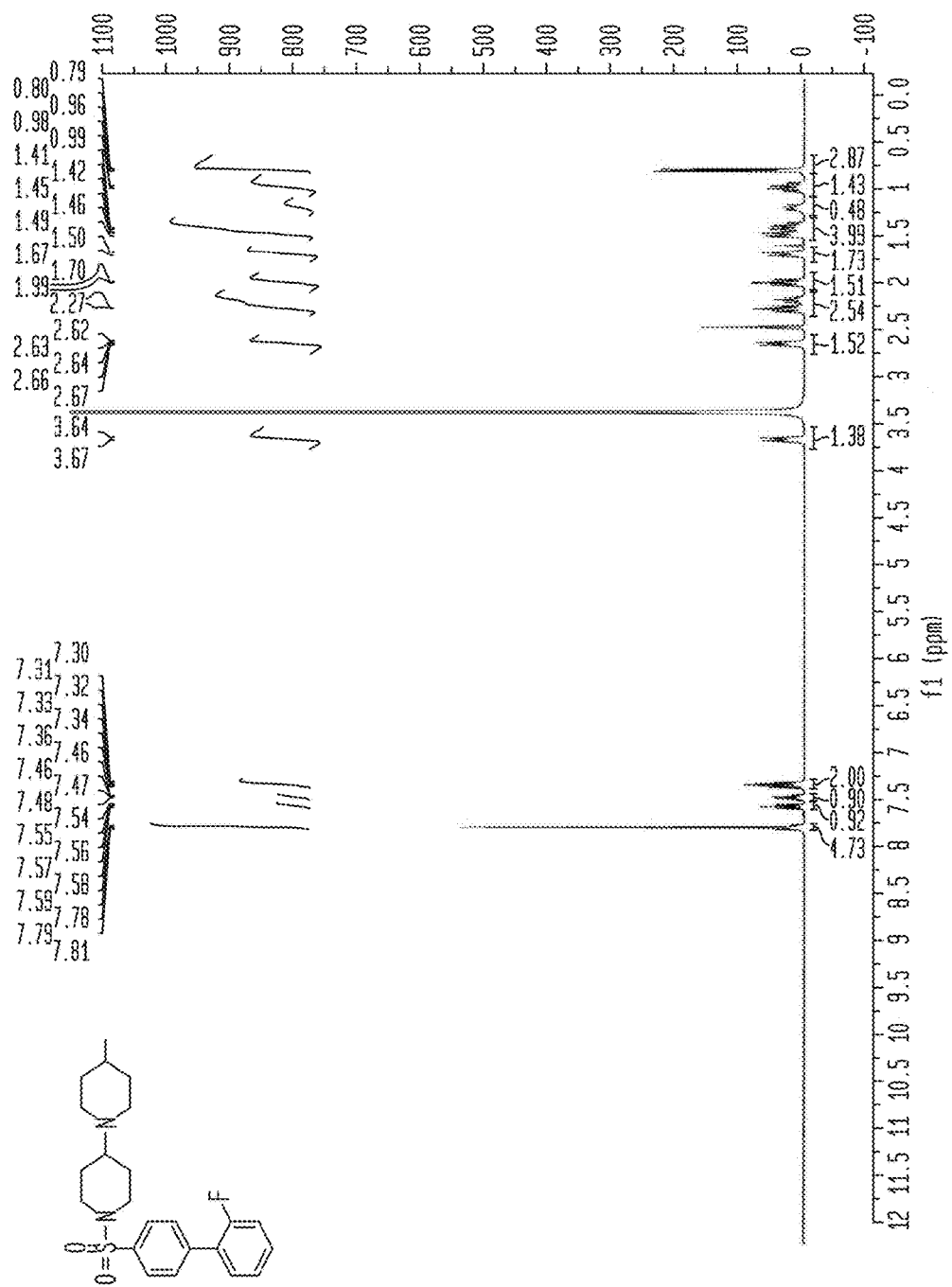
Figure 36A:
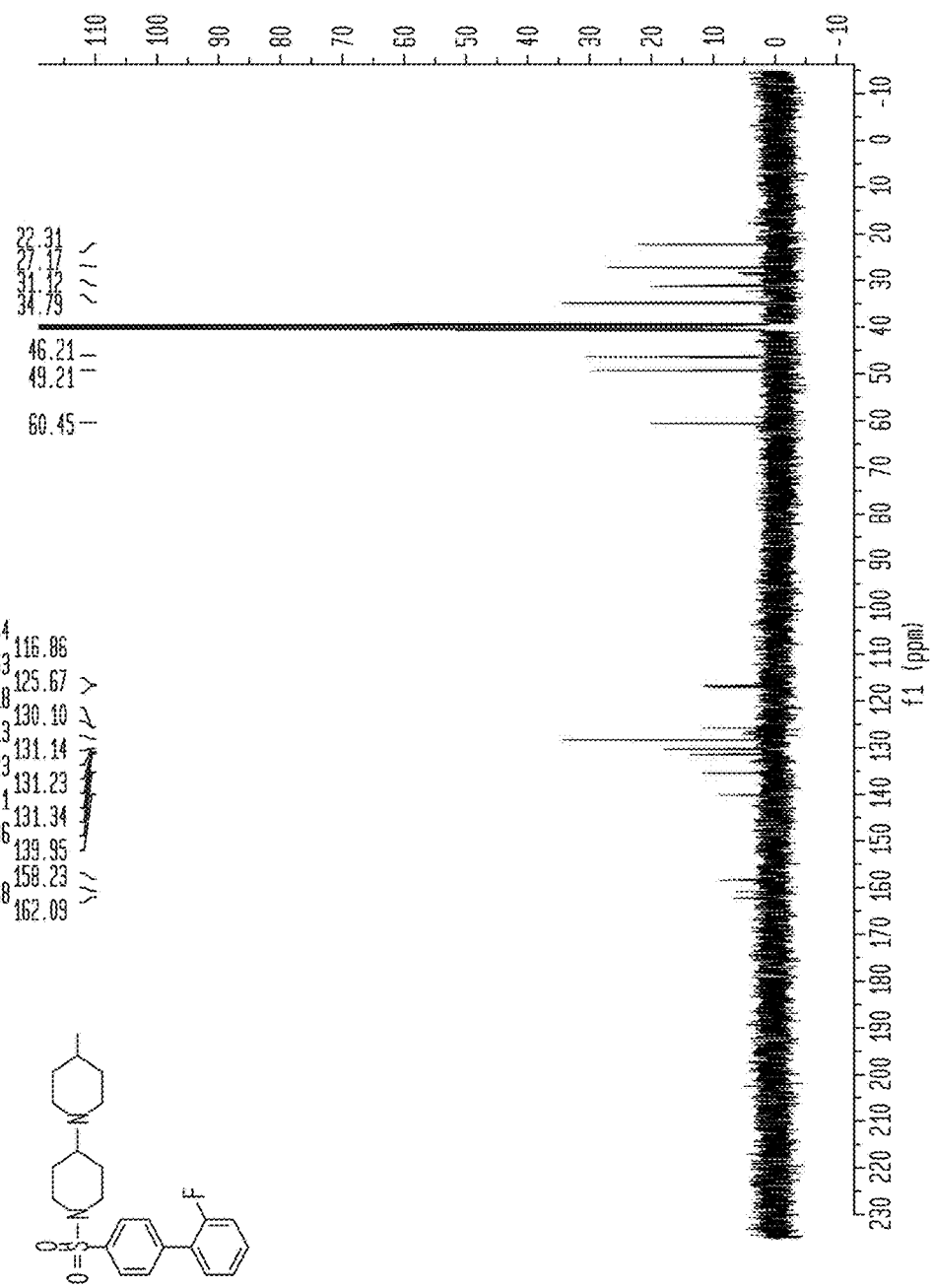
Figure 36A:
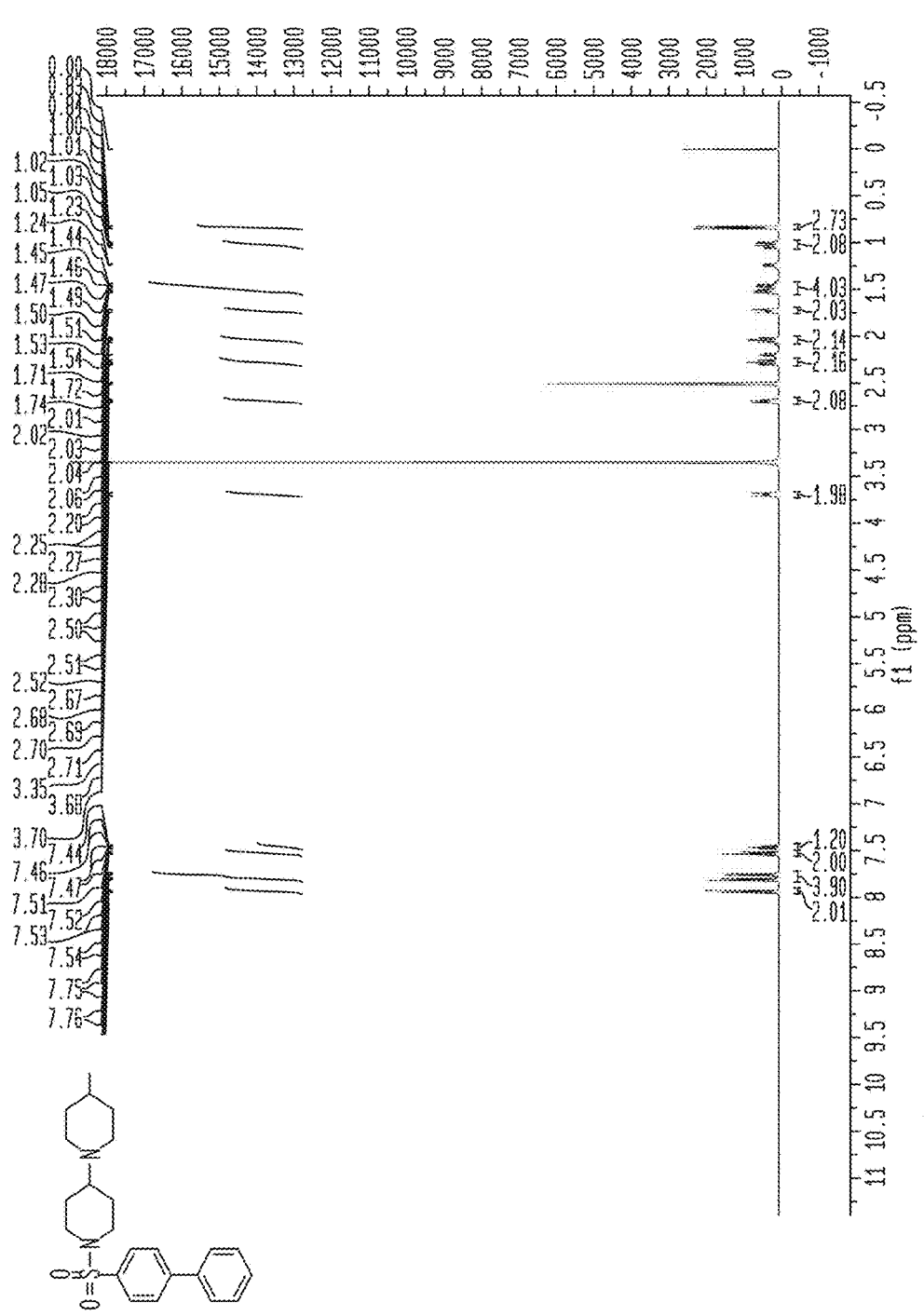
Figure 36A:
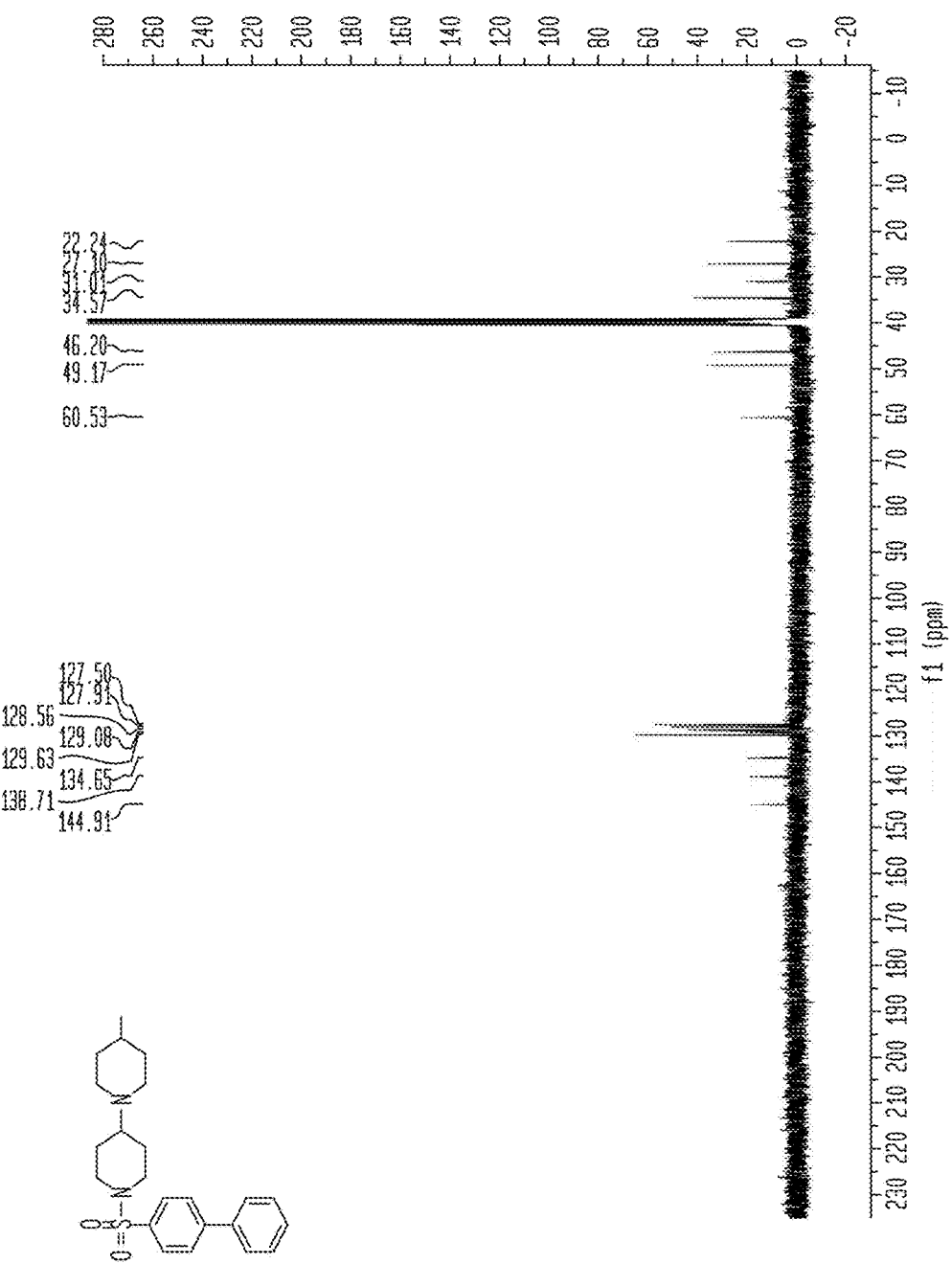
Figure 36B:
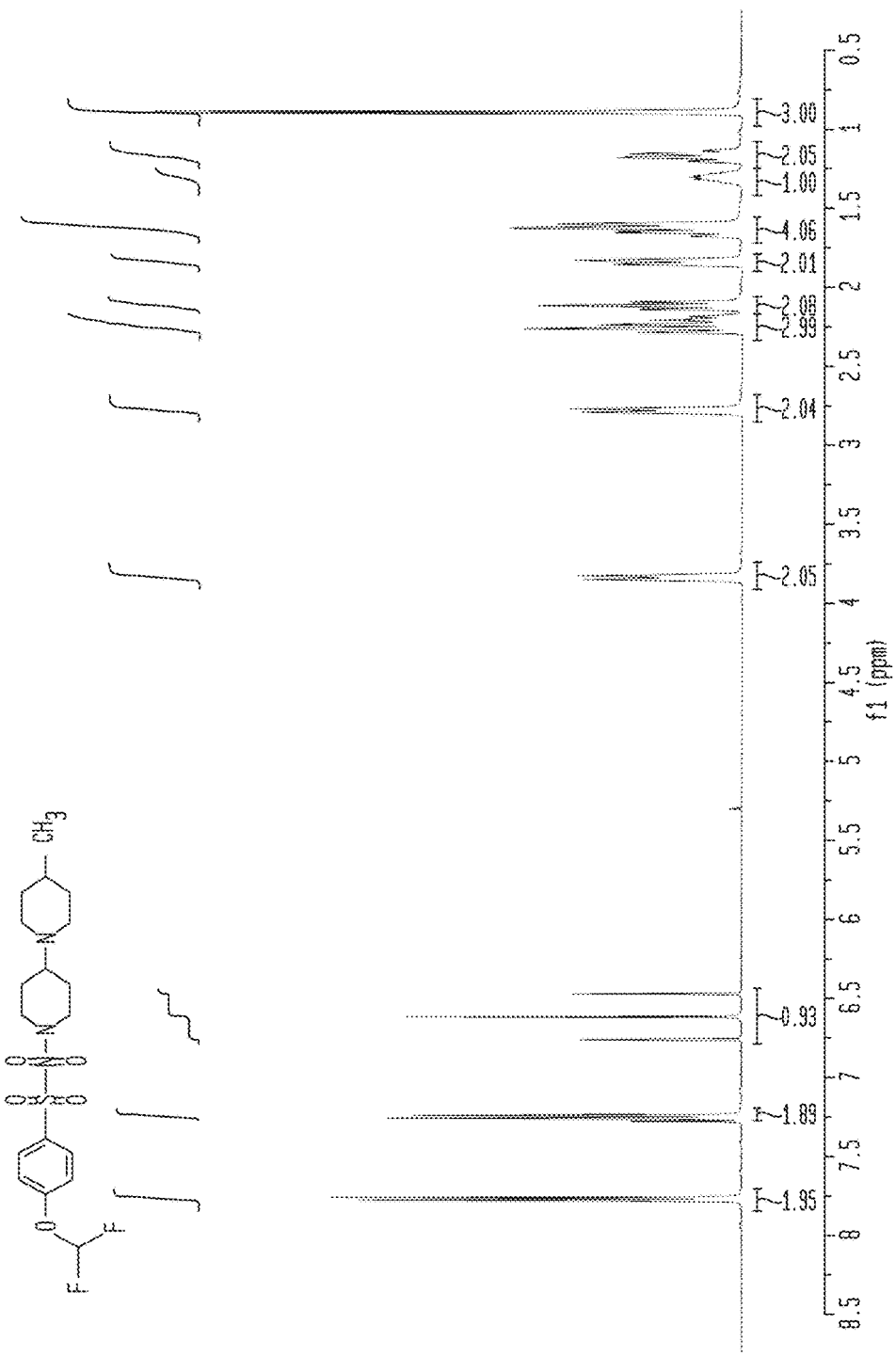
Figure 36B:
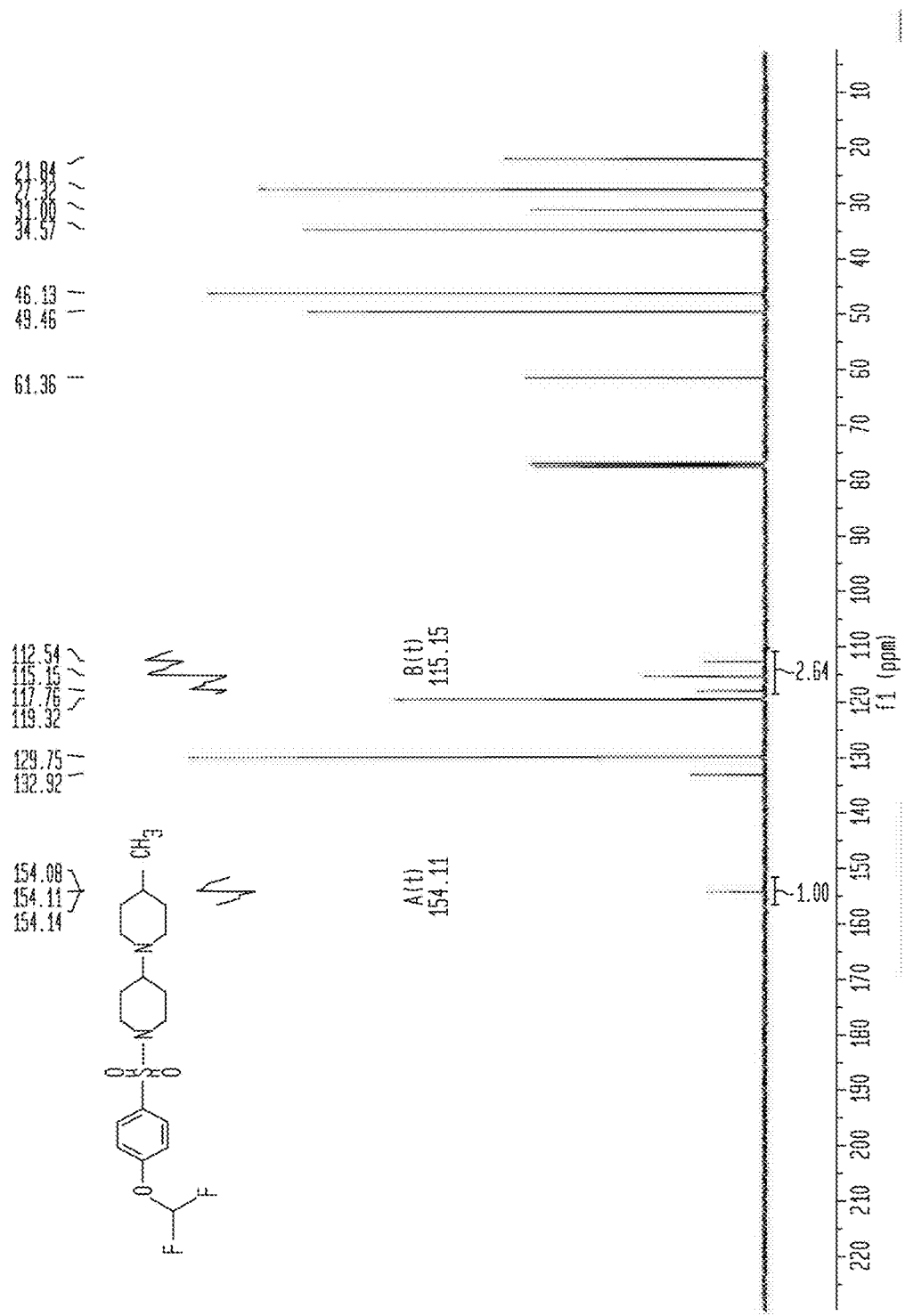

FIG. 36A-36BB show NMR spectra of exemplified compounds (a-bb).

DETAILED DESCRIPTION

The described invention can be better understood from the following description of exemplary embodiments, taken in conjunction with the accompanying figures and drawings. It should be apparent to those skilled in the art that the described embodiments of the described invention provided herein are merely exemplary and illustrative and not limiting.

Definitions:

Various terms used throughout this specification shall have the definitions set out herein.

The term "Adenomatous polyposis *coli* gene" or "APC gene" or "APC" as used herein refers to a mammalian DNA sequence coding for an APC protein. An example of a human APC gene is located at 5q21-q22 on chromosome 5, GenBank: M74088.1. Synonyms for the human APC gene include: BTPS2, DP2, DP2.5, DP3, PPP1R46 and "protein phosphatase 1, regulatory subunit 46". An example of a mouse APC gene is located at chromosome 18 B1, MGI: 88039. Synonyms for the mouse APC gene include: CC2, Min, mAPC, AI0147805, AU020952 and AW124434.

The term "anti-cancer compounds" as used herein refers to small molecule compounds that selectively target and inhibit the biological activity of truncated APCs.

The term "Adenomatous polyposis *coli* protein" or "APC protein" or "APC" as used herein refers to a mammalian protein sequence of 2843 amino acids. An example of a human APC sequence is GenBank: AAA03586. An example of a mouse APC sequence is GenBank: AAB59632.

The term "APC truncation" or "APC truncation mutant" or "APC truncation mutation" refers to a truncated protein product resulting from a mutation occurring within the APC gene. An APC truncation can be, for example, but not limited to, a 1309 amino acid product or a 1450 amino acid product.

The term "administering" as used herein includes in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be locally administered by means such as, but not limited to, injection, implantation, grafting, topical application, or parenterally.

The terms "analog" and "derivative" are used interchangeably to mean a compound produced from another compound of similar structure in one or more steps. A "derivative" or "analog" of a compound retains at least a degree of the desired function of the reference compound. Accordingly, an alternate term for "derivative" may be "functional derivative." Derivatives can include chemical modifications, such as akylation, acylation, carbamylation, iodination or any modification that derivatizes the compound. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The term "condition", as used herein, refers to a variety of health states and is meant to include disorders or diseases caused by any underlying mechanism or injury. Diseases associated with APC include, but are not limited to, colon cancer.

The term "disease" or "disorder", as used herein, refers to an impairment of health or a condition of abnormal functioning.

The term "drug" as used herein refers to a therapeutic agent or any substance used in the prevention, diagnosis, alleviation, treatment, or cure of disease.

As used herein, the term "enzymatic activity" refers to the amount of substrate consumed (or product formed) in a given time under given conditions. Enzymatic activity also may be referred to as "turnover number."

The term "inhibiting" as used herein refers to reducing or modulating the chemical or biological activity of a substance or compound.

The term "injury," as used herein, refers to damage or harm to a structure or function of the body caused by an outside agent or force, which may be physical or chemical.

The term "syndrome," as used herein, refers to a pattern of symptoms indicative of some disease or condition.

The term "therapeutic agent" as used herein refers to a drug, molecule, nucleic acid, protein, metabolite, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein. The active agent may be, for example, but not limited to, at least one of a compound of formula I, or a pharmaceutically acceptable salt thereof.

The term "modify" as used herein means to change, vary, adjust, temper, alter, affect or regulate to a certain measure or proportion in one or more particulars.

The term "modifying agent" as used herein refers to a substance, composition, extract, botanical ingredient, botanical extract, botanical constituent, therapeutic component, active constituent, therapeutic agent, drug, metabolite, active agent, protein, non-therapeutic component, non-active constituent, non-therapeutic agent, or non-active agent that reduces, lessens in degree or extent, or moderates the form, symptoms, signs, qualities, character or properties of a condition, state, disorder, disease, symptom or syndrome.

The term "modulate" as used herein means to regulate, alter, adapt, or adjust to a certain measure or proportion.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using Exemplary dispersing or wetting agents and suspending agents.

The term "reduce" or "reducing" as used herein refers to limit occurrence of a disorder in individuals at risk of developing the disorder.

As used herein, the terms "subject" or "individual" or "patient" are used interchangeably to refer to a member of an animal species of mammalian origin, including humans.

The term "symptom" as used herein refers to a phenomenon that arises from and accompanies a particular disease or disorder and serves as an indication of it.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50, which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

As used herein, the term "topical" refers to administration of a composition at, or immediately beneath, the point of application. The phrase "topically applying" describes application onto one or more surfaces(s) including epithelial surfaces. Although topical administration, in contrast to transdermal administration, generally provides a local rather than a systemic effect, the terms "topical administration" and "transdermal administration" as used herein, unless otherwise stated or implied, are used interchangeably.

As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The terms "mutants" and "variants" are used interchangeably herein to refer to nucleotide sequences with substantial identity to a reference nucleotide sequence. The differences in the sequences may by the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of techniques.

The term "pharmaceutical composition" as used herein refers to a preparation comprising a pharmaceutical product, drug, metabolite, or active ingredient.

As used herein the term "treating" includes abrogating, substantially inhibiting, slowing or reversing the progression of a condition, substantially ameliorating clinical symptoms of a condition, or substantially preventing the appearance of clinical symptoms of a condition. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder (s) in patients that have previously had the disorder(s); and (e) limiting recurrence of symptoms in patients that were previously asymptomatic for the disorder(s). The term "condition" as used herein refers to a variety of health states and is meant to include disorders or diseases caused by any underlying mechanism or disorder in which a truncated APC protein is expressed. A subject in need thereof is a patient having, or at risk of having a disorder related to APC mutation.

Compounds

According to one aspect, the described invention provides a small molecule anti-cancer compound of Formula I:

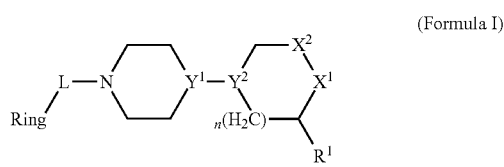

(Formula I)

wherein:

$Y^1$ and $Y^2$ are each independently CH or N;

L is $SO_2$, CO, $CH_2$, or CHMe;

$X^2$ is selected from the group consisting of $CH_2$, $CHR^2$, $NR^3$, O, S;

$X^1$ is selected from the group consisting of $CH_2$, $CHR^4$, $NR^5$, O, S;

n=0, 1, 2

$R^1$ and $R^2$ are each independently selected from the group consisting of H, $C_{1-4}$ alkyl, $C_{1-4}$ alkenyl, $C_{1-4}$ alkynyl, $CH_2$aryl, $CH_2$heteroaryl $R^3$, $R^4$ and $R^5$ are each independently selected from the group consisting of $C_{1-6}$ alkyl; $C_{1-6}$ cycloalkyl, $C_{1-6}$ alkenyl, $C_{1-6}$ alkynyl, aryl, heteroaryl, $CH_2$aryl, $CH_2$heteroaryl;

$R^3$ can form a methylene or ethylene bridge to one of the other ring atoms, thus providing a bicyclic ring structure; and the Ring connected to L can be aryl, heteroaryl, heterocyclyl, fused cycloalkylaryl, fused heterocyclylaryl, fused arylheterocyclyl, fused cycloalkylheteroaryl, fused heterocyclylheteroaryl, fused heteroarylheterocyclyl;

such that all possible stereoisomers, including optically active isomers, are included whenever stereogenic centers are present.

Exemplary small molecule anti-cancer compounds of formula I are found in Table A (SAR). All possible stereoisomers, including optically active isomers, are included whenever sterogenic centers are present.

According to one embodiment, the described invention provides a small molecule anti-cancer compounds of Formula I-a:

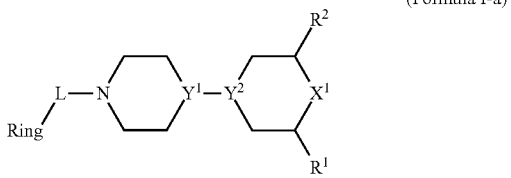

(Formula I-a)

wherein:

$Y^1$ and $Y^2$ are each independently CH or N;

L is $SO_2$, CO, $CH_2$, or CHMe;

$X^1$ is selected from the group consisting of $CH_2$, $CHR^4$, $NR^5$, O, S;

$R^1$ and $R^2$ are each independently H or Me;

$R^4$ and $R^5$ are each independently selected from the group consisting of $C_{1-6}$ alkyl; $C_{1-6}$ cycloalkyl, $C_{1-6}$ alkenyl, $C_{1-6}$ alkynyl, aryl, heteroaryl, $CH_2$aryl, $CH_2$heteroaryl;

the Ring connected to L can be aryl, heteroaryl, fused heterocyclylaryl;

such that all possible stereoisomers, including optically active isomers, are included whenever stereogenic centers are present.

According to another embodiment, the described invention provides a small molecule anti-cancer compound of Formula I-b:

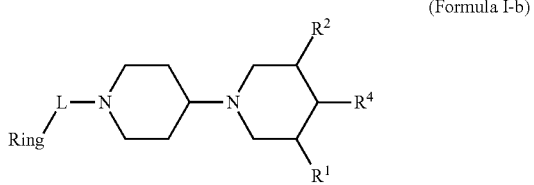

(Formula I-b)

wherein:

L is $SO_2$, CO, $CH_2$, or CHMe $R^1$ and $R^2$ are each independently H or Me;

$R^4$ selected from the group consisting of $C_{1-6}$ alkyl; $C_{1-6}$ alkynyl, aryl, $CH_2$aryl;

the Ring connected to L can be aryl, heteroaryl, fused heterocyclylaryl;

such that all possible stereoisomers, including optically active isomers, are included whenever sterogenic centers are present.

According to another embodiment, a small molecule anti-cancer compound of the described inbention is represented by Formula I-c:

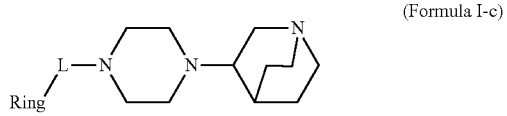

(Formula I-c)

wherein:

L is $SO_2$, $CH_2$, or CHMe;

the Ring connected to L can be aryl, heteroaryl, fused heterocyclylaryl;

such that all possible stereoisomers, including optically active isomers, are included whenever stereogenic centers are present.

According to another embodiment, a small molecule anti-cancer compound of the described invention is represented by Formula I-d:

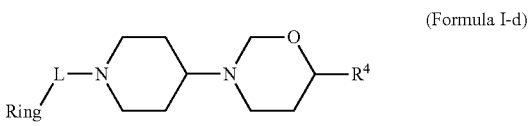

(Formula I-d)

wherein:

L is $SO_2$, $CH_2$, or CHMe;

$R^4$ selected from the group consisting of $C_{1-6}$ alkyl; $C_{1-6}$ alkynyl, aryl, $CH_2$aryl;

the Ring connected to L can be aryl, heteroaryl, fused heterocyclylaryl;

such that all possible stereoisomers, including optically active isomers, are included whenever stereogenic centers are present.

According to another embodiment, a small molecule anti-cancer compound of the described invention is represented by Formula I-e:

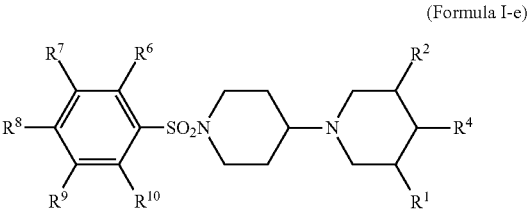

(Formula I-e)

wherein:

$R^1$ and $R^2$ are each independently H or Me;

$R^4$ is selected from the group consisting of H, Me, propargyl, isopropyl, cyclopropyl, $CH_2$aryl;

$R^{6-10}$ are each independently selected from the group consisting of H, F, Cl, Br, Me, Et, $CF_3$, cyclopropyl, isopropyl, tert-butyl, aryl, OMe, $OCF_3$, $OCHF_2$, OAryl, CN, $N_3$, COAryl, $CO_2H$, $CO_2R$, CHO, $CONH_2$, $CONR_2$, CONHR. In the context of this paragraph, R is independently selected from the group consisting of H, $C_{1-4}$ alkyl, $C_{1-4}$ cycloalkyl, Aryl, $CH_2$Aryl, $CH_2$Heteroaryl;

such that all possible stereoisomers, including optically active isomers, are included whenever stereogenic centers are present.

According to one embodiment of small molecule anti-cancer compounds represented by Formula I-e, $R^1$ and $R^2$ are each independently H or Me; $R^4$ is selected from H, Me, propargyl, isopropyl, cyclopropyl, $CH_2$aryl; $R^{6-10}$ are each independently selected from H, F, Cl, Br, Me, Et, $CF_3$, cyclopropyl, isopropyl, aryl, OMe, $OCF_3$, $OCHF_2$, OAryl;

According to another embodiment of small molecule anti-cancer compounds represented by Formula I-e, $R^1$ and $R^2$ are each independently H or Me; $R^4$ is selected from H, Me, propargyl, isopropyl, cyclopropyl, $CH_2$aryl; $R^6$ is Aryl, $R^{7-10}$ are each independently selected from H, F, Cl, $CF_3$, Me, cyclopropyl, isopropyl, OMe, $OCF_3$, $OCHF_2$;

According to another embodiment of small molecule anti-cancer compounds represented by Formula I-e, $R^1$ and $R^2$ are each independently H or Me; $R^4$ is selected from H, Me, propargyl, isopropyl, cyclopropyl, $CH_2$aryl; $R^7$ is Aryl, $R^6$, $R^8$, $R^9$ and $R^{10}$ are each independently selected from H, F, Cl, $CF_3$, Me, cyclopropyl, isopropyl, OMe, $OCF_3$, $OCHF_2$;

According to another embodiment of small molecule anti-cancer compounds represented by Formula I-e, $R^1$ and $R^2$ are each independently H or Me; $R^4$ is selected from H, Me, propargyl, isopropyl, cyclopropyl, $CH_2$aryl; $R^8$ is Aryl, $R^6$, $R^7$, $R^9$ and $R^{10}$ are each independently selected from H, F, Cl, $CF_3$, Me, cyclopropyl, isopropyl, OMe, $OCF_3$, $OCHF_2$;

According to another embodiment of small molecule anti-cancer compounds represented by Formula I-e, $R^1$ and $R^2$ are each independently H or Me; $R^4$ is selected from H, Me, propargyl, isopropyl, cyclopropyl, $CH_2$aryl; $R^7$ is COAryl, $R^6$, $R^8$, $R^9$ and $R^{10}$ are each independently selected from H, F, Cl, $CF_3$, Me, cyclopropyl, isopropyl, OMe, $OCF_3$, $OCHF_2$;

According to another embodiment, a small molecule anti-cancer compound of the described invention is represented by Formula I-f:

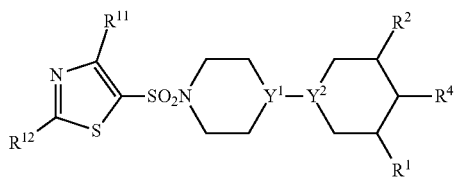

(Formula I-f)

wherein:
$Y^1$ and $Y^2$ are each independently CH or N;
$R^1$ and $R^2$ are each independently H or Me;
$R^4$ is selected from the group consisting of $C_{1-6}$ alkyl; $C_{1-6}$ cycloalkyl, $C_{1-6}$ alkenyl, $C_{1-6}$ alkynyl, $CH_2$aryl;
$R^{11}$ and $R^{12}$ are each independently selected from H, F, Cl, Br, Me, $CF_3$, cyclopropyl, aryl, heteroaryl;
such that all possible stereoisomers, including optically active isomers, are included whenever stereogenic centers are present.

According to an embodiment of small molecule anti-cancer compounds represented by Formula I-f, $Y^1$ is CH; $Y^2$ is N; $R^1$ and $R^2$ are each independently H or Me; $R^4$ is selected from H, Me, propargyl, isopropyl, cyclopropyl, $CH_2$aryl; $R^{11}$ is H, Me, $CF_3$, cyclopropyl, aryl; and $R^{12}$ is selected from H, F, Cl, $CF_3$, Aryl;

Chemical Substituents and Stereochemistry

The term "Aliphatic" as used herein, denotes a straight- or branched-chain arrangement of constituent carbon atoms, including, but not limited to paraffins (alkanes), which are saturated, olefins (alkenes or alkadienes), which are unsaturated, and acetylenes (alkynes), which contain a triple bond. In complex structures, the chains may be branched or cross-linked.

The term "lower" as used herein refers to a group having between one and six carbons.

As used herein, the term "alkyl" refers to a straight or branched chain hydrocarbon having from 1 to 25 carbon atoms, or of the numbers of carbon atoms specified (e.g. $C_{1-6}$ alkyl) or any numbers within this range. It is implicitely implied within the context of this application that such alkyl groups can be optionally substituted with substituents such as, but not limited to, halogen, perfluoroalkyl, lower alkyl, lower alkenyl, lower alkynyl, lower cycloalkyl, lower alkoxy, lower cycloalkoxy, lower alkylsulfanyl, oxo, hydroxyl. Examples of "alkyl" as used herein include, but are not limited to, methyl, trifluoromethyl, ethyl, propyl, n-butyl, t-butyl, n-pentyl, isobutyl, and isopropyl, methoxymethy, methoxyethyl, isopropoxybutyl, propynyloxyethyl, and the like.

The term "Alkenyl," as used herein, denotes a monovalent, straight (unbranched) or branched hydrocarbon chain having one or more double bonds therein where the double bond can be unconjugated or conjugated to another unsaturated group (e.g., a polyunsaturated alkenyl) and can be unsubstituted or substituted, with multiple degrees of substitution being allowed. It may be optionally substituted with substituents such as, but not limited to, halogen, perfluoroalkyl, lower alkyl, lower alkenyl, lower alkynyl, lower cycloalkyl, lower alkoxy, lower cycloalkoxy, lower alkylsulfanyl, oxo, hydroxyl. For example, and without limitation, the alkenyl can be vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, 6-methoxyhexenyl, 2-trifluoromethyl-3-butenyl, and the like.

As used herein, the term "alkynyl" refers to a hydrocarbon radical having at least one carbon-carbon triple bond, optionally substituted with substituents such as, without limitation, halogen, perfluoroalkyl, lower alkyl, lower alkenyl, lower alkynyl, lower cycloalkyl, lower alkoxy, lower cycloalkoxy, lower alkylsulfanyl, oxo, hydroxyl.

The term "aryl" as used herein refers to a benzene ring or to an optionally substituted benzene ring system fused to one or more optionally substituted benzene rings, with multiple degrees of substitution being allowed. Substituents include, but are not limited to, cyano, halogen, perfluoroalkyl, aryl, heteroaryl, heterocyclyl, cycloalkyl, lower alkyl, lower alkoxy, lower alkylsulfanyl, oxo, hydroxy, amino optionally substituted by alkyl or aryl or heteroaryl or heterocyclyl or cycloalkyl, aminocarbonyl (—NRC(O)R) optionally substituted by alkyl or aryl or heteroaryl or heterocyclyl or cycloalkyl, carboxy, acyl, acyloxy, alkoxycarbonyl, aryloxy, heteroaryloxy, heterocyclyloxy, aroyloxy, heteroaroyloxy, heterocycloyloxy, carbamoyl optionally substituted by alkyl or cycloalkyl or aryl or heteroaryl or heterocyclyl, aminosulfonyl optionally substituted by alkyl or cycloalkyl or aryl or heteroaryl or heterocyclyl. Examples of aryl include, but are not limited to, phenyl, 2-napthyl, 1-naphthyl, 1-anthracenyl, and the like.

It should be understood that wherever the terms "alkyl" or "aryl" or either of their prefix roots appear in a name of a substituent, they are to be interpreted as including those limitations given above for alkyl and aryl. Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, "cycloalkyl" (used interchangeably with "aliphatic cyclic" herein) refers to a non-aromatic monovalent, monocyclic or polycyclic ring structure having a total of from 3 to 10 carbon ring atoms (but no heteroatoms) optionally possessing one or more degrees of unsaturation, optionally substituted with substituents such as, without limitation, halogen, perfluoroalkyl, cycloalkyl, lower alkyl, lower alkoxy, lower alkylsulfanyl, oxo, hydroxyl. "Cycloalkyl" includes by way of example cyclopropyl, cyclobutyl, cyclopentyl, cyclopentenyl, cyclohexyl, cyclohehexenyl, adamantanyl, norbornyl, nobornenyl, cycloheptyl, or cyclooctyl, and the like.

The terms "heterocycle" and "heterocyclic" as used herein are used interchangeably to refer to a three to twelve-membered heterocyclic ring optionally possessing one or more degrees of unsaturation, containing one or more heteroatomic substitutions selected from —S—, —SO—, —SO$_2$—, —O—, or —N—, optionally substituted with substitutents, including, but not limited to, nitro, cyano, halogen, perfluoroalkyl, aryl, heteroaryl, heterocyclyl, cycloalkyl, lower alkyl, lower alkoxy, lower alkylsulfanyl, lower alkylsulfenyl, lower alkylsulfonyl, oxo, hydroxy, mercapto, amino optionally substituted by alkyl or aryl or heteroaryl or heterocyclyl or cycloalkyl, aminocarbonyl (—NRC(O)R) optionally substituted by alkyl or aryl or heteroaryl or heterocyclyl or cycloalkyl, carboxy, acyl, acyloxy, alkoxycarbonyl, aryloxy, heteroaryloxy, heterocyclyloxy, aroyloxy, heteroaroyloxy, heterocycloyloxy, carbamoyl optionally substituted by alkyl or cycloalkyl or aryl or heteroaryl or heterocyclyl, aminosulfonyl optionally substituted by alkyl or cycloalkyl or aryl or heteroaryl or heterocyclyl, silyloxy optionally substituted by alkyl or aryl, silyl optionally substituted by alkoxy or alkyl or aryl, multiple degrees of substitution being allowed. Such a ring optionally may be fused to one or more of another "heterocyclic" ring(s). Examples of "heterocyclic" include, but are not limited to, pyrrole, furan, thiophene, imidazole, oxazole, thiazole, pyrazole, 3-pyrroline, pyrrolidine, pyridine, pyrimidine, purine, quinoline, isoquinoline, carbazole, tetrahydrofuran, 1,4-dioxane, 1,3-dioxane, piperidine, pyrrolidine, morpholine, piperazine and the like.

Examples of heterocycles include, but are not limited to, pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, beta-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents including, but not limited to, nitro, cyano, halogen, perfluoroalkyl, aryl, heteroaryl, heterocyclyl, cycloalkyl, lower alkyl, lower alkoxy, lower alkylsulfanyl, lower alkylsulfenyl, lower alkylsulfonyl, oxo, hydroxy, mercapto, amino optionally substituted by alkyl or aryl or heteroaryl or heterocyclyl or cycloalkyl, aminocarbonyl (—NRC(O)R) optionally substituted by alkyl or aryl or heteroaryl or heterocyclyl or cycloalkyl, carboxy, acyl, acyloxy, alkoxycarbonyl, aryloxy, heteroaryloxy, heterocyclyloxy, aroyloxy, heteroaroyloxy, heterocycloyloxy, carbamoyl optionally substituted by alkyl or cycloalkyl or aryl or heteroaryl or heterocyclyl, aminosulfonyl optionally substituted by alkyl or cycloalkyl or aryl or heteroaryl or heterocyclyl, silyloxy optionally substituted by alkyl or aryl, silyl optionally substituted by alkoxy or alkyl or aryl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include, but are not limited to, 5-indanyl, 5,6,7,8-tetrahydro-2-naphthyl,

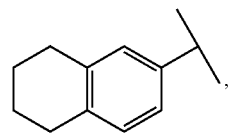

and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include, but are not limited to, 1-indanyl, 2-indanyl, 1-(1,2,3,4-tetrahydronaphthyl),

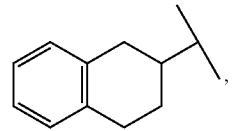

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include, but are not limited to, 3,4-methylenedioxy-1-phenyl,

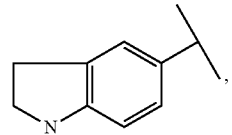

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include, but are not limited to, 2-(1,3-benzodioxolyl),

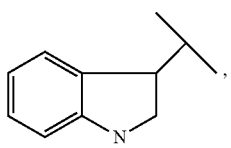

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include, but are not limited to, 5-aza-6-indanyl,

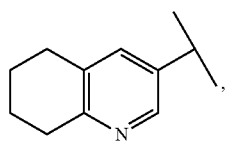

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include, but are not limited to, 5-aza-1-indanyl,

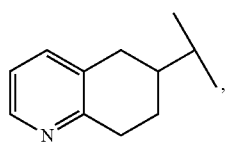

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include, but are not limited to, 1,2,3,4-tetrahydro-beta-carbolin-8-yl,

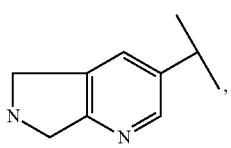

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include, but are not limited to, −5-aza-2,3-dihydrobenzofuran-2-yl,

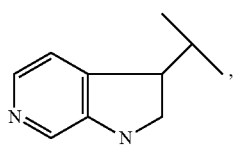

and the like.

As used herein, the term "direct bond", where part of a structural variable specification, refers to the direct joining of the substituents flanking (preceding and succeeding) the variable taken as a "direct bond".

As used herein, the term "O-linked moiety" means a moiety that is bonded through an oxygen atom. Thus, when an R group is an O-linked moiety, that R is bonded through oxygen and it thus can be an ether, an ester (e.g., —O—C(O)-optionally substituted alkyl), a carbonate or a carbamate (e.g., —O—C(O)—NH$_2$ or —O—C(O)—NH-optionally substituted alkyl) Similarly, the term "S-linked moiety" means a moiety that is bonded through a sulfur atom. Thus, when an R group is an S-linked moiety, that R is bonded through sulfur and it thus can be a thioether (e.g., —S-optionally substituted alkyl), a thioester (—S—C(O)-optionally substituted alkyl) or a disulfide (e.g., —S—S-optionally substituted alkyl). The term "N-linked moiety" means a moiety that is bonded through a nitrogen atom. Thus, when an R group is an N-linked moiety, the R group is bonded through nitrogen and one or more of these can thus be an N-linked amino acid such as —NH—CH$_2$—COOH, a carbamate such as —NH—C(O)—O-optionally substituted alkyl, an amine such as —NH-optionally substituted alkyl, an amide such as —NH—C(O)-optionally substituted alkyl or —N$_3$. The term "C-linked moiety" means a moiety that is bonded through a carbon atom. When one or more R group is bonded through carbon, one or more of these thus can be -optionally substituted alkyl such as —CH$_2$—CH$_2$—O—CH$_3$, —C(O)-optionally substituted alkyl hydroxyalkyl, mercaptoalkyl, aminoalkyl or =CH-optionally substituted alkyl.

The term "alkoxy" as used herein refers to the group $R_a$O—, where $R_a$ is alkyl.

The term "alkenyloxy" as used herein refers to the group $R_a$O—, where $R_a$ is alkenyl.

The term "alkynyloxy" as used herein refers to the group $R_a$O—, where $R_a$ is alkynyl.

The term "alkylsulfanyl" as used herein refers to the group $R_a$S—, where $R_a$ is alkyl.

The term "alkenylsulfanyl" as used herein refers to the group $R_a$S—, where $R_a$ is alkenyl.

The term "alkynylsulfanyl" as used herein refers to the group $R_a$S—, where $R_a$ is alkynyl.

The term "alkylsulfenyl" as used herein refers to the group $R_a$S(O)—, where $R_a$ is alkyl.

The term "alkenylsulfenyl" as used herein refers to the group $R_a$S(O)—, where $R_a$ is alkenyl.

The term "alkynylsulfenyl" as used herein refers to the group $R_a$S(O)—, where $R_a$ is alkynyl.

The term "alkylsulfonyl" as used herein refers to the group $R_a$SO$_2$—, where $R_a$ is alkyl.

The term "alkenylsulfonyl" as used herein refers to the group $R_a$SO$_2$—, where $R_a$ is alkenyl.

The term "alkynylsulfonyl" as used herein refers to the group $R_a$SO$_2$—, where $R_a$ is alkynyl.

The term "acyl" as used herein refers to the group $R_a$C(O)—, where $R_a$ is alkyl, alkenyl, alkynyl, cycloalkyl, cycloalkenyl, aryl, heteroaryl, or heterocyclyl.

The term "aroyl" as used herein refers to the group $R_aC(O)$—, where $R_a$ is aryl.

The term "heteroaroyl" as used herein refers to the group $R_aC(O)$—, where $R_a$ is heteroaryl.

The term "heterocycloyl" as used herein refers to the group $R_aC(O)$—, where $R_a$ is heterocyclyl.

The term "alkoxycarbonyl" as used herein refers to the group $R_aOC(O)$—, where $R_a$ is alkyl.

The term "acyloxy" as used herein refers to the group $R_aC(O)O$—, where $R_a$ is alkyl, alkenyl, alkynyl, cycloalkyl, cycloalkenyl, aryl, heteroaryl, or heterocyclyl.

The term "aroyloxy" as used herein refers to the group $R_aC(O)O$—, where $R_a$ is aryl.

The term "heteroaroyloxy" as used herein refers to the group $R_aC(O)O$—, where $R_a$ is heteroaryl.

The term "heterocycloyloxy" as used herein refers to the group $R_aC(O)O$—, where $R_a$ is heterocyclyl.

The term "substituted" as used herein refers to substitution with the named substituent or substituents, multiple degrees of substitution being allowed unless otherwise stated.

The terms "contain" or "containing" can as used herein refers to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$, —$CH_2$—NH—$CH_3$ and so forth.

The term "oxo" as used herein refers to the substituent =O.

The term "halogen" or "halo" as used herein includes iodine, bromine, chlorine and fluorine.

The term "mercapto" as used herein refers to the substituent —SH.

The term "carboxy" as used herein refers to the substituent —COOH.

The term "cyano" as used herein refers to the substituent —CN.

The term "aminosulfonyl" as used herein refers to the substituent —$SO_2NH_2$.

The term "carbamoyl" as used herein refers to the substituent —$C(O)NH_2$.

The term "sulfanyl" as used herein refers to the substituent —S—.

The term "sulfenyl" as used herein refers to the substituent —S(O)—.

The term "sulfonyl" as used herein refers to the substituent —$S(O)_2$—.

The term "ethoxy" as used herein refers to the substituent —O—$CH_2CH_3$.

The term "methoxy" as used herein refers to the substituent —O—$CH_3$.

As used herein, the term "optionally" means that the subsequently described event(s) may or may not occur, and includes both event(s) which occur and events that do not occur.

Compounds of structural formula I and formulas Ia-f may contain one or more asymmetric centers and can thus occur as racemates and racemic mixtures, single enantiomers, diastereomeric mixtures and individual diastereomers. The present invention is meant to comprehend all such isomeric forms of the compounds of structural formula I and formulas Ia-f.

Compounds of structural formula I and formulas Ia-f may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I and formulas Ia-f may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of generic Formula I and formulas Ia-f, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I and formulas Ia-g. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I and formulas Ia-f can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I and formulas Ia-f are meant to also include the pharmaceutically acceptable salts, and also salts that are not pharmaceutically acceptable when they are used as precursors to the free compounds or their pharmaceutically acceptable salts or in other synthetic manipulations.

Compositions

According to another aspect, the described invention provides pharmaceutical compositions comprising at least one of the small molecule anti-cancer compounds and a pharmaceutically acceptable carrier.

The term "active" as used herein refers to having pharmacological or biological activity or affect. The term "active ingredient" ("AI", "active pharmaceutical ingredient", or "bulk active") is the substance in a drug that is pharmaceutically active.

The terms "formulation" and "composition" are used interchangeably herein to refer to a product of the described invention that comprises all active and inert ingredients. The terms "pharmaceutical formulation" or "pharmaceutical composition" as used herein refer to a formulation or composition that is employed to prevent, reduce in intensity, cure or otherwise treat a target condition or disease.

As used herein, the term "binder" refers to substances that bind or "glue" powders together and make them cohesive by forming granules, thus serving as the "adhesive" in the formulation. Binders add cohesive strength already available in the diluent or bulking agent. Exemplary binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulo se; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

As used herein, the term "bioavailability" refers to the rate and extent to which the active drug ingredient or therapeutic moiety is absorbed into the systemic circulation from an administered dosage form as compared to a standard or control.

As used herein, the term "capsule" refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

As used herein, the term "coloring agents" refers to excipients that provide coloration to the composition or the dosage form. Such excipients can include food grade dyes and food grade dyes adsorbed onto a Exemplary adsorbent such as clay or aluminum oxide. The amount of the coloring agent can vary from about 0.1 to about 5% by weight of the composition, preferably from about 0.1 to about 1%.

As used herein, the term "diluent" refers to substances that usually make up the major portion of the composition or dosage form. Exemplary diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

As used herein, the term "disintegrant" refers to materials added to the composition to help it break apart (disintegrate) and release the medicaments. Exemplary disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

As used herein, the term "glident" refers to material that prevents caking and improves the flow characteristics of granulations, so that flow is smooth and uniform. Exemplary glidents include silicon dioxide and talc. The amount of glident in the composition can range from about 0.1% to about 5% by weight of the total composition, preferably from about 0.5 to about 2% by weight.

As used herein, the term "lubricant" refers to a substance added to the dosage form to enable the tablet, granules, etc. after it has been compressed, to release from the mold or die by reducing friction or wear. Exemplary lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

As used herein, the term "oral gel" refers to the active ingredients dispersed or solubilized in a hydrophillic semi-solid matrix.

As used herein, the term "tablet" refers to a compressed or molded solid dosage form containing the active ingredients with suitable diluents. The tablet can be prepared by compression of mixtures or granulations obtained by wet granulation, dry granulation or by compaction.

As used herein, the term "therapeutic amount" refers to the amount of a small molecule anti-cancer compound necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. The effective amount for any particular application may vary depending on such factors as the disease or condition being treated, the particular described compound, the size of the subject, or the severity of the disease or condition. One of ordinary skill in the art may determine empirically the therapeutically effective amount of a particular described compound and/or other therapeutic agent without necessitating undue experimentation. It is generally preferred that a maximum dose be used, that is, the highest safe dose according to some medical judgment. The terms "dose" and "dosage" are used interchangeably herein.

For any compound described herein the therapeutically effective amount can be initially determined from preliminary in vitro studies and/or animal models. A therapeutically effective dose can also be determined from human data for compounds of general structure I and structures Ia-f. The applied dose can be adjusted based on the relative bioavailability and potency of the administered compound. Adjusting the dose to achieve maximal efficacy based on the methods described above and other methods as are well-known in the art is within the capabilities of the ordinarily skilled artisan.

The formulations of inhibitors may be administered in pharmaceutically acceptable solutions, which may routinely contain pharmaceutically acceptable concentrations of salt, buffering agents, preservatives, compatible carriers, adjuvants, and optionally other therapeutic agents.

According to another embodiment, the compositions of the described invention can further include one or more additional compatible active ingredients. "Compatible" as used herein means that the components of such a composition are capable of being combined with each other in a manner such that there is no interaction that would substantially reduce the efficacy of the composition under ordinary use conditions. As used herein, the phrase "additional active ingredient" refers to an agent, other than the anti-cancer compounds of the described composition, that exerts a pharmacological, or any other beneficial activity. No limiting examples of such additional therapeutic agents include, without limitation, 5-fluorouracil, leucovorin, oxaliplatin capecitabine, leucovorin, irinotecan, capecitabine, oxaliplatin, bevacizumab, cetuximab, panitumumab, or a combination thereof.

Pharmaceutically Acceptable Carrier

The term "pharmaceutically-acceptable carrier" as used herein refers to one or more compatible solid or liquid filler, diluents or encapsulating substances which are exemplary for administration to a human or other vertebrate animal. The term "carrier" as used herein refers to an organic or inorganic ingredient, natural or synthetic, with which the active ingredient is combined to facilitate the application. According to some embodiments, the carrier can be inert, or it can possess pharmaceutical benefits.

The components of the pharmaceutical compositions also are capable of being commingled in a manner such that there is no interaction which would substantially impair the desired pharmaceutical efficiency.

The carrier can be liquid or solid and is selected with the planned manner of administration in mind to provide for the desired bulk, consistency, etc., when combined with an active and the other components of a given composition.

Administration

For use in therapy, a therapeutic amount of a small molecule anti-cancer compound may be administered to a subject by any mode. Administering the pharmaceutical composition may be accomplished by any means known to the skilled artisan. Routes of administration include, but are not limited to, parenteral oral, buccal, topical, by inhalation or insufflation (i.e., through the mouth or through the nose), or rectal.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord), intrasternal injection, or infusion techniques. A parenterally administered composition of the present invention is delivered using a needle, e.g., a surgical needle. The term "surgical needle" as used herein, refers to any needle adapted for delivery of fluid (i.e., capable of flow) compositions of the present invention into a selected anatomical structure. Injectable preparations, such as sterile injectable aqueous or oleaginous suspensions, may be formulated according to the known art using exemplary dispersing or wetting agents and suspending agents.

The compositions of the present invention may be in the form of a sterile injectable aqueous solution or oleaginous suspension. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion in which a finely-divided species is combined with another species, with the former being so finely divided and mixed that it doesn't rapidly settle out. The term "dispersion", as used herein, refers to a two-phase system, in which one phase is distributed as particles or droplets in the second, or continuous phase. In these systems, the dispersed phase frequently is referred to as the discontinuous or internal phase, and the continuous phase is called the external phase or dispersion medium. For example, in coarse dispersions, the particle size is 0.5 mm. In colloidal dispersions, size of the dispersed particle is in the range of approximately 1 nm to 0.5 mm. Molecular dispersion is a dispersion, in which the dispersed phase consists of individual molecules; if the molecules are less than colloidal size, the result is a true solution.

The compositions of the described invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or *arachis* oil, or a mineral oil, for example a liquid paraffin, or a mixture thereof. Exemplary emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate.

According to some embodiments, the composition may be formulated for parenteral administration by by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Exemplary lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension also may contain exemplary stabilizers or agents, which increase the solubility of the compounds to allow for the preparation of highly concentrated solutions. Alternatively, the active compounds may be in powder form for constitution with an exemplary vehicle, e.g., sterile pyrogen-free water, before use.

The pharmaceutical compositions also may comprise exemplary solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Exemplary liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are exemplary for use in a variety of drug delivery systems. For a brief review of methods for drug delivery, see Langer 1990 Science 249, 1527-1533, which is incorporated herein by reference.

Depending upon the structure, at least one small molecule anti-cancer compound of the described invention, and optionally at least one additional active agent, may be administered per se (neat) or, depending upon the structure of the inhibitor, in the form of a pharmaceutically acceptable salt. The inhibitors of the described invention may form pharmaceutically acceptable salts with organic or inorganic acids, or organic or inorganic bases. When used in medicine the salts should be pharmaceutically acceptable, but non-pharmaceutically acceptable salts conveniently may be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group.

By "pharmaceutically acceptable salt" is meant those salts which are, within the scope of sound medical judgment, exemplary for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002).

The salts may be prepared in situ during the final isolation and purification of the compounds described within the described invention or separately by reacting a free base function with a exemplary organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides, such as methyl, ethyl, propyl, and butyl chlorides, bromides and iodides; dialkyl sulfates like dimethyl, diethyl, dibutyl and diamyl sulfates; long chain halides, such as decyl, lauryl, myristyl and stearyl chlorides, bromides and iodides; arylalkyl halides, such as benzyl and phenethyl bromides, and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with an exemplary base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts may be also obtained using standard procedures well known in the art, for example by reacting a sufficiently basic compound such as an amine with an exemplary acid affording a physiologically acceptable anion. Alkali metal (for example, sodium, potassium or lithium) or alkaline earth metal (for example calcium or magnesium) salts of carboxylic acids may also be made.

The formulations may be presented conveniently in unit dosage form and may be prepared by any of the methods well known in the art of pharmacy. All methods include the step of bringing into association a composition, or a pharmaceutically acceptable salt or solvate thereof ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The pharmaceutical agent or a pharmaceutically acceptable ester, salt, solvate or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of exemplary aqueous and nonaqueous carriers, diluents, solvents or vehicles include water, ethanol, polyols (propylene glycol, polyethylene glycol, glycerol, and the like), exemplary mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

The therapeutic agent(s), including the composition(s) of the described invention may be provided in particles. The term "particles" as used herein refers to nano or microparticles (or in some instances larger) that may contain in whole or in part the composition or the other therapeutic agent(s) as described herein. The particles may contain the therapeutic agent(s) in a core surrounded by a coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the composition in a solution or in a semi-solid state. The particles may be of virtually any shape.

Both non-biodegradable and biodegradable polymeric materials may be used in the manufacture of particles for delivering the therapeutic agent(s). Such polymers may be natural or synthetic polymers. The polymer is selected based on the period of time over which release is desired. For example, bioadhesive polymers include bioerodible hydrogels as described by Sawhney et al in Macromolecules (1993) 26, 581-587, the teachings of which are incorporated herein by reference. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. The term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that can result in substantially constant blood levels of a drug over an extended time period. Alternatively, delayed absorption of a parenterally administered drug form is accomplished by dissolving or suspending the drug in an oil vehicle. The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

According to some embodiments, use of a long-term sustained release implant may be desirable for treatment of chronic conditions. The term "long-term" release, as used herein, means that the implant is constructed and arranged to deliver therapeutic levels of the active ingredient for at least 7 days, and preferably about 30 to about 60 days. Long-term sustained release implants are well-known to those of ordinary skill in the art and include some of the release systems described above.

Injectable depot forms are made by forming microencapsulated matrices of a described inhibitor in biodegradable polymers such as polylactide-polyglycolide. Depending upon the ratio of inhibitor to polymer and the nature of the particular polymer employed, the rate of drug release may be controlled. Such long acting formulations may be formulated with appropriate polymeric or hydrophobic materials (for example as an emulsion in an acceptable oil) or ion exchange resins, or as sparingly soluble derivatives, for example, as a sparingly soluble salt. Examples of other biodegradable polymers include poly(orthoesters) and poly(anhydrides). Depot injectable formulations also are prepared by entrapping the inhibitor of the described invention in liposomes or microemulsions, which are compatible with body tissues.

The injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Exemplary buffering agents include: acetic acid and a salt (1-2% w/v); citric acid and a salt (1-3% w/v); boric acid and a salt (0.5-2.5% w/v); and phosphoric acid and a salt (0.8-2% w/v). Exemplary preservatives include benzalkonium chloride (0.003-0.03% w/v); chlorobutanol (0.3-0.9% w/v); parabens (0.01-0.25% w/v) and thimerosal (0.004-0.02% w/v).

For oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, uitable binders, lubricants, disintegrating agents and coloring agents also may be incorporated in the mixture. Powders and tablets may be comprised of from about 5 to about 95 percent of the described composition. Exemplary binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

The compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

For buccal administration, the compositions of the present invention may take the form of tablets or lozenges formulated in a conventional manner for this route.

Liquid form preparations include solutions, suspensions and emulsions.

Liquid form preparations also may include solutions for intranasal administration.

The compositions of the present invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the present invention is placed within an exemplary dosage receptacle in an amount sufficient to provide a subject with a unit dosage treatment. The dosage receptacle is one that fits within an exemplary inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. Nos. 4,227,522; 4,192,309; and 4,105,027. Exemplary containers also include those used in conjunction with Glaxo's Ventolin® Rotohaler brand powder inhaler or Fison's Spinhaler® brand powder inhaler. Another exemplary unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). Each of these references is incorporated herein by reference.

The compositions of the present invention may be in the form of suppositories for rectal administration of the composition. "Rectal" or "rectally" as used herein refers to introduction into the body through the rectum where absorption occurs through the walls of the rectum. These compositions can be prepared by mixing the drug with an exemplary nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

The term "topical" refers to administration of an inventive composition at, or immediately beneath, the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably. For the purpose of this application, topical applications shall include mouthwashes and gargles.

Topical administration may also involve the use of transdermal administration such as transdermal patches or iontophoresis devices which are prepared according to techniques and procedures well known in the art. The terms "transdermal delivery system", transdermal patch" or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for postmenopausal indications, and nicotine for smoking cessation.

Exemplary patches for use in the present invention include, but are not limited to, (1) the matrix patch; (2) the reservoir patch; (3) the multi-laminate drug-in-adhesive patch; and (4) the monolithic drug-in-adhesive patch; TRANSDERMAL AND TOPICAL DRUG DELIVERY SYSTEMS, pp. 249-297 (Tapash K. Ghosh et al. eds., 1997), hereby incorporated herein by reference. These patches are well known in the art and generally available commercially.

Unless defined otherwise, all technical and scientific terms used herein have the same meaning as commonly understood by one of ordinary skill in the art to which this invention belongs. Although any methods and materials similar or equivalent to those described herein also can be used in the practice or testing of the described invention, the preferred methods and materials are now described. All publications mentioned herein are incorporated herein by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, parts are by weight, molecular weight is weight average molecular weight, temperature is in degrees Centigrade, and pressure is at or near atmospheric.

Example 1

Immortalized human colonic epithelial cell (HCEC) lines have been generated using exogenously introduced telomerase and cdk4 (Fearon, E. R. & Vogelstein, B. A genetic model for colorectal tumorigenesis. *Cell* 61, 759-767 (1990).). These cells are non-transformed, karyotypically diploid and have multipotent characteristics. When placed in Matrigel® in the absence of a mesenchymal feeder layer, individual cells divide and form self-organizing, crypt-like structures with a subset of cells exhibiting markers associated with mature epithelium.

Colonic Tissues

This study was approved by the institutional review board at the Dallas VA Medical center. Colon biopsies (20-30 samples, ~0.5 $cm^3$) from tissue not involved with endoscopically visible adenomas were obtained from patients undergoing routine screening colonoscopy after obtaining informed consent.

Growth Media and Tissue Culture Substrate

Cells were grown on basal DMEM, MEM or RPMI media (Gibco®, Hyclone, Logan, Utah) supplemented with EGF (25 ng/mL) (Peprotech, Inc, Rocky Hill, N.J.), hydrocortisone (1 µg/mL), insulin (10 µg/mL), transferrin (2 µg/mL), sodium selenite (5 nanomolar) (all from Sigma, St Louis, Mo.), 2% cosmic calf serum (Hyclone), and gentamicin sulfate (50 µg/ml) (Gemini Bio-Products, West Sacramento, Calif.). Cells were cultured in primaria flasks (BD Biosciences, San Jose, Calif.) and grown in 2%-5% oxygen and 7% carbon dioxide. HCT 116, BJ human skin fibroblasts, Hela cells, and immortalized human colonic fibroblast cells (C26Ci, population doubling 150) were maintained in DMEM, MEM or RPMI media (Gibco®, Hyclone, Logan, Utah) supplemented with 10% cosmic calf serum (Hyclone). C26Ci cells were treated with 10 µg/mL mitomycin c (Sigma) for 2 hours and used as feeder layers from the point of initial crypt attachment until the first passage.

For cleaved PARP detection and caspase 3 activity assay, cells were treated with 2.5 uM of TASIN-1 for 72 hours in the presence or absence of 12.5 uM of SP600125 (Millipore) or 5 uM of doxorubicin (Sigma) alone for 6 hours as positive controls. For mitotic synchronization, cells were synchronized at the G2/M boundary by treatment with the selective cdk1 small-molecule inhibitor, RO-3306 (9 uM) for 18 hours (Kim, Hyun S. et al. Systematic Identification of Molecular Subtype-Selective Vulnerabilities in Non-Small-Cell Lung cancer. *Cell* 155, 552-566 (2013).

Plasmids

CDK4, hTERT, pSRZ-shTP53 and pBABE-hyg-KRASV12 were described in Vassilev, L. T. and is hereby incorporated by reference (Vassilev, L. T. Cell cycle synchronization at the G2/M phase border by reversible inhibition of CDK1. *Cell cycle* 5, 2555-2556 (2006)).

Cell Isolation and Immortalization

Colonic biopsies were immersed in cold DMEM, MEM or RPMI media (Gibco®, Hyclone, Logan, Utah), brought to the laboratory within 40-60 minutes after colonoscopy, copiously washed with phosphate-buffered saline containing antibiotic/antimycotic solution (Gemini Bio-Products), and cut into multiple small pieces (~1 mm in size). After enzymatic digestion with collagenase 150 u/mL (Worthington Biochemical, Lakewood, N.J.) and dispase 40 µg/ml (Roche, Germany), crypts were resuspended in DMEM, MEM or RPMI media (Gibco®, Hyclone, Logan, Utah) with growth supplements including 2% serum, and plated in primaria culture dishes seeded 48 hours previously with 50% confluent colonic fibroblast feeder layers. During the first 10 days after attachment, cells were fed every 3 days, reducing the serum by 1% each change until 0% to prevent growth of unwanted cells such as fibroblasts. Once small nests of expanding epithelial cells were easily observed, cells were transduced with retroviral CDK4 and hTERT as described previously. When numerous cuboidal-appearing cell nests were observed (3-4 weeks after initial crypt seeding), cells were reseeded on primaria flasks. Feeder layers were not needed or used for routine tissue culture after the first passage.

APC Knockdown Experiments

HCECs isolated from normal colonic biopsies were immortalized by successive infections of CDK4 and hTERT followed by selection with respective antibiotics—G418 (250 µg/mL) and blastocidin (2.5 µg/mL). shRNAs against p53 were introduced with retroviruses and p53 knockdown efficiency was verified by Western analysis. Human colon cancer cell lines (HCT116, DLD-1, RKO) and virus-producing cell lines (293FT, Phoenix A) were cultured in basal medium supplemented with 10% serum. The identity of all cell lines was verified by DNA fingerprinting. 1 µg of shRNA together with 1 µg of helper plasmids (0.4 µg pMD2G and 0.6 µg psPAX2) were transfected into 293FT cells with Polyjet reagent (SignaGen). Viral supernatants were collected 48 hours after transfection and cleared through a 0.45-µm filter. Cells were infected with viral supernatants containing 4 µg/mL polybrene (Sigma) at a multiplicity of infection (MOI) of approximately 1. Successfully infected cells were selected with 1 ug/mL puromycin for 3 days. as described in: Eskiocak U, Kim S B, Ly P, Roig A I, Biglione S, Komurov K, Cornelius C, Wright W E, White M A, Shay J W. Functional parsing of driver mutations in the colorectal cancer genome reveals numerous suppressors of anchorage-independent growth. Cancer Res 2011; 71:4359-65, which is incorporated herein by reference.

Western Blot Analysis

After electrophoresis through 10% SDS-PAGE, separated proteins were transported onto a nitrocellulose (NC) membrane (Pierce, Rockford, USA). The membrane was incubated with primary antibody against poly(ADP-ribose) polymerase (PARP) (Millipore, Cell Signaling Technology, Santa Cruz, etc.), cytochrome C (Abcam, Cell Signaling Technology, Santa Cruz, etc.), voltage-dependent anion-selectivve channel protein −1 (VDAC) (Cell Signaling Technology, Abcam, Santa Cruz, etc.), phospho-JNK (Cell Signaling), JNK (Cell Signaling), or actin (Abcam, Santa Cruz, Cell Signaling, etc.) overnight at 4° C. After washing, the membrane was incubated with each corresponding secondary antibody before being visualized by chemiluminescence. Mouse monoclonal GAPDH (Promab, USA, 1:1000) was used as the primary antibody for control.

Caspase 3/7 Activity

Cells were treated with vehicle control or 2.5 uM of TASin-1 for 72 hours and subjected to Caspase-Glo 3/7 assay in 96-well plates (Promega). Specifically, 96-well places containing cells were removed from an incubator and equilibrated to room temperature. A reconstituted Caspase-Glo Reagent was also equilibrated to room temperature. A volume of Caspase-Glo reagent equal to the volume of cell culture medium was added to each well. The mixture was gently mixed using a plate shaker at 300-500 rpm for 30 seconds and then incubated at room temperature for 30 minutes to 3 hours. The plate was inserted into the Veritas to begin the assay. The RLU values were measured by the Veritas™. (Promega; A Veritas Microplate Luminometer Method for Prometa's caspase-Glo™ 3/7 assay).

Immunocytochemistry

Cells were fixed using 3.7% paraformaldehyde for 10 min, permeabilized with 0.5% Triton X-100 in PBS for 5 min and incubated with blocking solution (10% goat serum and 3% BSA in PBS containing 0.1% Triton X-100) for 60 min. Cells were then incubated with primary antibodies diluted in blocking solution for an hour. The following antibodies are used: anti-HURP (Santa Cruz Biotechnology), anti-α-tubulin (Cell Signaling), anti-active β-catenin (EMD Millipore). After incubation using secondary antibodies labeled with Alexa-568 or Alexa-488 (Invitrogen), slides were mounted with Mowiol 4-88(Calbiochem) solution (Eskiocak, U. et al. Functional parsing of driver mutations in the colorectal cancer genome reveals numerous suppressors of anchorage-independent growth. Cancer Res 71, 4359-4365 (2011)). Cells were observed under a fluorescence microscope, Axiovert 200M (Carl Zeiss). Nuclei were counterstained with DAPI (Vectashield, Vector Laboratories). Metaphase plate width, spindle width and cell width was determined using the line measurement tool in ImageJ software.

SuperTopFlash Assay

DLD1 cells were transiently transfected with DNA constructs encoding firefly luciferase (FL) and Gaussia luciferase (GL) proteins driven by a CMV promoter, incubated with DMSO or TASIN-1 for 18 h and then analyzed for GL and FL activities, respectively, 24 h later. (Longin, A., Souchier, C., Ffrench, M. & Bryon, P. A. Comparison of anti-fading agents used in fluorescence microscopy: image analysis and laser confocal microscopy study. *J Histochem Cytochem* 41, 1833-1840 (1993).)

Quantitative Reverse Transcription-PCR (qRT-PCR)

Total RNA was isolated from mouse tissue using RNeasy Plus Universal Mini kit (Qiagen) according to the manufacturer's protocol. Then 1 µg was converted to cDNA using a First Strand cDNA Synthesis Kit (Roche). Real-time quantitative PCR reactions were set up in triplicate with Ssofast Master Mix (Biorad) and run on a LightCycler® 480 (Roche). Restriction fragment length polymorphism (RFLP) analysis for detection of mutant Kras was performed by Sato et al., and is hereby incorporated by reference (Sato, M. et al. Multiple oncogenic changes (K-RAS(V12), p53 knockdown, mutant EGFRs, p16 bypass, telomerase) are not sufficient to confer a full malignant phenotype on human bronchial epithelial cells. *Cancer Res* 66, 2116-2128 (2006)). All the primers (Sigma) used in this study are listed in Data Table 3.

DATA TABLE 3 qPCR primer sets for inflammatory genes

| Genes | Forward primer (5'-3') | Reverse primer (5'-3') | SEQ ID NOs: |
|---|---|---|---|
| Il1rn | TTGTGCCAAGTCTGGAGATGTTCTCAGAGCGGAT GAAGGT | | 1, 2 |

DATA TABLE 3 -continued qPCR primer sets for inflammatory genes

| Genes | Forward primer (5'-3') | Reverse primer (5'-3') | SEQ ID NOs: |
|---|---|---|---|
| Lpo | TGACCTTGCTCCAGACTGC | TTGACCCAGACCTT GACCTC | 3, 4 |
| Opg | ATGAACAAGTGGCTGTGCTGTCACACAGGAGCTG | ATGACC | 5, 6 |
| Slc7a11 | TCTGGTCTGCCTGTGGAGTACAAAGGACCAAAGA | CCTCCA | 7, 8 |
| Sox4 | AATTGCACCAACTCCTCAGCTCGATTGCAGTTCA | CGAGAG | 9, 10 |
| Sox17 | TGAAATATGGCCCACTCACACTGTCTTCCCTGTC | TTGGTTG | 11, 12 |
| Tlr1 | GGACCTACCCTTGCAAACAATATCAGGACCCTCA | GCTTGG | 13, 14 |
| Tlr2 | GAGCATCCGAATTGCATCA | ACAGCGTTTGCTGA AGAGGA | 15, 16 |
| Tnfrsf1b | GTCTTCGAACTGCAGCTGTGTACCCAGGTTCCGG | TTTGTA | 17, 18 |
| Tnfrsf8 | GAGACTCGGGAAGCCAAGATGGTGGTCTTGAGTG | GTCGAT | 19, 20 |
| Troy | CGCTGCCATTCTCTTCCTACTCGATCCTTGAATT | CCTGCT | 21, 22 |

DATA TABLE 2 shRNA sequence against APC.

| shRNA | Mature sense sequence | Mature anti-sense sequence | SEQ ID NOs: |
|---|---|---|---|
| APC (B7) | TAATGAACACTACAGATAGAA | TTCTATCTGTAGTGTT CATTA | 23, 24 |
| APC (G3) | CCCAGTTTGTTTCTCAAGAAA | TTTCTTGAGAAACAAA CTGGG | 25, 26 |

In Vivo Pharmacokinetic Analysis

Female CD-1 mice were injected IP with 10 mg/kg TASIN-1, 0.2 mL/mouse formulated as 5% DMSO, 5% cremophor EL, and 90% $D_5W$ pH 7.4. Whole blood was harvested. Plasma was processed from whole blood by centrifugation of the ACD treated blood for 10 minutes at 10,000 rpm in a standard centrifuge. Large intestines with contents were harvested and large intestine contents were removed for further analysis. All harvested tissues were weighted and snap frozen in liquid nitrogen. Large intestinal contents (LIC) homogenate was prepared by mincing the intestinal contents and homogenizing in a 4-fold volume of PBS. 100 microliters LIC was mixed with 200 microliters of acetonitrile containing 0.15% formic acid and 37.5 ng/mL IS (IS final conc.=25 ng/ml). The samples were vortexed for 15 seconds, incubated at room temperature for 10 minutes and spun 2×13,200 rpm in a standard microcentrifuge. The supernatant was then analyzed by LC/MS/MS. Non-treated mice were used to collect tissue for blank homogenates in order to make standards and QCs.

Tissue Staining

Hematoxylin & Eosin Staining Protocol for Parrafin Sections

Prior to staining, slides were baked for at least twenty minutes at a minimum temperature of 70° C. to inhibit detachment of sections during the staining procedure. Sections were stained in Weigert's Hematoxylin, working solution, for 6 minutes, and drained. Slides were dehydrated in 70% Acid-Ethanol, pH 2.5, using two changes, three quick dips each. Slides were dehydrated in 70% Acid-DI, pH 2.5, using two changes, three quick dips each. The slides were washed in running tap water for 15 minutes and excess water was drained from the slides, and then stained in working Eosin-Phloxine solution for 2 minutes and drained. The slides were dehydrated in 95% ethanol, using two changes, at 30 seconds each, completely dehydrated in 100% ethanol, using three changes, three quick dips each, and cleared in Histoclear (National Diagnosics; AGTC Bioproducts, etc.), using two changes, at one minute each. Fresh Histoclear was used and the slides were coverslipped with mounting medium.

Hematoxylin & Eosin Staining Protocol for Frozen Tissue Sections

The sections were mounted on slides and air dried to remove moisture, stained with filtered 0.1% Mayers Hematoxylin (Sigma; MHS-16) for 10 minutes, and rinsed in cool running $ddH_2O$ for 5 minutes. The slides were dipped in 0.5% Eosin (1.5 g dissolved in 300 mL of 95% EtOH) 12 times, and then in distilled $H_2O$ until the eosin no longer streaked, dipped in 50% EtOH 10 times, then dipped in 70% EtOH 10 times, equilibrated in 95% EtOH for 30 seconds, equilibrated in 100% EtOH for 1 minute, dipped in xylene several times and then were cleaned off with a kimwipe and mounted with a coverslip using Cytoseal XYL (Stephens Scientific; cat#8312-4).

Standard Immunohistochemistry Staining Method: Avidin Biotin Complex (ABC) Method Slides containing deparaffinized or frozen sections were rinsed in PBS-Tween 20 for 2×2 min. Sections were incubated in normal serum of the same species as the secondary antibody. Sections were incubated in primary antibody, anti-caspase 3 (Millipore No. AB3623; Sigma-Aldrich No. C8487; etc.), at 1:100 in IHC-Tek™ Antibody Diluent (Cat# IW-1000 or IW-1001) or anti-cleaved caspase 3 (Cell signaling) for 1 hour at room temperature or overnight, and rinsed in PBS-Tween 20 for 3×2 min. The sections were incubated in peroxidase blocking solution for 10 minutes at room temperature, rinsed in PBS-Tween 20 for 3×2 min, and then incubated in Biotinylated secondary antibody in PBS for 30 minutes at room temperature. The sections were rinsed in PBS-Tween 20 for 3×2 min, and then incubated in ABC-Peroxidase Solution for 30 minutes at room temperature. The sections were rinsed in PBS-Tween 20 for 3×2 min, and then incubated in peroxidase substrate solution. The sections were rinsed in PBS-Tween 20 for 3×2 min, counterstained with counterstain solution, rinsed in running tap water for 2-5 minutes, dehydrated through 95% ethanol for 1 minute, 100% ethanol for 2×3 min, cleared in xylene for 2×5 min and coverslipped with mounting medium. Negative control slides were processed in the absence of the primary antibody. (Ren, Y. et al. Small molecule Wnt inhibitors enhance the efficiency of BMP-4-directed cardiac differentiation of human pluripotent stem cells. *Journal of molecular and cellular cardiology* 51, 280-287 (2011); Scholl, F. A. et al. Mek 1/2 MAPK kinases are essential for Mammalian development, homeostasis, and Raf-induced hyperplasia. Developmental cell 12, 615-629 (2007)).

Soft Agar Colony Formation Assay

DLD1 or HCT116 cells were plated in double-layer agar cultures in 35-mm dishes. The alpha modification of Eagle's minimal essential medium (Flow Laboratories, Invitrogen, Sigma-Aldrich, etc.) supplemented with 20% fetal calf serum (Sigma-Aldrich, Invitrogen, etc.) was used for all cultures. Growth factors and/or conditioned media were incorporated in the underlay at a maximum of 13.2% of the total culture volume of 1.5 mL per dish. Cultures were gassed with a 5% $O_2$-10% $CO_2$-85% $N_2$ mixture and incubated for 10 to 14 days. Only colonies containing 50 or more cells were scored.

Invasion Assays $10^5$ cells were serum-starved overnight, suspended in basal medium and plated onto 8.0-μm pore Matrigel® transwell (BD Biosciences). Five hundred microliters of medium containing 2% serum and growth supplements was added to the bottom well. Non-migratory cells were scraped off 24 hours later, and migratory cells were stained with 4',6-diamidino-2-phenylindole (DAPI). Experiments were performed in triplicate transwells for biological triplicates and quantified by averaging the number of stained cells per 4× field of view counting five fields per chamber.

Flow Cytometry

HCT116, DLD1, 1CTRPA and 1CTRPA A1309 cells were exposed to small molecule anti-cancer analogs PDSA-010, PDSA-011, PDSA-013 or PDSA-014 and analyzed by flow cytometry using a Beckman Coulter (Hialeah, Fla.) EPICS XL Flow Cytometer.

Cytochrome C Releasing Apoptosis Assay

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways.

The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. Loberg, R D, et al., J.

Biol. Chem. 277 (44): 41667-673 (2002). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon agregation and mitochondrial localization, induces cytochrome c release. Akt is a critical regulator of GSK-3, and phosphorylation and inactivation of GSK-3 may mediate some of the antiapoptotic effects of Akt.

Apoptosis was induced in cells as follows. Cells were collected ($5\times10^7$) by centrifugation at 600×g for 5 minutes at 4° C., washed with 10 ml of ice-cold PBS, centrifuged at 600×g for 5 minutes at 4° C. and the supernatant was removed. Cells were resuspended with 1.0 ml of 1× Cytosol Extraction Buffer Mix containing DTT and Protease Inhibitors and incubated on ice for 10 minutes. The cells were homogenized in an ice-cold Dounce tissue grinder on ice. The homogenate was transferred to a 1.5-ml microcentrifuge tube, and centrifuged at 700×g for 10 minutes at 4° C. Supernatant was collected into a fresh 1.5-ml tube, and centrifuged at 10,000×g for 30 minutes at 4° C. Supernatant was collected as a Cytosolic Fraction. The pellet was resuspended in 0.1-mL Mitochondrial Extraction Buffer Mix containing DTT and protease inhibitors, and vertexed for 10 seconds and saved as the Mitochondrial Fraction. 10 μg each of the cytosolic and mitochondrial fractions isolated from uninduced and induced cells were loaded on a 12% SDS-PAGE, and electrophoresed. A standard Western blot procedure was performed and the blot was probed with cytochrome c antibody (1 μg/mL). (BioVision; Cytochrome C Releasing Apoptosis Assay Kit; Catalog #K257-100)

Assay to Determine Absorption of TASIN-1

Samples from the content of the large intestine, plasma and large intestine were analyzed to determine retention of TASIN-1. Samples were taken at the following time points: 200, 400, 600, 800, 1000, 1200, 1400, and 1600 minutes. High-performance liquid chromatography (HPLC) was used to assess the presence of TASIN-1 in each of the samples.

Ethoxycoumarin (2 mM in DMSO) was incubated with Male ICR/CD-1 mouse hepatocytes (Lot HIC) and HI media for 0-240 minutes. Reactions were quenched with 0.2 mL (1:2) of methanol containing 0.2% formic acid and 100 ng/nl IS (IS final conc.=25 ng/ml). Samples were vortexed for 15 seconds, incubated at RT for 10 minutes, then spun in a table top, chilled centrifuge for 5 minutes at 13.2K rpm. Supernatant (185 μL) was transferred to an HPLA vial (with insert). The results were analyzed by a Qtrap 4000 mass spectrometer. The parameters for using the Qtrap 4000 were: Ethoxycoumarin+IS 050412.dam. The Ion Source/Gas parameters were as follows: CUR=45, CAD=low, IS=5500, TEM=600, GS1=60, and GS2=60. Buffer A was: water+0.1% formic acid; Buffer B was: MeOH+0.1% formic acid and the flow rate was 1.5 mL/min. The column that was used was the Agilent C18XDB column, 5 micron packing 50×4.6 mm size, 0-1.5 min 97% A, 1.5-2.0 minute gradient to 100% B, 2.0-3.0 minute 100% B, 3.0-3.3 minute gradient to 97% A, 3.3-4.5 minute gradient to 97% A; IS: n-benzylbenzamide (sigma-alderich, lot #02914LH, made Nov. 07, 2011 in MeOH, transition 212.1 to 91.1); compound transition 191.0 to 163.1.

Each of the compounds (2 mM in DMSO) was incubated with murine S9 (lot KWB) fraction and Phase I (NADPH Regenerating System) cofactors for 0-240 minutes. Reactions were quenched with 1 mL (1:1) methanol containing 0.2% formic acid and 100 ng/mL IS (IS final concentration=50 ng/mL). Samples were vortexed for 15 seconds, incubated at RT for 10 minutes and spun for 5 minutes at 2400 rpm. Supernatant (1 mL) was then transferred to an eppendorf tube and spun in a table top, chilled centrifuge for 5 minutes at 13.2K rpm. Supernatant (800 μL) was transferred to an HPLC vial (without insert). The results were analyzed by a Qtrap 4000 mass spectrometer. The parameters for using the Qtrap 4000 were: SW142282+IS053112.dam. The Ion Source/Gas parameters were as follows: CUR=45, CAD=low, IS=5500, TEM=600, GS1=60, GS2=60. Buffer A was: water+0.1% formic acid; Buffer B was: MeOH+0.1% formic acid and the flow rate was 1.5 mL/min. The column that was used was the Agilent C18XDB column, 5 micron packing 50×4.6 mm size, 0-1.5 min 97% A, 1.5-2.0 minute gradient to 100% B, 2.0-3.0 minute 100% B, 3.0-3.3 minute gradient to 97% A, 3.3-4.5 minute gradient to 97% A; IS: n-benzylbenzamide (sigma-alderich, lot #02914LH, made Nov. 07, 2011 in MeOH, transition 212.1 to 91.1); compound transition, e.g., 400.1 to 146.0, or, e.g. 354.2 to 171.0.

Animal Experiments

Subcutaneous (s.c.) xenografts were established in 5- to 6-week-old female nude mice (NCI) by inoculation of $2\times10^6$ CRC cells into both dorsal flanks of each mouse. When the tumors grew to 2 to 3 mm in diameter, the mice were injected i.p. with TASIN-1 at a dose of 40 mg/kg (dissolved in 0.2 mL solvent containing 10% DMSO, 10% cremophor) or solvent alone twice daily until the tumors grew to 15 mm in diameter in the control group. Tumor volumes were measured using calipers and calculated using formula $1\times w^2 \times 0.5$, where 1 and w represented the length and width of the tumor, respectively. The colorectal transgenic cancer mouse model, CDX2P-NLS Cre;APC$^{+/loxP}$ (CPC;Apc) mouse, was used (Kaplan, K. B. et al. A role for the Adenomatous Polyposis *Coli* protein in chromosome segregation. *Nature cell biology* 3, 429-432 (2001). Male CPC; Apc mice ~110 days old were injected i.p. with either solvent or 20 mg/kg/injection of TASIN-1 twice a week for 90 days. Weights were measured every 15 days over the treatment period.

In summary, female nude mice (NCI) with established xenografts were injected i.p. with TASIN-1 at a dose of 40 mg/kg (dissolved in 0.2 mL solvent containing 10% DMSO, 10% cremophor) or solvent alone twice daily. For the CPC; Apc mice experiments, mice were injected i.p. with either solvent or 20 mg/kg/injection of TASIN-1 twice a week for 90 days.

Tumor Development in Mice

Mice were injected with HCT116 cells, DLD1 or HT-29 cells on day 0 and on day 8, and then treated with either vehicle or compound at a dose of 10-40 mg/kg, twice daily. Tumor growth was assessed by excising and physically measuring the size of the tumor. Tumor growth rate was assessed by analyzing tumor size after the following time points after inoculation with HCT116 cells, DLD1 or HT-29: 12, 15, 19, 22 and 24 days.

Analogs were tested for tumor inhibition in mice. DLD1 or HCT116 cells were injected into mice to grow tumors. At day 6, when the tumor volume is approximately 50 mm$^3$, mice were either inoculated with a control or PDSA-014. PDSA-014 was administered by intraperitoneal injections to mice twice daily at 10 mg/kg. Tumors were removed on days 9, 12, 15, 18 and 21. Tumors were measured to determine tumor growth.

Mitotic Index

For determination of the mitotic index, DLD1 cells were methanol fixed 24 h after treatment with TASIN-1 at a concentration of 2.5 μL or 10 μL or Pitstop2 (abcam, ab120687) at a concentration of 10□□L, DNA was visualized by Hoechst 33342 staining, and cells were imaged on a microscope (Axiovert 200M; Carl Zeiss) using a LD 40×/NA 0.75/Ph2 Plan-Neofluor objective. Mitotic cells were identified in the UV channel by their condensed DNA content.

HCECs with TP53, APC knockdown, KRASV12 mutation (1CTRPA) together with ectopic expression of APC truncation 1309 (hereinafter "1CTRPA A1309") (table 1) have been developed (see Eskiocak U, Kim S B, Ly P, Roig A I, Biglione S, Komurov K, Cornelius C, Wright W E, White M A, Shay J W. Functional parsing of driver mutations in the colorectal cancer genome reveals numerous suppressors of anchorage-independent growth. Cancer Res 2011; 71:4359-65; Ly, P. Eskiocak, U., Parker, C. R., Harris, K. J., Wright, W. E. and Shay, J. W. RNAi screening of the human colorectal cancer genome identifies multifunctional tumor suppressors regulating epithelial cell invasion. Cell Res. 22:1605-1608, 2012, PubMed PMID: 23044803; Zhang, L., Komurov, K., Wright, W. E. and Shay, J. W. Identification of novel driver tumor suppressors through functional interrogation of putative passenger mutations in colorectal cancer. Int J Cancer. 132 (3):732-7, 2013. doi: 10.1002/ijc.27705. Epub 2012 Jul. 21. PMID: 22753261, each of which is incorporated herein by reference.) This APC mutation is strongly selected for in colon cancers and has been shown to be more resistant to caspase cleavage than other truncated forms of APC. APC-truncated HCEC cell line 1CTRPA A1309 exhibits an increase in growth rate, enhancement of soft agar growth and invasion through Matrigel® compared to matched parental HCECs (1CTRPA). However, knockdown of wt APC alone (1CTRPA) did not cause HCECs to gain oncogenic properties (data unpublished).

These observations lent support to the idea that APC truncations may cause cells to gain oncogenic properties, such as, for example, excessive or misregulated cellular proliferation.

These isogenic cell lines with defined genetic alterations have been used as a cellular model for identification of small molecules that target truncated APC proteins.

TABLE 1

Summary of the Isogenic Human Colonic
Epithelial Cells (HCECs) used in this screen

| Cell lines | Genetic alterations |
|---|---|
| 1CT | HCECs immortalized with CDK4 and hTERT |
| 1CTRPA | $Kras^{v12}$, shTP53, shAPC |
| 1CTRPA A1309 | $Kras^{v12}$, shTP53, shAPC, APC mutation (aa 1-1309) |

C: CDK4,
T: hTERT,
R: $Kras^{v12}$,
P: shTP53,
A: shAPC

Isogenic cell lines were used to carry out a cell-based high-throughput screen designed to identify small molecules and/or natural product fractions from within the University of Texas Southwestern (UTSW) compound file that can selectively inhibit cell growth of APC-truncated HCECs (FIG. 6). This compound library encompasses ~200,000 synthetic compounds that represent a large chemical space from several commercial vendors, including 1200 marketed drugs from the Prestwick Chemical Library®, and 600 compounds that went to pre-clinical tests from the NIH library. The isogenic cell lines used in the screen are listed in Table 1.

A primary screen was performed in 1CTRPA A1309. For the screen, cells were seeded as a monolayer at a density of 400 cells/well in 384 well plates [in Colonic Epithelial Cell Medium (CoEpiCM (ScienCell Research Laboratories; Innoprot, etc.)] which are commercially available (Invitrogen; BioRad; Corning etc.). Twenty four hours later candidate compounds were added at a concentration of 2.5 μM per well and cells were incubated for 4 days at physiologic oxygen conditions (~3-5% $O_2$). A luminescence-based Cell-titer-Glo® assay was performed to measure cell viability, using ATP levels as the readout. In brief, opaque-walled multiwell plates with mammalian cells in culture medium (25 μl per well, 384-well plates) were prepared. Control wells containing medium without cells were prepared to obtain a value for background luminescence. Test compounds were added to experimental wells, and incubated according to culture protocol. The plate and its contents were incubated at room temperature for approximately 30 minutes. An ATP standard curve was generated immediately prior to adding the CellTiter-Glo® Reagent. A volume of CellTiter-Glo® Reagent equal to the volume of cell culture medium present in each well (25 μl of reagent to 25 μl of medium containing cells for a 384-well plate) was added. The contents were mixed for 2 minutes on an orbital shaker to induce cell lysis. The plate was allowed to incubate at room temperature for 10 minutes to stabilize the luminescent signal and luminescence recorded. (e.g. GloMax®, Lumistar, SPECTROstar, PHERAstar FS). The primary screen yielded 6704 positive hits (based on a z-score of <−3, which means that the z-score of −3 was 3 standard deviations below the mean).

Compounds that inhibited >40% of the proliferation of normal human epithelial cells were excluded based on the screening facility database and previous experience. The remaining 5381 compounds were re-screened against 1CTRPA A1309 (to validate the primary screen results) and 1CTRPA (to exclude those compounds that are not specific to APC truncations). To eliminate the possible general toxicity properties of these compounds, the compounds were also counter screened against normal diploid HCECs (1CT). This counter screen identified 126 compounds that inhibit cell growth of CTRPA A1309>50% more than that of 1CTRPA and 1CT. An additional screen of these selectively toxic compounds was carried out against the same panel of HCECs at a 1:3 fold dilution series of concentrations, ranging from 2.5 um to 30 nm. This secondary counter screen yielded 14 candidate compounds that showed selective inhibition of 1CTRPA A1309 cells at concentrations of 30 nm or 90 nm but without noticeable impact on 1CTRPA or 1CT cells. The overall screening strategy is shown in the flow chart (FIG. 6).

Figure 7F:
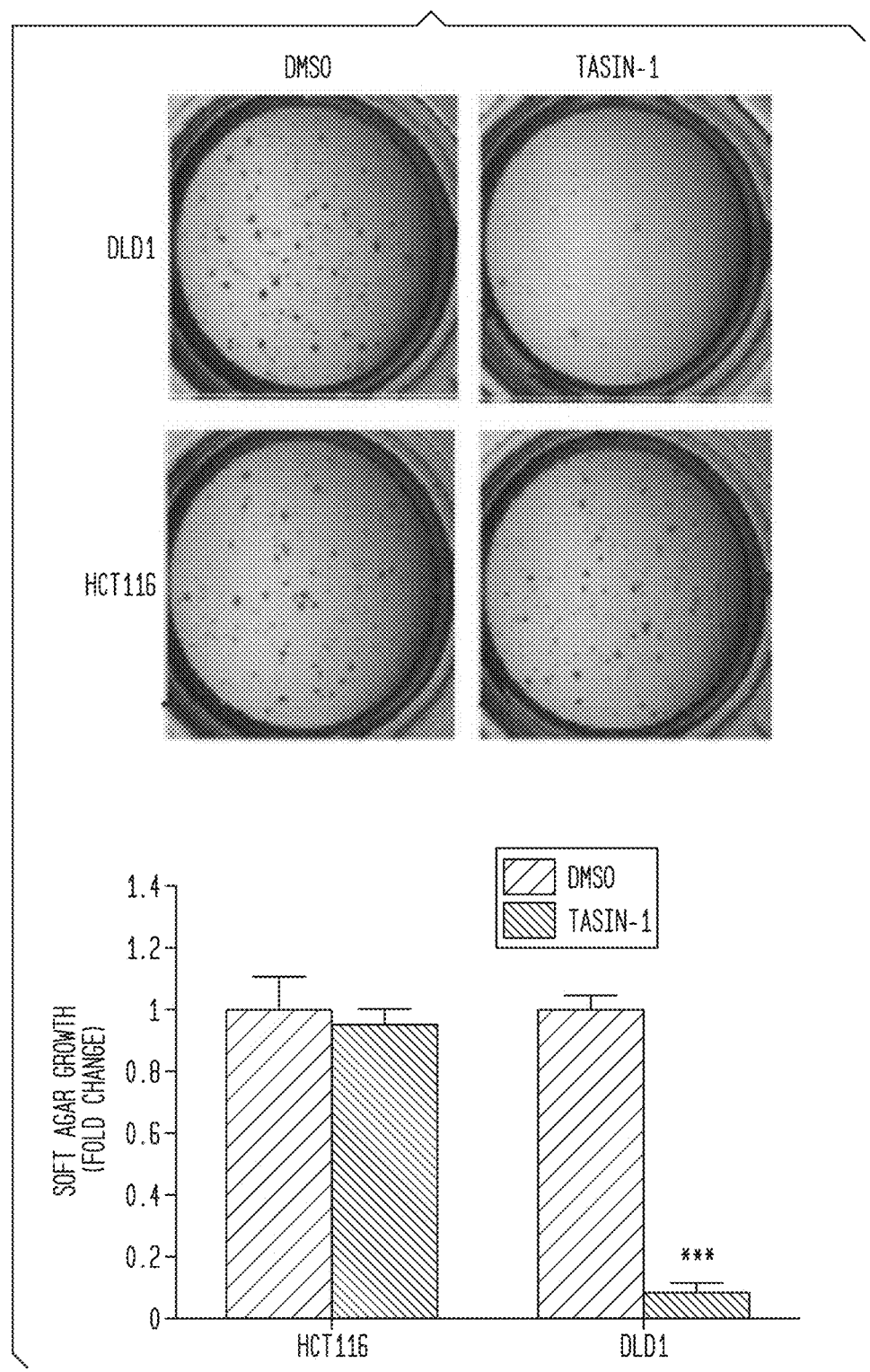

These 14 compounds then were obtained commercially and their $IC_{50}$ determined by performing dose response studies with half log dilution series at 12 concentration points in two authentic CRC lines: HCT116 (wt APC) and DLD1 (truncated APC). Anti-cancer compounds A and B showed selective toxicity towards DLD1 with $IC_{50}$ 63 nm and 131 nm, respectively, as shown in FIG. 7. These two compounds served as initial lead compounds for analog development and for additional studies.

Exemplary Compounds Resulting from these Substitutions are Shown in Table A

I. General Information $^1$H and $^{13}$C NMR spectra were obtained using either Varian Inova-400 MHz or 500 MHz spectrometer. Abbreviations for signal couplings are as follows: s, singlet; br, broad; d, doublet; t, triplet, q, quartet and m, multiplet.

Melting point of solid samples was performed using Fisher-Johns Melting Point Apparatus. Analytical thin layer chromatography (TLC) was performed on precoated plates purchased from E. Merck (TLC silica 60 PF254, 25 Glass plates 20×20 cm). The chromatograms were visualized under UV light or by staining with iodide or KMnO4. Flash chromatography was performed either on the basis of the description of Still et al (Still, W. C. et al. J. Org. Chem. 1978, 43, 2923-2925) using E. Merck silica gel 60 (230-400 mesh) or on an Isco Combiflash system using Redisep®Rf Flash column with the size ranging from 4 grams to 80 grams. All air sensitive reactions were carried out under argon environment. Unless otherwise noted, all common reagents and solvents purchased from commercial sources were used without further purification. All glassware used for moisture-sensitive reactions were either oven dried overnight or flame-dried.

II. General Procedure for the Preparation of Sulfonamides from Sulfonyl Chlorides and Amines A mixture of amine (1.0 mmol), sulfonyl chloride (1.1 mmol), N,N-diisopropyl ethylamine (1.5 mmol), and $CH_2Cl_2$ (5 mL) was stirred at room temperature overnight. The reaction solution was then poured into saturated $NaHCO_3$ solution (20 ml) and extracted by $CH_2Cl_2$ (3×20 mL). The combined organic layers were dried over $Na_2SO_4$, filtered and concentrated under reduced pressure. The residue was purified either through flash chromatography on silica gel with a $MeOH:CH_2Cl_2$ (or MeOH:EtOAc) mixture as eluent or by recrystallization from a mixture of $CH_2Cl_2$ and hexane to provide the sulfonamides.

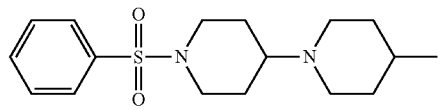

4-methyl-1'-(phenylsulfonyl)-1,4'-bipiperidine: This compound was obtained as a pale yellow solid (92%) through flash chromatography (1 : 9 MeOH:EtOAc) after the reaction between 4-methyl-1,4'-bipiperidine and benzenesulfonyl chloride. mp 154-156° C.; $^1$H NMR (500 MHz, CDCl3) δ 7.77 (dd, J=8.3, 1.4 Hz, 2 H), 7.65-7.58 (m, 1 H), 7.54 (dd, J=8.4, 7.0 Hz, 2H), 3.87 (d, J=11.9 Hz, 2 H), 2.80 (d, J=11.8 Hz, 2 H), 2.26 (m, 3 H), 2.14 (t, J=11.4 Hz, 2 H), 1.86 (d, J=11.7 Hz, 2 H), 1.72-1.59 (m, 4 H), 1.40-1.28 (m, 1 H), 1.23 (m, 2 H), 0.91 (d, J=6.4 Hz, 3 H); $^{13}$C NMR (100 MHz, CDCl$_3$) δ 136.0, 132.7, 129.0, 127.6, 61.3, 49.1, 46.1, 33.9, 30.8, 26.9, 21.7; MS (ESI) m/z 323.2 (100%, [M+H]+).

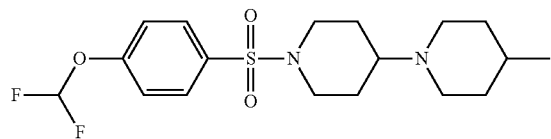 [SMILES: CC1CCN(C2CCN(S(=O)(=O)c3ccc(OC(F)F)cc3)CC2)CC1]

1'-((4-(difluoromethoxy)phenyl)sulfonyl)-4-methyl-1,4'-bipiperidine: This compound was obtained as a light orange solid (69%) through flash chromatography (1:19 MeOH:$CH_2Cl_2$) after the reaction between 4-methyl-1,4'-bipiperidine and 4-(difluoromethoxy)benzene-1-sulfonyl chloride. mp 132-135° C.; $^1$H NMR (500 MHz, CDCl$_3$) δ 7.76 (d, J=8.8 Hz, 2 H), 7.24 (d, J=8.8 Hz, 2 H), 6.61 (t, J=72.6 Hz, 1 H), 3.83 (d, J=12.1 Hz, 2 H), 2.77 (d, J=11.7 Hz, 2 H), 2.33-2.16 (m, 3 H), 2.11 (td, J=11.6, 2.5 Hz, 2 H), 1.84 (d, J=13.2 Hz, 2 H), 1.64 (m, 4 H), 1.30 (dddt, J=13.3, 9.7, 6.5, 3.5 Hz, 1 H), 1.16 (qd, J=12.0, 3.8 Hz, 2 H), 0.89 (d, J=6.5 Hz, 3 H); $^{13}$C NMR (100 MHz, CDCl$_3$) δ 154.1 (t, J=2.9 Hz), 132.9, 129.8, 119.3, 115.2 (t, J=262.5 Hz), 61.4, 49.5, 46.1, 34.6, 31.0, 27.3, 21.8; MS (ESI) m/z 389.2 (100%, [M+H]+).

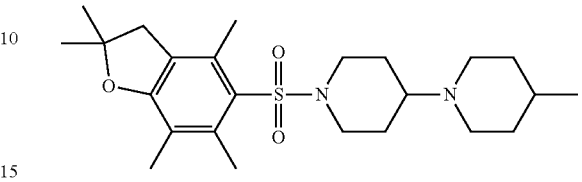

4-methyl-1'-((2,2,4,6,7-pentamethyl-2,3-dihydrobenzofuran-5-yl)sulfonyl)-1,4'-bipiperidine: This compound was obtained as a pale yellow oil (95%) through flash chromatography (1:9 MeOH:EtOAc) after the reaction between 4-methyl-1,4'-bipiperidine and 2,2,4,6,7-pentamethyl-2,3-dihydrobenzofuran-5-sulfonyl chloride. $^1$H NMR (400 MHz, CDCl$_2$) δ 3.63 (d, J=12.0 Hz, 2 H), 2.97 (s, 2 H), 2.89 (s, br, 2 H), 2.75 (dt, J=12.0, 4.0 Hz, 2 H), 2.50 (s, 3 H), 2.46 (s, 3 H), 2.41 (s, br, 1 H), 2.14 (s, br, 2 H), 2.10 (s, 3 H), 1.90 (d, J=12.0 Hz, 2 H), 1.64 (d, J=12.0 Hz, 2 H), 1.51 (m, 2 H), 1.48 (s, 6 H), 1.40-1.08 (m, 3 H), 0.87 (d, J=4.0 Hz, 3 H); $^{13}$C NMR (100 MHz, CDCl$_3$) δ 159.9, 140.8, 135.3, 125.8, 125.0, 117.9, 86.8, 61.9, 49.6, 43.9, 43.1, 34.5, 31.0, 28.6, 27.7, 21.8, 19.2, 17.6, 12.5; MS (ESI) m/z 435.3 (100%, [M+H]+).

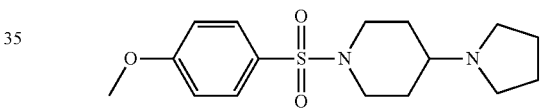

1-((4-methoxyphenyl)sulfonyl)-4-(pyrrolidin-1-yl)piperidine: This compound was obtained as a pale yellow oil (70%) through flash chromatography (1:9 MeOH:EtOAc then 1:9 MeOH:$CH_2Cl_2$) after the reaction between 4-(pyrrolidin-1-yl)piperidine and 4-methoxybenzene-1-sulfonyl chloride. $^1$H NMR (400 MHz, CDCl$_3$) δ 7.68 (d, J=8.0 Hz, 2 H), 6.97 (d, J=8.0 Hz, 2 H), 3.86 (s, 3 H), 3.68 (d, J=12.0 Hz, 2 H), 2.51 (s, 4 H), 2.36 (dt, J=12.0, 4.0 Hz, 2 H), 1.90 (m, 3 H), 1.75 (s, 4 H), 1.61 (q, J=12.0 Hz, 1H); $^{13}$C NMR (100 MHz, CDCl$_3$) δ 162.9, 129.8, 127.8, 114.1, 60.8, 55.6, 51.3, 45.0, 30.4, 23.2; MS (ESI) m/z 325.2 (100%, [M+H]+).

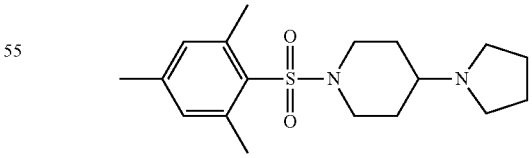

1-(mesitylsulfonyl)-4-(pyrrolidin-1-yl)piperidine: This compound was obtained as a yellow oil (59%) through flash chromatography (1:9 MeOH:EtOAc) after the reaction between 4-(pyrrolidin-1-yl)piperidine and 2,4,6-trimethyl-benzene-1-sulfonyl chloride. $^1$H NMR (400 MHz, CDCl$_3$) δ 6.92 (s, 2 H), 3.53 (d, J=12.0 Hz, 2 H), 2.80 (td, J=12.0, 2.6 Hz, 2 H), 2.59 (s, 6 H), 2.56 (s, 4 H), 2.28 (s, 3 H), 2.11 (s, br, 1 H), 1.93 (d, J=12.0 Hz, 2 H), 1.77 (s, 4 H), 1.50 (m, 2 H); ¹³C NMR (100 MHz, CDCl₃) δ 142.5, 140.6, 131.9, 131.6, 61.2, 51.4, 42.9, 30.7, 23.2, 22.7, 21.0; MS (ESI) m/z 337.2 (100%, [M+H]+).

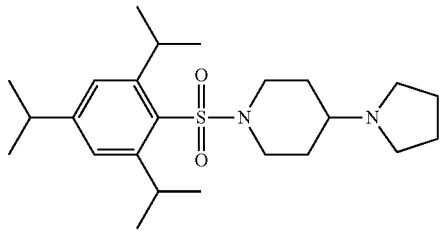 [SMILES: CC(C)c1cc(C(C)C)c(S(=O)(=O)N2CCC(N3CCCC3)CC2)c(C(C)C)c1]

4-(pyrrolidin-1-yl)-1-((2,4,6-triisopropylphenyl)sulfonyl) piperidine: This compound was obtained as a yellow solid (>95%) through flash chromatography (1:9 MeOH:EtOAc) after the reaction between 4-(pyrrolidin-1-yl)piperidine and 2,4,6-triisopropylbenzene-1-sulfonyl chloride. mp 118-122° C.; ¹H NMR (400 MHz, CDCl₃) δ 7.15 (s, 2 H), 4.16 (m, 2 H), 3.58 (d, J=12.0 Hz, 2 H), 2.85 (m, 3 H), 2.62 (s, 4 H), 2.16 (s, br, 1 H), 1.98 (d, J=12.0 Hz, 2 H), 1.81 (s, 4 H)m 1.55 (d, J=12.0 Hz, 2 H), 1.24 (m, 18 H); ¹³C NMR (100 MHz, CDCl₃) δ 153.2, 151.8, 129.7, 123.9, 61.5, 51.4, 42.9, 34.2, 29.3, 24.9, 23.6, 23.2; MS (ESI) m/z 421.2 (100%, [M+H]+).

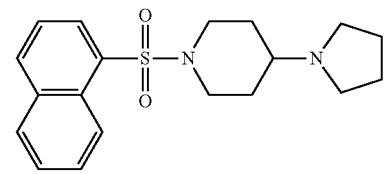 [SMILES: O=S(=O)(c1cccc2ccccc12)N1CCC(N2CCCC2)CC1]

1-(naphthalen-1-ylsulfonyl)-4-(pyrrolidin-1-yl)piperidine: This compound was obtained as a white solid (67%) through flash chromatography (1:9 MeOH:EtOAc) after the reaction between 4-(pyrrolidin-1-yl)piperidine and naphthalene-1-sulfonyl chloride. mp 151-154° C.; ¹H NMR (400 MHz, CDCl₃) δ 8.70 (d, J=12.0 Hz, 1 H), 8.20 (dd, J=7.3, 1.4 Hz, 1 H), 8.05 (d, J=12.0 Hz, 1 H), 7.90 (dd, J=7.3, 1.4 Hz, 1 H), 7.58 (m, 3H), 3.81 (d, J=12.0 Hz, 2 H), 2.65 (m, 6 H), 2.19 (s, br, 1 H), 1.92 (m, 2 H), 1.79 (s, 4 H), 1.59 (m, 2 H); ¹³C NMR (100 MHz, CDCl₃) δ 134.5, 134.3, 132.8, 130.5, 128.9, 128.8, 128.1, 126.9, 125.2, 124.1, 60.8, 51.1, 44.2, 30.0, 23.2; MS (ESI) m/z 345.2 (100%, [M+H]+).

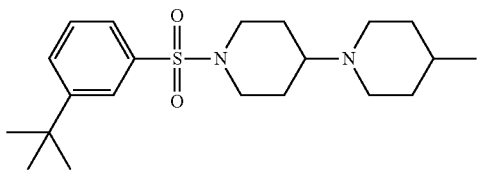

1'-((3-(tert-butyl)phenyl)sulfonyl)-4-methyl-1,4'-bipiperidine: This compound was obtained as a yellow solid (90%) through flash chromatography (1:9 MeOH:EtOAc) after the reaction between 4-(pyrrolidin-1-yl)piperidine and 3-(tert-butyl)benzene-1-sulfonyl chloride. mp 100-102° C.; ¹H NMR (400 MHz, CDCl₃) δ 7.73 (s, 1 H), 7.57 (m, 2 H), 7.43 (m, 1 H), 3.84 (d, J=12.0 Hz, 2 H), 2.78 (d, J=12.0 Hz, 2 H), 2.22 (td, J=12.0, 2.5 Hz, 3 H), 2.12 (t, J=12.0 Hz, 2 H), 1.82 (d, J=12.0 Hz, 2 H), 1.63 (m, 4 H), 1.33 (s, 9 H), 1.28 (m, 1 H), 1.19 (m, 2 H), 0.88 (d, J=8.0 Hz, 3 H); ¹³C NMR (100 MHz, CDCl₃) δ 152.5, 135.9, 129.7, 128.7, 124.7, 124.4, 61.5, 49.4, 46.0, 35.0, 34.4, 31.1, 31.0, 27.2, 21.8; MS (ESI) m/z 379.2 (100%, [M+H]+).

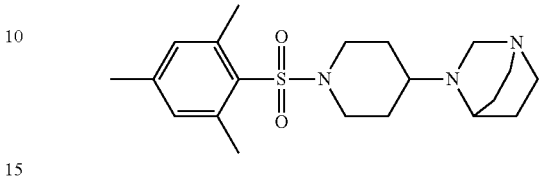

3-(4-(mesitylsulfonyl)piperazin-1-yl)quinuclidine: This compound was obtained as a white solid (42%) through flash chromatography (1:9 MeOH:EtOAc) after the reaction between 3-piperazin-1-ylquinuclidine trihydrochloride hemihydrate (1.0 mmol) and 2,4,6-trimethylbenzenesulfonyl chloride (1.1 mmol) in CH₂Cl₂ in the presence of N,N-diisopropyl ethylamine (1.5 mmol). mp higher than 300° C.; ¹H NMR (400 MHz, CDCl₃) δ 6.96 (s, 2 H), 3.34-3.12 (m, 9 H), 3.04 (dd, J=12.0, 4.0 Hz, 1 H), 2.60 (s, 6 H), 2.45 (s, 5 H), 2.30 (s, 4 H), 2.05 (m, 2 H), 1.79 (m, 1 H), 1.68 (m, 1 H); ¹³C NMR (100 MHz, CDCl₃) δ 142.8, 140.5, 132.0, 131.0, 59.1, 52.8, 50.3, 46.6, 45.6, 44.1, 23.0, 22.9, 22.1, 20.9, 17.7; MS (ESI) m/z 378.2 (100%, [M+H]+).

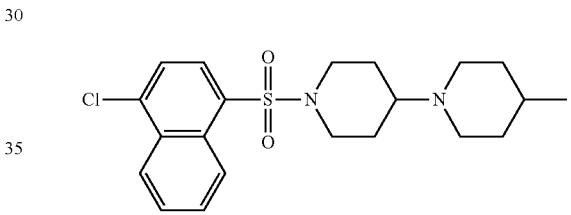

1'-((4-chloronaphthalen-1-yl)sulfonyl)-4-methyl-1,4'-bipiperidine: This compound was obtained as a white solid (71%) through flash chromatography (1:9 MeOH:EtOAc) after the reaction between 4-methyl-1,4'-bipiperidine and 4-chloronaphthalene-1-sulfonyl chloride. mp 129-132° C.; ¹H NMR (400 MHz, CDCl₃) δ 8.76 (m, 1H), 8.39 (ddd, J=6.5, 3.4, 0.7 Hz, 1 H), 8.11 (d, J=8.0 Hz, 1 H), 7.69 (dd, J=6.6, 3.3 Hz, 2 H), 7.64 (d, J=8.0 Hz, 1 H), 3.87 (d, J=12.4 Hz, 2 H), 2.75 (d, J=11.0 Hz, 2 H), 2.55 (td, J=12.2, 2.4 Hz, 2 H), 2.23 (t, J=12.0 Hz, 1 H), 2.06 (t, J=11.3 Hz, 2 H), 1.81 (d, J=13.1 Hz, 2 H), 1.55 (m, 4 H), 1.27 (dd, J=17.6, 9.0 Hz, 1 H), 1.15 (dd, J=13.4, 9.6 Hz, 2 H), 0.87 (d, J=6.4 Hz, 3 H).; ¹³C NMR (100 MHz, CDCl₃) δ 138.4, 132.3, 131.5, 130.1, 130.0, 128.7, 127.9, 125.7, 125.4, 124.6, 61.5, 49.5, 45.5, 34.5, 31.0, 27.7, 21.8; MS (ESI) m/z 407.1 (100%, [M+H]+).

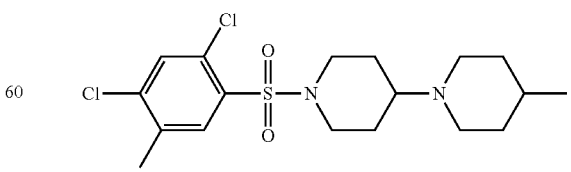

1'-((2,4-dichloro-5-methylphenyl)sulfonyl)-4-methyl-1,4'-bipiperidine: This compound was obtained as a white solid (83%) through flash chromatography (1:9 MeOH:EtOAc)

after the reaction between 4-methyl-1,4'-bipiperidine and 2,4-dichloro-5-methylbenzene-1-sulfonyl chloride. mp 120-123° C.; $^1$H NMR (400 MHz, CDCl$_3$) δ 7.89 (s, 1H), 7.49 (s, 1H), 3.87 (d, J=12.9 Hz, 2 H), 2.82 (d, J=11.2 Hz, 2H), 2.71 (td, J=12.4, 2.4 Hz, 2H), 2.38 (s, 3 H), 2.34 (m, 1 H), 2.15 (t, J=11.2 Hz, 2H), 1.83 (d, J=11.6 Hz, 2H), 1.59 (m, 4H), 1.31 (m, 1H), 1.06 (t, J=12.0 Hz, 2H), 0.89 (d, J=6.0 Hz, 3H); $^{13}$C NMR (100 MHz, CDCl$_3$) δ 139.3, 135.5, 134.6, 133.6, 132.0, 129.9, 61.7, 49.5, 45.6, 34.5, 31.0, 27.7, 21.8, 19.6; MS (ESI) m/z 405.1 (100%, [M+H]+).

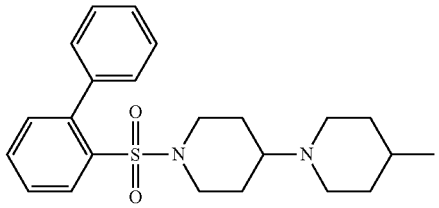

1'-([1,1'-biphenyl]-2-ylsulfonyl)-4-methyl-1,4'-bipiperidine: This compound was obtained as a yellow solid (>95%) through flash chromatography (1:9 MeOH:EtOAc) after the reaction between 4-methyl-1,4'-bipiperidine and [1,1'-biphenyl]-2-sulfonyl chloride. mp 106-109° C.; $^1$H NMR (400 MHz, CDCl$_3$) δ 8.12 (dd, J=8.0, 1.6 Hz, 1H), 7.56 (td, J=7.6, 1.6 Hz, 1H), 7.46 (td, J=7.6, 1.6 Hz, 1 H), 7.39 (m, 5 H), 7.30 (dd, J=7.6, 1.6 Hz, 1 H), 3.29 (d, J=12.8, 2 H), 2.71 (d, J=10.8 Hz, 2 H), 2.22 (td, J=12.6, 2.5 Hz, 3 H), 2.09 (t, J=10.4 Hz, 2 H), 1.90-1 49 (m, 4 H), 1.21 (m, 5 H), 0.88 (d, J=6.0 Hz, 3 H); $^{13}$C NMR (100 MHz, CDCl$_3$) δ 141.6, 139.7, 137.1, 133.0, 132.2, 130.3, 129.6, 127.7, 127.5, 61.7, 49.3, 44.4, 34.4, 31.0, 27.2, 21.8; MS (ESI) m/z 399.2 (100%, [M+H]+).

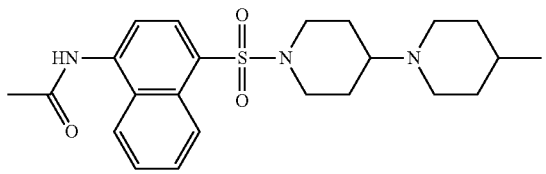 [SMILES: CC(=O)Nc1ccc(S(=O)(=O)N2CCC(N3CCC(C)CC3)CC2)c2ccccc12]

N-(4-((4-methyl-[1,4'-bipiperidin]-1'-yl)sulfonyl)naphthalen-1-yl)acetamide: This compound was obtained as a yellow solid (64%) through flash chromatography (1:9 MeOH:CH$_2$Cl$_2$) after the reaction between 4-methyl-1,4'-bipiperidine and 4-acetamidonaphthalene-1-sulfonyl chloride. mp 113-117° C.; $^1$H NMR (400 MHz, CDCl$_3$) δ 8.51 (d, J=8.8 Hz, 1H), 8.09 (m, 2H), 7.87 (s, 1 H), 7.66 (d, J=7.6 Hz, 1 H), 7.48 (m, 2 H), 3.86 (d, J=9.6 Hz, 2 H), 2.80 (d, J=11.6 Hz, 2 H), 2.52 (t, J=12.4 Hz, 2 H), 2.36 (t, J=12.8 Hz, 1 H), 2.31 (s, 3 H), 2.15 (t, J=11.6 Hz, 3 H), 1.83 (d, J=13.6 Hz, 2 H), 1.56 (m, 4 H), 1.24 (m, 3 H), 0.88 (d, J=6.0 Hz, 3 H); 13C NMR (100 MHz, CDCl$_3$) δ 169.5, 133.3, 133.2, 130.6, 129.5, 129.4, 128.1, 127.7, 124.3, 123.9, 123.4, 61.6, 49.3, 45.3, 33.7, 30.7, 27.2, 24.0, 21.6; MS (ESI) m/z 430.2 (100%, [M+H]+).

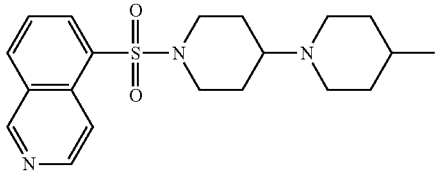 [SMILES: CC1CCN(C2CCN(S(=O)(=O)c3cccc4cnccc34)CC2)CC1]

5-((4-methyl-[1,4'-bipiperidin]-1'-yl)sulfonyl)isoquinoline: This compound was obtained as a white solid (51%) through flash chromatography (1:9 MeOH:EtOAc) after the reaction between 4-methyl-1,4'-bipiperidine and isoquinoline-5-sulfonyl chloride. mp 123-126° C.; $^1$H NMR (400 MHz, CDCl$_3$) δ 9.33 (s, 1 H), 8.66 (d, J=6.0 Hz, 1 H), 8.48 (d, J=6.0 hz, 1 H), 8.36 (dd, J=7.6, 1.6 Hz, 1 H), 8.19 (d, J=6.0 Hz, 1 H), 7.69 (dd, J=8.2, 7.4 Hz, 1H), 3.90 (d, J=12.4 Hz, 2 H), 2.74 (d, J=10.8 Hz, 2 H), 2.51 (td, J=12.0, 2.4 Hz, 2 H), 2.21 (m, 1 H), 2.06 (m, 2 H), 1.81 (d, J=11.6 Hz, 2 H), 1.56 (m, 4 H), 1.27 (m, 1 H), 1.15 (m, 2 H), 0.86 (d, J=6.4 Hz, 3 H); $^{13}$C NMR (100 MHz, CDCl$_3$) δ 153.2, 145.1, 134.0, 133.7, 132.6, 131.9, 129.1, 125.8, 117.7, 61.4, 49.9, 45.6, 34.5, 31.0, 27.7, 21.6; MS (ESI) m/z 374.2 (100%, [M+H]+).

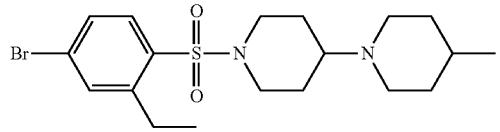 [SMILES: CCc1cc(Br)ccc1S(=O)(=O)N1CCC(N2CCC(C)CC2)CC1]

1'-((4-bromo-2-ethylphenyl)sulfonyl)-4-methyl-1,4'-bipiperidine: This compound was obtained as a white solid (92%) through flash chromatography (1:9 MeOH:EtOAc) after the reaction between 4-methyl-1,4'-bipiperidine and 4-bromo-2-ethylbenzene-1-sulfonyl chloride. mp 87-91° C.; $^1$H NMR (400 MHz, CDCl$_3$) δ7.73 (d, J=8.4 Hz, 1 H), 7.50 (d, J=2.0 Hz, 1 H), 7.42 (dd, J=8.4, 2.0 Hz, 1 H), 3.75 (d, J=12.4 Hz, 2 H), 2.96 (q, J=7.6 Hz, 2 H), 2.83 (d, J=7.6 Hz, 2 H), 2.60 (td, J=12.4, 2.4 Hz, 2 H), 2.34 (m, 1 H), 2.13 (m, 2 H), 1.84 (d, J=7.6 Hz, 2 H), 1.57 (m, 4 H), 1.25 (m, 6 H), 0.89 (d, J=6.4 Hz, 3 H); $^{13}$C NMR (100 MHz, CDCl$_3$) δ 145.2, 134.8, 133.9, 131.7, 129.0, 127.8, 61.6, 49.5, 45.1, 34.4, 30.9, 27.7, 25.9, 21.8, 15.4; MS (ESI) m/z 429.1 (100%, [M+]+), 431.1 (100%, [M+2]+).

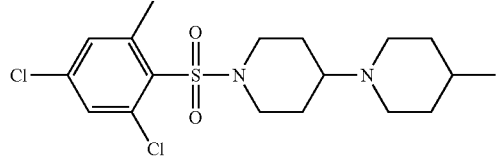 [SMILES: Cc1cc(Cl)cc(Cl)c1S(=O)(=O)N1CCC(N2CCC(C)CC2)CC1]

1'-((2,4-dichloro-6-methylphenyl)sulfonyl)-4-methyl-1,4'-bipiperidine: This compound was obtained as a white solid (93%) through flash chromatography (1:9 MeOH:EtOAc) after the reaction between 4-methyl-1,4'-bipiperidine and 2,4-dichloro-6-methylbenzene-1-sulfonyl chloride. mp 89-91° C.; $^1$H NMR (400 MHz, CDCl$_3$) δ 7.37 (d, J=2.3 Hz, 1H), 7.19 (dd, J=2.3, 0.9 Hz, 1H), 3.79 (d, J=12.7 Hz, 2H), 2.93-2.73 (m, 4H), 2.67 (s, 3H), 2.45-2.27 (m, 1H), 2.14 (td, J=11.3, 2.5 Hz, 2H), 1.83 (dd, J=12.3, 3.4 Hz, 2H), 1.57 (dtd, J=24.4, 11.6, 4.0 Hz, 4H), 1.30 (ddt, J=12.8, 6.4, 3.7 Hz, 1H), 1.18 (qd, J=12.0, 3.9 Hz, 2H), 0.89 (d, J=6.9 Hz, 3H);

$^{13}$C NMR (100 MHz, CDCl$_3$) δ 143.7, 137.7, 135.3, 134.2, 131.6, 130.2, 61.7, 49.5, 45.0, 34.6, 31.0, 27.9, 24.0, 21.8; MS (ESI) m/z 405.1 (100%, [M+H]+).

1.79-1.46 (m, 7H), 0.88-0.75 (m, 1H), 0.83 (d, J=6.4 Hz, 3H); $^{13}$C NMR (100 MHz, CDCl$_3$) δ 162.9, 129.8, 127.7, 114.1, 61.6, 57.3, 55.6, 49.4, 46.1, 33.1, 31.2, 27.0, 25.6, 19.8.; MS (ESI) m/z 353.2 (100%, [M+H]+).

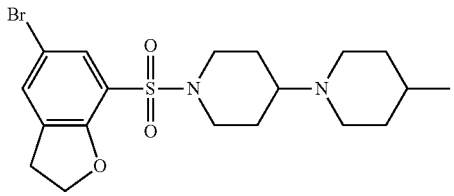 [SMILES: CC1CCN(C2CCN(S(=O)(=O)c3cc(Br)cc4c3OCC4)CC2)CC1]

1'-((5-bromo-2,3-dihydrobenzofuran-7-yl)sulfonyl)-4-methyl-1,4'-bipiperidine: This compound was obtained as a white solid (86%) through flash chromatography (1:9 MeOH:EtOAc) after the reaction between 4-methyl-1,4'-bipiperidine and 5-bromo-2,3-dihydrobenzofuran-7-sulfonyl chloride. mp 128-132° C.; $^1$H NMR (400 MHz, CDCl$_3$) δ 7.62 (s, 1 H), 7.43 (s, 1 H), 4.70 (t, J=8.9 Hz, 2 H), 3.89 (d, J=12.3 Hz, 2 H), 3.24 (t, J=9.0 Hz, 2 H), 2.79 (d, J=11.9 Hz, 2 H), 2.50 (t, J=12.4 Hz, 2 H), 2.27 (tt, J=11.7, 3.7 Hz, 1 H), 2.12 (t, J=11.5 Hz, 2H), 1.82 (d, J=11.2 Hz, 2H), 1.60 (m, 4H), 1.30 (m, 1H), 1.17 (qd, J=11.9, 3.7 Hz, 2 H), 0.88 (d, J=6.3 Hz, 3 H); $^{13}$C NMR (100 MHz, CDCl$_3$) δ 156.4, 132.3, 132.2, 130.7, 121.0, 111.8, 73.0, 61.7, 49.5, 46.0, 34.6, 31.0, 29.0, 27.6, 21.9; MS (ESI) m/z 443.1 (90%, [M+]+), 445.1 (100%, [M+2]+).

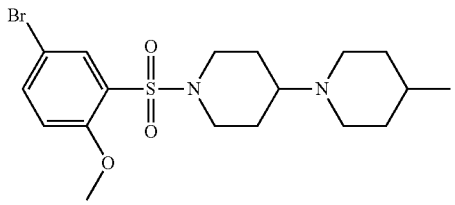 [SMILES: COc1ccc(Br)cc1S(=O)(=O)N1CCC(N2CCC(C)CC2)CC1]

1'-((5-bromo-2-methoxyphenyl)sulfonyl)-4-methyl-1,4'-bipiperidine: This compound was obtained as a yellow solid (92%) through flash chromatography (1:19 MeOH:CH$_2$Cl$_2$) after the reaction between 4-methyl-1,4'-bipiperidine and 5-bromo-2-methoxybenzene-1-sulfonyl chloride. mp 98-102° C.; $^1$H NMR (400 MHz, CDCl$_3$) δ8.01 (d, J=2.6, Hz, 1 H), 7.59 (dd, J=8.8, 2.6 Hz, 1 H), 6.88 (d, J=8.8 Hz, 1 H), 3.96-3.88 (d, J=13.6 Hz, 2 H), 3.90 (s, 3 H), 2.84 (d, J=10.9 Hz, 2 H), 2.64 (td, J=12.5, 2.5 Hz, 2 H), 2.38 (d, J=12.2 Hz, 1 H), 2.17 (t, J=11.7 Hz, 2 H), 1.85 (d, J=12.7 Hz, 2 H), 1.60 (m, 4 H), 1.40-1.14 (m, 3 H), 0.91 (d, J=6.2 Hz, 3 H); $^{13}$C NMR (100 MHz, CDCl$_3$) δ 155.9, 136.8, 133.8, 128.7, 114.1, 112.3, 61.8, 56.3, 49.5, 45.9, 34.6, 31.0, 28.0, 21.9; MS (ESI) m/z 431.1 (100%, [M+]+), 433.1 (100%, [M+2]+).

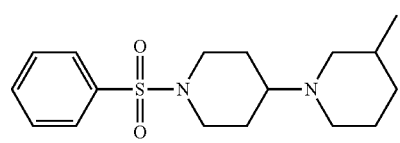

3-methyl-1'-(phenylsulfonyl)-1,4'-bipiperidine: This compound was obtained as a yellow solid (63%) through flash chromatography (1:9 MeOH:EtOAc) after the reaction between 3-methyl-1,4'-bipiperidine and benzenesulfonyl chloride. mp 132-135° C.; $^1$H NMR (400 MHz, CDCl$_3$) δ 7.79-7.69 (m, 2 H), 7.62-7.55 (m, 1 H), 7.55-7.44 (m, 2 H), 3.84 (d, J=11.9 Hz, 2H), 2.89-2.51 (m, 2 H), 2.36-2.09 (m, 3 H), 2.02 (td, J=11.2, 2.7 Hz, 1 H), 1.88-1.76 (m, 2 H), 1.75-1.44 (m, 7 H), 0.85-0.73 (m, 1 H), 0.81 (d, J=6.4 Hz, 3 H); $^{13}$C NMR (100 MHz, CDCl$_3$) δ 136.3, 132.6, 129.0, 127.6, 61.5, 57.6, 49.5, 46.2, 33.29, 31.5, 27.2, 27.1, 25.9, 19.8; MS (ESI) m/z 323.2 (100%, [M+H]+).

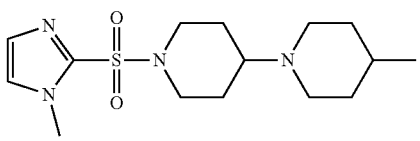 [SMILES: CC1CCN(C2CCN(S(=O)(=O)c3nccn3C)CC2)CC1]

4-methyl-1'-((1-methyl-1H-imidazol-2-yl)sulfonyl)-1,4'-bipiperidine: This compound was obtained as a white solid (51%) through flash chromatography (1:19 MeOH:CH$_2$Cl$_2$) after the reaction between 4-methyl-1,4'-bipiperidine and 1-methyl-1H-imidazole-2-sulfonyl chloride. mp 153-156° C.; $^1$H NMR (400 MHz, CDCl$_3$) δ 7.03 (d, J=1.1 Hz, 1H), 6.92 (d, J=1.1 Hz, 1H), 3.96 (d, J=12.2 Hz, 2H), 3.89 (s, 3H), 3.05 (t, J=12.5 Hz, 2H), 2.89 (d, J=10.8 Hz, 2H), 2.54 (s, 1H), 2.24 (s, 2H), 1.94 (d, J=12.5 Hz, 2H), 1.81-1.58 (m, 4H), 1.31 (s, 3H), 1.06-0.79 (d, J=8.0 Hz, 3H); $^{13}$C NMR (100 MHz, CDCl$_3$) δ 142.8, 128.2, 124.4, 61.8, 49.4, 46.6, 34.8, 34.1, 30.9, 27.3, 21.7; MS (ESI) m/z 327.2 (100%, [M+H]+).

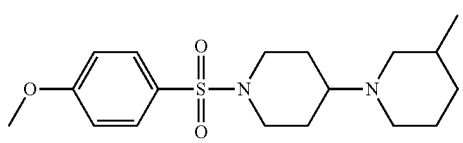

1'-((4-methoxyphenyl)sulfonyl)-3-methyl-1,4'-bipiperidine: This compound was obtained as a yellow solid (74%) through flash chromatography (1:19 MeOH:CH$_2$Cl$_2$) after the reaction between 3-methyl-1,4'-bipiperidine and 4-methoxybenzene-1-sulfonyl chloride. mp 114-117° C.; $^1$H NMR (400 MHz, CDCl$_3$) δ 7.69 (d, J=8.8 Hz, 2H), 6.98 (d, J=8.8 Hz, 2H), 3.87 (s, 3H), 3.82 (d, J=12.0 Hz, 2H), 2.87-2.62 (m, 2H), 2.22 (td, J=12.0, 2.5 Hz, 2H), 2.06 (td, J=11.8, 10.7, 2.9 Hz, 1H), 1.90-1.79 (d, J=12.4 Hz, 2H),

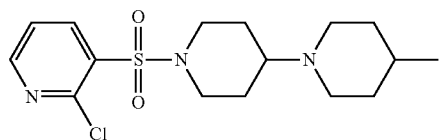

1'-((2-chloropyridin-3-yl)sulfonyl)-4-methyl-1,4'-bipiperidine: This compound was obtained as a white solid (71%) through flash chromatography (1:19 MeOH:CH$_2$Cl$_2$) after the reaction between 4-methyl-1,4'-bipiperidine and 2-chloropyridine-3-sulfonyl chloride. mp 122-124° C.; $^1$H NMR (500 MHz, CDCl$_3$) δ 8.55 (d, J=4.9 Hz, 1 H), 8.38 (d, J=7.8 Hz, 1 H), 7.40 (dd, J=7.8, 4.8 Hz, 1 H), 3.92 (d, J=13.0 Hz, 2 H), 2.83 (t, J=12.5 Hz, 4 H), 2.38 (t, J=11.5 Hz, 1H), 2.15 (t, J=11.0 Hz, 2H), 1.86 (d, J=12.5 Hz, 2H), 1.72-1.53 (m, 4 H), 1.32 (m, 1 H), 1.18 (m, 2 H), 0.90 (d, J=6.5 Hz, 3 H).; $^{13}$C NMR (100 MHz, CDCl$_3$) δ 148.4, 144.5, 136.9, 130.5, 118.5, 57.6, 45.6, 41.9, 30.7, 27.1, 24.0, 17.9; MS (ESI) m/z 358.1 (100%, [M+H]+).

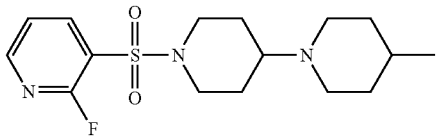 [SMILES: CC1CCN(C2CCN(S(=O)(=O)c3cccnc3F)CC2)CC1]

1'-((2-fluoropyridin-3-yl)sulfonyl)-4-methyl-1,4'-bipiperidine: This compound was obtained as a white solid (>95%) through flash chromatography (1:19 MeOH:CH$_2$Cl$_2$) after the reaction between 4-methyl-1,4'-bipiperidine and 2-fluoropyridine-3-sulfonyl chloride. mp 120-123° C.; $^1$H NMR (500 MHz, CDCl$_3$) δ 8.41 (d, J=4.9 Hz, 1 H), 8.29 (dd, J=9.2, 7.6 Hz, 1 H), 7.37 (dd, J=7.6, 4.9 Hz, 1 H), 3.96 (d, J=12.6 Hz, 2 H), 2.81 (d, J=11.5 Hz, 2 H), 2.67 (t, J=12.4 Hz, 2 H), 2.34 (ddd, J=11.5, 8.0, 3.5 Hz, 1 H), 2.15 (t, J=10.4 Hz, 2 H), 1.87 (d, J=12.1 Hz, 2 H), 1.74-1.55 (m, 4 H), 1.32 (ddt, J=10.3, 6.9, 4.1 Hz, 1 H), 1.27-1.11 (m, 2 H), 0.91 (d, J=6.4 Hz, 3 H); $^{13}$C NMR (100 MHz, CDCl$_3$) δ 154.75 (d, J=244.0 Hz), 147.68 (d, J=14.3 Hz), 138.2, 118.2, 117.9, 57.5, 45.6, 41.9, 30.7, 27.1, 23.8, 17.9; MS (ESI) m/z 342.2 (100%, [M+H]+).

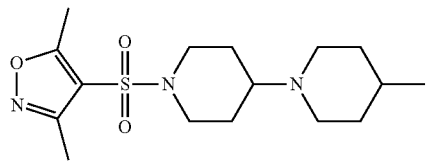 [SMILES: Cc1noc(C)c1S(=O)(=O)N1CCC(N2CCC(C)CC2)CC1]

3,5-dimethyl-4-((4-methyl-[1,4'-bipiperidin]-1'-yl)sulfonyl)isoxazole: This compound was obtained as a white solid (28%) through recrystallization in a mixture of CH$_2$Cl$_2$ and hexane after the reaction between 4-methyl-1,4'-bipiperidine and 3,5-dimethylisoxazole-4-sulfonyl chloride. mp 158-161° C.; $^1$H NMR (400 MHz, CDCl$_3$) δ 3.78 (d, J=11.9 Hz, 2H), 2.80 (d, J=11.5 Hz, 2H), 2.61 (s, 3H), 2.50 (t, J=12.0 Hz, 2H), 2.38 (s, 3H), 2.27 (tt, J=11.4, 3.5 Hz, 1H), 2.14-2.06 (m, 2H), 1.87 (d, J=11.6 Hz, 2H), 1.72-1.50 (m, 4H), 1.30 (m, 1H), 1.25-1.09 (m, 2H), 0.89 (d, J=6.4 Hz, 3H); $^{13}$C NMR (100 MHz, CDCl$_3$) δ 173.5, 158.0, 113.7, 61.3, 49.6, 45.4, 34.6, 31.0, 27.5, 21.9, 13.0, 11.4; MS (ESI) m/z 342.2 (100%, [M+H]+).

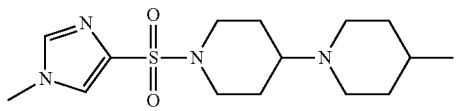

4-methyl-1'-((1-methyl-1H-imidazol-4-yl)sulfonyl)-1,4'-bipiperidine: This compound was obtained as a yellow solid (61%) through recrystallization in a mixture of CH$_2$Cl$_2$ and hexane after the reaction between 4-methyl-1,4'-bipiperidine and 1-methyl-1H-imidazole-4-sulfonyl chloride. mp 139-142° C.; $^1$H NMR (500 MHz, CDCl$_3$) δ 7.48 (s, 1H), 7.42 (s, 1H), 3.90 (d, J=13.0 Hz, 2H), 3.75 (s, 3H), 2.80 (d, J=9.9

Hz, 2H), 2.57 (t, J=12.1 Hz, 2H), 2.26 (t, J=11.5 Hz, 1H), 2.13 (t, J=10.5 Hz, 2H), 1.83 (d, J=12.1 Hz, 2H), 1.64 (m, 4H), 1.31 (s, br, 1H), 1.26-1.12 (m, 2H), 0.90 (d, J=6.4 Hz, 3H); $^{13}$C NMR (100 MHz, CDCl$_3$) δ 139.0, 138.3, 124.4, 61.7, 49.5, 46.3, 34.6, 34.0, 31.1, 27.4, 21.9; MS (ESI) m/z 327.2 (100%, [M+H]+).

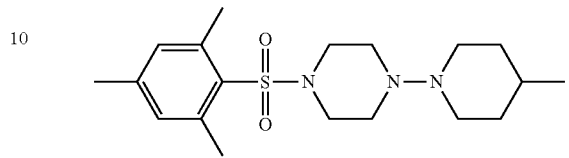

1-(mesitylsulfonyl)-4-(1-methylpiperidin-4-yl)piperazine: This compound was obtained as a colorless gel (>95%) through flash chromatography (1:9 MeOH:CH$_2$Cl$_2$) after the reaction between 1-(1-methylpiperidin-4-yl)piperazine (1.0 mmol) and 2,4,6-trimethylbenzenesulfonyl chloride (1.1 mmol) in CH$_2$Cl$_2$ in the presence of N, N-diisopropyl ethylamine (1.5 mmol). $^1$H NMR (400 MHz, CDCl$_3$) δ 6.91 (s, 2 H), 3.23-3.04 (m, 4 H), 2.85 (d, J=12.2 Hz, 2 H), 2.59 (s, 6 H), 2.57-2.48 (m, 4 H), 2.26 (s, 3 H), 2.22 (s, 3 H), 2.19 (m, 1 H), 1.89 (t, J=12.0 Hz, 2 H), 1.69 (d, J=11.0 Hz, 2 H), 1.51 (qd, J=12.3, 3.9 Hz, 2 H).; $^{13}$C NMR (100 MHz, CDCl$_3$) δ 142.5, 140.4, 131.9, 131.3, 61.4, 55.3, 48.4, 46.1, 44.7, 28.0, 23.0, 21.0.; MS (ESI) m/z 366.2 (60%, [M+H]+), 414.2 (100%, [M+K]+).

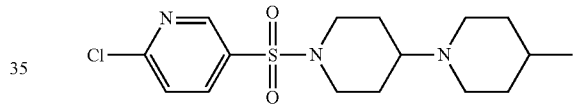

1'-((6-chloropyridin-3-yl)sulfonyl)-4-methyl-1,4'-bipiperidine: This compound was obtained as a white solid (80%) through flash chromatography (1:9 MeOH:CH$_2$Cl$_2$) after the reaction between 4-methyl-1,4'-bipiperidine and 6-chloropyridine-3-sulfonyl chloride. mp 178-182° C. $^1$H NMR (500 MHz, CDCl$_3$) δ 8.75 (s, 1H), 7.99 (dd, J=8.4, 2.3 Hz, 1H), 7.51 (d, J=8.3 Hz, 1H), 3.87 (d, J=12.0 Hz, 2H), 2.81 (d, J=8.5 Hz, 2H), 2.35 (t, J=12.0 Hz, 2H), 2.25 (t, J=11.4 Hz, 1H), 2.14 (t, J=11.3 Hz, 2H), 1.89 (d, J=11.3 Hz, 2H), 1.75-1.58 (m, 4H), 1.33 (s, br, 1H), 1.21 (m, 2H), 0.91 (d, J=6.6 Hz, 3H); $^{13}$C NMR (100 MHz, CDCl$_3$) δ 155.6, 148.6, 137.7, 132.1, 124.7, 61.3, 49.5, 46.0, 34.4, 30.9, 27.3, 21.8; MS (ESI) m/z 358.1 (100%, [M+H]+).

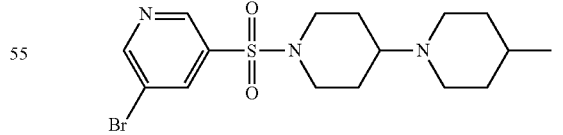

1'-((5-bromopyridin-3-yl)sulfonyl)-4-methyl-1,4'-bipiperidine: This compound was obtained as a white solid (79%) through flash chromatography (1:9 MeOH:CH$_2$Cl$_2$) after the reaction between 4-methyl-1,4'-bipiperidine and 5-bromopyridine-3-sulfonyl chloride. mp 171-173° C.; $^1$H NMR (500 MHz, CDCl$_3$) δ 8.81 (s, 2 H), 8.18 (t, J=2.0 Hz, 1 H), 3.89 (d, J=11.6 Hz, 2 H), 2.81 (d, J=11.0 Hz, 2 H), 2.39 (td, J=12.0, 2.5 Hz, 2 H), 2.25 (d, J=11.9 Hz, 1 H), 2.14 (t, J=11.6 Hz, 2 H), 1.90 (d, J=12.8 Hz, 2 H), 1.78-1.57 (m, 4 H), 1.43-1.29 (m, 1 H), 1.20 (m, 2 H), 0.91 (d, J=6.4 Hz, 3 H); $^{13}$C NMR (100 MHz, CDCl$_3$) δ 154.4, 146.2, 137.4, 134.5, 121.0, 61.2, 49.5, 46.0, 34.5, 31.0, 27.3, 21.8; MS (ESI) m/z 402.1 (100%, [M+]+), 404.1 (100%, [M+2]+).

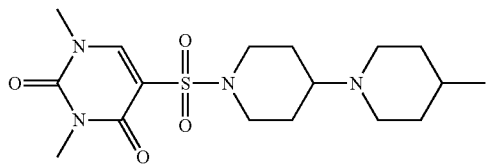 [SMILES: CC1CCN(C2CCN(S(=O)(=O)c3cn(C)c(=O)n(C)c3=O)CC2)CC1]

1,3-dimethyl-5-((4-methyl-[1,4'-bipiperidin]-1'-yl)sulfonyl) pyrimidine-2,4 (1H,3H)-dione: This compound was obtained as a white solid (78%) through flash chromatography (1:9 MeOH:CH$_2$Cl$_2$) after the reaction between 4-methyl-1,4'-bipiperidine and 1,3-dimethyl-2,4-dioxo-1,2,3,4-tetrahydropyrimidine-5-sulfonyl chloride. mp 212-215° C.; $^1$H NMR (500 MHz, CDCl$_3$) δ 8.07 (s, 1H), 3.94 (d, J=12.8 Hz, 2 H), 3.50 (s, 3 H), 3.35 (s, 3 H), 2.93 (d, J=11.6 Hz, 2 H), 2.85 (t, J=12.7 Hz, 2 H), 2.56 (t, J=11.7 Hz, 1 H), 2.26 (t, J=11.9 Hz, 2 H), 1.92 (d, J=11.9 Hz, 2 H), 1.75-1.58 (m, 4H), 1.48-1.20 (m, 3H), 0.93 (d, J=6.0 Hz, 3H); $^{13}$C NMR (100 MHz, CDCl$^3$) δ 158.2, 150.8, 148.1, 112.6, 61.6, 49.2, 46.0, 37.9, 33.8, 30.7, 28.3, 27.5, 21.7; MS (ESI) m/z 385.2 (100%, [M+H]+).

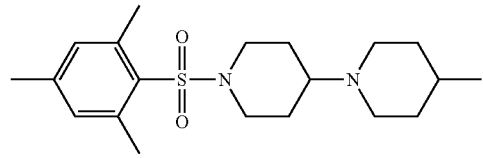

1'-(mesitylsulfonyl)-4-methyl-1,4'-bipiperidine: This compound was obtained as a yellow solid (>95%) through flash chromatography (1:19 MeOH:CH$_2$Cl$_2$) after the reaction between 4-methyl-1,4'-bipiperidine and 2,4,6-trimethylbenzene-1-sulfonyl chloride. mp 62-65° C.; $^1$H NMR (500 MHz, CDCl$_3$) δ 6.94 (s, 2 H), 3.62 (d, J=12.5 Hz, 2 H), 2.85 (d, J=12.4 Hz, 2 H), 2.75 (t, J=12.4 Hz, 2 H), 2.61 (s, 6 H), 2.34 (t, J=11.5 Hz, 1 H), 2.29 (s, 3 H), 2.12 (t, J=11.4 Hz, 2 H), 1.86 (d, J=11.1 Hz, 2H), 1.63 (d, J=13.4 Hz, 2 H), 1.50 (qd, J=12.3, 4.0 Hz, 2H), 1.39-1.27 (s, br, 1 H), 1.27-1.13 (m, 2 H), 0.90 (d, J=6.6 Hz, 3 H); $^{13}$C NMR (100 MHz, CDCl$_3$) δ 142.4, 140.4, 131.8, 131.7, 61.8, 49.6, 44.0, 34.6, 31.0, 27.7, 22.8, 21.9, 20.9; MS (ESI) m/z 365.2 (100%, [M+H]+).

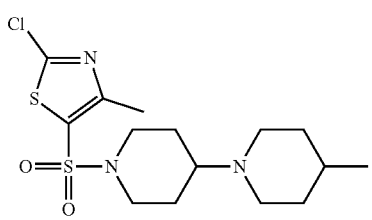 [SMILES: Cc1nc(Cl)sc1S(=O)(=O)N1CCC(N2CCC(C)CC2)CC1]

2-chloro-4-methyl-5-((4-methyl-[1,4'-bipiperidin]-1'-yl)sulfonyl)thiazole: This compound was obtained as a white solid (64%) through flash chromatography (1:19 MeOH:CH$_2$Cl$_2$) after the reaction between 4-methyl-1,4'-bipiperidine and 2-chloro-4-methylthiazole-5-sulfonyl chloride. mp 117-119° C.; $^1$H NMR (400 MHz, CDCl$_3$) δ 3.85 (d, J=13.5 Hz, 2 H), 2.82 (d, J=11.0 Hz, 2 H), 2.60 (s, 3 H), 2.53 (t, J=12.0 Hz, 2 H), 2.34 (t, J=11.9 Hz, 1 H), 2.15 (t, J=11.4 Hz, 2 H), 1.91 (d, J=12.7 Hz, 2 H), 1.65 (m, 4 H), 1.45-1.29 (m, 1 H), 1.22 (m, 2 H), 0.89 (d, J=6.2 Hz, 3 H); $^{13}$C NMR (100 MHz, CDCl$_3$) δ 155.4, 154.4, 128.9, 61.3, 49.5, 46.0, 34.3, 30.9, 27.3, 21.8, 16.8; MS (ESI) m/z 378.1 (100%, [M+H]+).

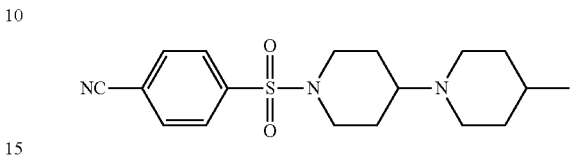

4-((4-methyl-[1,4'-bipiperidin]-1'-yl)sulfonyl)benzonitrile: This compound was obtained as a white solid (86%) through flash chromatography (1:19 MeOH:CH$_2$Cl$_2$) after the reaction between 4-methyl-1,4'-bipiperidine and 4-cyanobenzene-1-sulfonyl chloride. mp 184-186° C.; $^1$H NMR (400 MHz, CDCl$_3$) δ 7.84 (q, J=8.5 Hz, 4 H), 3.85 (d, J=12.1 Hz, 2 H), 2.77 (d, J=11.6 Hz, 2 H), 2.31 (t, J=12.0 Hz, 2 H), 2.22 (tt, J=11.6, 3.6 Hz, 1 H), 2.11 (t, J=12.2 Hz, 2 H), 1.85 (d, J=11.6 Hz, 2 H), 1.71-1.55 (m, 4 H), 1.31 (m, 1 H), 1.25-1.10 (m, 2 H), 0.89 (d, J=6.4 Hz, 3 H); $^{13}$C NMR (100 MHz, CDCl$_3$) δ 140.9, 132.8, 128.1, 117.3, 116.4, 61.2, 49.5, 46.1, 34.6, 31.0, 27.4, 21.8; MS (ESI) m/z 348.2 (100%, [M+H]+).

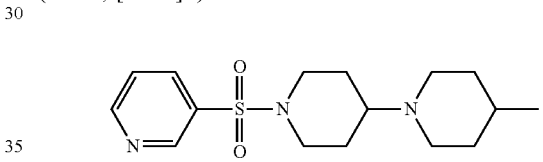

4-methyl-1'-(pyridin-3-ylsulfonyl)-1,4'-bipiperidine: This compound was obtained as a yellow solid (86%) through flash chromatography (1:9 MeOH:CH$_2$Cl$_2$) after the reaction between 4-methyl-1,4'-bipiperidine and pyridine-3-sulfonyl chloride. mp 144-147° C.; $^1$H NMR (500 MHz, CDCl$_3$) δ 8.98 (s, 1 H), 8.82 (d, J=4.9 Hz, 1 H), 8.04 (d, J=8.1 Hz, 1 H), 7.49 (dd, J=8.0, 4.9 Hz, 1 H), 3.88 (d, J=12.3 Hz, 2 H), 2.78 (d, J=11.9 Hz, 2 H), 2.32 (td, J=12.0, 2.4 Hz, 2 H), 2.22 (tt, J=11.6, 3.6 Hz, 1H), 2.12 (t, J=11.6 Hz, 2 H), 1.86 (d, J=11.9 Hz, 2 H), 1.75-1.55 (m, 4 H), 1.31 (m, 1 H), 1.17 (qd, J=12.0, 3.7 Hz, 2 H), 0.89 (d, J=6.5 Hz, 3 H); $^{13}$C NMR (100 MHz, CDCl$_3$) δ 153.3, 148.4, 135.2, 133.1, 123.7, 61.3, 49.5, 46.0, 34.5, 31.0, 27.3, 21.8; MS (ESI) m/z 324.2 (100%, [M+H]+).

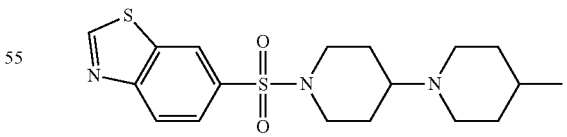

6-((4-methyl-[1,4'-bipiperidin]-1'-yl)sulfonyl)benzo[d]thiazole: This compound was obtained as a yellow solid (93%) through flash chromatography (1:19 MeOH:CH$_2$Cl$_2$) after the reaction between 4-methyl-1,4'-bipiperidine and benzo[d]thiazole-6-sulfonyl chloride. mp 197-199° C.; $^1$H NMR (400 MHz, CDCl$_3$) δ 9.19 (s, 1 H), 8.41 (d, J=1.8 Hz, 1 H), 8.24 (d, J=8.6 Hz, 1 H), 7.86 (dd, J=8.5, 1.8 Hz, 1 H), 3.89 (d, J=12.3, 2 H), 2.75 (d, J=10.7 Hz, 2 H), 2.45-2.02 (m, 5

H), 1.84 (d, J=12.4 Hz, 2 H), 1.76-1.51 (m, 4 H), 1.44-1.05 (m, 3 H), 0.87 (d, J=6.3 Hz, 3 H); $^{13}$C NMR (100 MHz, CDCl$_3$) δ 157.8, 155.5, 134.3, 133.5, 125.2, 124.1, 122.4, 61.4, 49.4, 46.2, 34.4, 30.9, 27.3, 21.8; MS (ESI) m/z 380.1 (100%, [M+H]+).

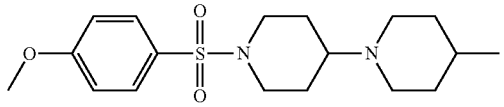

1'-((4-methoxyphenyl)sulfonyl)-4-methyl-1,4'-bipiperidine: This compound was obtained as a white solid (94%) through flash chromatography (1:19 MeOH:CH$_2$Cl$_2$) after the reaction between 4-methyl-1,4'-bipiperidine and 4-methoxybenzene-1-sulfonyl chloride. mp 109-112° C.; $^1$H NMR (400 MHz, CDCl$_3$) δ7.67 (d, J=8.8 Hz, 2H), 6.97 (d, J=8.8 Hz, 2H), 3.85 (s, 3H), 3.83-3.74 (d, J=12.0 Hz, 2H), 2.76 (d, J=11.7 Hz, 2H), 2.28-2.04 (m, 5H), 1.88-1.75 (d, J=12.9 Hz, 2H), 1.72-1.54 (m, 4H), 1.28 (m, 1H), 1.23-1.08 (m, 2H), 0.87 (d, J=6.3 Hz, 3H); $^{13}$C NMR (100 MHz, CDCl$_3$) δ 162.9, 129.8, 127.6, 114.1, 61.5, 55.6, 49.5, 46.2, 34.6, 31.0, 27.3, 21.9; MS (ESI) m/z 353.2 (100%, [M+H]+).

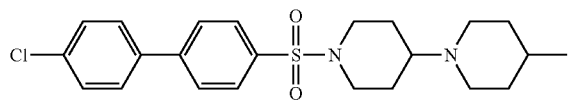 [SMILES: CC1CCN(C2CCN(S(=O)(=O)c3ccc(-c4ccc(Cl)cc4)cc3)CC2)CC1]

1'-((4'-chloro-[1,1'-biphenyl]-4-yl)sulfonyl)-4-methyl-1,4'-bipiperidine: This compound was obtained as a white solid (87%) through flash chromatography (1:9 MeOH:CH$_2$Cl$_2$) after the reaction between 4-methyl-1,4'-bipiperidine and 4'-chloro-[1,1'-biphenyl]-4-sulfonyl chloride. mp 205-207° C.; $^1$H NMR (400 MHz, CDCl$_3$) δ 7.88-7.75 (m, 2 H), 7.67 (d, J=8.4 Hz, 2 H), 7.51 (d, J=8.5 Hz, 2 H), 7.43 (d, J=8.5 Hz, 2 H), 3.87 (d, J=12.0 Hz, 2 H), 2.76 (d, J=10.9 Hz, 2 H), 2.41-2.02 (m, 5 H), 1.83 (dd, J=12.3, 3.6 Hz, 2 H), 1.70-1.46 (m, 4 H), 1.37-1.05 (m, 3 H), 0.87 (d, J=6.3 Hz, 3H); $^{13}$C NMR (100 MHz, CDCl$_3$) δ 144.2, 137.7, 135.1, 134.7, 129.2, 128.5, 128.3, 127.4, 61.4, 49.5, 46.2, 34.6, 31.0, 27.3, 21.8; MS (ESI) m/z 433.2 (100%, [M+H]+).

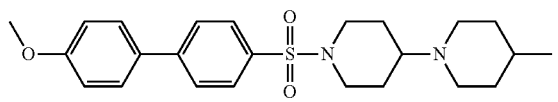

1'-((4'-methoxy-[1,1'-biphenyl]-4-yl)sulfonyl)-4-methyl-1, 4'-bipiperidine: This compound was obtained as a white solid (92%) through flash chromatography (1:9 MeOH: CH$_2$Cl$_2$) after the reaction between 4-methyl-1,4'-bipiperidine and 4'-methoxy-[1,1'-biphenyl]-4-sulfonyl chloride. mp 195-198° C.; $^1$H NMR (400 MHz, CDCl$_3$) δ 7.85-7.72 (m, 2 H), 7.66 (d, J=8.5 Hz, 2 H), 7.53 (d, J=8.7 Hz, 2 H), 7.04-6.88 (m, 2 H), 3.88 (d, J=12.0 Hz, 2 H), 3.84 (s, 3 H), 2.76 (d, J=11.6 Hz, 2 H), 2.40-1.95 (m, 5 H), 1.83 (d, J=10.7 Hz, 2 H), 1.71-1.48 (m, 4 H), 1.29 (m, 1 H), 1.23-1.04 (m, 2 H), 0.87 (d, J=6.3 Hz, 3 H).; $^{13}$C NMR (100 MHz, CDCl$_3$) δ 160.0, 145.1, 133.9, 131.6, 128.4, 128.2, 126.9, 114.5, 61.5, 55.4, 49.5, 46.2, 34.6, 31.0, 27.4, 21.9; MS (ESI) m/z 429.2 (100%, [M+H]+).

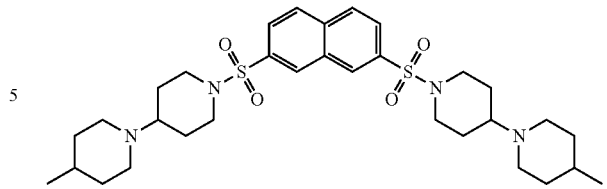

2,7-bis((4-methyl-[1,4'-bipiperidin]-1'-yl)sulfonyl)naphthalene: This compound was obtained as a white solid (92%) through flash chromatography (1:19 MeOH:CH$_2$Cl$_2$) after the reaction of 4-methyl-1,4'-bipiperidine (0.39 mmol) with naphthalene-2,7-disulfonyl dichloride (0.15 mmol) in CH$_2$Cl$_2$ (2.5 mL) in the presence of N, N-diisopropyl ethylamine (0.52 mmol). mp 265-268° C.; $^1$H NMR (400 MHz, CDCl$_3$) δ 8.42 (s, 2 H), 8.04 (d, J=8.7 Hz, 2 H), 7.89 (dd, J=8.6, 1.7 Hz, 2 H), 3.92 (d, J=12.3 Hz, 4 H), 2.75 (d, J=11.7 Hz, 4 H), 2.32 (td, J=12.1, 2.4 Hz, 4 H), 2.25-1.99 (m, 6 H), 1.84 (d, J=11.5 Hz, 4 H), 1.72-1.51 (m, 8 H), 1.37-1.21 (m, 2 H), 1.21-1.07 (m, 4 H), 0.86 (d, J=6.3 Hz, 6 H); $^{13}$C NMR (100 MHz, CDCl$_3$) δ 136.0, 135.5, 131.3, 129.7, 129.2, 125.8, 61.4, 49.5, 46.2, 34.5, 31.0, 27.4, 21.8; MS (ESI) m/z 617.3 (100%, [M+H]+)

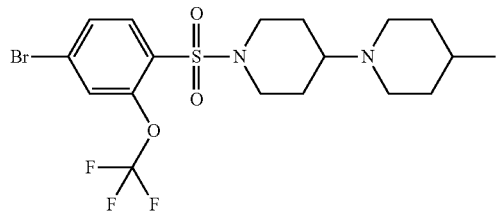

1'-((4-bromo-2-(trifluoromethoxy)phenyl)sulfonyl)-4-methyl-1,4'-bipiperidine was obtained as a yellow solid (67%) through flash chromatography (1:19 MeOH:CH$_2$Cl$_2$) after the reaction between 4-methyl-1,4'-bipiperidine and 4-bromo-2-(trifluoromethoxy)benzene-1-sulfonyl chloride. mp 108-110° C.; $^1$H NMR (400 MHz, CDCl$_3$) δ 7.83 (d, J=8.9 Hz, 1 H), 7.58-7.45 (m, 2 H), 3.85 (d, J=12.7 Hz, 2 H), 2.78 (dt, J=11.9, 3.3 Hz, 2 H), 2.59 (td, J=12.5, 2.5 Hz, 2 H), 2.29 (tt, J=11.5, 3.6 Hz, 1 H), 2.11 (td, J=11.5, 2.4 Hz, 2 H), 1.82 (dt, J=12.7, 2.7 Hz, 2 H), 1.69-1.45 (m, 4 H), 1.40-1.24 (m, 1 H), 1.23-1.05 (m, 2 H), 0.88 (d, J=6.3 Hz, 3 H); $^{13}$C NMR (100 MHz, CDCl$_3$) δ 146.2, 132.7, 130.1, 129.8, 127.9, 123.90, 121.3, 61.5, 49.5, 45.7, 34.59, 31.0, 27.8, 21.8; MS (ESI) m/z 485.1 (100%, [M+H]+)

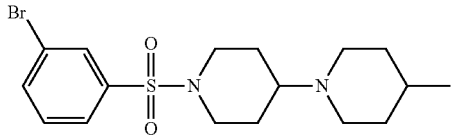 [SMILES: CC1CCN(C2CCN(S(=O)(=O)c3cccc(Br)c3)CC2)CC1]

1'-((3-bromophenyl)sulfonyl)-4-methyl-1,4'-bipiperidine was obtained as a white solid (65%) through flash chromatography (1:19 MeOH:CH$_2$Cl$_2$) after the reaction between 4-methyl-1,4'-bipiperidine and 3-bromobenzene-1-sulfonyl chloride. mp 125-126° C.; $^1$H NMR (400 MHz, CDCl$_3$) δ 7.85 (s, 1 H), 7.66 (dd, J=13.3, 7.9 Hz, 2 H), 7.37 (t, J=7.9 Hz, 1 H), 3.80 (d, J=11.7 Hz, 2 H), 2.74 (d, J=11.0 Hz, 2 H), 2.16 (dt, J=73.4, 11.4 Hz, 5 H), 1.81 (d, J=12.7 Hz, 2 H), 1.60 (td, J=12.4, 8.1 Hz, 4 H), 1.27 (dt, J=11.0, 5.9 Hz, 1 H), 1.20-1.02 (m, 2 H), 0.85 (d, J=6.2 Hz, 3 H); $^{13}$C NMR (100 MHz, CDCl$_3$) δ 138.2, 135.7, 130.5, 130.3, 126.1, 123.1, 61.3, 49.5, 46.1, 34.6, 31.0, 27.4, 21.9; MS (ESI) m/z 401.1 (100%, [M+]+), 403.1 (100%, [M+2]+).

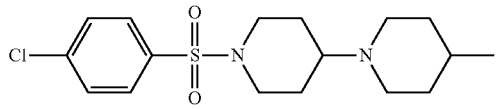 [SMILES: CC1CCN(C2CCN(S(=O)(=O)c3ccc(Cl)cc3)CC2)CC1]

1'-((4-chlorophenyl)sulfonyl)-4-methyl-1,4'-bipiperidine was obtained as a white solid (67%) through recrystallization in a mixture of CH$_2$Cl$_2$ and hexane after the reaction between 4-methyl-1,4'-bipiperidine and 4-chlorobenzene-1-sulfonyl chloride. mp 152-155° C.; $^1$H NMR (400 MHz, CDCl$_3$) δ 7.66 (d, J=8.5 Hz, 2 H), 7.47 (d, J=8.5 Hz, 2 H), 3.93-3.69 (m, 2 H), 2.80 (dt, J=11.6, 3.4 Hz, 2 H), 2.23 (td, J=12.0, 2.5 Hz, 3 H), 2.15 (t, J=11.3 Hz, 2 H), 1.84 (d, J=12.6 Hz, 2 H), 1.71-1.54 (m, 4 H), 1.42-1.26 (m, 1 H), 1.25-1.12 (m, 2 H), 0.87 (d, J=6.2 Hz, 3H); $^{13}$C NMR (100 MHz, CDCl$_3$) δ 139.3, 134.6, 129.3, 129.0, 61.4, 49.4, 46.0, 34.2, 30.8, 27.2, 21.7; MS (ESI) m/z 357.2 (100%, [M+H]+).

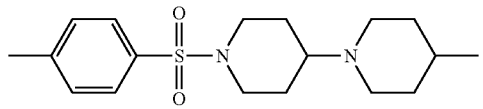

4-methyl-1'-tosyl-1,4'-bipiperidine was obtained as a white solid (67%) through recrystallization in a mixture of CH$_2$Cl$_2$ and hexane after the reaction between 4-methyl-1,4'-bipiperidine and 4-methylbenzene-1-sulfonyl chloride. mp 139-142° C.; $^1$H NMR (400 MHz, CDCl$_3$) δ 7.59 (d, J=8.2 Hz, 2 H), 7.28 (d, J=8.2 Hz, 2 H), 3.80 (d, J=11.9 Hz, 2 H), 2.79 (d, J=11.1 Hz, 2 H), 2.39 (s, 3 H), 2.30-2.07 (m, 5 H), 1.84 (d, J=10.9 Hz, 2 H), 1.69-1.53 (m, 4 H), 1.40-1.09 (m, 3 H), 0.86 (d, J=6.2 Hz, 3 H); $^{13}$C NMR (100 MHz, CDCl$_3$) δ 143.5, 132.9, 129.6, 127.7, 61.6, 49.4, 46.0, 34.1, 30.8, 27.1, 21.7, 21.5; MS (ESI) m/z 337.2 (100%, [M+H]+).

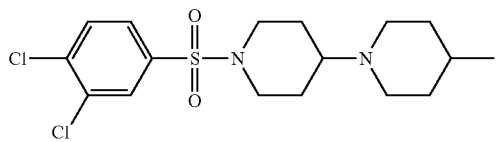

1'-((3,4-dichlorophenyl)sulfonyl)-4-methyl-1,4'-bipiperidine was obtained as a light brown solid (86%) through flash chromatography (1:19 MeOH:CH$_2$Cl$_2$) after the reaction between 4-methyl-1,4'-bipiperidine and 3,4-dichlorobenzene-1-sulfonyl chloride. mp 160-162° C.; $^1$H NMR (400 MHz, CDCl$_3$) δ 7.81 (d, J=1.9 Hz, 1 H), 7.66-7.44 (m, 2 H), 3.81 (d, J=12.1 Hz, 2 H), 2.76 (d, J=11.2 Hz, 2 H), 2.29 (td, J=11.9, 2.5 Hz, 2 H), 2.20 (tt, J=11.5, 3.5 Hz, 1 H), 2.10 (td, J=11.5, 2.4 Hz, 2 H), 1.84 (d, J=11.5 Hz, 2 H), 1.62 (ddt, J=16.3, 12.5, 5.6 Hz, 4 H), 1.28 (tdd, J=12.8, 10.3, 5.5 Hz, 1 H), 1.15 (qd, J=11.8, 11.2, 3.7 Hz, 2 H), 0.87 (d, J=6.5 Hz, 3 H); $^{13}$C NMR (100 MHz, CDCl$_3$) δ 137.5, 136.2, 133.8, 131.1, 129.4, 126.6, 61.3, 49.5, 46.1, 34.6, 31.0, 27.4, 21.8; MS (ESI) m/z 391.1 (100%, [M+H]+).

III. General Procedure for the Preparation of Sulfonamides from Sulfonyl Chlorides and Amine Hydrochloride Salts Sulfonyl chloride (1.2 mmol), amine hydrochloride salt (1.0 mmol), CHCl$_3$ (2 mL), water (2 mL) and K$_2$CO$_3$ (2.5 mmol) were added to a 15 ml flask sequentially. The bi-phase reaction solution was stirred vigorously at room temperature for 20 h after which the reaction solution was transferred to a separatory funnel and 25 mL saturated NaHCO$_3$ solution was added. The resulting bi-phase solution was extracted by CH$_2$Cl$_2$ (3×20 mL) and the combined organic layers were dried over Na$_2$SO$_4$, filtered and concentrated under reduced pressure. The residue was purified through flash chromatography on silica gel with a Hexane:EtOAc (or MeOH:CH$_2$Cl$_2$) mixture as eluent to provide the sulfonamide product.

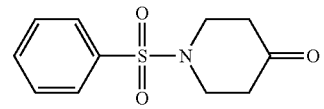 [SMILES: O=C1CCN(S(=O)(=O)c2ccccc2)CC1]

1-(phenylsulfonyl)piperidin-4-one: This compound was obtained as a white solid (93%) through flash chromatography (1:1 Hexane:EtOAc). mp 105-108° C.; $^1$H NMR (400 MHz, CDCl$_3$) δ 7.85-7.73 (m, 2 H), 7.66-7.58 (m, 1 H), 7.58-7.48 (m, 2 H), 3.39 (t, J=6.2 Hz, 4 H), 2.52 (t, J=6.2 Hz, 4 H); $^{13}$C NMR (126 MHz, CDCl$_3$) δ 205.6, 136.3, 133.2, 129.3, 127.5, 45.9, 40.7. The analytical data were consistent with the literature report (Ellis, G. L. et al. J. Med. Chem. 2008, 51, 2170-2177).

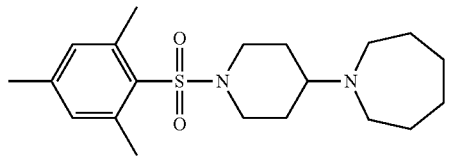 [SMILES: Cc1cc(C)c(S(=O)(=O)N2CCC(N3CCCCCC3)CC2)c(C)c1]

1-(1-(mesitylsulfonyl)piperidin-4-yl)azepane: This compound was obtained as an orange gel (90%) through flash chromatography (1:19 MeOH:CH$_2$Cl$_2$). $^1$H NMR (400 MHz, CDCl$_3$) δ 6.94 (s, 2 H), 3.71 (d, J=11.8 Hz, 2 H), 3.62 (s, br, 1 H), 3.18-2.89 (s, 4 H), 2.77 (t, J=12.7 Hz, 2 H), 2.58 (s, 6 H), 2.29 (s, 3 H), 2.10 (d, J=12.5 Hz, 2 H), 1.82 (s, 4 H), 1.76-1.54 (m, 6 H); $^{13}$C NMR (100 MHz, CDCl$_3$) δ 142.8, 140.3, 132.0, 132.0, 132.0, 131.5, 63.3, 51.2, 43.8, 26.9, 26.6, 26.4, 22.8, 21.0. MS (ESI) m/z 365.2 (100%, [M+H]+).

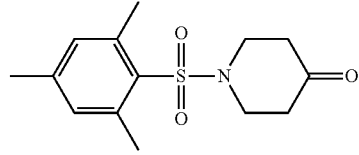 [SMILES: Cc1cc(C)c(S(=O)(=O)N2CCC(=O)CC2)c(C)c1]

1-(mesitylsulfonyl)piperidin-4-one: This compound was obtained as a white solid (95%) through flash chromatography ((1:19 MeOH:CH$_2$Cl$_2$). mp 102-105° C.; $^1$H NMR (400 MHz, CDCl$_3$) δ 6.95 (s, 2 H), 3.50 (t, J=6.2 Hz, 4 H), 2.61 (s, 6 H), 2.52 (t, J=6.2 Hz, 4 H), 2.29 (s, 3 H); $^{13}$C NMR (100 MHz, CDCl$_3$) δ 201.6, 138.3, 135.6, 127.4, 126.8, 39.6, 36.3, 18.1, 16.2; MS (ESI) m/z 282.1 (100%, [M+H]+).

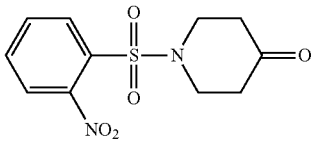

1-((2-nitrophenyl)sulfonyl)piperidin-4-one: This compound was obtained as a white solid (88%) through flash chromatography ((1:19 MeOH:CH$_2$Cl$_2$). mp 107-109° C.; $^1$H NMR (400 MHz, CDCl$_3$) δ 8.13-7.96 (m, 1 H), 7.81-7.58 (m, 3 H), 3.64 (t, J=6.3 Hz, 4 H), 2.63-2.45 (t, J=6.3 Hz, 4 H); $^{13}$C NMR (100 MHz, CDCl$_3$) δ 205.4, 134.1, 131.9, 131.9, 130.9, 124.4, 45.5, 41.2; MS (ESI) m/z 285.0 (100%, [M+H]+).

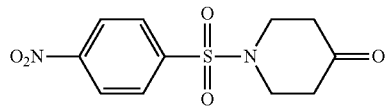 [SMILES: O=C1CCN(S(=O)(=O)c2ccc([N+](=O)[O-])cc2)CC1]

1-((4-nitrophenyl)sulfonyl)piperidin-4-one: This compound was obtained as a white solid (82%) through flash chromatography ((1:19 MeOH:CH$_2$Cl$_2$). mp 192-195° C.; $^1$H NMR (400 MHz, CDCl$_3$) δ 8.47-8.33 (m, 2 H), 7.98 (d, J=8.8 Hz, 2 H), 3.46 (t, J=6.2 Hz, 4 H), 2.56 (t, J=6.2 Hz, 4 H); $^{13}$C NMR (100 MHz, CDCl$_3$) δ 204.5, 150.4, 142.7, 128.6, 124.6, 45.8, 40.7; MS (ESI) m/z 285.1 (100%, [M+H]+).

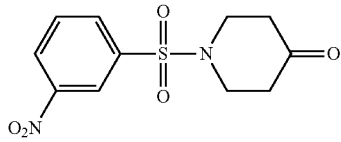

1-((3-nitrophenyl)sulfonyl)piperidin-4-one: This compound was obtained as a white solid (90%) through flash chromatography ((1:19 MeOH:CH$_2$Cl$_2$). mp 141-143° C.; $^1$H NMR (400 MHz, CDCl$_3$) δ 8.60 (s, 1 H), 8.48-8.43 (m, 1 H), 8.14-8.07 (m, 1 H), 7.78 (t, J=8.0 Hz, 1H), 3.46 (t, J=6.2 Hz, 4 H), 2.56 (t, J=6.2 Hz, 4 H); $^{13}$C NMR (100 MHz, CDCl$_3$) δ 204.6, 148.5, 139.1, 132.8, 130.8, 127.6, 122.5, 45.8, 40.7; MS (ESI) m/z 285.1 (100%, [M+H]+).

IV. General Procedure for the Methylation of Tertiary Amines

Tertiary amine (0.1 mmol) was dissolved in acetonitrile (3 mL) and CH$_3$I (0.3 mmol) was added dropwise. The resulting mixture was stirred at reflux for 4 h. Upon evaporation of the organic solvent in vacuo, the corresponding quaternary ammonium salt was obtained without further purification unless noted otherwise.

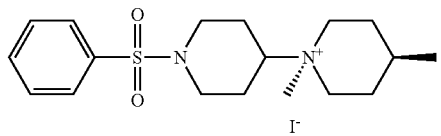

1,4-dimethyl-1-(1-(phenylsulfonyl)piperidin-4-yl)piperidin-1-ium iodide(N-methyl and C-methyl are trans): This trans isomer was obtained as a yellow solid (58%) through flash chromatography (1:9 EtOH:CH$_2$Cl$_2$) after the methylation of 4-methyl-1'-(phenylsulfonyl)-1,4'-bipiperidine. mp 201-204° C.; $^1$H NMR (400 MHz, DMSO-d6) δ 7.73 (m, 3 H), 7.65 (m, 2 H), 3.78 (d, J=12.0 Hz, 2 H), 3.36 (d, J=12.0 Hz, 3 H), 3.07 (t, J=12.0 Hz, 2 H), 2.84 (s, 3 H), 2.18 (t, J=12.4 Hz, 4 H), 1.78 (qd, J=12.0, 3.9 Hz, 2 H), 1.67 (d, J=12.0 Hz, 2 H), 1.54 (m, 3H), 0.91 (d, J=4.0 Hz, 3 H); $^{13}$C NMR (100 MHz, DMSO-d6) δ 135.1, 133.9, 130.0, 128.0, 72.0, 58.5, 45.6, 41.1, 27.9, 27.6, 24.6, 20.7; MS (ESI) m/z 337.2 (100%, [M−I]+).

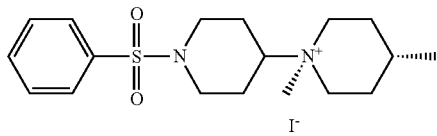 [SMILES: C[C@H]1CC[N@+](C)(C2CCN(S(=O)(=O)c3ccccc3)CC2)CC1 ; [I-]]

1,4-dimethyl-1-(1-(phenylsulfonyl)piperidin-4-yl)piperidin-1-ium iodide(N-methyl and C-methyl are cis): This cis isomer was obtained as a white solid (28%) through flash chromatography (1:9 EtOH:CH$_2$Cl$_2$) after the methylation of 4-methyl-1'-(phenylsulfonyl)-1,4'-bipiperidine. mp 264-266° C.; $^1$H NMR (400 MHz, DMSO-d6) δ 7.74 (m, 3 H), 7.65 (m, 2 H), 3.75 (m, 3 H), 3.53 (d, J=16.0 Hz, 2 H), 3.16 (t, J=12.0 Hz, 2 H), 2.81 (s, 3 H), 2.40 (t, J=12.0 Hz, 2 H), 1.99 (d, J=12.0, 2 H), 1.75 (m, 2 H), 1.51 (m, 5 H), 0.87 (d, J=4.0 Hz, 3 H); $^{13}$C NMR (100 MHz, DMSO-d6) δ 135.8, 133.8, 130.1, 128.0, 59.8, 58.3, 47.2, 45.0, 28.0, 26.9, 24.0, 20.5; MS (ESI) m/z 337.2 (100%, [M−I]+).

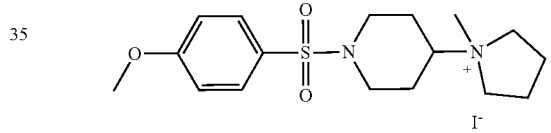

1-(1-((4-methoxyphenyl)sulfonyl)piperidin-4-yl)-1-methylpyrrolidin-1-ium iodide: This compound was obtained as a yellow solid (>95%). mp 82-85° C.; $^1$H NMR (400 MHz, DMSO-d6) δ 7.67 (d, J=8.0 Hz, 2 H), 7.15 (d, J=8.0 Hz, 2 H), 3.82 (s, 3 H), 3.72 (d, J=12.0 Hz, 2 H), 3.49 (dd, J=12.0, 8.0 Hz, 2 H), 3.30 (s, br, 3 H), 2.79 (s, 3 H), 2.17 (t, J=12.0 Hz, 2 H), 2.02 (m, 6 H), 1.84 (m, 2 H); $^{13}$C NMR (100 MHz, DMSO-d6) δ 163.4, 130.3, 126.6, 115.1, 70.1, 63.5, 56.3, 45.4, 43.3, 26.2, 21.3; MS (ESI) m/z 339.2 (100%, [M−I]+).

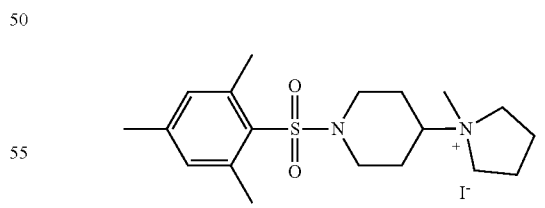

1-(1-(mesitylsulfonyl)piperidin-4-yl)-1-methylpyrrolidin-1-ium iodide: This compound was obtained as a yellow solid (83%). mp 263-266° C.; $^1$H NMR (400 MHz, DMSO-d6) δ 7.07 (s, 2 H), 3.60-3.43 (m, 5 H), 3.34 (dd, J=19.2, 8.0 Hz, 2 H), 2.80 (s, 3 H), 2.73 (td, J=12.6, 2.1 Hz, 2 H), 2.56 (s, 6 H), 2.25 (s, 3 H), 2.05 (m, 6 H), 1.71 (m, 2 H); $^{13}$C NMR (100 MHz, DMSO-d6) δ 143.1, 140.1, 132.4, 131.6, 70.6, 63.4, 43.4, 43.2, 26.5, 22.8, 21.2, 20.9; MS (ESI) m/z 351.2 (100%, [M−I]+).

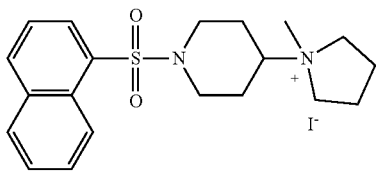

1-methyl-1-(1-(naphthalen-1-ylsulfonyl)piperidin-4-yl)pyrrolidin-1-ium iodide: This compound was obtained as a yellow solid (91%). mp 285-288° C.; $^1$H NMR (400 MHz, DMSO-d6) δ 8.67 (dd, J=8.4, 1.2 Hz, 1 H), 8.29 (dd, J=8.4, 1.2 Hz, 1 H), 8.12 (m, 2 H), 7.69 (m, 3 H), 3.90 (d, J=12.8 Hz, 2 H), 3.46 (dd, J=9.6, 4.8 Hz, 2 H), 3.26 (m, 3 H), 2.75 (s, 3 H), 2.42 (s, 1 H), 2.02 (m, 7 H), 1.78 (m, 2 H); $^{13}$C NMR (100 MHz, DMSO-d6) δ 135.2, 134.5, 132.1, 130.8, 129.6, 128.8, 128.6, 127.5, 125.2, 125.0, 70.1, 63.4, 45.0, 43.2, 26.6, 21.2; MS (ESI) m/z 359.2 (100%, [M−I]+).

V. General Procedure for the Preparation of Tertiary Amine Hydrochloride Salts

Tertiary amide (0.5 mmol) was dissolved in minimum amount of DCM and the resulting solution was stirred vigorously during which HCl in 1,4-dioxane (4 M, 2 mL) was added dropwise. Upon removal of solvents, the title amine hydrochloric acid salt was obtained as a white solid without further purification.

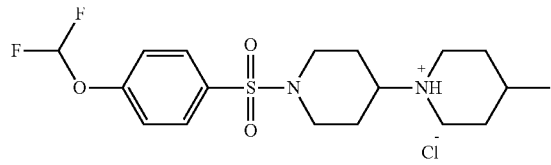

1-(1-((4-(difluoromethoxy)phenyl)sulfonyl)piperidin-4-yl)-4-methylpiperidin-1-ium chloride: This compound was obtained as a white solid (>95%). mp 251-254° C.; $^1$H NMR (400 MHz, CDCl$_3$) δ 12.08 (s, 1 H), 7.73 (d, J=8.0 Hz, 2 H), 7.25 (d, J=7.9 Hz, 2 H), 6.63 (t, J=72.4 Hz, 1 H), 3.93 (d, J=9.9 Hz, 2 H), 3.33 (d, J=9.8 Hz, 2H), 3.03 (s, 1 H), 2.70 (s, 2H), 2.35 (d, J=11.7 Hz, 4 H), 2.20-1.90 (m, 2 H), 1.81 (t, J=15.8 Hz, 4 H), 1.55 (s, 1 H), 0.99 (d, J=6.0 Hz, 3 H); $^{13}$C NMR (100 MHz, CDCl$_3$) δ 154.5, 132.4, 129.7, 119.7, 115.2 (triplet), 62.8, 49.5, 45.1, 30.7, 29.7, 25.3, 20.9; MS (ESI) m/z 389.2 (100%, [M−Cl]+).

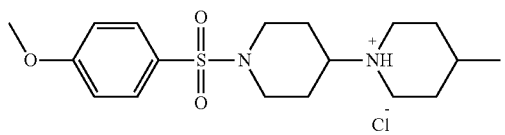

1-(1-((4-methoxyphenyl)sulfonyl)piperidin-4-yl)-4-methylpiperidin-1-ium chloride: This compound was obtained as a white solid (>95%). mp 247-250° C.; $^1$H NMR (400 MHz, CDCl$_3$) δ 12.03 (s, 1 H), 7.63 (d, J=8.8 Hz, 2 H), 6.98 (d, J=8.1 Hz, 2 H), 3.98-3.87 (s, 2 H), 3.85 (s, 3 H), 3.30 (s, 2 H), 2.99 (s, 1 H), 2.72 (s, 2 H), 2.30 (s, 4 H), 2.10-1.92 (s, 2 H), 1.78 (m, 4 H), 1.55 (s, 1 H), 1.13-0.89 (s, 3 H); $^{13}$C NMR (100 MHz, CDCl$_3$) δ 163.4, 129.8, 126.8, 114.5, 63.0, 55.8, 49.4, 45.2, 30.8, 29.8, 25.3, 20.9; MS (ESI) m/z 353.2 (100%, [M−Cl]+).

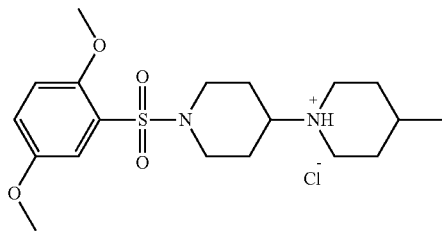 [SMILES: COc1ccc(OC)c(S(=O)(=O)N2CCC(N3CCC(C)CC3)CC2)c1 ; Cl]

1-(1-((2,5-dimethoxyphenyl)sulfonyl)piperidin-4-yl)-4-methylpiperidin-1-ium chloride: This compound was obtained as a white solid (73%). mp 207-210° C.; $^1$H NMR (400 MHz, CDCl$_3$) δ 11.90 (s, 1 H), 7.31 (s, 1 H), 6.96 (d, J=32.2 Hz, 2 H), 4.16-3.90 (s, 2 H), 3.83 (s, 3 H), 3.73 (s, 3 H), 3.24 (d, br, J=75.5 Hz, 3H), 2.70 (s, 4 H), 2.46-2.18 (s, 2 H), 2.16-1.90 (s, 2 H), 1.88-1.68 (s, 4 H), 1.69-1.41 (s, 1 H), 0.96 (s, 3 H); $^{13}$C NMR (100 MHz, CDCl$_3$) δ 152.98, 150.81, 126.50, 120.42, 115.98, 114.02, 63.41, 57.05, 56.07, 49.66, 45.11, 30.79, 29.68, 26.09, 20.93; MS (ESI) m/z 383.2 (100%, [M−Cl]+).

1-(1-(mesitylsulfonyl)piperidin-4-yl)-4-methylpiperidin-1-ium chloride: This compound was obtained as a white solid (69%). mp 259-262° C.; $^1$H NMR (400 MHz, CDCl$_3$) δ 11.73 (s, 1 H), 6.85 (s, 2 H), 3.93-3.46 (s, br, 2 H), 3.33 (s, br, 3 H), 2.74 (s, 3 H), 2.46 (s, 6H), 2.18 (d, J=4.3 Hz, 5 H), 2.06-1.07 (m, 8 H), 0.89 (s, 3 H); $^{13}$C NMR (100 MHz, CDCl$_3$) δ 142.99, 140.20, 132.08, 131.01, 63.44, 49.91, 43.52, 30.77, 29.54, 25.70, 22.85, 20.96; MS (ESI) m/z 365.2 (100%, [M−Cl]+).

FIG. 30 shows NMR spectra of exemplified compounds.

VI. General Procedure for Reductive Amination

A mixture of ketone (or acetone) (1.0 mmol), amine (1.0 mmol), AcOH (1.0 mmol), and CH$_2$Cl$_2$ (or DCE) (5 ml) was stirred at room temperature for 15 min before NaBH(OAc)$_3$ (1.5 mmol) was added. The resulting suspension was stirred at room temperature with a reaction time ranged from 20 h to 89 h. The reaction was then quenched by dropwsie adding saturated NaHCO3 solution at 0° C. and the generated bi-phase solution was extracted by CH$_2$Cl$_2$ (3×30 ml). The combined organic layers were dried over Na$_2$SO$_4$, filtered and concentrated under reduced pressure. The residue was purified through flash chromatography on silica gel with a MeOH:CH$_2$Cl$_2$ (or Hexane:EtOAc) mixture as eluent to provide the reductive amination product.

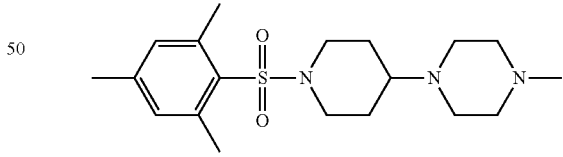

1-(1-(mesitylsulfonyl)piperidin-4-yl)-4-methylpiperazine: This compound was obtained as a colorless gel (74%) through flash chromatography (1:9 MeOH:CH$_2$Cl$_2$) after the reductive amination between 1-(mesitylsulfonyl)piperidin-4-one and 1-methylpiperazine with the reaction time of 20 h. $^1$H NMR (400 MHz, CDCl$_3$) δ 6.91 (s, 2 H), 3.59 (d, J=12.6 Hz, 2 H), 2.73 (t, J=12.3 Hz, 2 H), 2.58 (s, 6 H), 2.55 (s, br, 4 H), 2.49-2.35 (s, br, 4 H), 2.36-2.29 (s, 1 H), 2.26 (s, 3 H), 2.25 (s, 3 H), 1.84 (d, J=11.6 Hz, 2 H), 1.59-1.34 (m, 2 H); $^{13}$C NMR (100 MHz, CDCl$_3$) δ 142.5, 140.4, 131.8, 131.7, 61.2, 55.3, 48.9, 45.9, 43.7, 27.8, 22.8, 20.9; MS (ESI) m/z 366.2 (100%, [M+H]+).

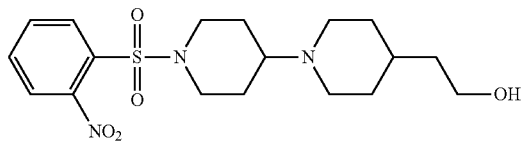 [SMILES: O=[N+]([O-])c1ccccc1S(=O)(=O)N1CCC(N2CCC(CCO)CC2)CC1]

2-(1'-((2-nitrophenyl)sulfonyl)-[1,4'-bipiperidin]-4-yl)ethanol: This compound was obtained as a pale yellow solid (37%) through flash chromatography (1:9 MeOH:CH$_2$Cl$_2$) after the reductive amination between 1-((2-nitrophenyl)sulfonyl)piperidin-4-one and 2-(piperidin-4-yl)ethanol with the reaction time of 38 h. mp 130-133° C.; $^1$H NMR (400 MHz, CDCl$_3$) δ 7.96 (d, J=7.3 Hz, 1 H), 7.74-7.61 (m, 2 H), 7.61-7.51 (m, 1 H), 3.88 (d, J=12.9 Hz, 2 H), 3.65 (t, J=6.6 Hz, 2 H), 2.82 (d, J=11.6 Hz, 2 H), 2.73 (t, J=12.5 Hz, 2 H), 2.33 (tt, J=11.5, 3.6 Hz, 1 H), 2.14 (t, J=11.6 Hz, 2 H), 1.84 (d, J=10.7 Hz, 2 H), 1.73-1.65 (m, 2 H), 1.59 (qd, J=12.3, 4.2 Hz, 3 H), 1.48 (q, J=6.6 Hz, 2 H), 1.38 (m, 1 H), 1.20 (qd, J=12.1, 3.8 Hz, 2 H); $^{13}$C NMR (100 MHz, CDCl$_3$) δ 148.3, 133.5, 131.8, 131.5, 130.9, 124.0, 61.4, 60.5, 49.4, 45.9, 39.4, 32.6, 32.6, 27.7; MS (ESI) m/z 398.2 (100%, [M+H]+).

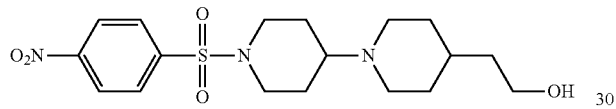

2-(1'-((4-nitrophenyl)sulfonyl)-[1,4'-bipiperidin]-4-yl)ethanol: This compound was obtained as a pale yellow solid (20%) through flash chromatography (1:9 MeOH:CH$_2$Cl$_2$) after the reductive amination 1-((4-nitrophenyl)sulfonyl)piperidin-4-one and 2-(piperidin-4-yl)ethanol with the reaction time of 71 h. mp 126-129° C.; $^1$H NMR (400 MHz, CDCl$_3$) δ 8.36 (d, J=8.8 Hz, 2 H), 7.92 (d, J=8.9 Hz, 2 H), 3.88 (d, J=11.8 Hz, 2 H), 3.66 (t, J=6.5 Hz, 2 H), 2.82 (d, J=11.0 Hz, 2 H), 2.33 (td, J=11.9, 2.2 Hz, 2 H), 2.25 (m, 1 H), 2.14 (t, J=11.4 Hz, 2 H), 1.87 (d, J=12.7 Hz, 2 H), 1.66 (m, 4 H), 1.48 (q, J=6.6 Hz, 2 H), 1.40 (m, 1H), 1.32-1.13 (m, 3 H); $^{13}$C NMR (100 MHz, CDCl$_3$) δ 150.1, 142.4, 128.7, 124.3, 61.2, 60.4, 49.4, 46.1, 39.3, 32.5, 27.3; MS (ESI) m/z 398.2 (100%, [M+H]+).

2-(1'-((3-nitrophenyl)sulfonyl)-[1,4'-bipiperidin]-4-yl)ethanol: This compound was obtained as a pale yellow solid (25%) through flash chromatography (1:9 MeOH:CH$_2$Cl$_2$) after the reductive amination 1-((3-nitrophenyl)sulfonyl)piperidin-4-one and 2-(piperidin-4-yl)ethanol with the reaction time of 64 h. mp 128-131° C.; $^1$H NMR (500 MHz, CDCl$_3$) δ 8.59 (s, 1 H), 8.46 (d, J=8.2 Hz, 1 H), 8.09 (d, J=7.8 Hz, 1 H), 7.77 (t, J=8.0 Hz, 1 H), 3.92 (d, J=11.8 Hz, 2 H), 3.68 (t, J=6.6 Hz, 2 H), 2.84 (m, J=11.2 Hz, 2 H), 2.35 (t, J=12.0 Hz, 2 H), 2.27 (tt, J=11.6, 3.5 Hz, 1 H), 2.16 (t, J=11.7 Hz, 3 H), 1.89 (d, J=11.2 Hz, 2 H), 1.69 (m, 4 H), 1.50 (q, J=6.7 Hz, 2 H), 1.47-1.35 (m, 1 H), 1.23 (qd, J=12.0, 3.8 Hz, 2 H); $^{13}$C NMR (100 MHz, CDCl$_3$) δ 148.3, 138.8, 133.0, 130.5, 127.2, 122.6, 61.2, 60.4, 49.4, 46.1, 39.2, 32.5, 32.4, 27.3; MS (ESI) m/z 398.2 (100%, [M+H]+).

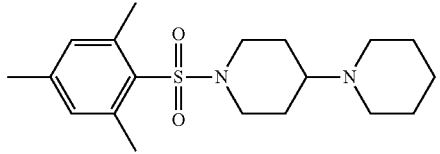 [SMILES: Cc1cc(C)c(S(=O)(=O)N2CCC(N3CCCCC3)CC2)c(C)c1]

1'-(mesitylsulfonyl)-1,4'-bipiperidine: This compound was obtained as a colorless gel (67%) through flash chromatography (1:9 MeOH:CH$_2$Cl$_2$) after the reductive amination between 1-(mesitylsulfonyl)piperidin-4-one and piperidine with the reaction time of 24 h. $^1$H NMR (500 MHz, CDCl$_3$) δ 6.93 (s, 2 H), 3.62 (d, J=11.7 Hz, 2 H), 2.74 (t, J=12.1 Hz, 2 H), 2.60 (s, 6 H), 2.52-2.40 (s, 4 H), 2.38-2.30 (m, 1 H), 2.28 (s, 3 H), 1.85 (d, J=11.5 Hz, 2 H), 1.56 (m, 4 H), 1.52-1.44 (m, 2 H), 1.41 (m, 2 H); $^{13}$C NMR (100 MHz, CDCl$_3$) δ 142.4, 140.4, 131.8, 131.8, 62.2, 50.2, 44.1, 27.5, 26.3, 24.6, 22.8, 20.9; MS (ESI) m/z 351.2 (100%, [M+H]+).

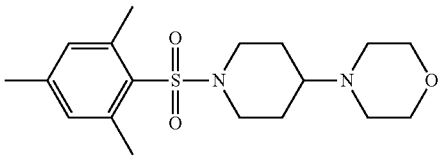 [SMILES: Cc1cc(C)c(S(=O)(=O)N2CCC(N3CCOCC3)CC2)c(C)c1]

4-(1-(mesitylsulfonyl)piperidin-4-yl)morpholine: This compound was obtained as a colorless gel (74%) through flash chromatography (1:9 MeOH: CH$_2$Cl$_2$) after the reductive amination between 1-(mesitylsulfonyl)piperidin-4-one and morpholine with the reaction time of 89 h. $^1$H NMR (500 MHz, CDCl$_3$) δ 6.92 (s, 2 H), 3.68 (s, 4 H), 3.60 (d, J=12.9 Hz, 2 H), 2.75 (t, J=12.3 Hz, 2 H), 2.59 (s, 6 H), 2.55-2.45 (s, 4 H), 2.27 (s, 4 H), 1.87 (d, J=14.5 Hz, 2H), 1.46 (qd, J=11.6, 3.4 Hz, 2 H); $^{13}$C NMR (100 MHz, CDCl$_3$) δ 142.5, 140.4, 140.4, 131.9, 131.6, 67.1, 61.5, 49.7, 43.6, 27.7, 22.8, 20.9; MS (ESI) m/z 353.2 (100%, [M+H]+).

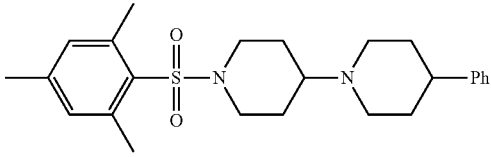

1'-(mesitylsulfonyl)-4-phenyl-1,4'-bipiperidine:
This compound was obtained as a white solid (90%) through flash chromatography (2:1 Hexane:EtOAc) after the reductive amination between 1-(mesitylsulfonyl)piperidin-4-one and 4-phenylpiperidine with the reaction time of 48 h. mp 141-144° C.; $^1$H NMR (400 MHz, CDCl$_3$) δ 7.34-7.26 (m, 2 H), 7.25-7.16 (m, 3 H), 6.95 (s, 2 H), 3.66 (d, J=12.5 Hz, 2 H), 3.03 (d, J=11.0 Hz, 2 H), 2.78 (t, J=12.5 Hz, 2 H), 2.62 (s, 6 H), 2.47 (m, 2 H), 2.30 (s, 3 H), 2.30-2.20 (m, 2 H), 1.99-1.66 (m, 6 H), 1.56 (qd, J=12.2, 4.3 Hz, 2H); $^{13}$C NMR (100 MHz, CDCl$_3$) δ 142.5, 140.5, 131.9, 131.7, 128.4, 126.8, 126.2, 61.9, 50.0, 44.0, 42.9, 33.7, 27.7, 22.8, 21.0; MS (ESI) m/z 427.2 (100%, [M+H]+).

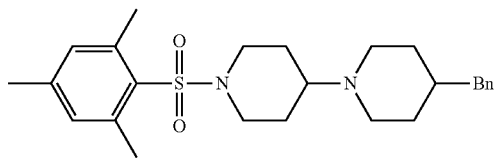 [SMILES: Cc1cc(C)c(S(=O)(=O)N2CCC(N3CCC(Cc4ccccc4)CC3)CC2)c(C)c1]

4-benzyl-1'-(mesitylsulfonyl)-1,4'-bipiperidine: This compound was obtained as a light brown oil (68%) through flash chromatography (2:1 Hexane:EtOAc) after the reductive amination between 1-(mesitylsulfonyl)piperidin-4-one and 4-benzylpiperidine with the reaction time of 48 h. $^1$H NMR (400 MHz, CDCl$_3$) δ 7.36-7.22 (m, 2 H), 7.21-7.06 (m, 3 H), 6.92 (s, 2 H), 3.61 (d, J=12.4 Hz, 2 H), 2.92 (s, 2 H), 2.72 (td, J=12.5, 2.4 Hz, 2 H), 2.58 (s, 6 H), 2.50 (d, J=7.0 Hz, 2 H), 2.40-2.26 (s, br, 1 H), 2.28 (s, 3 H), 2.08 (t, J=17.9 Hz, 1 H), 1.85 (d, J=12.8 Hz, 2 H), 1.64 (d, J=12.8 Hz, 2 H), 1.49 (d, J=11.5 Hz, 3 H), 1.41-1.12 (s, br, 2H); $^{13}$C NMR (100 MHz, CDCl$_3$) δ 142.5, 140.5, 140.4, 131.9, 131.7, 129.1, 128.2, 125.8, 61.9, 49.6, 44.0, 43.1, 38.1, 32.3, 27.6, 22.8, 21.0; MS (ESI) m/z 441.3 (100%, [M+H]+).

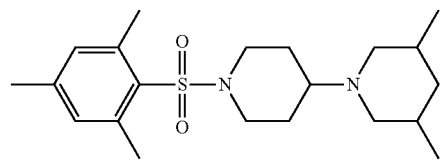

1'-(mesitylsulfonyl)-3,5-dimethyl-1,4'-bipiperidine: This compound was obtained as a colorless oil (36%) through flash chromatography (1:19 MeOH:CH$_2$Cl$_2$) after the reductive amination between 3,5-dimethylpiperidine and 1-(mesitylsulfonyl)piperidin-4-one with the reaction time of 88 h. $^1$H NMR (400 MHz, CDCl$_3$) δ 6.92 (s, 2 H), 3.61 (d, J=12.4 Hz, 2 H), 2.87-2.66 (m, 4 H), 2.59 (s, 6 H), 2.47-2.29 (m, 1 H), 2.27 (s, 3 H), 1.82 (d, J=13.6 Hz, 2 H), 1.74-1.39 (m, 7 H), 0.81 (d, J=5.8 Hz, 6 H), 0.47 (q, J=11.4 Hz, 1H); $^{13}$C NMR (100 MHz, CDCl$_3$) δ 142.4, 140.4, 131.8, 131.8, 61.8, 57.2, 44.1, 42.3, 31.4, 27.5, 22.8, 20.9, 19.7; MS (ESI) m/z 379.3 (100%, [M+H]+).

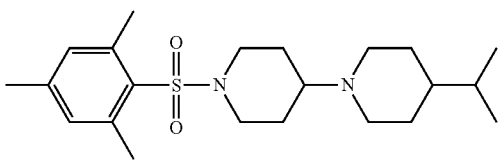 [SMILES: Cc1cc(C)c(S(=O)(=O)N2CCC(N3CCC(C(C)C)CC3)CC2)c(C)c1]

4-isopropyl-1'-(mesitylsulfonyl)-1,4'-bipiperidine: This compound was obtained as a yellow oil (46%) through flash chromatography (1:19 MeOH:CH$_2$Cl$_2$) after the reductive amination between 4-isopropylpiperidine and 1-(mesitylsulfonyl)piperidin-4-one with the reaction time of 30 h. $^1$H NMR (400 MHz, CDCl$_3$) δ 6.91 (s, 2 H), 3.60 (d, J=12.7 Hz, 2 H), 2.90 (dd, J=11.5 Hz, 2 H), 2.72 (t, J=12.4 Hz, 2 H), 2.59 (d, J=2.3 Hz, 6 H), 2.38-2.29 (m, 1 H), 2.28 (s, 3 H), 2.06 (t, J=10.6 Hz, 2 H), 1.85 (d, J=11.2 Hz, 2 H), 1.63 (d, J=11.3 Hz, 2 H), 1.49 (td, J=12.1, 4.1 Hz, 2H), 1.44-1.32 (m, 1 H), 1.30-1.14 (m, 2 H), 0.95 (m, 1 H), 0.83 (d, J=6.7 Hz, 6 H); $^{13}$C NMR (100 MHz, CDCl$_3$) δ 142.4, 140.4, 131.8, 131.7, 61.8, 50.0, 44.0, 42.6, 32.4, 29.6, 27.7, 22.8, 20.9, 19.8; MS (ESI) m/z 393.3 (100%, [M+H]+).

VII. Synthesis of 1'-(phenylsulfonyl)-2-(2-(prop-2-yn-1-yloxy)ethyl)-1,4'-bipiperidine and 1'-(phenylsulfonyl)-2-(prop-2-yn-1-yl)-1,4'-bipiperidine

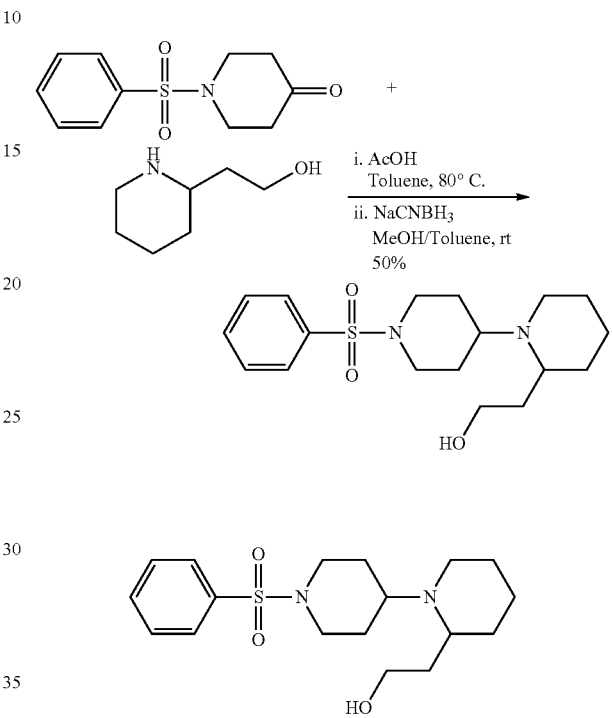

2-(1'-(phenylsulfonyl)-[1,4'-bipiperidin]-2-yl)ethan-1-ol: 1-(phenylsulfonyl)piperidin-4-one (0.6004 g, 2.51 mmol) and 2-(piperidin-2-yl)ethan-1-ol (0.9701 g, 7.52 mmol) were dissolved in toluene (5 mL), followed by the addition of AcOH (0.62 ml, 10.84 mmol). The resulting solution was stirred at 80° C. for 3 h and was then cooled to room temperature. NaCNBH$_3$ (0.2031 g, 3.22 mmol) in methanol (5 mL) was added dropwise and the reaction mixture was stirred for 30 min. The reaction was quenched by saturated NaHCO$_3$ solution (20 mL) at 0° C. The resulting bi-phase solution was extracted by CH$_2$Cl$_2$ (3×25 mL) and the combined organic layers were dried over Na$_2$SO$_4$, filtered and concentrated under reduced pressure. The residue was purified through flash chromatography on silica gel with a mixture of 1:19 MeOH:CH$_2$Cl$_2$ as eluent to provide the reductive amination product as a yellow oil (0.4445 g, 50%). $^1$H NMR (400 MHz, CDCl$_3$) δ 7.74 (d, J=8.5 Hz, 2 H), 7.65-7.57 (m, 1 H), 7.56-7.47 (m, 2 H), 3.86 (dd, J=11.1, 4.7 Hz, 3 H), 3.64 (dt, J=11.1, 5.6 Hz, 1 H), 3.05-2.87 (m, 3 H), 2.44-2.30 (m, 2 H), 2.26 (td, J=12.1, 2.5 Hz, 1 H), 1.88-1.29 (m, 12 H); $^{13}$C NMR (100 MHz, CDCl$_3$) δ 135.9, 132.9, 129.1, 127.6, 60.7, 56.7, 56.0, 46.1, 45.8, 44.9, 31.1, 29.7, 28.5, 25.0, 24.2, 22.4; MS (ESI) m/z 353.2 (100%, [M+H]+).

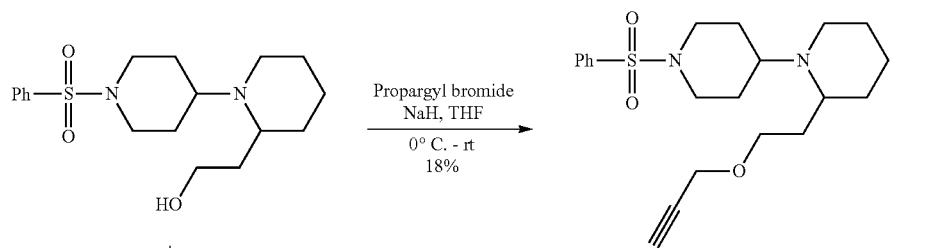

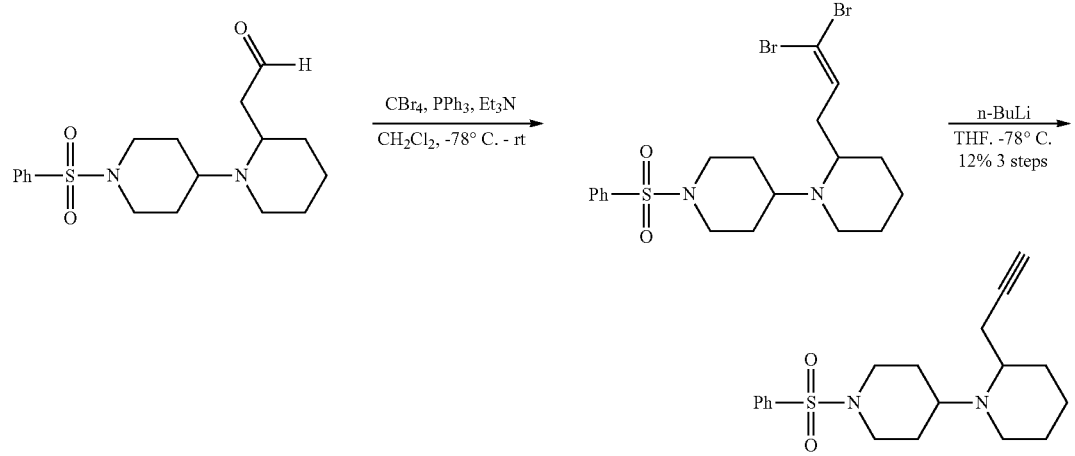

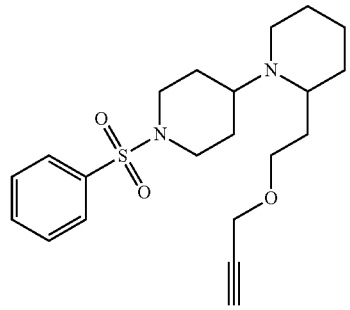 [SMILES: C#CCOCCC1CCCCN1C1CCN(S(=O)(=O)c2ccccc2)CC1]

1'-(phenylsulfonyl)-2-(2-(prop-2-yn-1-yloxy)ethyl)-1,4'-bipiperidine: 2-(1'-(phenylsulfonyl)-[1,4'-bipiperidin]-2-yl)ethan-1-ol (0.0830 g, 0.24 mmol) was dissolved in anhydrous THF (2 mL), followed by the addition of NaH (60%, 0.0192 g, 0.48 mmol) at 0° C. The flask was then immediately flushed by argon flow and sealed by a rubber septum fitted with an argon balloon. The reaction solution was stirred at 0° C. for 15 min and propargyl bromide (80% in toluene, 0.075 ml, 0.67 mmol) was added via syringe. The reaction solution was stirred at 0° C. for another 30 min and was allowed to warm to room temperature and stirred for 3 h before a second portion of NaH (60%, 0.0175 g, 0.44 mmol) in anhydrous THF (1 mL) was introduced. The reaction solution was then stirred for 18 h at room temperature and water (10 mL) was added to quench the reaction, followed by the extraction with CH$_2$Cl$_2$ (3×10 mL). The combined organic layers were dried over Na$_2$SO$_4$, filtered and concentrated under reduced pressure. After the purification by flash chromatography on silica gel (1:19 CH$_3$OH:CH$_2$Cl$_2$), the product was obtained as a yellow gel (0.0132 g, 18%). $^1$H NMR (400 MHz, CDCl$_3$) δ 7.82-7.69 (m, 2 H), 7.64-7.56 (m, 1 H), 7.53 (m, 2 H), 4.06 (d, J=2.4 Hz, 2 H), 3.83 (d, J=11.9 Hz, 2 H), 3.58-3.37 (m, 2 H), 2.73 (dd, J=39.3, 10.5 Hz, 3 H), 2.35 (t, J=2.4 Hz, 1 H), 2.25 (dtd, J=26.4, 12.1, 11.7, 2.9 Hz, 3 H), 1.88-1.70 (m, 4 H), 1.69-1.19 (m, 8 H); $^{13}$C NMR (100 MHz, CDCl$_3$) δ 136.0, 132.8, 129.1, 127.6, 79.6, 74.4, 67.1, 58.2, 55.5, 55.0, 46.4, 45.9, 45.4, 30.3, 29.8, 29.7, 25.6, 24.2, 23.0; MS (ESI) m/z 391.2 (100%, [M+H]+).

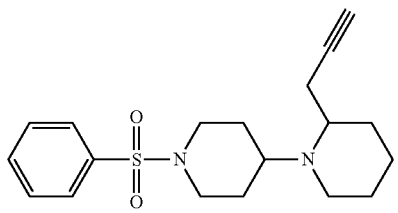 [SMILES: C#CCC1CCCCN1C1CCN(S(=O)(=O)c2ccccc2)CC1]

1'-(phenylsulfonyl)-2-(prop-2-yn-1-yl)-1,4'-bipiperidine: A 25 mL flame-dried flask equipped with a magnetic stirring bar was purged by argon and was then sealed with a rubber septum fitted with an argon balloon. Anhydrous CH$_2$Cl$_2$ (1 mL) and oxalyl chloride (0.039 ml, 0.45 mmol) were added via syringe sequentially. The resulting solution was cooled to −78° C. in a dry ice-acetone bath. Anhydrous DMSO (0.066 ml, 0.93 mmol) was introduced and the solution was stirred for 1.5 h at −78° C. 2-(1'-(phenylsulfonyl)-[1,4'-bipiperidin]-2-yl)ethanol (0.1344 g, 0.38 mmol) in 1 mL anhydrous CH$_2$Cl$_2$ was added dropwise. After the reaction mixture was stirred at −78° C. for 1 h, Et$_3$N (0.20 mL, 1.44 mmol) was added and after 15 min, the reaction solution was allowed to warm to room temperature and stirred for 2 h, before being quenched by 6 mL water. Saturated NaHCO$_3$ solution (10 mL) was added and the resulting solution was exacted by CH$_2$Cl$_2$ (3×20 mL). The combined organic layers were dried over Na$_2$SO$_4$, filtered and concentrated under reduced pressure to afford the aldehyde intermediate which was used directly for next step without further purification.

To a solution of triphenylphosphine (0.4429 g, 1.69 mmol) in anhydrous CH$_2$Cl$_2$ (2 mL), a solution of carbon tetrabromide (0.2653 g, 0.80 mmol) in CH$_2$Cl$_2$ (1 mL) was added dropwise at room temperature and the resulting solution was stirred for 30 min after which Et3N (0.45 mL, 3.39 mmol) was added via syringe. The solution was then cooled to −78° C. under which the aldehyde intermediate above dissolved in CH$_2$Cl$_2$ (2 mL) was added dropwise. The reaction mixture was allowed to warm to room temperature and stirred overnight before being filtered through a pad of Celite. The filtrate was concentrated and purified by flash chromatography (two times, 1:19 CH$_3$OH:CH$_2$Cl$_2$ then 1:1 Hexane:EtOAc) to afford the corresponding dibromide (0.0505 g) as colorless oil.

The above dibromide was dissolved in anhydrous THF (1 mL) and was cooled to −78° C. n-BuLi (0.090 mL, 2.5 M in Hexane, 0.225 mmol) was introduced via syringe. The reaction mixture was stirred for 2.5 h at the same temperature and was quenched by adding saturated NH$_4$Cl (15 mL) solution. The mixture was then extracted by EtOAc (3×15 mL). The combined organic layers were dried by Na$_2$SO$_4$, filtered and concentrated under reduced pressure. The residue was purified by flash chromatography (1:1 Hexane:EtOAc) to afford the final alkyne (0.0165 g, 12% three steps). $^1$H NMR (400 MHz, CDCl$_3$) δ 7.82-7.70 (m, 2 H), 7.63-7.57 (m, 1 H), 7.57-7.50 (m, 2 H), 3.85 (d, J=12.1 Hz, 2 H), 2.78-2.57 (m, 3 H), 2.36-2.19 (m, 4 H), 1.94 (t, J=2.7 Hz, 1 H), 1.89-1.39 (m, 9 H), 1.35-1.19 (m, 2 H); $^{13}$C NMR (100 MHz, CDCl$_3$) δ 136.2, 232.7, 129.0, 127.6, 82.1, 70.0, 56.4, 55.5, 46.5, 46.0, 45.2, 31.8, 30.1, 26.0, 24.2, 23.2, 21.7; MS (ESI) m/z 347.2 (100%, [M+H]+).

VIII. Synthesis of 1'-(phenylsulfonyl)-4-(2-(prop-2-yn-1-yloxy)ethyl)-1,4'-bipiperidine and 1'-(phenylsulfonyl)-4-(prop-2-yn-1-yl)-1,4'-bipiperidine

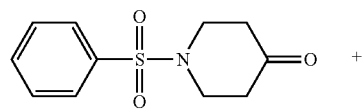

+

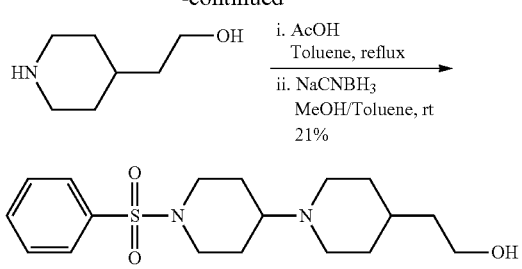

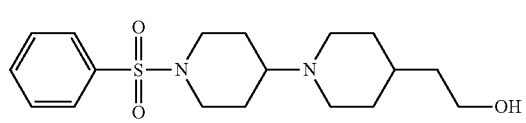 [SMILES: O=S(=O)(c1ccccc1)N1CCC(N2CCC(CCO)CC2)CC1]

2-(1'-(phenylsulfonyl)-[1,4'-bipiperidin]-4-yl)ethanol:
1-(phenylsulfonyl)piperidin-4-one (0.4923 g, 2.06 mmol) and AcOH (0.24 mL, 4.20 mmol) were dissolved in toluene (4 mL) and the resulting solution was stirred under reflux condition for 30 min, followed by addition of 2-(piperidin-4-yl)ethanol (0.2562 g, 1.99 mmol). The reaction mixture was stirred for 2 more hours under reflux condition and was then cooled to room temperature. NaCNBH$_3$ (0.1590 g, 2.52 mmol) in methanol (4 mL) was added dropwise and the solution was stirred for 50 min. The reaction was quenched by saturated NaHCO$_3$ solution (10 mL) at 0° C. The resulting solution was extracted by CH$_2$Cl$_2$ (3×15 mL) and the combined organic layers were dried over Na$_2$SO$_4$, filtered and concentrated under reduced pressure. The flash chromatography on silica gel (1:19 CH$_3$OH:CH$_2$Cl$_2$) provided the desired product as a yellow oil (0.1613 g, 21%). $^1$H NMR (400 MHz, CDCl$_3$) δ 7.78-7.72 (m, 2 H), 7.62-7.56 (m, 1 H), 7.53 (ddt, J=8.4, 6.7, 1.4 Hz, 2H), 3.85 (d, J=12.1 Hz, 2 H), 3.66 (t, J=6.6 Hz, 2 H), 2.81 (d, J=11.6 Hz, 2 H), 2.32-2.04 (m, 5 H), 1.83 (d, J=13.0 Hz, 3 H), 1.75-1.54 (m, 4 H), 1.49 (q, J=6.6 Hz, 2 H), 1.45-1.32 (m, 1 H), 1.29-1.14 (m, 2 H); $^{13}$C NMR (100 MHz, CDCl$_3$) δ 136.1, 132.7, 129.0, 127.6, 61.4, 60.4, 49.4, 46.1, 39.3, 32.5, 27.3; MS (ESI) m/z 353.2 (100%, [M+H]+).

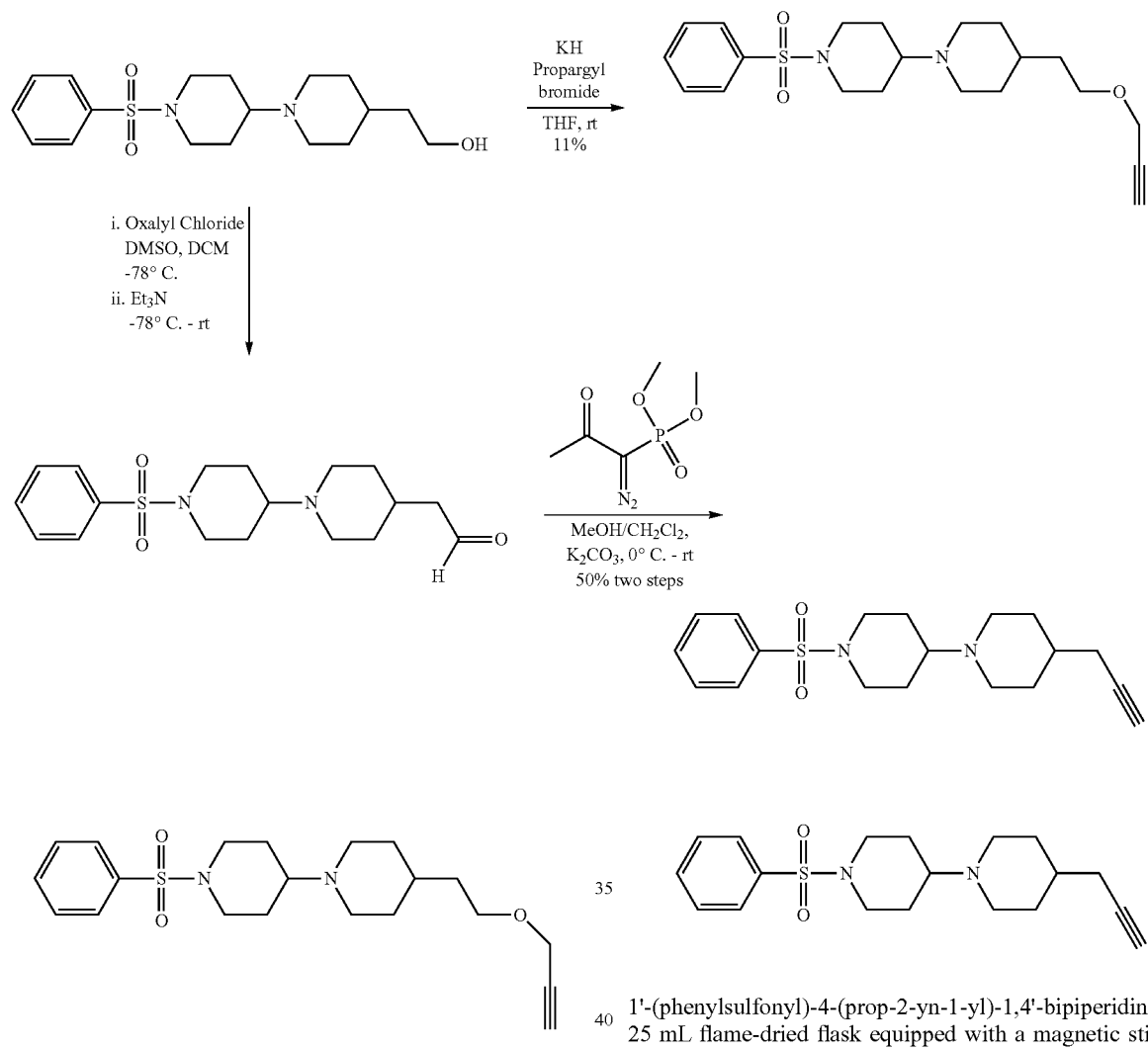

1'-(phenylsulfonyl)-4-(2-(prop-2-yn-1-yloxy)ethyl)-1,4'-bipiperidine: 2-(1'-(phenylsulfonyl)-[1,4'-bipiperidin]-4-yl)ethanol (0.0585 g, 0.17 mmol) was dissolved in anhydrous THF (1 mL), The flask was then immediately flushed by argon flow and sealed by a rubber septum fitted with an argon balloon. KH (30% in mineral oil, 0.0275 g, 0.21 mmol) suspended in anhydrous THF (0.5 mL) was added via syringe at room temperature. The reaction solution was stirred at room temperature for 45 min and propargyl bromide (80% in toluene, 0.038 mL, 0.43 mmol) was added dropwise via syringe. The solution was stirred at room temperature for 7.5 h. After the evaporation of solvent, the residue was purified by flash chromatography on silica gel (1:19 $CH_3OH:CH_2Cl_2$) afforded the desired product as a yellow gel (0.0072 g, 11%). $^1$H NMR (400 MHz, $CDCl_3$) δ 7.83-7.69 (m, 2 H), 7.63-7.57 (m, 1 H), 7.57-7.49 (m, 2 H), 4.11 (d, J=2.3 Hz, 2 H), 3.95-3.80 (m, 2 H), 3.53 (t, J=6.4 Hz, 2 H), 2.85 (d, J=10.7 Hz, 2 H), 2.41 (t, J=2.4 Hz, 1 H), 2.22 (m, 5 H), 1.87 (d, J=12.6 Hz, 2 H), 1.79-1.59 (m, 4 H), 1.52 (q, J=6.5 Hz, 2 H), 1.45-1.36 (m, 1 H), 1.25 (m, 2H); $^{13}$C NMR (100 MHz, $CDCl_3$) δ 136.06, 132.74, 129.01, 127.63, 79.89, 74.18, 67.58, 61.57, 58.05, 49.34, 46.08, 35.88, 32.57, 32.15, 27.11; MS (ESI) m/z 391.1 (100%, [M+H]+).

1'-(phenylsulfonyl)-4-(prop-2-yn-1-yl)-1,4'-bipiperidine: A 25 mL flame-dried flask equipped with a magnetic stirring bar was purged by argon and was then sealed with a rubber septum fitted with an argon balloon. Anhydrous $CH_2Cl_2$ (1.5 mL) and oxalyl chloride (0.10 mL, 2 M in $CH_2Cl_2$, 0.20 mmol) were added via syringe sequentially. The resulting solution was cooled to −78° C. in a dry ice-acetone bath. Anhydrous DMSO (0.030 mL, 0.42 mmol) was introduced and the solution was stirred for 40 min at −78° C. 2-(1'-(phenylsulfonyl)-[1,4'-bipiperidin]-4-yl)ethanol (0.0570 g, 0.16 mmol) in 1.5 mL anhydrous $CH_2Cl_2$ was added dropwise. After the reaction mixture was stirred at −78° C. for 2 h, $Et_3N$ (0.085 mL, 0.61 mmol) was added and the reaction solution was allowed to warm to room temperature and stirred for 2 hours, before being quenched by 25 mL saturated $NaHCO_3$ solution. The resulting solution was exacted by $CH_2Cl_2$ (3×25 mL). The combined organic layers were dried over $Na_2SO_4$, filtered and concentrated under reduced pressure to afford the aldehyde intermediate which was used directly for next step without further purification.

Bestmann Ohira reagent (dimethyl (1-diazo-2-oxopropyl) phosphonate) was prepared in advance according to the experimental procedure reported by Pietruszka, J. et al. [Pietruszka, J. et al. Synthesis 2006, 24, 4266-4268]. Bestmann Ohira reagent (0.0441 g, 0.023 mmol) and methanol (2 mL) were mixed at 0° C., followed by addition of the adehyde (dissolved in 0.5 mL $CH_2Cl_2$) and $K_2CO_3$ (0.0523 g, 0.38 mmol). The reaction solution was then allowed to warm up to room temperature and stirred overnight. The slurry solution was filtered and poured into a separatory funnel, diluted with 25 mL CH$_2$Cl$_2$, washed by 1 N NaOH (25 mL). The organic layer was dried over Na$_2$SO$_4$, filtered and concentrated. The residue was purified through flash chromatography on silica gel (1:9 CH$_3$OH:CH$_2$Cl$_2$) to afford the entitled product as a yellow solid (0.0282 g, 50%). If the product is not pure enough, it could be sonicated with a small amount of hexane and the supernatant of hexane layer could be removed by glass pipette to get rid of the impurities. mp 109-111° C.; $^1$H NMR (500 MHz, CDCl$_3$) δ 7.82-7.73 (m, 2 H), 7.67-7.59 (m, 1 H), 7.55 (dd, J=8.4, 7.0 Hz, 2 H), 3.88 (d, J=12.0 Hz, 2 H), 2.84 (s, 2 H), 2.35-2.03 (m, 7 H), 1.97 (t, J=2.7 Hz, 1 H), 1.92-1.74 (m, 4 H), 1.67 (tt, J=15.6, 7.8 Hz, 2 H), 1.46 (s, br, 1 H), 1.30 (s, br, 2 H).; $^{13}$C NMR (100 MHz, CDCl$_3$) δ 136.1, 132.8, 129.0, 127.6, 82.5, 69.5, 61.6, 49.1, 46.0, 35.4, 31.5, 27.0, 25.2; MS (ESI) m/z 347.2 (100%, [M+H]+).

IX. Synthesis of (3-((4-methyl-[1,4'-bipiperidin]-1'-yl)sulfonyl)-4-(prop-2-yn-1-yloxy)phenyl)(phenyl)methanone

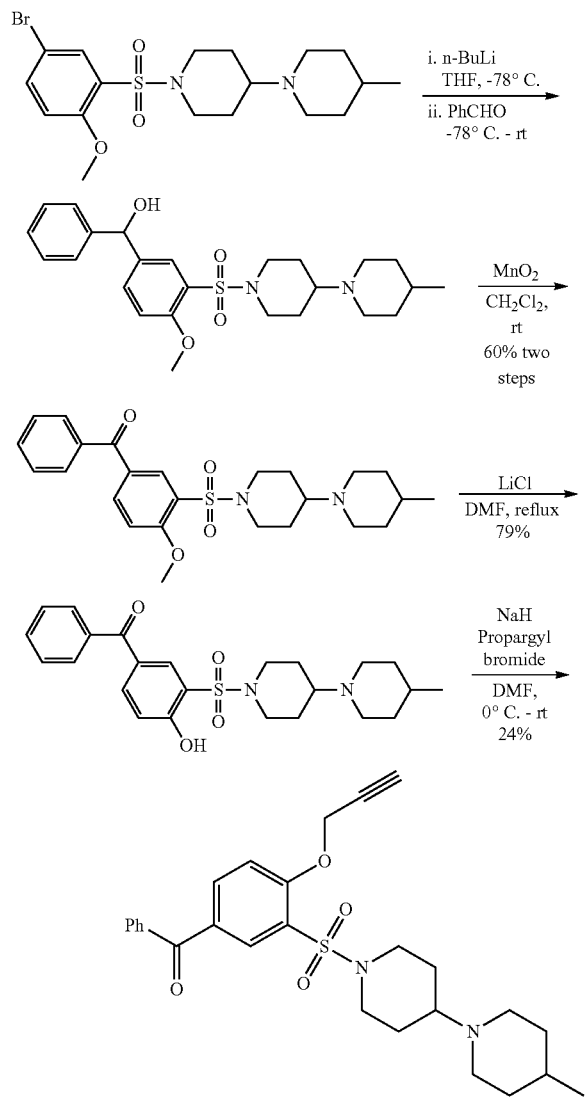

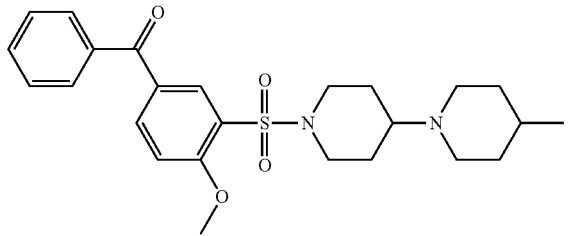 [SMILES: COc1ccc(C(=O)c2ccccc2)cc1S(=O)(=O)N1CCC(N2CCC(C)CC2)CC1]

(4-methoxy-3-((4-methyl-[1,4'-bipiperidin]-1'-yl)sulfonyl)phenyl)(phenyl)methanone: A 25 ml flame-dried flask equipped with a magnetic stirring bar were added 1'-((5-bromo-2-methoxyphenyl)sulfonyl)-4-methyl-1,4'-bipiperidine (0.3686 g, 0.86 mmol) and anhydrous THF (2.5 mL). The flask was purged by argon and was then sealed with a rubber septum fitted with an argon balloon. The resulting solution was cooled to −78° C. in a dry ice-acetone bath and n-BuLi (0.68 mL, 2.5 M in Hexane, 1.70 mmol) was introduced via syringe. The reaction mixture was stirred for 50 min at the temperature. Benzaldehyde (0.125 mL, 1.23 mmol) was added via syringe. The reaction mixture was stirred for 10 min before it was allowed to warm to room temperature and stirred over 3 h. The reaction was then quenched by 20 mL saturated NaHCO$_3$ solution and the resulting solution was exacted by CH$_2$Cl$_2$ (3×20 mL). The combined organic layers were dried over Na$_2$SO$_4$, filtered and concentrated under reduced pressure. The residue was purified by flash chromatography (1:19 Methanol:CH$_2$Cl$_2$) to afford the alcohol intermediate as colorless gel.

Manganese (IV) dioxide (2.0087 g, 22.32 mmol) was added to a solution of the alcohol intermediate in CH$_2$Cl$_2$ (7 mL). The suspension solution was stirred at room temperature for 36 h. The reaction mixture was then filtered through a pad of Celite and the filtrate was concentrated under reduced pressure to give the desired product as a white solid (0.2329 g, 60% two steps). mp 52-56° C.; $^1$H NMR (400 MHz, CDCl$_3$) δ 8.33 (d, J=2.2 Hz, 1 H), 8.04 (dd, J=8.6, 2.2 Hz, 1 H), 7.82-7.67 (m, 2 H), 7.67-7.54 (m, 1 H), 7.48 (m, 2 H), 7.09 (d, J=8.7 Hz, 1 H), 4.00 (s, 3 H), 3.91 (d, J=12.7 Hz, 2 H), 2.79 (d, J=11.1 Hz, 2 H), 2.63 (td, J=12.5, 2.4 Hz, 2 H), 2.30 (tt, J=11.6, 3.2 Hz, 1 H), 2.12 (t, J=10.2 Hz, 2 H), ), 1.81 (d, J=12.7 Hz, 2 H), 1.60-1.48 (m, 4 H), 1.29 (m, 1 H), 1.18 (qd, J=11.6, 7.9 Hz, 2 H), 0.88 (d, J=6.4 Hz, 3 H); $^{13}$C NMR (100 MHz, CDCl$_3$) δ 194.3, 159.9, 137.2, 136.4, 133.8, 132.6, 129.9, 129.8, 128.5, 127.0, 112.0, 61.8, 56.4, 49.5, 45.9, 34.6, 31.0, 28.0, 21.9; MS (ESI) m/z 457.1 (100%, [M+H]+).

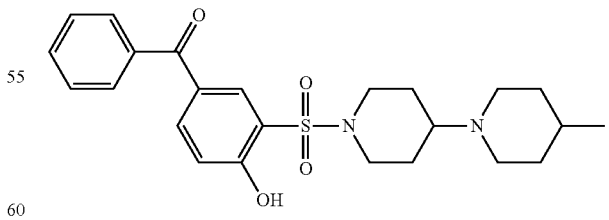

(4-hydroxy-3-((4-methyl-[1,4'-bipiperidin]-1'-yl)sulfonyl)phenyl)(phenyl)methanone: LiCl (0.0672 g, 1.6 mmol) in a 15 mL flask was flame dried under vacuum and the flask was then refilled with argon. (4-methoxy-3-((4-methyl-[1,4'-bipiperidin]-1'-yl)sulfonyl)phenyl)(phenyl)methanone (0.0733 g, 0.16 mmol) in anhydrous DMF (3 mL) was added into the flask via syringe. The flask was then equipped with a reflux condenser fitted with an argon balloon. The reaction was carried out under reflux condition for 21.5 h. After the reaction mixture was cooled to room temperature, the suspension was filtered through a pad of Celite, washed by $CH_2Cl_2$. After evaporation of solvents, the residue was purified by flash chromatography on silica gel (1:19 Methanol: $CH_2Cl_2$) to provide the desired product as an orange solid (0.0560 g, 79%). mp 153-156° C.; $^1$H NMR (400 MHz, $CDCl_3$) δ 8.11 (d, J=2.1 Hz, 1 H), 7.91 (dd, J=8.6, 2.2 Hz, 1 H), 7.75-7.69 (m, 2 H), 7.63-7.55 (m, 1 H), 7.48 (ddd, J=8.2, 6.6, 1.3 Hz, 2 H), 7.21 (d, J=8.6 Hz, 1 H), 3.94 (d, J=12.9 Hz, 2 H), 3.32 (d, J=11.3 Hz, 2 H), 3.06 (t, J=12.3 Hz, 1 H), 2.79-2.50 (m, 4 H), 2.25 (d, J=12.3 Hz, 2 H), 1.83 (s, br, 6 H), 1.57 (m, 1 H), 0.98 (d, J=6.4 Hz, 3 H); $^{13}$C NMR (100 MHz, $CDCl_3$) δ 194.3, 161.0, 137.4, 136.9, 133.2, 132.5, 129.7, 128.5, 128.1, 122.6, 119.1, 62.7, 49.5, 44.8, 30.9, 29.1, 26.0, 20.7; MS (ESI) m/z 443.1 (100%, [M+H]+).

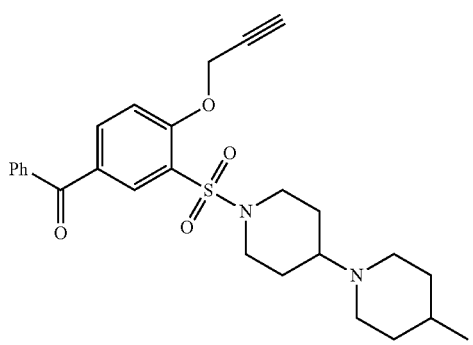 [SMILES: C#CCOc1ccc(C(=O)c2ccccc2)cc1S(=O)(=O)N1CCC(N2CCC(C)CC2)CC1]

(3-((4-methyl-[1,4'-bipiperidin]-1'-yl)sulfonyl)-4-(prop-2-yn-1-yloxy)phenyl)(phenyl)methanone: (4-hydroxy-3-((4-methyl-[1,4'-bipiperidin]-1'-yl)sulfonyl)phenyl)(phenyl) methanone (0.1103 g, 0.25 mmol) was dissolved in anhydrous DMF (1.5 mL), followed by the addition of NaH (95%, 0.0095 g, 0.38 mmol) at 0° C. The flask was then immediately flushed by argon flow and sealed by a rubber septum fitted with an argon balloon. The reaction solution was allowed to warm up to room temperature and stirred for 30 min. The solution was then cooled to 0° C. and propargyl bromide (80% in toluene, 0.032 ml, 0.29 mmol) was added via syringe. The solution was allowed to gradually warm up to room temperature and stirred for 17 h. The reaction solution was diluted with $CH_2Cl_2$ (25 mL) and washed by saturated $NaHCO_3$ solution (25 ml) and 20% LiCl solution (25 mL). The organic layer were dried over $Na_2SO_4$, filtered and concentrated under reduced pressure. The flash chromatography on silica gel (1:19 Methanol:$CH_2Cl_2$) afforded the desired product as a yellow oil (0.0290 g, 24%). $^1$H NMR (500 MHz, $CDCl_3$) δ 8.37 (d, J=2.2 Hz, 1 H), 8.07 (dd, J=8.6, 2.2 Hz, 1 H), 7.76 (dd, J=8.0, 1.5 Hz, 2 H), 7.67-7.58 (m, 1 H), 7.51 (t, J=7.7 Hz, 2 H), 7.24 (d, J=8.6 Hz, 1 H), 4.93 (d, J=2.4 Hz, 2 H), 3.96 (d, J=12.5 Hz, 2 H), 2.89 (d, J=12.7 Hz, 2 H), 2.72 (t, J=12.5 Hz, 2 H), 2.62 (t, J=2.3 Hz, 1 H), 2.46 (s, 1 H), 2.24 (t, J=11.4 Hz, 2 H), 1.90 (d, J=11.4 Hz, 2 H), 1.73-1.56 (m, 4 H), 1.44-1.27 (m, 3 H), 0.93 (d, J=5.8 Hz, 3 H); $^{13}$C NMR (100 MHz, $CDCl_3$) δ 194.2, 157.6, 137.0, 136.1, 133.9, 132.7, 130.8, 129.8, 128.5, 127.7, 113.5, 77.4, 77.4, 62.0, 56.8, 49.4, 45.9, 34.2, 30.9, 27.8, 21.7; MS (ESI) m/z 481.2 (100%, [M+H]+).

X. Synthesis of 1'-(3-azido-4-(prop-2-yn-1-yloxy)benzyl)-4-methyl-1,4'-bipiperidine

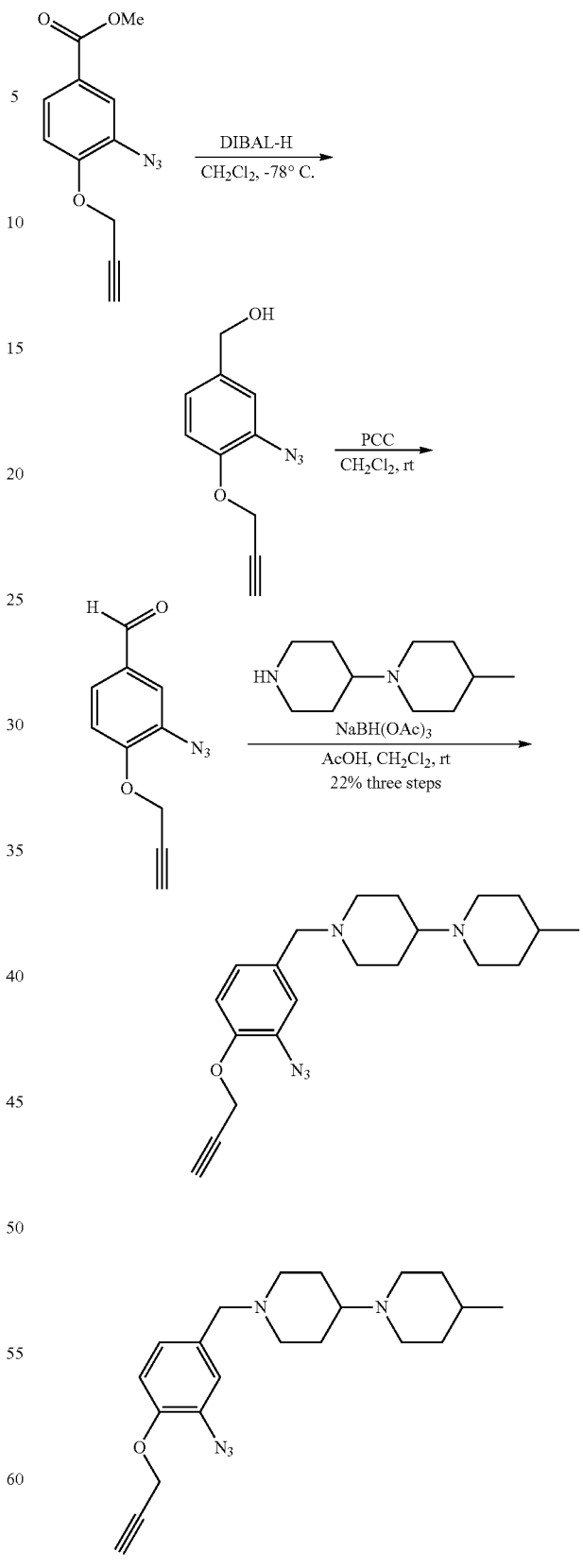

1'-(3-azido-4-(prop-2-yn-1-yloxy)benzyl)-4-methyl-1,4'-bipiperidine: Methyl 3-azido-4-(prop-2-yn-1-yloxy)benzoate (0.1085 g, 0.47 mmol) was dissolved in anhydrous $CH_2Cl_2$ (2 mL) and the solution was cooled to −78° C. DIBAL-H (1.2 M in hexane, 1.1 mL, 1.32 mmol) was dropwise added via syringe. The reaction mixture was then stirred at −78° C. for 1 h before it was quenched by slowly adding 1.5 mL CH$_3$OH and 15 mL HCl (2.5 M). The resulting solution was extracted with CH$_2$Cl$_2$ (4×15 mL). The the combined organic layers were dried over Na$_2$SO$_4$, filtered and concentrated under reduced pressure to afford the (3-azido-4-(prop-2-yn-1-yloxy)phenyl)methanol which was used directly for next step.

To a solution of (3-azido-4-(prop-2-yn-1-yloxy)phenyl) methanol (above) in CH$_2$Cl$_2$ (2 mL) was added pyridinium chlorochromate (PCC) (0.3103 g, 1.44 mmol). The reaction mixture was stirred for 30 min at room temperature and was diluted with 1:1 hexane: EtOAc. The resulting suspension was filtered through a short pad of silica gel and the filtered cake was washed by 1:1 Et$_2$O: Hexane and Et$_2$O. The evaporation of solvents gave the 3-azido-4-(prop-2-yn-1-yloxy)benzaldehyde which was confirmed by proton NMR and was used directly for next step.

A mixture of 3-methyl-1,4′-bipiperidine (0.0865 g, 0.048 mmol), the 3-azido-4-(prop-2-yn-1-yloxy)benzaldehyde (above), CH$_2$Cl$_2$ (2 mL), AcOH (0.027 mL, 0.47 mmol) and NaBH(OAc)$_3$ (0.1425 g, 0.67 mmol) was stirred at room temperature for 28 h. The reaction was then quenched by saturated NaHCO$_3$ solution (20 ml) at 0° C. and the generated bi-phase solution was extracted with CH$_2$Cl$_2$ (4×15 mL). The the combined organic layers were dried over Na$_2$SO$_4$, filtered and concentrated under reduced pressure. The flash chromatography on silica gel (1:9 Methanol: CH$_2$Cl$_2$) provided the desired product as a yellow gel (0.0378 g, 22% over three steps). $^1$H NMR (400 MHz, CDCl$_3$) δ 7.10-6.87 (m, 3 H), 4.72 (d, J=2.4 Hz, 2 H), 3.38 (s, 2 H), 3.03-2.85 (m, 4 H), 2.51 (t, J=2.4 Hz, 1 H), 2.41 (s, 1 H), 2.24 (d, J=11.8 Hz, 2 H), 1.93 (td, J=11.9, 2.2 Hz, 2 H), 1.84 (d, J=9.9 Hz, 2 H), 1.61 (m, 5 H), 1.37 (s, 2 H), 0.91 (d, J=5.4 Hz, 3H); $^{13}$C NMR (100 MHz, CDCl$_3$) δ 148.5, 133.0, 128.9, 125.9, 120.9, 114.1, 78.0, 76.1, 62.7, 61.9, 56.9, 53.1, 49.4, 33.8, 30.8, 27.5, 21.7; MS (ESI) m/z 368.2 (100%, [M+H]+).

XI. 1′-((5-azido-2-(prop-2-yn-1-yloxy)phenyl)sulfonyl)-4-methyl-1,4′-bipiperidine

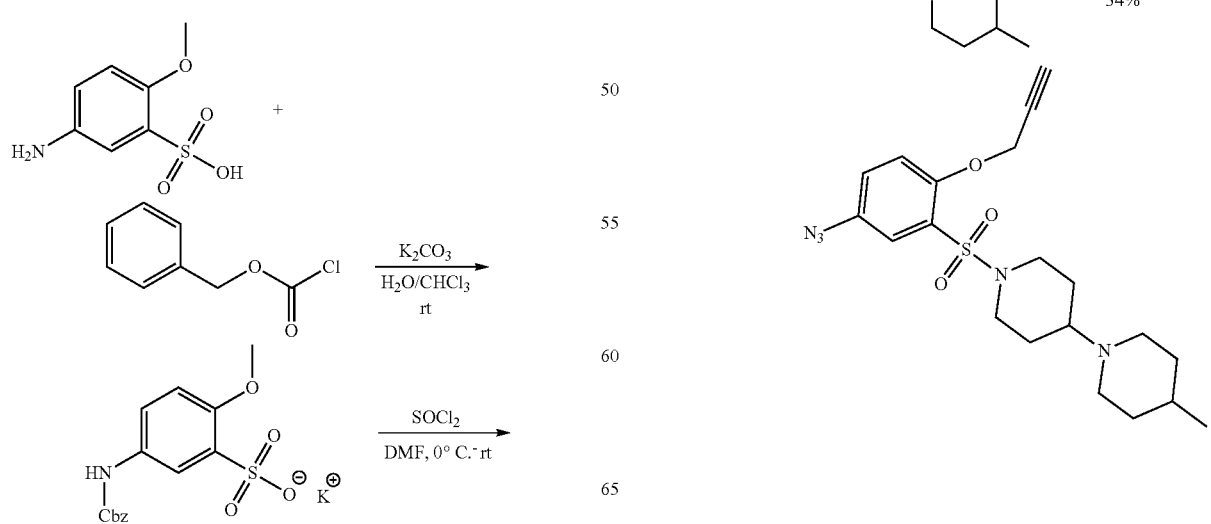

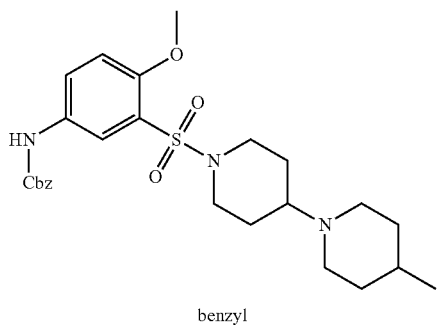 [SMILES: COc1ccc(NC(=O)OCc2ccccc2)cc1S(=O)(=O)N1CCC(N2CCC(C)CC2)CC1]

benzyl (4-methoxy-3-((4-methyl-[1,4'-bipiperidin]-1'-yl)sulfonyl)phenyl)carbamate: p-Anisidine-3-sulfonic acid (1.2215 g, 6.02 mmol), water (10 mL), benzyl chloroformate (1.03 mL, 7.21 mmol), $K_2CO_3$ (2.0854 g, 15.11 mmol) and $CHCl_3$ (10 mL) were added sequentially into a flask. The two-phase solution was stirred vigorously for 71 h. After addition of 75 mL water, the solution was washed by $CHCl_3$ (2×75 mL) and the aqueous solution was concentrated in vacuo to form 5-(((benzyloxy)carbonyl)amino)-2-methoxybenzenesulfonate potassium salt as yellow solid.

The salt was mixed with DMF (20 mL) and the suspension was cooled to 0° C. $SOCl_2$ (1.80 mL, 25.02 mmol) was added dropwise within 15 min. The reaction mixture was then allowed to warm to room temperature and stirred for 3 hours. The reaction solution was poured into ice water (50 mL) and was extracted by $CH_2Cl_2$ (3×60 ml). The combined organic layers were dried over $Na_2SO_4$, filtered and concentrated under reduced pressure, to form benzyl (3-(chlorosulfonyl)-4-methoxyphenyl)carbamate which was used without further purification.

A mixture of 4-methyl-1,4'-bipiperidine (1.2090 g, 6.64 mmol), benzyl (3-(chlorosulfonyl)-4-methoxyphenyl)carbamate (above), N, N-diisopropyl ethylamine (3 mL, 18.19 mmol), and $CH_2Cl_2$ (15 mL) were stirred at room temperature for 21 h. The solution was then diluted with $CH_2Cl_2$ (20 mL) and washed by saturated $NaHCO_3$ solution (35 mL) and brine (35 mL). The organic layer was dried over $Na_2SO_4$, filtered and concentrated under reduced pressure. The residue was purified by flash chromatography on silica gel (1:19 Methanol:$CH_2Cl_2$) to afford the desired product as a white solid (2.3318 g, 77% three steps). mp 124-127° C.; $^1H$ NMR (400 MHz, $CDCl_3$) δ 7.80 (s, br, 1 H), 7.67 (d, J=2.8 Hz, 1 H), 7.43-7.30 (m, 4 H), 6.95 (d, J=9.0 Hz, 1 H), 6.89 (s, 1 H), 5.18 (s, 2 H), 3.89 (s, J=3.4 Hz, 1 H), 3.87 (s, 3 H), 2.79 (d, J=11.5 Hz, 2 H), 2.66-2.53 (m, 2 H), 2.29 (tt, J=11.6, 3.5 Hz, 1 H), 2.19-2.06 (m, 2 H), 1.96-1.72 (m, 3 H), 1.68-1.48 (m, 4 H), 1.31 (ddt, J=14.5, 6.7, 3.7 Hz, 1 H), 1.25-1.10 (m, 2 H), 0.89 (d, J=6.3 Hz, 3 H); $^{13}C$ NMR (100 MHz, $CDCl_3$) δ 153.6, 153.0, 135.9, 130.8, 128.6, 128.4, 128.3, 126.9, 125.1, 122.2, 113.2, 67.2, 61.8, 56.4, 49.5, 45.9, 34.6, 31.1, 27.9, 21.9; MS (ESI) m/z 502.2 (100%, [M+H]+).

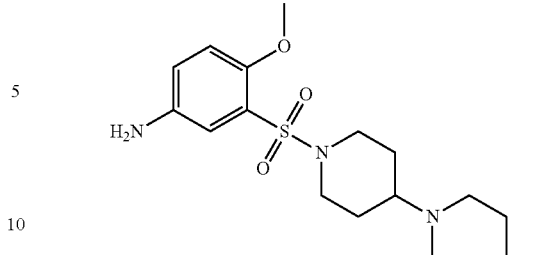

4-methoxy-3-((4-methyl-[1,4'-bipiperidin]-1'-yl)sulfonyl)aniline: To a flask were added methanol (6 mL), Benzyl (4-methoxy-3-((4-methyl-[1,4'-bipiperidin]-1'-yl)sulfonyl)phenyl)carbamate (0.5270 g, 1.05 mmol), and 3 spatula palladium on carbon (10 wt %). The flask was sealed with a rubber septum, followed by evacuating air using vacuum and refilling hydrogen using a hydrogen balloon. The reaction mixture was stirred for 27 hours and was filtered through a pad of Celite, washed by $CH_2Cl_2$. The evaporation of solvents afforded the product as a yellow solid (0.3591 g, 93%). mp 54-57° C.; $^1H$ NMR (500 MHz, $CDCl_3$) δ 7.24 (d, J=2.5 Hz, 1 H), 6.89-6.79 (m, 2 H), 3.91 (d, J=13.0 Hz, 2 H), 3.84 (s, 3 H), 3.59 (s, 2 H), 2.84 (d, J=9.3 Hz, 2 H), 2.60 (t, J=12.5 Hz, 2 H), 2.36 (t, J=11.9 Hz, 1 H), 2.19 (td, J=11.6, 10.0, 2.7 Hz, 2 H), 1.84 (d, J=12.5 Hz, 2 H), 1.70-1.50 (m, 4 H), 1.35 (s, br, 1 H), 1.26 (m, 2 H), 0.92 (d, J=6.3 Hz, 3 H); $^{13}C$ NMR (100 MHz, $CDCl_3$) δ 149.6, 140.0, 126.8, 120.8, 117.7, 114.3, 62.7, 56.7, 49.2, 45.4, 32.3, 30.1, 26.8, 21.2; MS (ESI) m/z 502.2 (100%, [M+H]+).

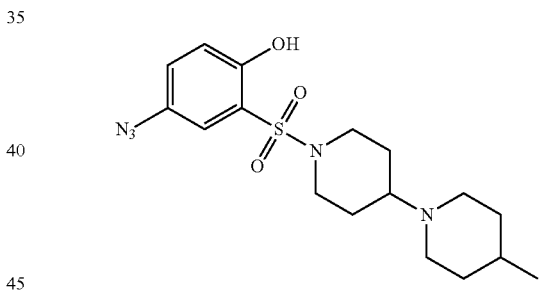

4-azido-2-((4-methyl-[1,4'-bipiperidin]-1'-yl)sulfonyl)phenol: To a 25 ml flame-dried flask equipped with a reflux condenser were added 4-methoxy-3-((4-methyl-[1,4'-bipiperidin]-1'-yl)sulfonyl)aniline (0.2546 g, 0.69 mmol), anhydrous toluene (6 mL), anhydrous $CH_2Cl_2$ (1.5 mL) and $BBr_3$ (1 M in $CH_2Cl_2$, 3.5 mL, 3.5 mmol). The resulting solution was carried out at 70° C. in an oil bath for 3 h before it was cooled to 0° C. and was quenched by 6 mL methanol. The solution was filtered through a pad of Celite, washed by methanol. After evaporation of solvents, the residue was purified through flash chromatograph on silica gel (1.5:8.5 Methanol:$CH_2Cl_2$) to afford the demethylated product. $^1H$ NMR (400 MHz, Methanol-d4) δ 7.79 (d, J=2.7 Hz, 1 H), 7.51 (dd, J=8.8, 2.7 Hz, 1 H), 7.13 (d, J=8.7 Hz, 1 H), 3.95 (d, J=13.2 Hz, 2 H), 3.49 (d, J=10.8 Hz, 2 H), 3.40 (m, 1 H), 3.26 (m, 2 H), 3.05 (t, J=13.7 Hz, 2 H), 2.82 (t, J=12.5 Hz, 2 H), 2.21 (dd, J=11.6, 3.3 Hz, 2 H), 1.88 (d, J=14.7 Hz, 2 H), 1.75 (d, J=14.2 Hz, 3 H), 1.53 (q, J=12.7 Hz, 2 H), 0.94 (d, J=6.2 Hz, 3 H); $^{13}C$ NMR (100 MHz, Methanol-d4) δ 155.9, 129.3, 125.2, 125.0, 121.6, 118.8, 62.9, 49.8, 44.5, 31.1, 28.5, 26.3, 20.0.

To the flask containing the demethylated product (above) were added 6 M HCl (3 mL), THF (3 mL) and DMF (3 mL). The mixture was cooled to 0° C. and NaNO$_2$ (0.0612 g, 0.89 mmol) in H$_2$O (1 mL) was added dropwise in 5 min. The reaction solution was stirred for 40 min at 0° C. and NaN$_3$ (0.0699 g, 1.08 mmol) in H$_2$O (1 mL) was added dropwise. The resulting solution was then allowed to warm up to room temperature and stirred overnight after which the reaction solution was diluted with water (10 mL) and was basified by 1 M NaOH solution. The resulting solution was extracted by CH$_2$Cl$_2$ (3×25 mL) and the combined organic layers were dried over Na$_2$SO$_4$, filtered and concentrated under reduced pressure. The residue was purified through flash chromatograph on silica gel (1:9 Methanol:CH$_2$Cl$_2$) to afford the desired product (0.1921 g, 73% two steps) as a green oil. $^1$H NMR (400 MHz, CDCl$_3$) δ 7.15 (dd, J=2.1, 1.0 Hz, 1 H), 7.12-7.08 (m, 2 H), 3.85 (d, J=12.5 Hz, 2 H), 3.05 (d, J=10.9 Hz, 2 H), 2.67 (t, J=11.8 Hz, 1 H), 2.51 (td, J=12.4, 2.4 Hz, 2 H), 2.40 (t, J=10.4 Hz, 2 H), 2.04 (d, J=11.1 Hz, 2 H), 1.83-1.61 (m, 4 H), 1.46 (dt, J=19.6, 7.8 Hz, 3 H), 0.91 (d, J=5.5 Hz, 3 H); $^{13}$C NMR (100 MHz, CDCl$_3$) δ 152.8, 132.1, 125.9, 121.3, 120.5, 118.8, 61.8, 49.4, 45.4, 32.7, 30.1, 26.5, 21.3; MS (ESI) m/z 380.2 (100%, [M+H]+).

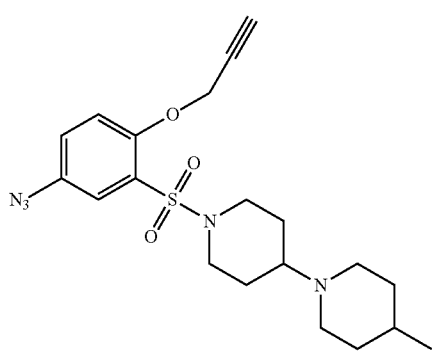 [SMILES: C#CCOc1ccc(N=[N+]=[N-])cc1S(=O)(=O)N1CCC(N2CCC(C)CC2)CC1]

1'-((5-azido-2-(prop-2-yn-1-yloxy)phenyl)sulfonyl)-4-methyl-1,4'-bipiperidine: 4-azido-2-((4-methyl-[1,4'-bipiperidin]-1'-yl)sulfonyl)phenol (0.1190 g, 0.31 mmol) was dissolved in anhydrous DMF (2.5 mL), followed by addition of NaH (60%, 0.163 g, 0.41 mmol) at 0° C. The flask was then immediately flushed by argon flow and sealed by a rubber septum fitted with an argon balloon. The reaction solution was stirred at 0° C. for 15 min and propargyl bromide (80% in toluene, 0.035 mL, 0.31 mmol) was added via syringe. The solution was allowed to gradually warm up to room temperature and stirred overnight. The reaction was then quenched by adding saturated NaHCO$_3$ solution (20 mL), followed by the extraction with EtOAc (3×25 mL). The combined organic layers were washed by water (40 mL) and brine (40 mL) after which the organic phase was dried over Na$_2$SO$_4$, filtered and concentrated under reduced pressure. The flash chromatography on silica gel (1:19 Methanol:CH$_2$Cl$_2$) afforded the desired product (0.0442 g, 34%) as a yellow gel. $^1$H NMR (400 MHz, CDCl$_3$) δ 7.57 (dd, J=2.1, 1.1 Hz, 1 H), 7.17-7.07 (m, 2 H), 4.77 (d, J=2.4 Hz, 2 H), 3.90 (d, J=12.9 Hz, 2 H), 2.80 (d, J=11.3 Hz, 2 H), 2.66 (td, J=12.5, 2.4 Hz, 2 H), 2.54 (t, J=2.4 Hz, 1 H), 2.34 (tt, J=11.6, 3.5 Hz, 1 H), 2.15 (td, J=11.5, 2.7 Hz, 2 H), 1.90-1.75 (m, 2 H), 1.71-1.52 (m, 4 H), 1.42-1.27 (m, 1 H), 1.27-1.11 (m, 2 H), 0.88 (d, J=6.3 Hz, 3 H); $^{13}$C NMR (125 MHz, CDCl$_3$) δ 151.7, 133.8, 129.5, 124.2, 122.0, 115.9, 77.3, 76.9, 61.9, 57.2, 49.4, 46.0, 34.4, 31.0, 27.8, 21.9; MS (ESI) m/z 418.2 (100%, [M+H]+).

XII. Synthesis of 1'-(phenylsulfonyl)-4-(prop-2-yn-1-yl)-1,4'-bipiperidine compound with aryl azide

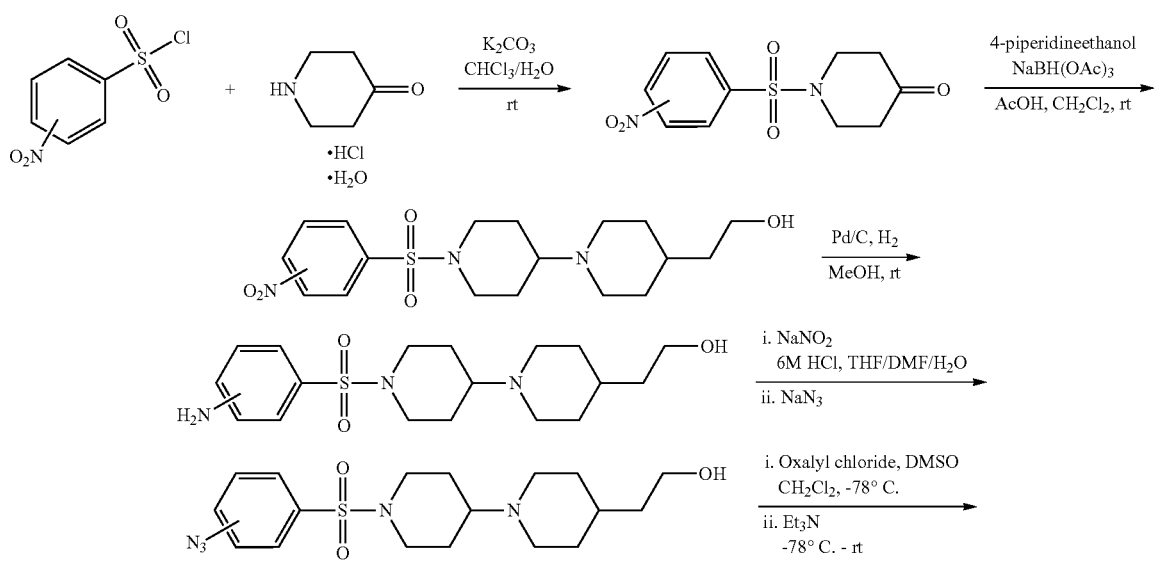

-continued

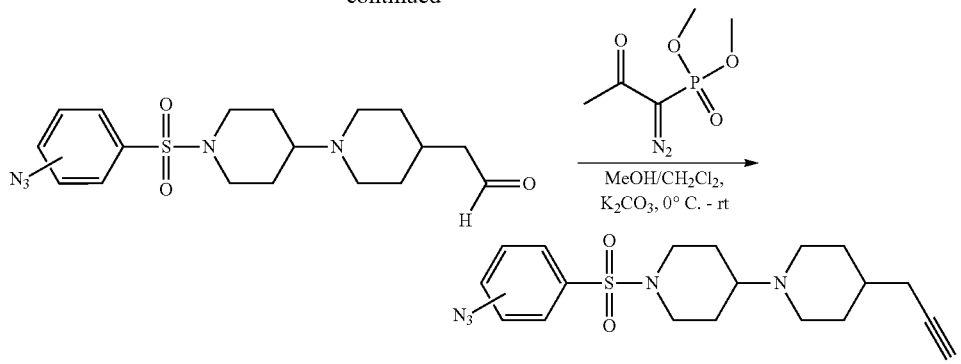

The synthetic experimental procedure is represented by the preparation of 1'-((4-azidophenyl)sulfonyl)-4-(prop-2-yn-1-yl)-1,4'-bipiperidine.

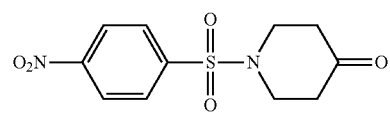 [SMILES: O=C1CCN(S(=O)(=O)c2ccc([N+](=O)[O-])cc2)CC1]

1-((4-nitrophenyl)sulfonyl)piperidin-4-one was prepared according to the general procedure for the preparation of sulfonamides from sulfonyl chlorides and amine hydrochloride salts with the detailed characterization above.

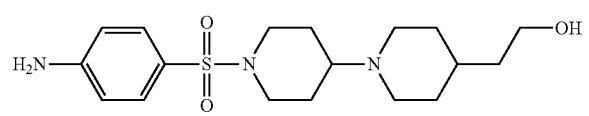 [SMILES: Nc1ccc(S(=O)(=O)N2CCC(N3CCC(CCO)CC3)CC2)cc1]

2-(1'-((4-nitrophenyl)sulfonyl)-[1,4'-bipiperidin]-4-yl)ethanol was prepared according to the general procedure for reductive amination with the detailed characterization above.

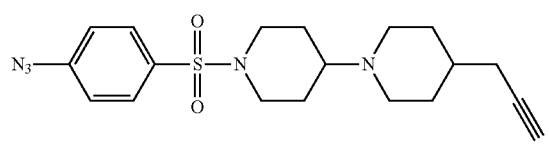

2-(1'-((4-aminophenyl)sulfonyl)-[1,4'-bipiperidin]-4-yl) ethanol: To a 10 mL flask were added 2-(1'-((4-nitrophenyl)sulfonyl)-[1,4'-bipiperidin]-4-yl)ethanol (0.1002 g, 0.25 mmol), methanol (3.5 mL) and 1 spatula palladium on carbon (10 wt %). The flask was sealed with a rubber septum, followed by evacuating air using vacuum and refilling hydrogen using a hydrogen balloon. The reaction mixture was stirred for 21 hours and was filtered through a pad of Celite, washed by $CH_2Cl_2$. The evapoaration of solvents afforded the product as a yellow solid (0.0815 g, 88%). mp 59-62° C.; $^1$H NMR (500 MHz, CDCl$_3$) δ 7.53 (d, J=8.6 Hz, 2 H), 6.70 (d, J=8.6 Hz, 2 H), 4.15 (s, 2 H), 3.80 (dt, J=10.9, 3.1 Hz, 2 H), 3.68 (t, J=6.7 Hz, 2 H), 2.82 (d, J=10.7 Hz, 2), 2.30-2.06 (m, 5 H), 1.83 (d, J=11.8 Hz, 2 H), 1.67 (m, 4 H), 1.50 (q, J=6.7 Hz, 2H), 1.45-1.35 (m, 1 H), 1.35-1.15 (m, 3 H); $^{13}$C NMR (100 MHz, CDCl$_3$) δ 150.5, 129.8, 124.2, 113.9, 61.6, 60.5, 49.4, 46.1, 39.3, 32.6, 32.5, 27.3; MS (ESI) m/z 368.2 (100%, [M+H]+).

2-(1'-((4-azidophenyl)sulfonyl)-[1,4'-bipiperidin]-4-yl)ethanol: To a 25 mL flask containing 2-(1'-((4-aminophenyl)sulfonyl)-[1,4'-bipiperidin]-4-yl)ethanol (0.1822 g, 0.50 mmol) were added 6 M HCl (2 mL), THF (2 mL) and DMF (2 mL). The mixture was cooled to 0° C. and NaNO$_2$ (0.0445 g, 0.64 mmol) in H$_2$O (0.7 mL) was added dropwise in 5 min. The reaction solution was stirred for 20 min at 0° C. and NaN$_3$ (0.0521 g, 0.80 mmol) was added. The resulting solution was then allowed to warm up to room temperature gradually and stirred overnight. The reaction was then quenched by adding 1 M NaOH (30 mL), followed by the extraction with CH$_2$Cl$_2$ (3×30 mL). The combined organic layers were dried over Na$_2$SO$_4$, filtered and concentrated under reduced pressure. The residue was dissolved in EtOAc (30 mL), washed by 10% LiCl solution (30 mL) and brine (3×30 mL) to afford the entitled product (0.0719 g, 36%) as a pale yellow solid. mp 165-167° C.; $^1$H NMR (400 MHz, CDCl$_3$) δ 7.72 (d, J=8.6 Hz, 2 H), 7.12 (d, J=8.6 Hz, 2 H), 3.81 (d, J=11.5 Hz, 2 H), 3.65 (t, J=6.6 Hz, 2 H), 2.80 (d, J=10.9 Hz, 2 H), 2.33-2.04 (m, 5 H), ), 1.82 (d, J=12.1 Hz, 2H), 1.64 (m, 5 H), 1.47 (q, J=6.6 Hz, 2 H), 1.38 (m, 1 H), 1.18 (ddd, J=15.4, 10.3, 3.7 Hz, 2 H); $^{13}$C NMR (100 MHz, CDCl$_3$) δ 144.8, 132.3, 129.5, 119.4, 61.4, 60.4, 49.4, 46.1, 39.3, 32.6, 32.5, 27.3; MS (ESI) m/z 394.2 (100%, [M+H]+).

1'-((4-azidophenyl)sulfonyl)-4-(prop-2-yn-1-yl)-1,4'-bipiperidine: A 25 ml flame-dried flask equipped with a magnetic stirring bar was purged by argon and was then sealed with a rubber septum fitted with an argon balloon. Anhydrous CH$_2$Cl$_2$ (1.5 mL) and oxalyl chloride (0.30 mL, 2 M in CH$_2$Cl$_2$, 0.60 mmol) were added via syringe sequentially. The resulting solution was cooled to −78° C. in a dry ice-acetone bath. Anhydrous DMSO (0.085 mL, 1.20 mmol) was introduced and the solution was stirred for 25 min at −78° C. 2-(1'-((4-azidophenyl)sulfonyl)-[1,4'-bipiperidin]-4-yl)ethanol (0.1910 g, 0.49 mmol) in 2 mL CH$_2$Cl$_2$ was added dropwise. After the reaction mixture was stirred at −78° C. for 1 h, Et$_3$N (0.24 mL, 1.73 mmol) was added and the reaction solution was allowed to warm up to room temperature and stirred for 1.5 hours, before being quenched by 20 mL saturated NaHCO$_3$ solution. The resulting biphase solution was exacted by CH$_2$Cl$_2$ (3×20 mL). The combined organic layers were dried over Na$_2$SO$_4$, filtered and concentrated under reduced pressure to afford the aldehyde intermediate which was used directly for next step without further purification.

The generated aldehyde was dissolved in 2 mL CH$_2$Cl$_2$ and half of it was for Bestmann Ohira reagent reaction. The procedure of Bestmann Ohira reagent reaction is described as following. Bestmann Ohira reagent (dimethyl (1-diazo-2-oxopropyl)phosphonate) (0.0570 g, 0.030 mmol) and methanol (2 mL) were mixed at 0° C., followed by addition of the adehyde (dissolved in 1 mL CH$_2$Cl$_2$) and K$_2$CO$_3$ (0.0670 g, 0.49 mmol). The reaction suspension was then allowed to warm up to room temperature and stirred overnight. The slurry solution was filtered and poured into a separatory funnel, diluted with 20 mL CH$_2$Cl$_2$, washed by Saturated NaHCO3 solution (20 ml) and 1 N NaOH (20 mL). The organic layer was dried by Na$_2$SO$_4$, filtered and concentrated in vacuo. The residue was sonicated with a small amount of hexane and the supernatant of hexane layer was removed by glass pipette and was then purified through flash chromatography on silica gel (1:9 CH$_3$OH:CH$_2$Cl$_2$) to afford the entitled product as a yellow solid (0.0454 g, 48%). $^1$H NMR (400 MHz, CDCl$_3$) δ 7.74 (d, J=8.7 Hz, 2 H), 7.15 (d, J=8.7 Hz, 2 H), 3.85 (dd, J=11.5, 3.8 Hz, 2 H), 2.87 (s, 2 H), 2.39-2.05 (m, 7 H), 1.97 (t, J=2.1 Hz, 1 H), 1.85 (m, 4 H), 1.67 (q, J=12.5 Hz, 2 H), 1.46 (s, br, 1 H), 1.30 (s, br, 2 H); $^{13}$C NMR (100 MHz, CDCl$_3$) δ 144.8, 132.3, 129.5, 119.4, 82.6, 69.4, 61.5, 49.2, 46.0, 35.4, 31.7, 27.2, 25.3; MS (ESI) m/z 388.2 (100%, [M+H]+).

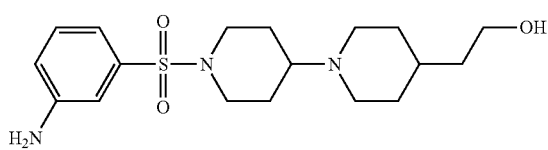

2-(1'-((3-aminophenyl)sulfonyl)-[1,4'-bipiperidin]-4-yl)ethanol was prepared as a yellow solid (91%) according to the experimental procedure of the synthesis of 2-(1'-((4-aminophenyl)sulfonyl)-[1,4'-bipiperidin]-4-yl)ethanol. mp 61-64° C.; $^1$H NMR (400 MHz, CD$_3$OD) δ 7.27 (t, J=7.9 Hz, 1 H), 7.03 (s, 1 H), 6.97 (d, J=7.7 Hz, 1 H), 6.91 (dd, J=8.1, 2.3 Hz, 1 H), 3.82 (d, J=12.8 Hz, 2 H), 3.60 (t, J=6.4 Hz, 2H), 3.32 (s, 2 H), 3.05 (d, J=11.5 Hz, 2 H), 2.49 (t, J=11.7 Hz, 1 H), 2.45-2.26 (m, 4 H), 1.97 (d, J=11.8 Hz, 2 H), 1.80 (d, J=13.3 Hz, 2 H), 1.62 (qd, J=12.3, 4.1 Hz, 2 H), 1.57-1.50 (m, 1 H), 1.48 (q, J=6.4 Hz, 2 H), 1.37-1.22 (m, 2 H); $^{13}$C NMR (100 MHz, CD$_3$OD) δ 149.2, 136.3, 129.4, 118.5, 115.4, 112.5, 61.6, 58.9, 49.2, 45.6, 38.4, 31.7, 31.0, 26.6; MS (ESI) m/z 368.2 (100%, [M+H]+).

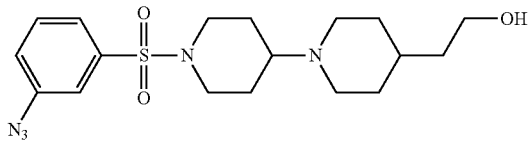 [SMILES: [N-]=[N+]=Nc1cccc(S(=O)(=O)N2CCC(N3CCC(CCO)CC3)CC2)c1]

2-(1'-((3-azidophenyl)sulfonyl)-[1,4'-bipiperidin]-4-yl)ethanol was prepared as a pale yellow solid (>95%) according to the experimental procedure of the synthesis of 2-(1'-((4-azidophenyl)sulfonyl)-[1,4'-bipiperidin]-4-yl)ethanol. mp 168-171° C.; $^1$H NMR (400 MHz, CDCl$_3$) δ 7.54-7.45 (m, 2 H), 7.36 (s, 1 H), 7.24-7.18 (m, 1 H), 3.83 (d, J=12.4 Hz, 2 H), 3.65 (t, J=6.6 Hz, 2 H), ), 2.79 (d, J=11.0 Hz, 2 H), 2.37-2.07 (m, 5 H), 1.83 (d, J=11.0 Hz, 2H), 1.72-1.54 (m, 5 H), 1.47 (q, J=6.6 Hz, 2 H), 1.43-1.34 (m, 1 H), 1.20 (tdd, J=15.5, 9.6, 4.2 Hz, 2 H); $^{13}$C NMR (100 MHz, CDCl$_3$) δ 141.4, 138.2, 130.5, 123.8, 123.0, 118.0, 61.4, 60.4, 49.4, 46.1, 39.3, 32.6, 32.5, 27.3; MS (ESI) m/z 394.2 (100%, [M+H]+).

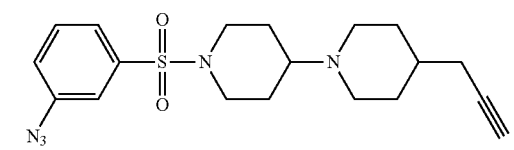 [SMILES: C#CCC1CCN(C2CCN(S(=O)(=O)c3cccc(N=[N+]=[N-])c3)CC2)CC1]

1'-((3-azidophenyl)sulfonyl)-4-(prop-2-yn-1-yl)-1,4'-bipiperidine was prepared as a yellow solid (49%) according to the experimental procedure of the synthesis of 1'-((4-azidophenyl)sulfonyl)-4-(prop-2-yn-1-yl)-1,4'-bipiperidine. $^1$H NMR (500 MHz, CDCl$_3$) δ 7.59-7.48 (m, 2 H), 7.38 (s, 1 H), 7.27-7.23 (m, 1 H), 3.90 (d, J=11.8 Hz, 2 H), 3.02 (s, 2 H), 2.53 (s, br, 1 H), 2.33 (m, 4 H), 2.16 (s, 2 H), 2.04 (d, J=11.8 Hz, 2 H), 1.99 (t, J=2.6 Hz, 1 H), 1.89 (d, J=10.7 Hz, 2 H), 1.73 (qd, J=12.3, 4.2 Hz, 2 H), 1.66-1.46 (s, br, 3 H); $^{13}$C NMR (100 MHz, CDCl$_3$) δ 141.6, 137.9, 130.6, 123.7, 123.2, 118.0, 82.1, 69.8, 61.8, 49.0, 45.7, 35.0, 30.6, 26.6, 25.0; MS (ESI) m/z 388.1 (100%, [M+H]+).

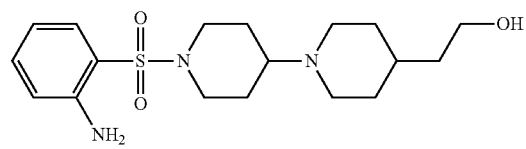 [SMILES: Nc1ccccc1S(=O)(=O)N1CCC(N2CCC(CCO)CC2)CC1]

2-(1'-((2-aminophenyl)sulfonyl)-[1,4'-bipiperidin]-4-yl)ethanol was prepared as a yellow solid (90%) according to the experimental procedure of the synthesis of 2-(1'-((4-aminophenyl)sulfonyl)-[1,4'-bipiperidin]-4-yl)ethanol. mp 204-206° C.; $^1$H NMR (400 MHz, CDCl$_3$) δ 7.52 (dd, J=8.1, 1.6 Hz, 1 H), 7.37-7.18 (m, 1 H), 6.85-6.58 (m, 2 H), 5.04 (s, 2 H), 3.84 (d, J=12.4 Hz, 2 H), 3.64 (t, J=6.4 Hz, 2 H), 2.86 (d, J=10.7 Hz, 2 H), 2.45 (td, J=12.3, 2.4 Hz, 2 H), 2.34 (t, J=11.8 Hz, 1 H), 2.26-2.13 (m, 2 H), 1.86 (d, J=13.3 Hz, 2 H), 1.70 (d, J=11.4 Hz, 2 H), 1.60 (qd, J=12.3, 4.1 Hz, 2 H), 1.52-1.20 (m, 6 H); $^{13}$C NMR (100 MHz, CDCl$_3$) δ 146.2, 134.2, 130.3, 117.8, 117.6, 117.2, 61.7, 60.3, 49.4, 45.8, 39.1, 32.3, 32.0, 27.0; MS (ESI) m/z 368.2 (100%, [M+H]+).

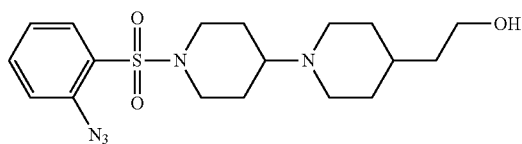

2-(1'-((2-azidophenyl)sulfonyl)-[1,4'-bipiperidin]-4-yl)ethanol was prepared as pale yellow solid (78%) according the experimental procedure of the synthesis of 2-(1'-((4-azidophenyl)sulfonyl)-[1,4'-bipiperidin]-4-yl)ethanol. mp 152-155° C.; $^1$H NMR (400 MHz, CDCl$_3$) δ 7.92 (dd, J=7.9, 1.5 Hz, 1 H), 7.56 (td, J=7.7, 1.6 Hz, 1 H), 7.38-7.12 (m, 2 H), 3.94 (d, J=13.0 Hz, 2 H), ), 3.67 (s, 2 H), 2.87 (d, J=10.9 Hz, 2 H), 2.66 (td, J=12.7, 2.4 Hz, 2 H), 2.35 (d, J=12.5 Hz, 1 H), 2.18 (t, J=11.3 Hz, 2 H), 1.87 (d, J=12.6 Hz, 2 H), 1.71 (d, J=10.8 Hz, 2 H), 1.66-1.54 (m, 2 H), 1.54-1.21 (m, 6 H); $^{13}$C NMR (125 MHz, CDCl$_3$) δ 138.3, 133.9, 131.7, 129.3, 124.6, 119.9, 61.9, 60.4, 49.4, 45.8, 39.2, 32.4, 32.3, 27.8; MS (ESI) m/z 394.2 (100%, [M+H]+).

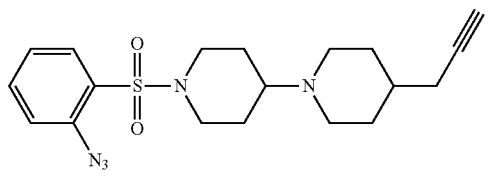 [SMILES: C#CCC1CCN(C2CCN(S(=O)(=O)c3ccccc3N=[N+]=[N-])CC2)CC1]

1'-((2-azidophenyl)sulfonyl)-4-(prop-2-yn-1-yl)-1,4'-bipiperidine was prepared as yellow solid (40%) according to the experimental procedure of the synthesis of 1'-((4-azidophenyl)sulfonyl)-4-(prop-2-yn-1-yl)-1,4'-bipiperidine. $^1$H NMR (400 MHz, CDCl$_3$) δ 7.94 (dd, J=7.9, 1.6 Hz, 1 H), 7.57 (td, J=7.8, 1.6 Hz, 1 H), 7.31-7.27 (m, 1 H), 7.23 (td, J=7.7, 1.1 Hz, 1 H), 3.94 (d, J=12.7 Hz, 2 H), 2.87 (d, J=11.0 Hz, 2 H), 2.67 (td, J=12.4, 2.4 Hz, 2 H), 2.34 (ddt, J=11.5, 7.3, 3.7 Hz, 1 H), 2.12 (m, 3 H), 1.96 (t, J=2.6 Hz, 1 H), 1.82 (t, J=15.2 Hz, 4 H), 1.60 (qd, J=12.1, 4.2 Hz, 2 H), 1.46 (m, 1 H), 1.29 (ddd, J=24.3, 12.1, 3.7 Hz, 3 H); $^{13}$C NMR (100 MHz, CDCl$_3$) δ 138.3, 133.8, 131.7, 129.4, 124.6, 119.9, 82.8, 69.3, 61.6, 49.2, 45.9, 35.6, 32.0, 28.0, 25.4; MS (ESI) m/z 388.1 (100%, [M+H]+).

XIII. Synthesis of 3-(1'-(mesitylsulfonyl)-[1,4'-bipiperidin]-4-yl)propanenitrile

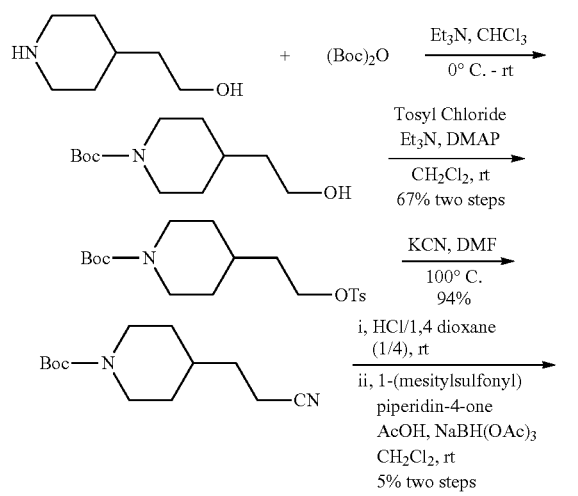

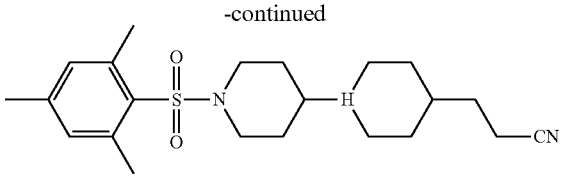

tert-butyl 4-(2-(tosyloxy)ethyl)piperidine-1-carboxylate 2-(piperidin-4-yl)ethanol (1.3091 g, 10.15 mmol), Et$_3$N (4.20 mL, 30.19 mmol) and CHCl$_3$ (10 mL) were mixed and stirred at 0° C., followed by dropwise addition of Di-tert-butyl-dicarbonate (2.5770 g, 11.81 mmol) in CHCl$_3$ (4 mL) in 30 min. The reaction solution was then allowed to warm up to room temperature and stirred for 9 h. The reaction solution was poured into saturated NaHCO$_3$ solution (30 mL) and extracted by CHCl$_3$ (3×30 mL). The combined organic layers were dried over Na$_2$SO$_4$, filtered and concentrated under reduced pressure to obtain the Boc protected 2-(piperidin-4-yl)ethanol which was used for next step without further purification.

The Boc protected 2-(piperidin-4-yl)ethanol was stirred with tosyl chloride (3.8988 g, 20.46 mmol) and DMAP (0.2514 g, 2.06 mmol) in CH$_2$Cl$_2$ (20 ml), followed by dropwise addition of Et$_3$N (4.25 mL, 30.55 mmol) in 10 min. The reaction solution was stirred for 14 h and was slowly poured into saturated NaHCO$_3$ solution (70 mL), extracted by CH$_2$Cl$_2$ (3×70 mL). The combined organic layers were dried over Na$_2$SO$_4$, filtered and concentrated under reduced pressure. The residue was purified through through flash chromatography (1:4 EtOAc:Hexane) to obtain the entitled product (2.6127 g, 67% two steps) as a yellow oil. $^1$H NMR (400 MHz, CDCl$_3$) δ 7.76 (d, J=8.3 Hz, 2 H), 7.33 (d, J=8.3 Hz, 2 H), 4.21-3.86 (m, 4 H), 2.58 (t, J=12.8 Hz, 2 H), 2.43 (s, 3 H), 1.65-1.46 (m, 5 H), 1.46-1.30 (s, 9 H), 1.14-0.87 (m, 2 H); $^{13}$C NMR (100 MHz, CDCl$_3$) δ 154.7, 144.8, 132.9, 129.8, 127.9, 79.3, 68.0, 43.7, 35.2, 32.1, 31.6, 28.4, 21.6; MS (ESI) m/z 406.2 (100%, [M+H]+).

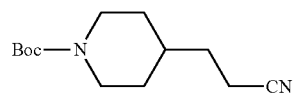

tert-butyl 4-(2-cyanoethyl)piperidine-1-carboxylate: To a 15 ml flask were added tert-butyl 4-(2-(tosyloxy)ethyl)piperidine-1-carboxylate (0.4975 g, 1.30 mmol), KCN (0.6981 g, 10.74 mmol) and DMF (5 mL). The resulting suspension was stirred vigorously at 100° C. for 4 h and was cooled down to room temperature. The suspension was then slowly poured into saturated NaHCO$_3$ solution (30 mL) and extracted by CH$_2$Cl$_2$ (3×30 mL).). The combined organic layers were dried over Na$_2$SO$_4$, filtered and concentrated under reduced pressure. Flash chromatography on silica gel (2:1 Hexane:EtOAc) provided the desired product (0.2901 g, 94%) as a colorless gel. $^1$H NMR (400 MHz, CDCl$_3$) δ 4.09 (s, 2 H), 2.67 (t, J=12.4 Hz, 2 H), 2.36 (td, J=7.1, 0.9 Hz, 2 H), 1.80-1.50 (m, 5 H), 1.42 (s, 9 H), 1.08 (qd, J=12.2, 4.2

Hz, 2 H); $^{13}$C NMR (100 MHz, CDCl$_3$) δ 154.7, 119.5, 79.4, 43.6, 34.9, 31.7, 31.4, 28.4, 14.5.

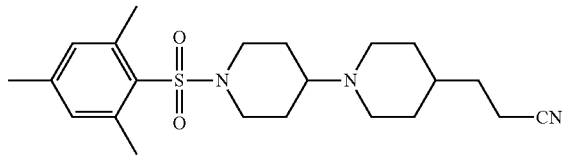 [SMILES: Cc1cc(C)c(S(=O)(=O)N2CCC(N3CCC(CCC#N)CC3)CC2)c(C)c1]

3-(1'-(mesitylsulfonyl)-[1,4'-bipiperidin]-4-yl)propanenitrile tert-butyl 4-(2-cyanoethyl)piperidine-1-carboxylate (0.3280 g, 1.38 mmol) was mixed and stirred with HCl (1 mL) in 1, 4-dioxane (4 mL) at room temperature for 2 hours. After the evaporation of solvents, the generated 4-(2-cyanoethyl)piperidine hydrochloride acid salt was neutralized by saturated NaHCO$_3$ solution at 0° C., followed by extraction with CH$_2$Cl$_2$ (3×25 mL). The combined organic layers were dried over Na$_2$SO$_4$, filtered and concentrated under reduced pressure (low vacuum) to provide the 3-(piperidin-4-yl)propanenitrile which was used for next step without further purification.

3-(piperidin-4-yl)propanenitrile above, 1-(mesitylsulfonyl)piperidin-4-one (0.3860 g, 1.37 mmol), CH$_2$Cl$_2$ (4 mL), AcOH (0.080 mL, 1.40 mmol) was stirred at room temperature for 25 min and NaBH(OAc)$_3$ (0.4298 g, 2.03 mmol) was added. The resulting solution was stirred at room temperature for 50 h. The reaction was then quenched by saturated NaHCO3 solution at 0° C., followed by extraction with CH$_2$Cl$_2$ (3×25 mL). The the combined organic layers were dried over Na$_2$SO$_4$, filtered and concentrated under reduced pressure. The residue was purified through flash chromatography (1:19 MeOH:CH$_2$Cl$_2$) to provide the desired product (0.0252 g, 5% two steps) as a white gel. $^1$H NMR (400 MHz, CDCl$_3$) δ 6.94 (s, 2 H), 3.63 (d, J=12.3 Hz, 2 H), 2.90 (d, J=10.7 Hz, 2 H), 2.74 (td, J=12.4, 2.4 Hz, 2 H), 2.60 (s, 6 H), 2.35 (t, J=7.2 Hz, 3 H), 2.29 (s, 3 H), 2.14 (t, J=9.6 Hz, 2 H), 1.84 (d, J=12.7 Hz, 2 H), 1.71 (d, J=12.3 Hz, 2 H), 1.63-1.34 (m, 5 H), 1.24 (m, 2 H); $^{13}$C NMR (100 MHz, CDCl$_3$) δ 142.5, 140.4, 131.9, 131.7, 119.7, 61.8, 49.2, 44.0, 34.8, 31.8, 31.7, 27.6, 22.8, 21.0, 14.6; MS (ESI) m/z 404.2 (100%, [M+H]+).

XIV. Synthesis of 3-(1-(mesitylsulfonyl)piperidin-4-yl)-6-methyl-1,3-oxazinane

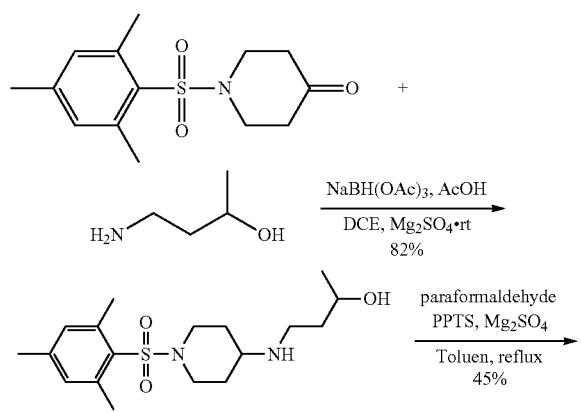

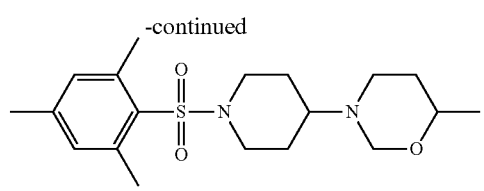

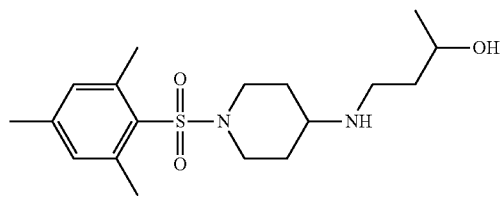 [SMILES: Cc1cc(C)c(S(=O)(=O)N2CCC(NCCC(C)O)CC2)c(C)c1]

4-((1-(mesitylsulfonyl)piperidin-4-yl)amino)butan-2-ol was obtained as a white solid (82%) through flash chromatography (1:19 MeOH:CH$_2$Cl$_2$) after the reductive amination between 4-aminobutan-2-ol and 1-(mesitylsulfonyl)piperidin-4-one with the reaction time of 27 h. mp 105-108° C.; $^1$H NMR (500 MHz, CDCl$_3$) δ 6.95 (s, 2 H), 3.96 (ddd, J=8.9, 5.8, 2.4 Hz, 1 H), 3.55 (d, J=12.5 Hz, 2 H), 3.05 (dt, J=11.9, 4.2 Hz, 1 H), 2.83 (tt, J=12.5, 3.3 Hz, 2 H), 2.76 (td, J=11.1, 2.9 Hz, 1 H), 2.61 (s, 7H), 2.30 (s, 3 H), 1.96 (t, J=12.8 Hz, 2 H), 1.63 (d, J=14.9 Hz, 1 H), 1.47 (m, 1 H), 1.34 (m, 2 H), 1.16 (d, J=6.2 Hz, 3 H); $^{13}$C NMR (100 MHz, CDCl$_3$) δ 142.6, 140.4, 131.9, 131.6, 69.5, 54.4, 45.5, 43.1, 43.0, 37.0, 31.8, 31.5, 23.6, 22.8, 21.0; MS (ESI) m/z 355.2 (100%, [M+H]+).

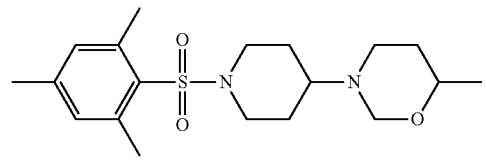

3-(1-(mesitylsulfonyl)piperidin-4-yl)-6-methyl-1,3-oxazinane: To a 15 mL flask equipped with a reflux condenser were added 4-((1-(mesitylsulfonyl)piperidin-4-yl)amino)butan-2-ol (0.1192 g, 0.34 mmol), paraformaldehyde (0.0143 g, 0.48 mmol), Mg$_2$SO$_4$ (0.2091 g, 1.74 mmol), pyridinium ptoluenesulfonate (PPTS) (0.0025 g, 0.01 mmol), and anhydrous toluene (4 mL). The suspension was stirred under reflux for 3 h and was allowed to cool to room temperature. The suspension was then poured into a separatory funnel containing 30 mL saturated NaHCO$_3$ solution, followed by extraction with CH$_2$Cl$_2$ (3×30 mL). The combined organic layers were dried over Na$_2$SO$_4$, filtered and concentrated under reduced pressure. The residue was purified through flash chromatography on silica gel (1:19 MeOH:CH$_2$Cl$_2$) to provide the desired product as a colorless gel (0.0555 g, 45%). $^1$H NMR (400 MHz, CDCl$_3$) δ 6.91 (s, 2 H), 4.61 (dd, J=10.0, 2.3 Hz, 1 H), 4.16 (d, J=10.1 Hz, 1 H), 3.57 (m, 3 H), 3.11 (ddt, J=13.4, 4.4, 2.2 Hz, 1 H), 2.89-2.68 (m, 4 H), 2.58 (s, 6 H), 2.27 (s, 3 H), 1.92 (dp, J=12.2, 2.8 Hz, 2 H), 1.65-1.29 (m, 4 H), 1.15 (d, J=6.1 Hz, 3 H); $^{13}$C NMR (100 MHz, CDCl$_3$) δ 142.5, 140.4, 131.9, 131.6, 81.6, 73.6, 55.0, 46.5, 43.4, 30.3, 29.8, 29.2, 22.8, 21.8, 20.9; MS (ESI) m/z 367.2 (100%, [M+H]+).

XV. Synthesis of 1'-([1,1'-biphenyl]-4-ylsulfonyl)-4-methyl-1,4'-bipiperidine

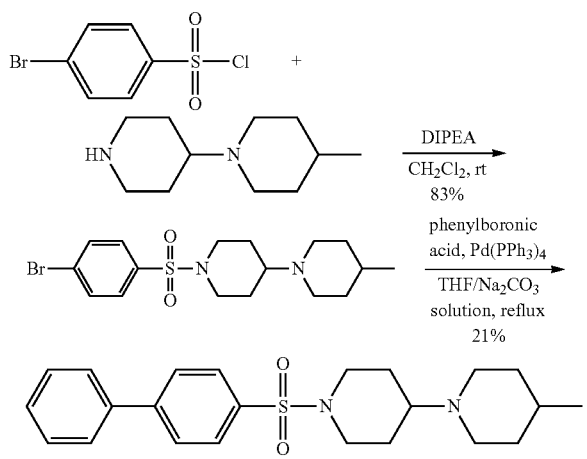

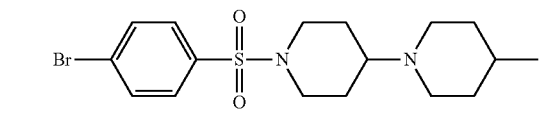

1'-((4-bromophenyl)sulfonyl)-4-methyl-1,4'-bipiperidine was obtained as a white solid (83%) through flash chromatography (1:19 MeOH:CH$_2$Cl$_2$) after the sulfonamide formation reaction between 4-bromobenzene-1-sulfonyl chloride and 4-methyl-1,4'-bipiperidine. mp 165-1 68° C.; $^1$H NMR (400 MHz, CDCl$_3$) δ 7.75-7.45 (m, 4 H), 3.81 (d, J=11.9 Hz, 2 H), 2.75 (d, J=11.5 Hz, 2 H), 2.38-1.96 (m, 5 H), 1.81 (d, J=11.8 Hz, 2 H), 1.73-1.52 (m, 4 H), 1.28 (m, 1 H), 1.22-1.06 (m, 2 H), 0.87 (d, J=6.4 Hz, 3 H); $^{13}$C NMR (100 MHz, CDCl$_3$) δ 135.2, 132.3, 129.1, 127.7, 61.3, 49.5, 46.1, 34.6, 31.0, 27.3, 21.9; MS (ESI) m/z 403.1 (100%, [M+H]+).

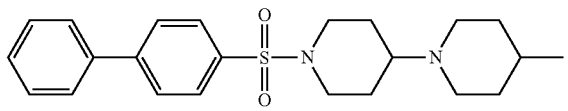 [SMILES: CC1CCN(C2CCN(S(=O)(=O)c3ccc(-c4ccccc4)cc3)CC2)CC1]

1'-([1,1'-biphenyl]-4-ylsulfonyl)-4-methyl-1,4'-bipiperidine: To a flame-dried flask equipped with a reflux condenser were added 1'-((4-bromophenyl)sulfonyl)-4-methyl-1,4'-bipiperidine (0.2200 g, 0.55 mmol), phenylboronic acid (0.1065 g, 0.87 mmol), Tetrakis(triphenylphosphine)palladium (0.0609 g, 0.053 mmol), THF (8 mL) and Na$_2$CO$_3$ (2 M, 0.8 mL). The mixture was degassed through Freeze-Pump-Thaw cycling and was refluxed for 3 h. After being cooled down to room temperature, the reaction suspension was diluted with water (25 mL), stirred for 10 min and was extracted with DCM (3×30 mL). The combined organic layers were dried over Na$_2$SO$_4$, filtered and concentrated and the residue was purified through flash chromatography on silica gel (1:19 MeOH:CH$_2$Cl$_2$) to afford the title product as a white solid (0.0433 g, 21%). mp 178-181° C.; $^1$H NMR (400 MHz, CDCl$_3$) δ 7.81 (d, J=8.4 Hz, 2 H), 7.72 (d, J=8.4 Hz, 2 H), 7.64-7.56 (m, 2 H), 7.52-7.45 (m, 2 H), 7.45-7.37 (m, 1 H), 3.90 (d, J=12.1 Hz, 2 H), 2.84 (d, J=10.8 Hz, 2 H), 2.32 (td, J=12.1, 2.5 Hz, 3 H), 2.20 (t, J=11.9 Hz, 2 H), 1.91 (d, J=12.6 Hz, 2 H), 1.77-1.57 (m, 4 H), 1.42-1.12 (m, 3 H), 0.90 (d, J=5.9 Hz, 3 H); $^{13}$C NMR (100 MHz, CDCl$_3$) δ 145.6, 139.2, 134.6, 129.1, 129.1, 128.5, 128.2, 127.6, 127.3, 61.6, 49.4, 46.1, 34.1, 30.8, 27.1, 21.7; m/z 399.2 (100%, [M+H]+).

Example 2. In Vitro APC Inhibition Assay

The small molecule anti-cancer compounds were evaluated for the ability to inhibit the activity of APC in an in vitro assay. Table A shows the IC$_{50}$ measured for each exemplified compound.

Reagents required for the assay are: (3-[4,5-Dimethylthiazol-2-yl]-2,5-diphenyltetrazolium bromide; Thiazolyl blue; RPI corp., cat# M92050); RPMI-1640 or Medium of Choice (i.e. DMEM) without phenol red; 1M Hepes; 100 mM NaPyruvate; 1000× Gentamicin (50 mg/ml); 100× Penicillin/Streptomycin/Fungizone; 1×PBS; Triton X-100; 1N HCl and Isopropanol. To make the MTT solution (10×), MTT powder was dissolved into complete RPMI (or DMEM solution) to a final concentration of 5 mg/mL and was sterilized by filtration with a 0.2 μm filter. The MTT solubilization solution contained 10% Triton X-100, 0.1N and 80% isopropanol. MTT solution was diluted to 1× with complete medium at 12 mL per plate. The culture dishes (96 wells) were removed from the incubator and the media was discarded. The plates were washed three times with 1×PBS. 100 μl of 1×MTT solution was added to each well and the plates were incubated in a tissue culture incubator for 2-4 hours, depending on the cell line. The cells were removed from the incubator and the MTT solution was discarded. 200 μl of 1×MTT solubilization solution was added to each well using a multi-channel pipetor and the cells were placed on an orbital shaker for 10 minutes. The results were read on a microtiter plate reader (absorbance=570 nm, reference=700 nm) and data was exported.

Percent inhibition was determined relative to control reactions without inhibitor, and half maximal inhibitory concentration (IC$_{50}$) values were determined using a standard four parameter fit to the inhibition data. The term "IC$_{50}$" as used herein refers to a quantitative measure of the effectiveness of a compound in inhibiting biological or biochemical function that indicates the amount that is needed to inhibit a given biological process (or component of a process) by 50%.

TABLE A

Analogs for treatment of colon cancer.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 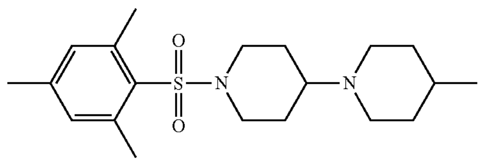 | 364.6 | | 0.03 | | 5 |
| 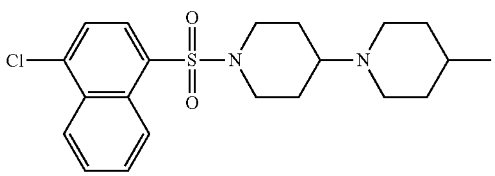 [SMILES: CC1CCN(C2CCN(S(=O)(=O)c3ccc(Cl)c4ccccc34)CC2)CC1] | 407 | | 0.1 | | 14 |
| 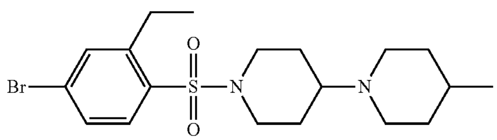 [SMILES: CCc1cc(Br)ccc1S(=O)(=O)N1CCC(N2CCC(C)CC2)CC1] | 429.4 | | 0.6 | | 9.1 |
| 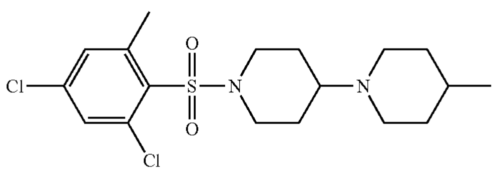 [SMILES: Cc1cc(Cl)cc(Cl)c1S(=O)(=O)N1CCC(N2CCC(C)CC2)CC1] | 405.4 | | 0.6 | | 9.1 |
| 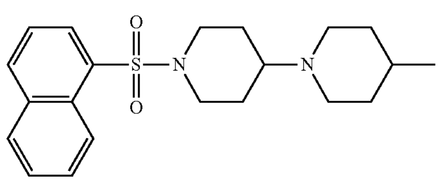 [SMILES: CC1CCN(C2CCN(S(=O)(=O)c3cccc4ccccc34)CC2)CC1] | 372.5 | | 0.65 | | <5 |
| 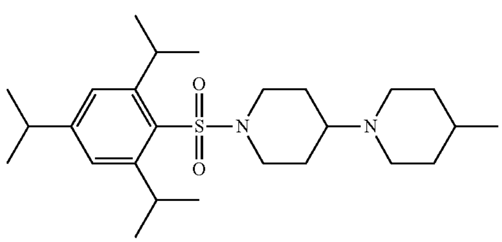 [SMILES: CC1CCN(C2CCN(S(=O)(=O)c3c(C(C)C)cc(C(C)C)cc3C(C)C)CC2)CC1] | 448.7 | | 0.7 | | 59 |
| 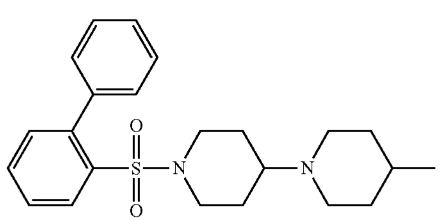 [SMILES: CC1CCN(C2CCN(S(=O)(=O)c3ccccc3-c3ccccc3)CC2)CC1] | 398.6 | | 0.96 | | <6 |
| 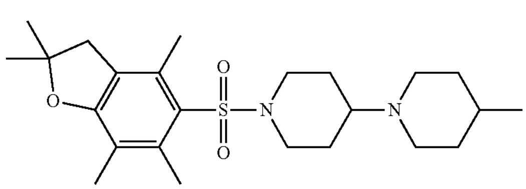 | 434.6 | | 1.2 | | 67 |

TABLE A-continued

Analogs for treatment of colon cancer.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 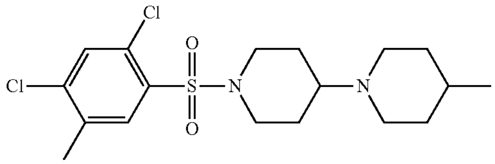 [SMILES: Cc1cc(S(=O)(=O)N2CCC(N3CCC(C)CC3)CC2)c(Cl)cc1Cl] | 405.4 | | 2 | | 6.5 |
| 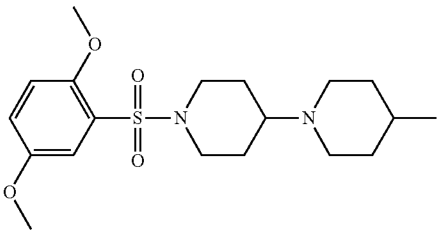 [SMILES: COc1ccc(OC)c(S(=O)(=O)N2CCC(N3CCC(C)CC3)CC2)c1] | 382.5 | | 4.5 | | 9.4 |
| 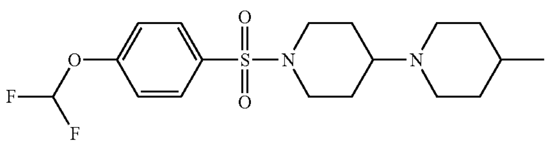 [SMILES: CC1CCN(C2CCN(S(=O)(=O)c3ccc(OC(F)F)cc3)CC2)CC1] | 388.5 | | 4.8 | | 144 |
| 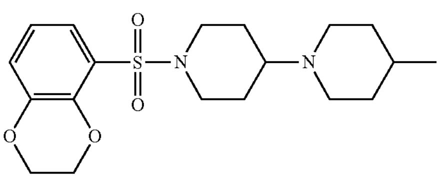 [SMILES: CC1CCN(C2CCN(S(=O)(=O)c3cccc4c3OCCO4)CC2)CC1] | 380.5 | | 10 | | 22.6 |
| 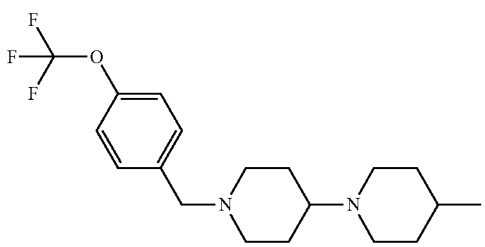 [SMILES: CC1CCN(C2CCN(Cc3ccc(OC(F)(F)F)cc3)CC2)CC1] | 356.4 | | 19 | | |
| 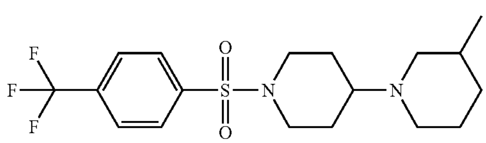 [SMILES: CC1CCCN(C2CCN(S(=O)(=O)c3ccc(C(F)(F)F)cc3)CC2)C1] | 390.5 | | 29 | | |
| 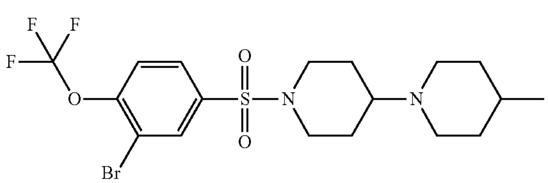 | 485.4 | | 29 | | |
| 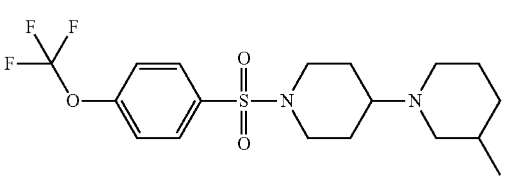 [SMILES: CC1CCCN(C2CCN(S(=O)(=O)c3ccc(OC(F)(F)F)cc3)CC2)C1] | 406.5 | | 31 | | |

TABLE A-continued
Analogs for treatment of colon cancer.
| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 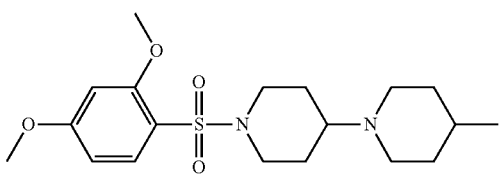 | 382.5 | | 41 | | |
| 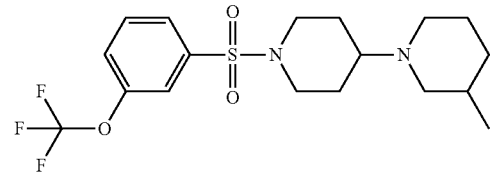 [SMILES: CC1CCCN(C2CCN(S(=O)(=O)c3cccc(OC(F)(F)F)c3)CC2)C1] | 406.5 | | 56 | | |
| 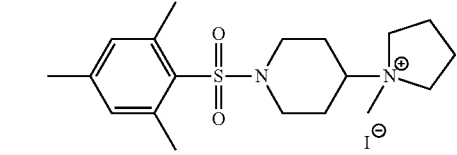 [SMILES: Cc1cc(C)c(S(=O)(=O)N2CCC([N+]3(C)CCCC3)CC2)c(C)c1 ; [I-]] | 478.4 | | 69 | | |
| 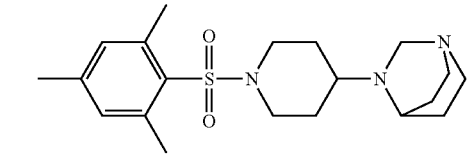 [SMILES: Cc1cc(C)c(S(=O)(=O)N2CCC(N3CN4CCC3CC4)CC2)c(C)c1] | 377.5 | | 84 | | |
| 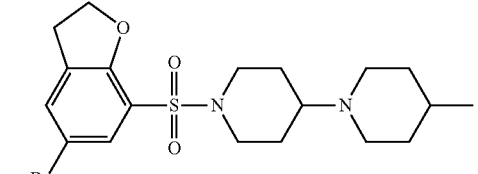 | 443.4 | | 96 | | |
| 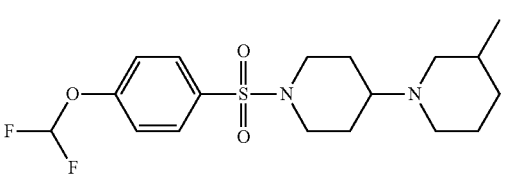 [SMILES: CC1CCCN(C2CCN(S(=O)(=O)c3ccc(OC(F)F)cc3)CC2)C1] | 388.5 | | 105 | | |
| 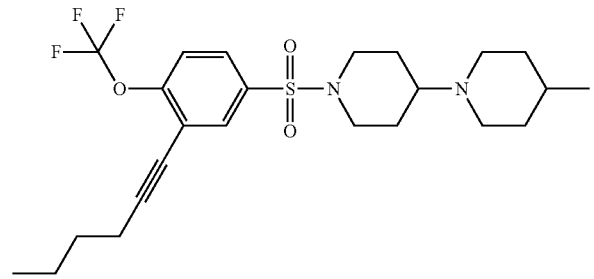 [SMILES: CCCCC#Cc1cc(S(=O)(=O)N2CCC(N3CCC(C)CC3)CC2)ccc1OC(F)(F)F] | 486.6 | | 147 | | |

TABLE A-continued

Analogs for treatment of colon cancer.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 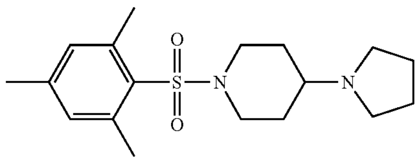 [SMILES: Cc1cc(C)c(S(=O)(=O)N2CCC(N3CCCC3)CC2)c(C)c1] | 336.5 | | 172.2 | | |
| 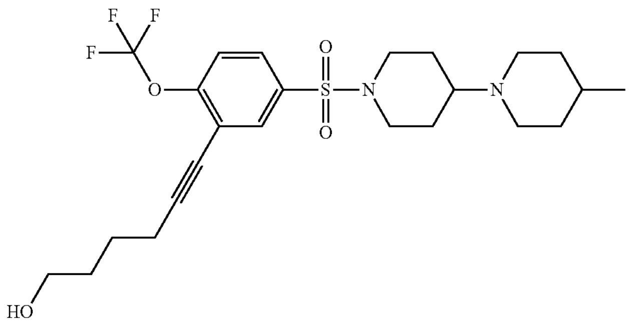 [SMILES: CC1CCN(C2CCN(S(=O)(=O)c3ccc(OC(F)(F)F)c(C#CCCCCO)c3)CC2)CC1] | 502.6 | | 205 | | |
| 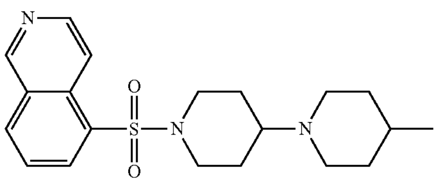 [SMILES: CC1CCN(C2CCN(S(=O)(=O)c3cccc4cnccc34)CC2)CC1] | 373.5 | | 225 | | |
| | 414.6 | | 244 | | |
| | 414.6 | | 253 | | |
| 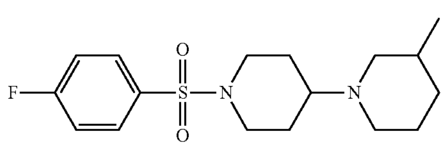 [SMILES: CC1CCCN(C2CCN(S(=O)(=O)c3ccc(F)cc3)CC2)C1] | 340.5 | | 255 | | |
| 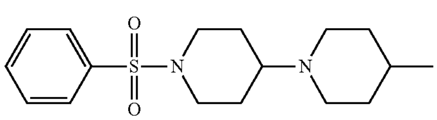 | 322.5 | | 293.9 | | |
| 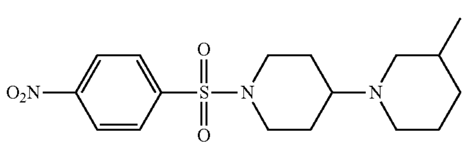 [SMILES: CC1CCCN(C2CCN(S(=O)(=O)c3ccc([N+](=O)[O-])cc3)CC2)C1] | 367.5 | | 366 | | |

TABLE A-continued

Analogs for treatment of colon cancer.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 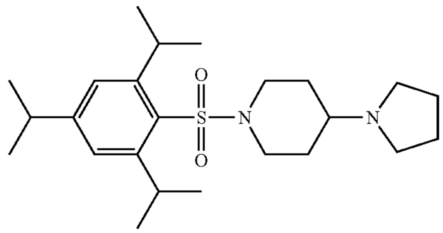 [SMILES: CC(C)c1cc(C(C)C)c(S(=O)(=O)N2CCC(N3CCCC3)CC2)c(C(C)C)c1] | 420.7 | 374 | | | |
| 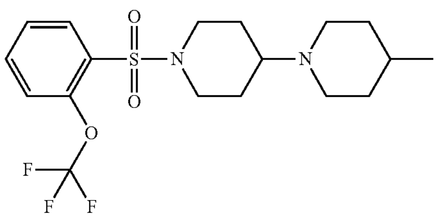 [SMILES: CC1CCN(C2CCN(S(=O)(=O)c3ccccc3OC(F)(F)F)CC2)CC1] | 406.5 | 421 | | | |
| 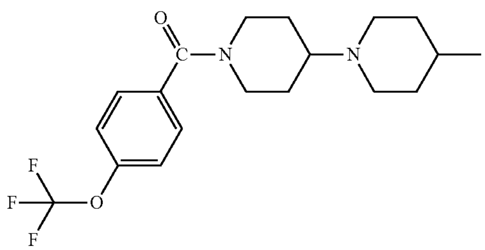 [SMILES: CC1CCN(C2CCN(C(=O)c3ccc(OC(F)(F)F)cc3)CC2)CC1] | 370.4 | 426 | | | |
| 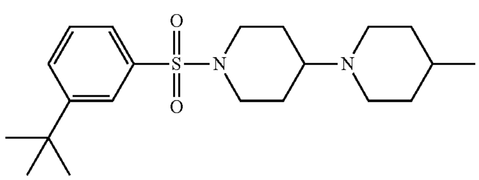 [SMILES: CC1CCN(C2CCN(S(=O)(=O)c3cccc(C(C)(C)C)c3)CC2)CC1] | 378.6 | 463 | | | |
| 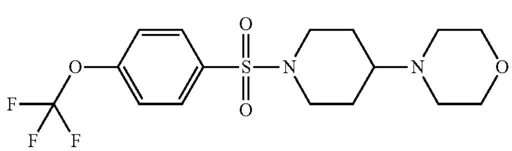 | 394.4 | 501 | | | |
| 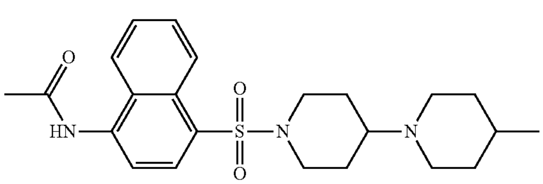 [SMILES: CC(=O)Nc1ccc(S(=O)(=O)N2CCC(N3CCC(C)CC3)CC2)c2ccccc12] | 429.6 | 1100 | | | |
| 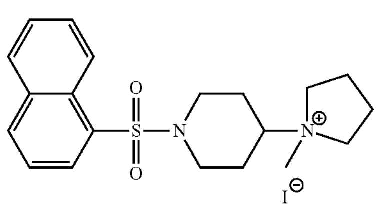 [SMILES: C[N+]1(C2CCN(S(=O)(=O)c3cccc4ccccc34)CC2)CCCC1 ; [I-]] | 486.4 | 2300 | | | |

TABLE A-continued

Analogs for treatment of colon cancer.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| (structure) | 324.4 | | 3203 | | |
| (structure) | 344.5 | | 3896 | | |
| (structure) | 464.4 | | ~7963 | | |
| (structure) | 464.4 | | >10,000 | | |
| (structure) | 466.4 | | >10000 | | |
| (structure) | 352.5 | >10,000 | 63 | 53 | |
| (structure) | 346.5 | >10,000 | 5300 | 1100 | |
| (structure) | 390.5 | >10,000 | 85 | 35 | |
| (structure) | 390.5 | >10,000 | 7900 | 2300 | |

TABLE A-continued
Analogs for treatment of colon cancer.
| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 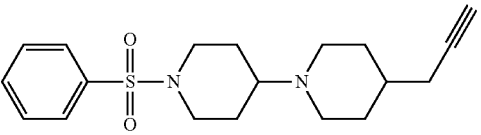 [SMILES: C#CCC1CCN(C2CCN(S(=O)(=O)c3ccccc3)CC2)CC1] | 346.5 | >10,000 | 18 | 4 | 25.2 |
| 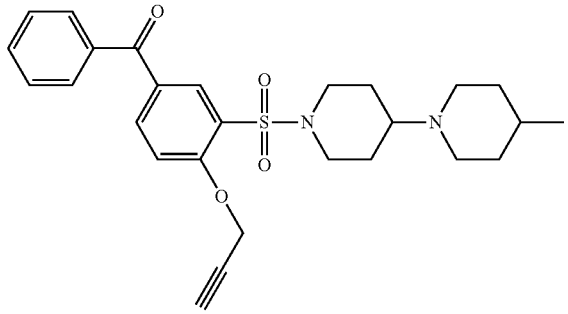 [SMILES: C#CCOc1ccc(C(=O)c2ccccc2)cc1S(=O)(=O)N1CCC(N2CCC(C)CC2)CC1] | 480.6 | >10,000 | 504 | 185 | |
| 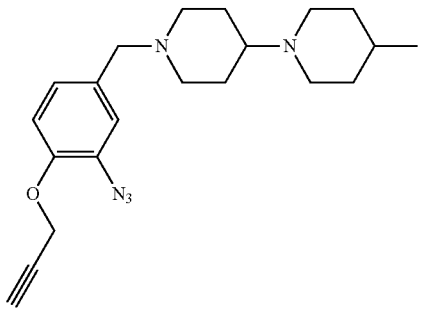 [SMILES: C#CCOc1ccc(CN2CCC(N3CCC(C)CC3)CC2)cc1N=[N+]=[N-]] | 367.5 | >10,000 | 921 | 437 | |
| 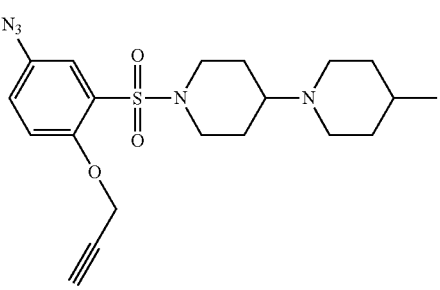 [SMILES: C#CCOc1ccc(N=[N+]=[N-])cc1S(=O)(=O)N1CCC(N2CCC(C)CC2)CC1] | 417.5 | >10,000 | 15000 | 4500 | |
| 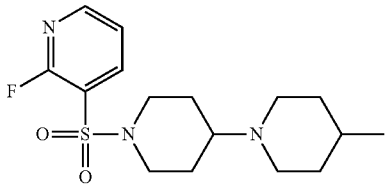 [SMILES: CC1CCN(C2CCN(S(=O)(=O)c3cccnc3F)CC2)CC1] | 341.4 | | >10,000 | | |
| 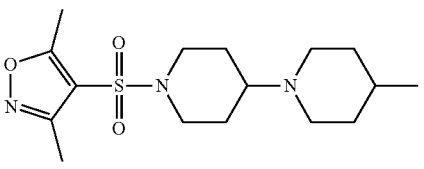 | 341.5 | | >10,000 | | |

TABLE A-continued

Analogs for treatment of colon cancer.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 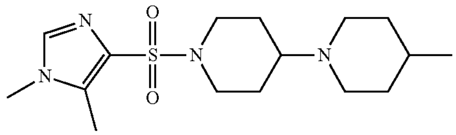 | 326.5 | | >10,000 | | |
| 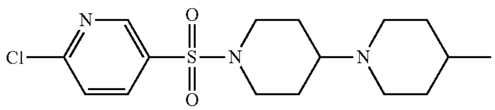 [SMILES: CC1CCN(C2CCN(S(=O)(=O)c3ccc(Cl)nc3)CC2)CC1] | 357.9 | | 3700 | | |
| 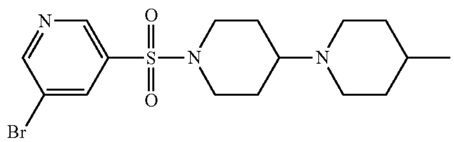 [SMILES: CC1CCN(C2CCN(S(=O)(=O)c3cncc(Br)c3)CC2)CC1] | 402.4 | | 7200 | | |
| 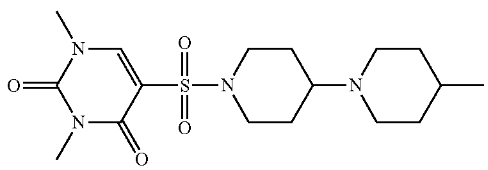 [SMILES: CC1CCN(C2CCN(S(=O)(=O)c3cn(C)c(=O)n(C)c3=O)CC2)CC1] | 384.5 | | >10,000 | | |
| | 387.5 | | 5300 | | |
| | 387.5 | | 235 | | |
| | 387.5 | | 1900 | | |
| | 365.5 | | 1100 | | |
| | 365.5 | | 426 | | |

TABLE A-continued

Analogs for treatment of colon cancer.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 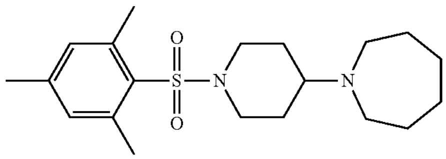 [SMILES: Cc1cc(C)c(S(=O)(=O)N2CCC(N3CCCCCC3)CC2)c(C)c1] | 364.6 | | 3300 | | |
| 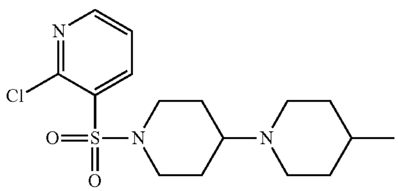 [SMILES: CC1CCN(C2CCN(S(=O)(=O)c3cccnc3Cl)CC2)CC1] | 357.9 | | >10,000 | | |
| 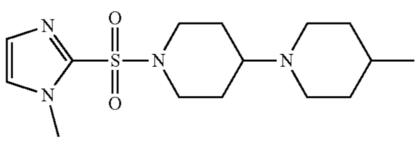 [SMILES: CC1CCN(C2CCN(S(=O)(=O)c3nccn3C)CC2)CC1] | 326.5 | | >10,000 | | |
| 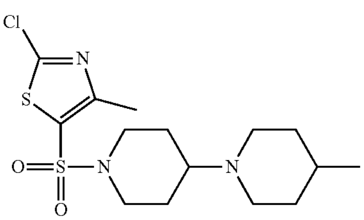 [SMILES: Cc1nc(Cl)sc1S(=O)(=O)N1CCC(N2CCC(C)CC2)CC1] | 378 | >10,000 | 1.6 | 1.5 | |
| 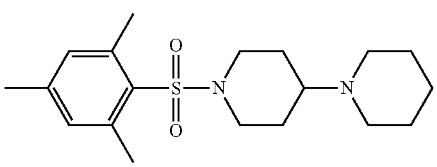 [SMILES: Cc1cc(C)c(S(=O)(=O)N2CCC(N3CCCCC3)CC2)c(C)c1] | 350.5 | >10,000 | 2200 | | |
| 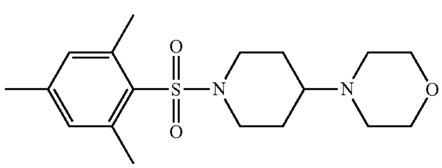 [SMILES: Cc1cc(C)c(S(=O)(=O)N2CCC(N3CCOCC3)CC2)c(C)c1] | 352.5 | >10,000 | 3100 | | |
| 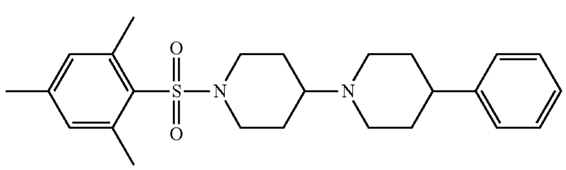 [SMILES: Cc1cc(C)c(S(=O)(=O)N2CCC(N3CCC(c4ccccc4)CC3)CC2)c(C)c1] | 426.6 | >10,000 | 865 | | |
| 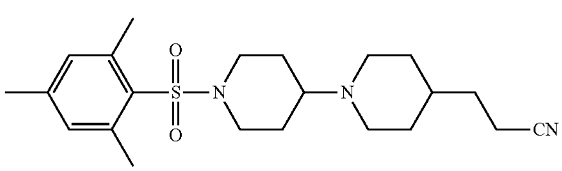 [SMILES: Cc1cc(C)c(S(=O)(=O)N2CCC(N3CCC(CCC#N)CC3)CC2)c(C)c1] | 403.6 | >10,000 | 7400 | | |

TABLE A-continued

Analogs for treatment of colon cancer.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| [NC-phenyl-SO₂-N(piperidine)-N(4-methylpiperidine)] | 347.5 | >10,000 | 2800 | | |
| [F₂HCO-phenyl-SO₂-N(piperidine)-NH⁺(4-methylpiperidine) Cl⁻] | 424.9 | >10,000 | 63 | 79 | |
| [pyridyl-SO₂-N(piperidine)-N(4-methylpiperidine)] | 323.5 | >10,000 | 2400 | 2,200 | |
| [naphthalene-2,7-bis(SO₂-N(piperidine)-N(4-methylpiperidine))] | 616.9 | TBD | TBD | | |
| [2,4,6-trimethylphenyl-SO₂-N(piperidine)-N(2-methylmorpholine)] | 366.5 | >10,000 | 92 | 61 | |
| [benzothiazole-SO₂-N(piperidine)-N(4-methylpiperidine)] | 379.5 | >10,000 | 38 | 26 | |
| [Br-phenyl-SO₂-N(piperidine)-N(4-methylpiperidine)] | 401.4 | >10,000 | 3.1 | 1.2 | |
| [biphenyl-SO₂-N(piperidine)-N(4-methylpiperidine)] | 398.6 | >10,000 | 258 | 234 | |
| [2,4,6-trimethylphenyl-SO₂-N(piperidine)-N(4-benzylpiperidine)] | 440.6 | >10,000 | 3.5 | 3 | |

TABLE A-continued

Analogs for treatment of colon cancer.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 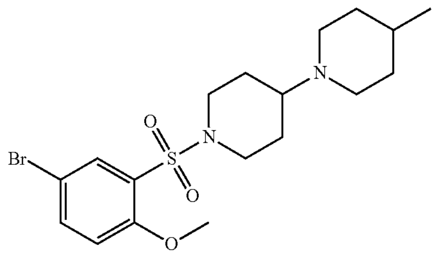 [SMILES: COc1ccc(Br)cc1S(=O)(=O)N1CCC(N2CCC(C)CC2)CC1] | 431.4 | >10,000 | 2 | 2 | |
| 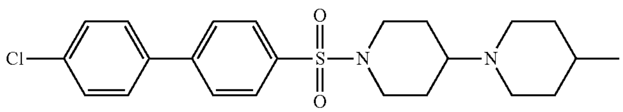 | 433 | >10,000 | 105 | 112 | |
| 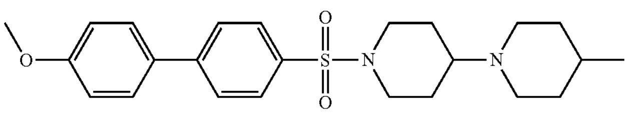 | 428.6 | >10,000 | 263 | 288 | |
| 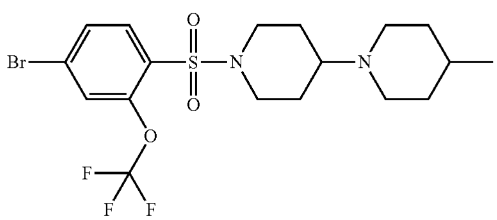 [SMILES: CC1CCN(C2CCN(S(=O)(=O)c3ccc(Br)cc3OC(F)(F)F)CC2)CC1] | 485.4 | >10,000 | 5 | 4 | |
| 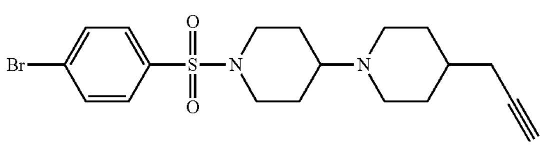 | 425.4 | >10,000 | 0.2 | 0.12 | |
| 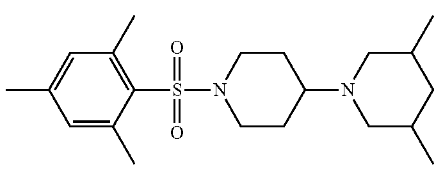 | 378.6 | >10,000 | 17 | 15 | |
| 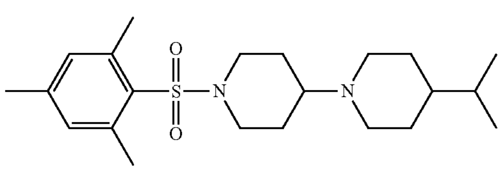 [SMILES: Cc1cc(C)c(S(=O)(=O)N2CCC(N3CCC(C(C)C)CC3)CC2)c(C)c1] | 392.6 | >10,000 | 0.3 | 0.2 | |
| 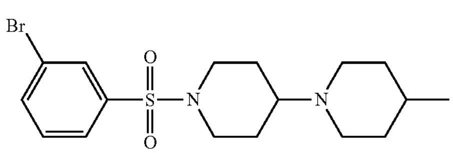 [SMILES: CC1CCN(C2CCN(S(=O)(=O)c3cccc(Br)c3)CC2)CC1] | 401.4 | >10,000 | 3.2 | 1.2 | |

TABLE A-continued

Analogs for treatment of colon cancer.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 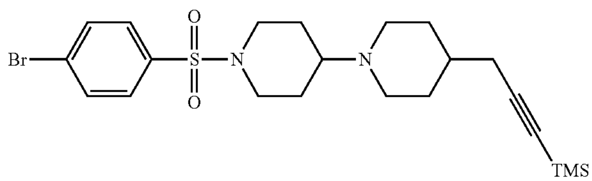 [SMILES: C[Si](C)(C)C#CCC1CCN(C2CCN(S(=O)(=O)c3ccc(Br)cc3)CC2)CC1] | 497.6 | >10,000 | 2.9 | 1.7 | |
| 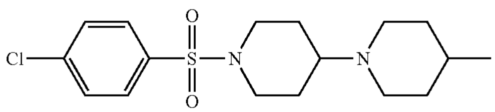 | 356.9 | >10,000 | 2.2 | 5.6 | |
| 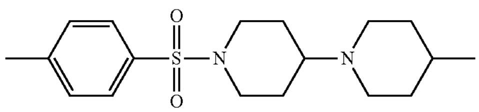 | 336.5 | >10,000 | 9.1 | 14 | |
| 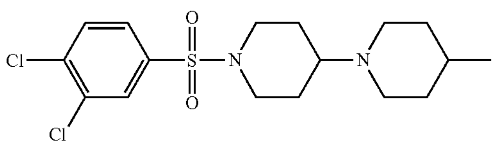 [SMILES: CC1CCN(C2CCN(S(=O)(=O)c3ccc(Cl)c(Cl)c3)CC2)CC1] | 391.4 | >10,000 | 2.9 | 2.2 | |
| 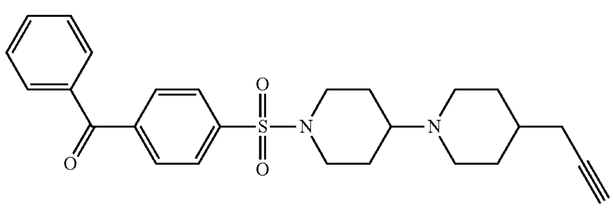 [SMILES: C#CCC1CCN(C2CCN(S(=O)(=O)c3ccc(C(=O)c4ccccc4)cc3)CC2)CC1] | 450.6 | >10,000 | 4.8 | 5.2 | |
| 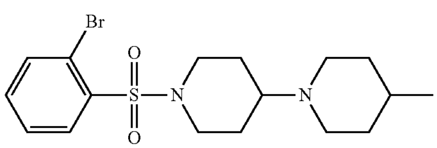 [SMILES: CC1CCN(C2CCN(S(=O)(=O)c3ccccc3Br)CC2)CC1] | 401.4 | >10,000 | 3 | 3 | |
| 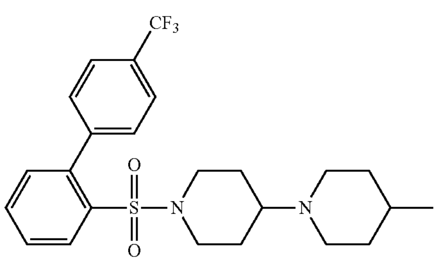 [SMILES: CC1CCN(C2CCN(S(=O)(=O)c3ccccc3-c3ccc(C(F)(F)F)cc3)CC2)CC1] | 466.6 | >10,000 | 122 | 57 | |
| 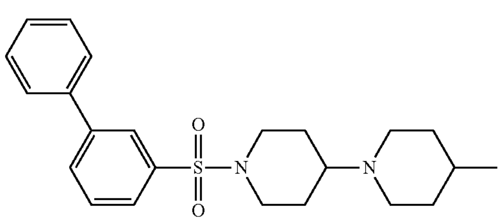 [SMILES: CC1CCN(C2CCN(S(=O)(=O)c3cccc(-c4ccccc4)c3)CC2)CC1] | 398.6 | >10,000 | 2 | 2 | |

TABLE A-continued

Analogs for treatment of colon cancer.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| [2'-methoxy-biphenyl-4-sulfonyl-piperidine-piperidine structure] | 428.6 | >10,000 | 26 | 19 | |
| [2'-fluoro-biphenyl-4-sulfonyl-piperidine-piperidine structure] | 416.6 | >10,000 | 5 | 6 | |
| [2,5-dimethoxy-phenyl-sulfonyl-piperidine-piperidinium chloride structure] | 419 | | 45 | 7 | |
| [2,4,6-trimethyl-phenyl-sulfonyl-piperidine-piperidinium chloride structure] | 401 | | 908 | 2 | |
| [4-methoxy-phenyl-sulfonyl-piperidine-piperidinium chloride structure] | 389 | | 494 | 6 | |

Analogs with an IC50 under 100 nM in DLD-1 are indicated in bold typeface.

Example 3. Truncated APC Selective Inhibitor-1 (TASIN-1) Kills CRC Lines with APC Truncations while Sparing Normal Human Colonic Epithelial Cells (HCECs) and Other Cancer Cells with Wild Type (WT) APC, Interferes with Proper Mitotic Spindle Formation, and Induces JNK-Dependent Apoptotic Cell Death in APC Truncated Cells Dose response analysis in two authentic CRC cell lines: HCT116 (WT APC) and DLD1 (truncated APC), led to identification of the lead compound TASIN-1 (truncated APC selective inhibitor) (FIG. 7 (d)). This compound exhibited potent and selective toxicity towards DLD1 cells (IC50=63 nM) but not towards HCT116 cells (IC$_{50}$>10 μM) (FIG. 7(e)). Sustained treatment of TASIN-1 inhibited soft agar growth in DLD1 but not in HCT116 cells (FIGS. 7 (f), 11)

Figure 8A:
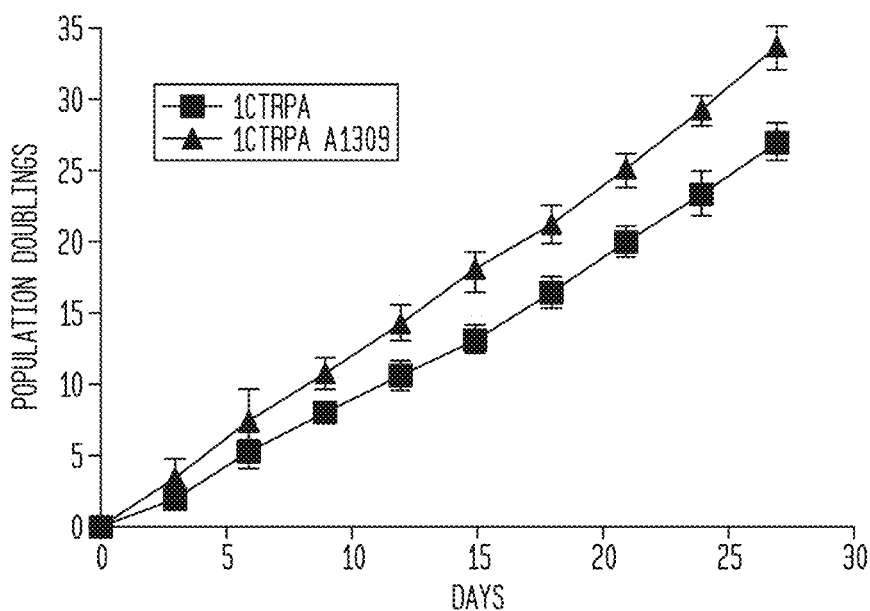
FIG. 8A-8C illustrates that ectopic expression of APC truncation confers tumorigenic properties. (a) Ectopic expression of APC truncation increased growth rate in 1CTRPA A1309 cells compared to 1CTRPA. Fold change in soft agar colony formation efficiency (b) or invasion through Matrigel® (c) in 1CTRPA A1309 cells compared to 1CTRPA. Data represent mean±s.d., n=3. Student's t-test, *P<0.05, P<0.01, *P<0.001.
Figure 8B:
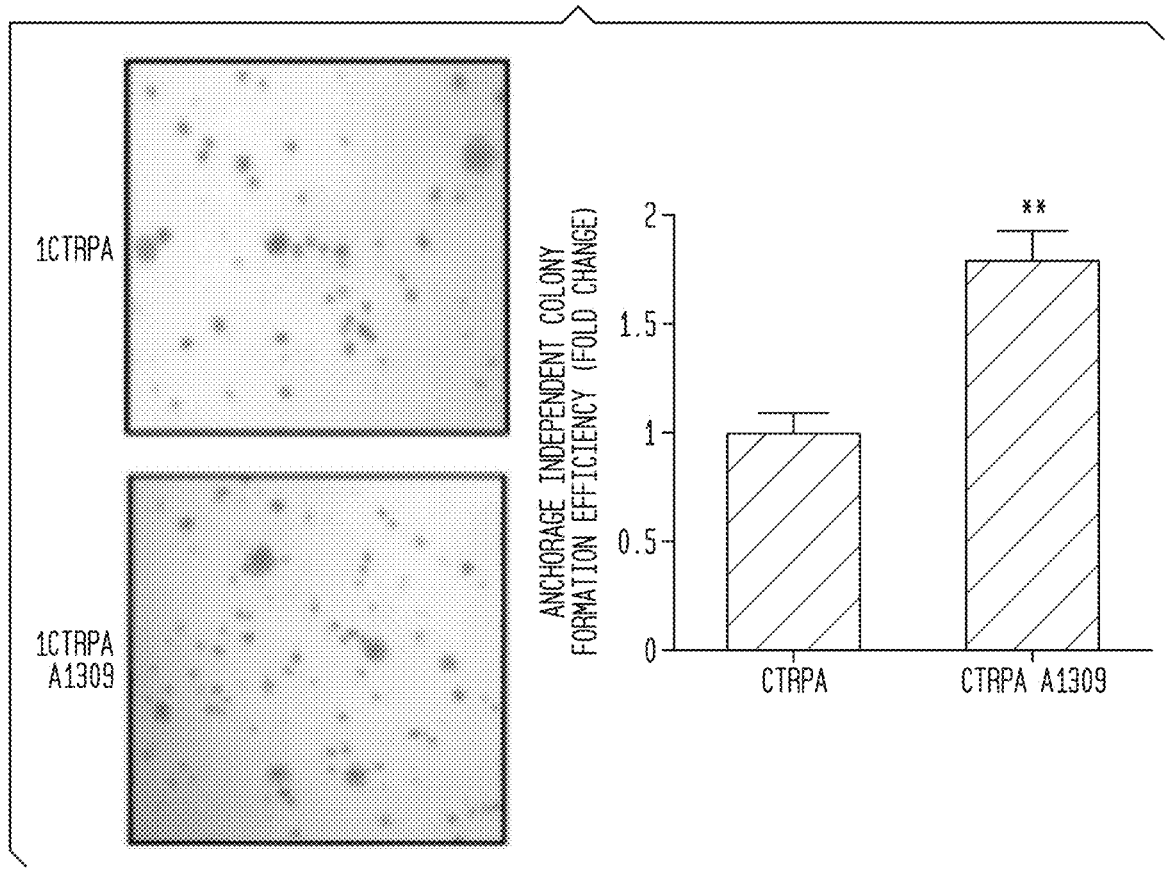
Figure 8C:
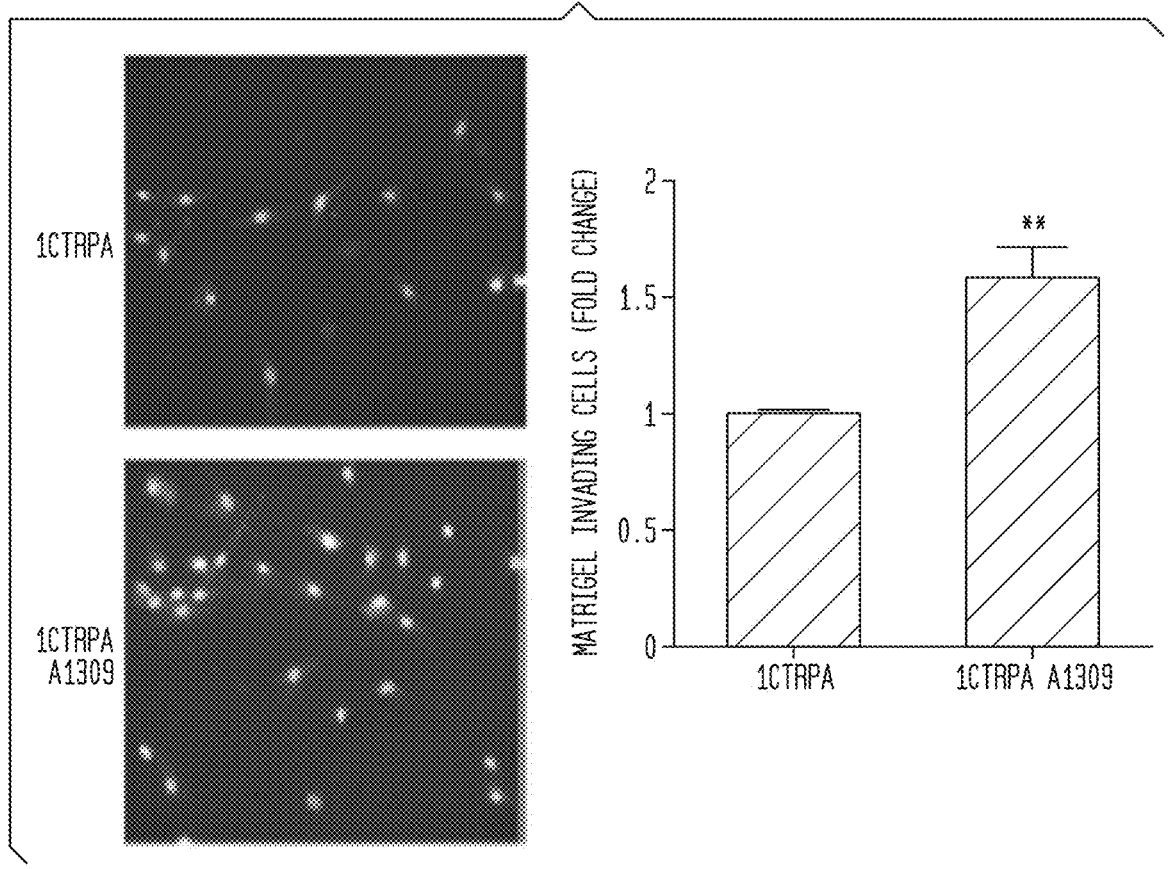
Figure 9:
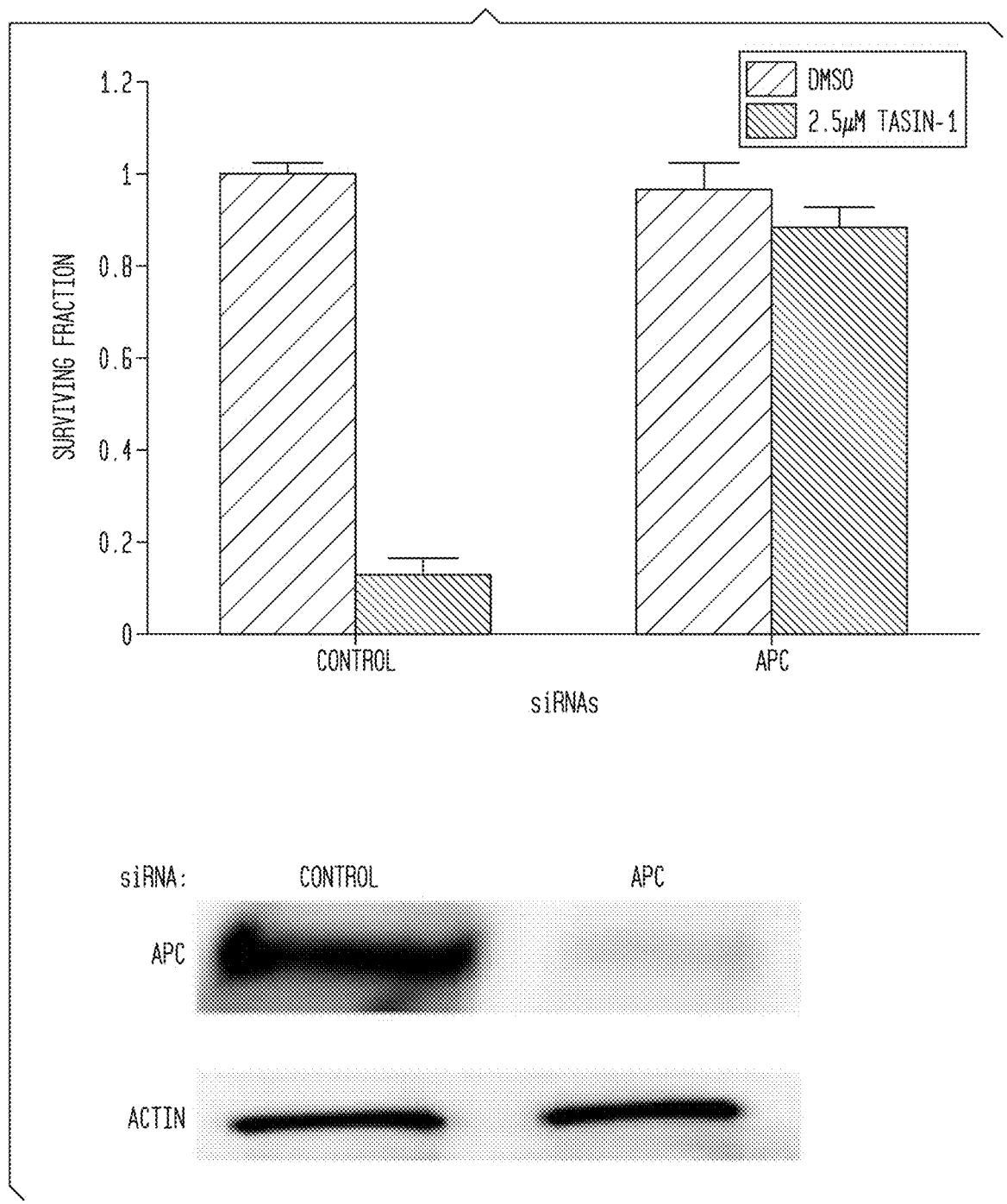
FIG. 9 illustrates that the knockdown of truncated APC desensitizes DLD1 cells to TASIN-1, providing evidence that APC is the target of TASIN-1.

To validate APC truncation dependency, two independent stable knockdown DLD1 cell lines expressing shRNAs were generated against truncated APC. Knockdown of truncated APC expression desensitized DLD1 cells to TASIN-1 with a protein reduction of >90% (FIGS. 8, 9), supporting that APC or a protein(s) in a relevant APC-dependent pathway is the target of TASIN-1. Similar effects were observed in HT29 cells depleted of truncated APC protein (FIG. 9a). In addition, ectopic expression of truncated APC partially sensitizes HCT116 and HCT116 p53 null cells to TASIN-1 (FIG. 9).

Figure 10A:
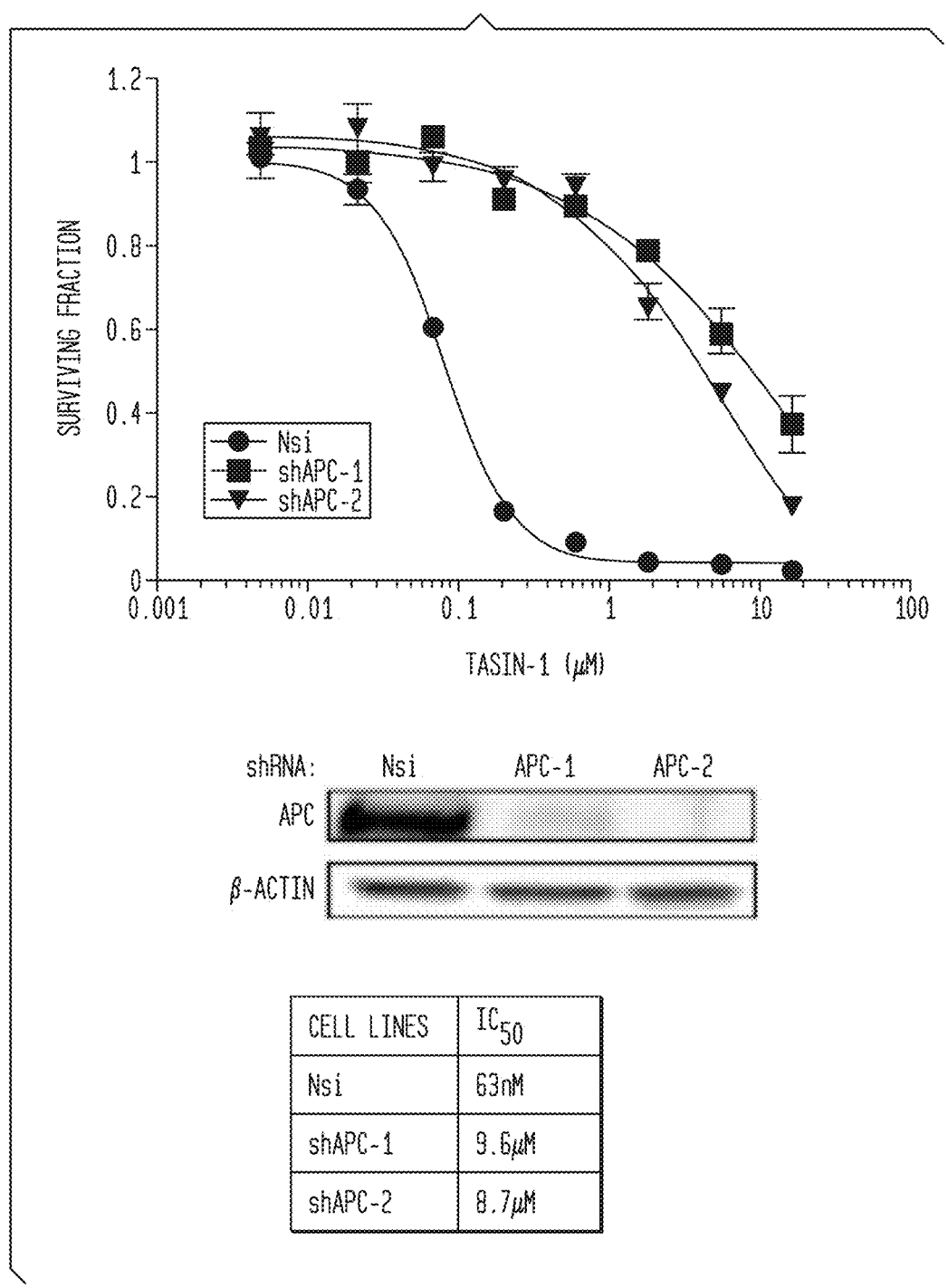
FIG. 10A-10C shows that APC truncation is required for TASIN-1's cytotoxic effects. (a) Dose response curve of DLD1 cells expressing non-silencing (Nsi) shRNA or shRNAs against APC. The table (a) lists the $IC_{50}$ value for each cell line. (b) Dose response curve of HCT116 and HCT116 p53−/− cells, a null mutant for tumor protein 53 (which is a known tumor suppressor), infected with a lentiviral vector expressing truncated APC A1309 were used to express either Beta-galactoside transacetylase (LacA) or the APC truncation mutant A1309. LacA was ectopically expressed in the cell lines as a negative control. Data represent means±s.d., n=3. Knockdown and ectopic expression were demonstrated by Western blot. (c) Left bar graph shows the surviving fraction for each cell line treated with DMSO, 2.5M or 5 uM of TASIN-1 for 72 h. Right table (c) lists the average $IC_{50}$ values for each cell line from biological triplicates. Statistical significance was determined between average of $IC_{50}$ values of the cell lines with WT APC and cell lines with truncated APC. Student's t-test, ****P<0.0001. The status of APC in each cell line is based on published data (Chandra, S. H., Wacker, I. Appelt, U.K., Behrens, J. & Schneikert, J. A common role for various human truncated adenomatous polyposis coli isoforms in the control of beta-catenin activity and cell proliferation. PloS one 7, e34479 (2012)) and the Cancer Genome Project Database (www.sanger.ac.uk/genetics/CGP).
Figure 10B:
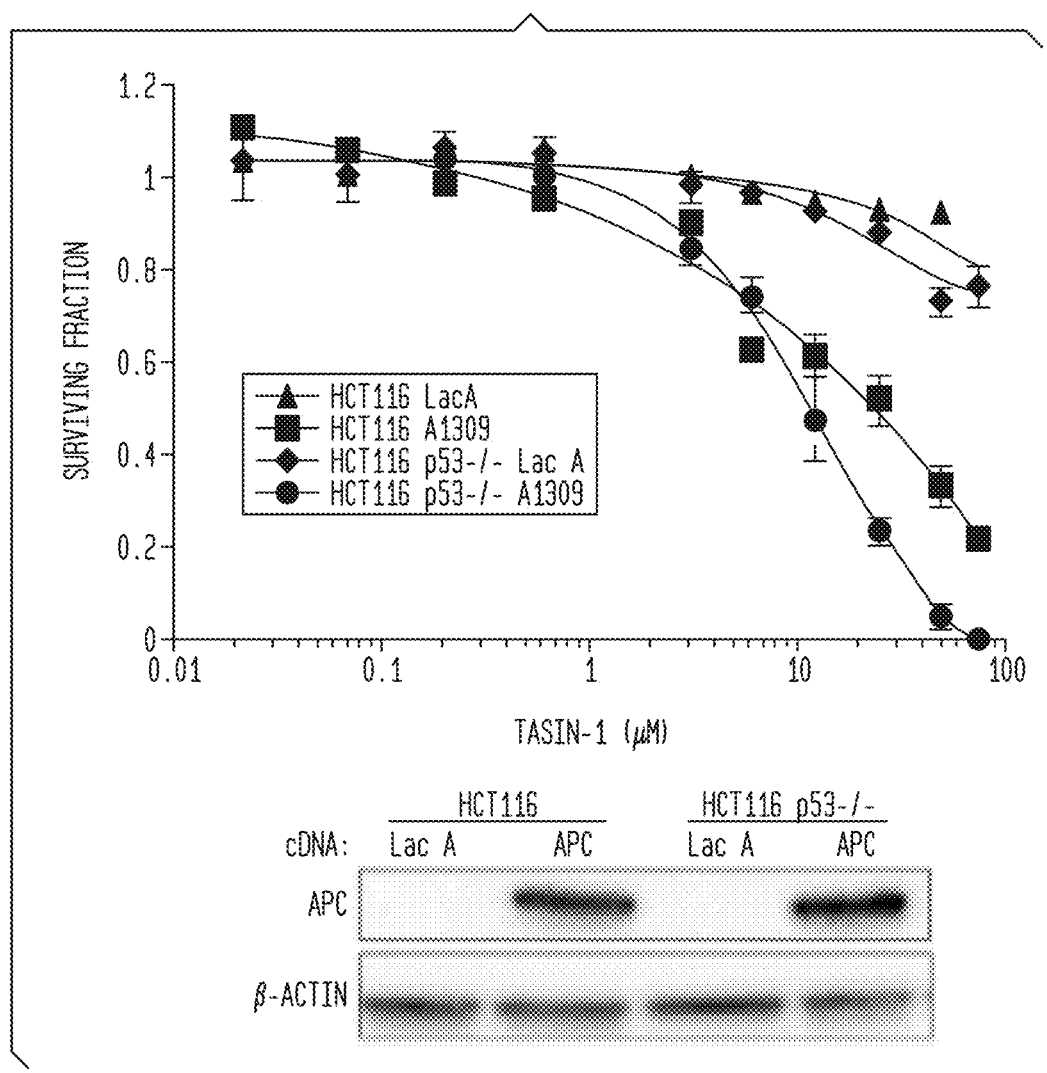
Figure 10C:
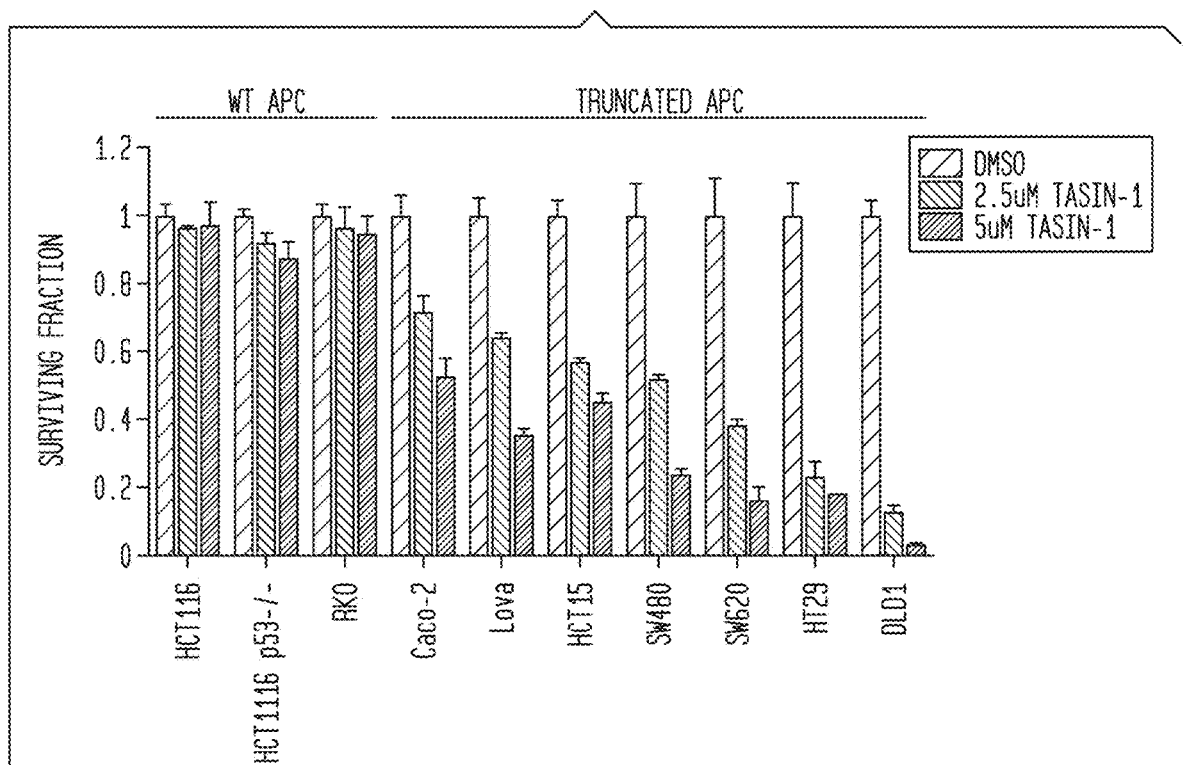
Figure 11A:
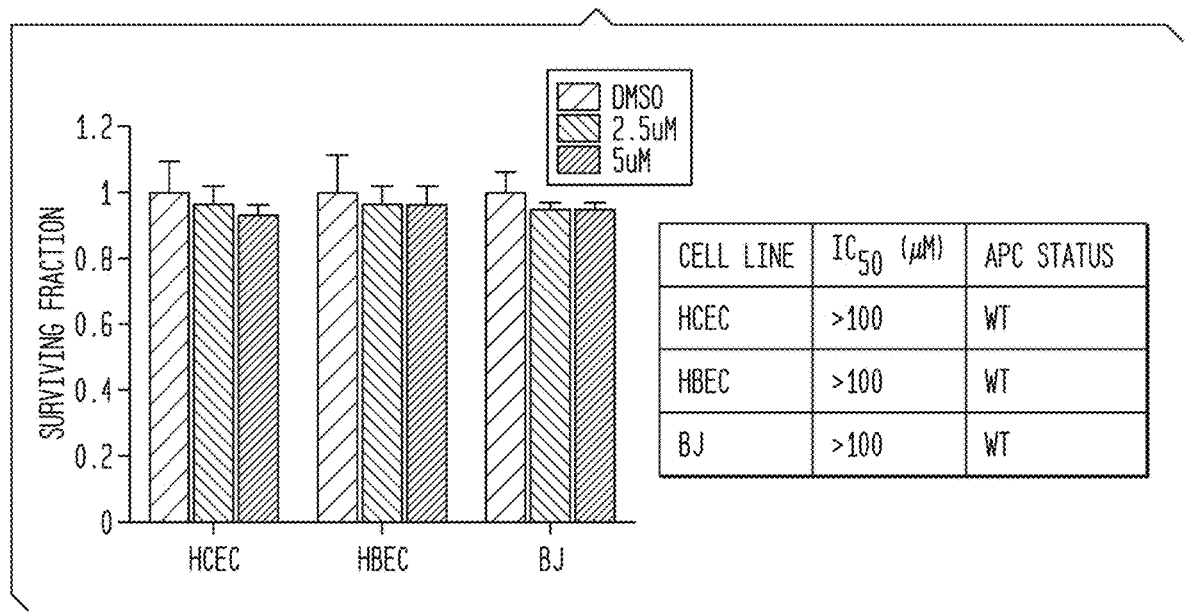
FIG. 11A-11B shows that TASIN-1 is selectively toxic towards cells with truncated APC. TASIN-1 does not affect viability of normal cell lines (a) and other cancer type cells (b) with WT APC but kills DU4457 cells with truncated APC. Data represent mean±s.d., n=3. Student's t-test, ***P<0.001.
Figure 11B:
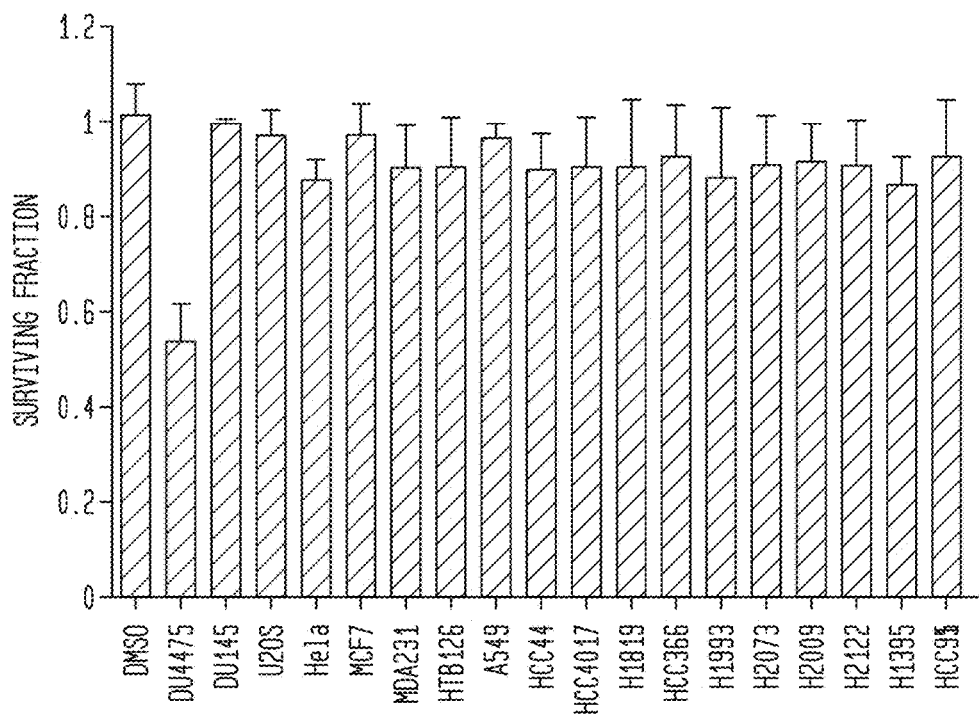

TASIN-1 was tested in a panel of CRC cell lines with varied APC status. Despite the highly heterogeneous genetic backgrounds, the results showed a consistent correlation between TASIN-1 sensitivity and APC status (FIGS. 9, 10). TASIN-1 did not affect the viability of HCECs, human bronchial epithelial cells (HBEC) and BJ fibroblast cells which are derived from normal tissues as well as other cancer cell types with WT APC. However, DU4475, a breast cancer cell line expressing truncated APC 15 was sensitive to TASIN-1, again supporting APC truncation dependency (FIG. 9', Data Table 1).

| Data Table 1. APC status and origin of other cancer types. | | |
|---|---|---|
| Cell line | APC status | Tumor type |
| DU4475 | aa1577 | Breast carcinoma |
| MCF7 | WT | Breast carcinoma |
| MDA231 | WT | Breast carcinoma |
| HTB126 | WT | Breast carcinoma |
| U2OS | WT | Osteosarcoma |
| DU145 | WT | Prostate carcinoma |

-continued

Data Table 1. APC status and origin of other cancer types.

| Cell line | APC status | Tumor type |
| --- | --- | --- |
| Hela | WT | Cervical carcinoma |
| A549 | WT | Lung carcinoma |
| HCC366 | WT | Lung carcinoma |
| HCC44 | WT | Lung carcinoma |
| HCC4017 | WT | Lung carcinoma |
| HCC95 | WT | Lung carcinoma |
| H1819 | WT | Lung carcinoma |
| H1993 | WT | Lung carcinoma |
| H2073 | WT | Lung carcinoma |
| H2009 | WT | Lung carcinoma |
| H2122 | WT | Lung carcinoma |
| H1395 | WT | Lung carcinoma |

Figure 12:
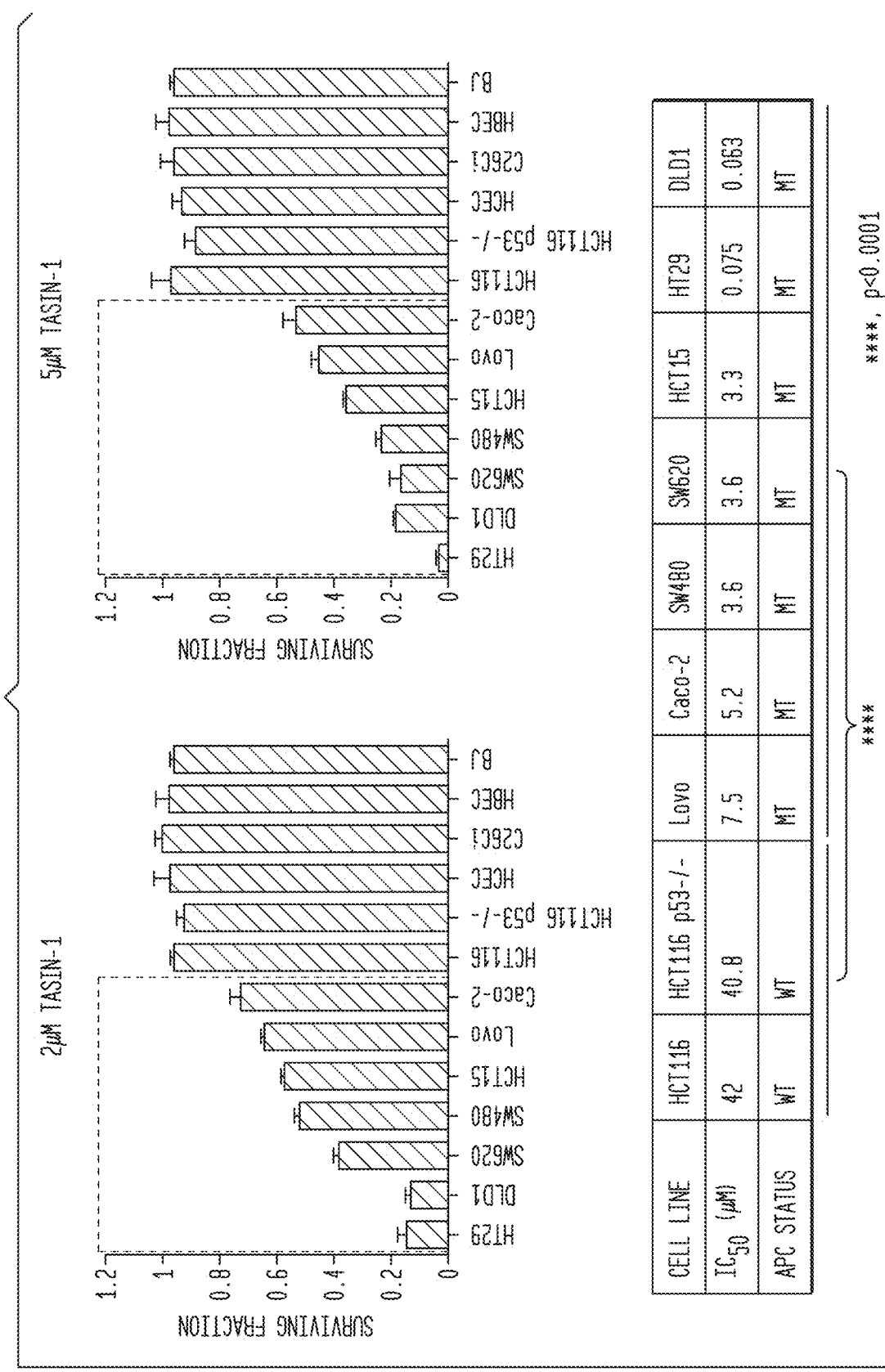
FIG. 12 illustrates responses of colorectal cancer cell lines with varying APC status to TASIN-1. Human colon epithelial cell lines expressing truncated APC HT-29, DLD1, SW620, SW480, HCT15, Lovo and Caco-2, and cells expressing wild type APC, HCT116, HCT116 p53−/−, HCEC, C26Ci, HBEC and BJ, were treated with TASIN-1 and the surviving cell fraction was assessed. Note that HCT116, HCT116 p53−/−, HCEC and C26Ci are colonic cell lines, whereas HBEC and BJ cell lines are bronchial epithelial cell lines and foreskin fibroblasts, respectively. In both 2 μM and 5 μM TASIN-1 conditions, all cell lines expressing truncated APC demonstrated sensitivity to TASIN-1, whereas cell lines expressing wild type APC did not demonstrate sensitivity to TASIN-1. This suggests that normal cells containing wild type levels of APC should be unaffected by TASIN-1.
Figure 13:
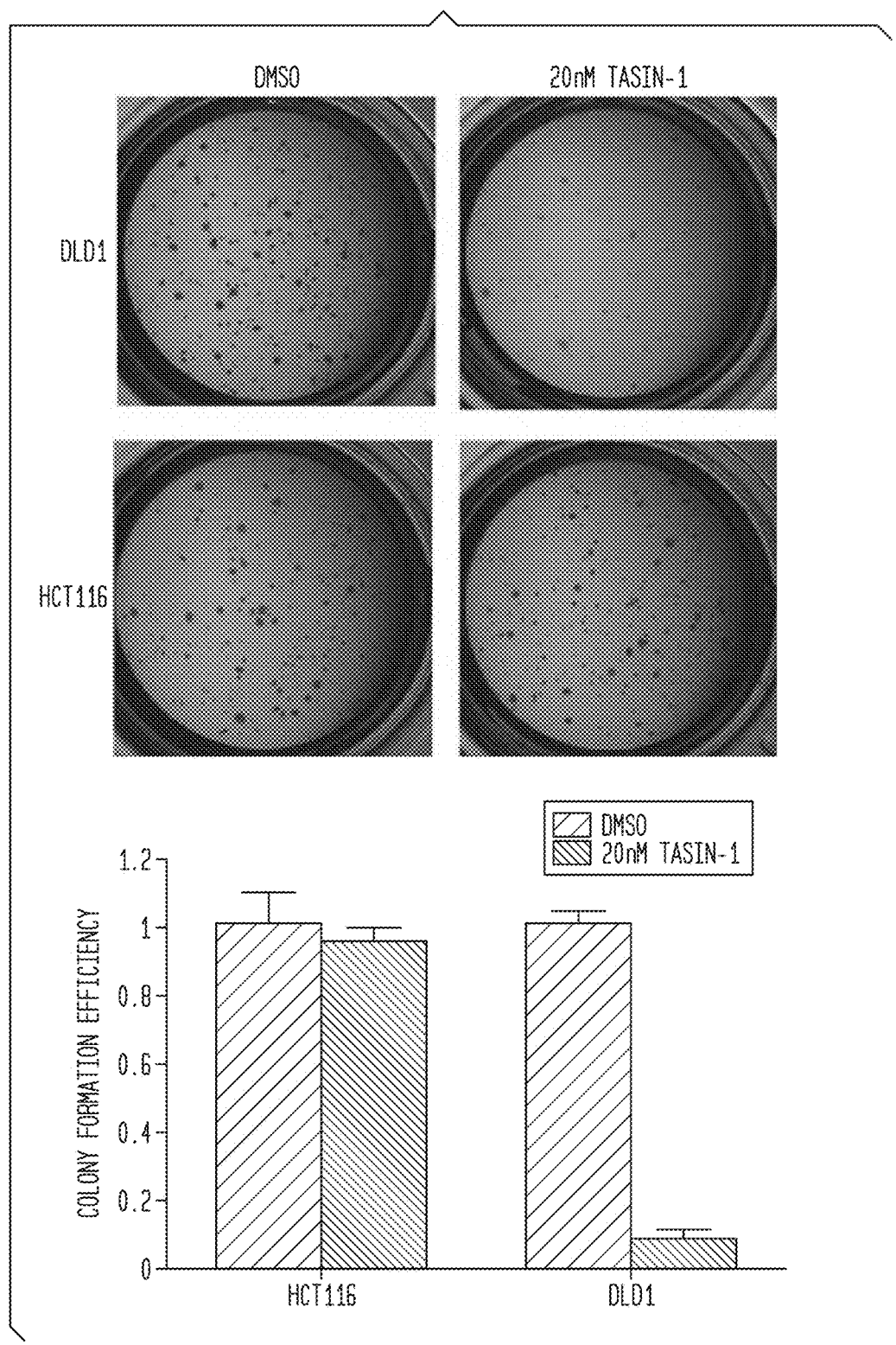
FIG. 13 shows that sustained treatment with low dose TASIN-1 suppressed anchorage-independent growth in DLD1 cells.
Figure 14:
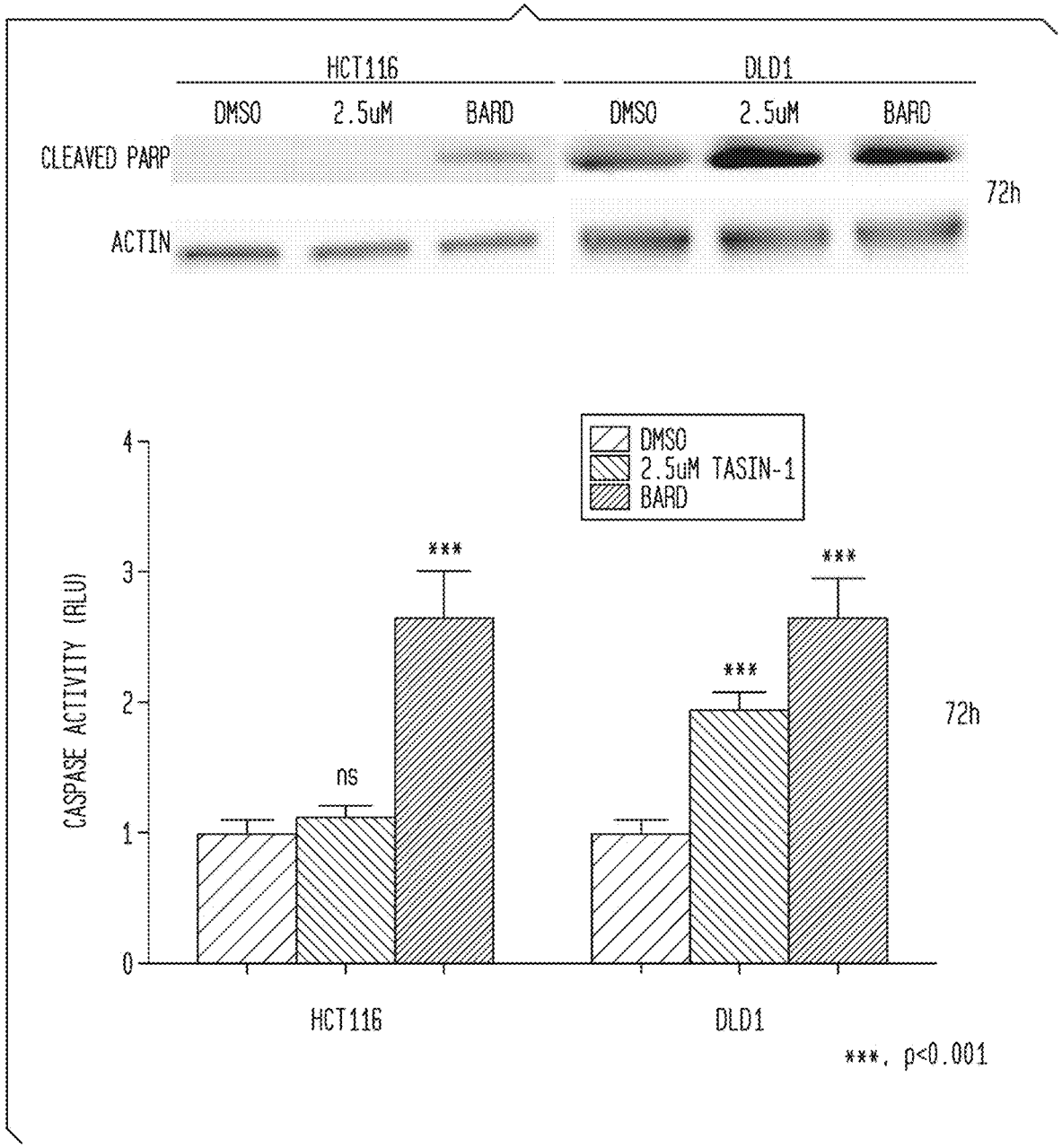
FIG. 14 shows that TASIN-1 induces apoptosis in DLD1 cells. After 72 hours of incubation of HCT116 or DLD1 cells with DMSO, 2.5 μM TASIN-1 or BARD, levels of cleaved PARP were analyzed by western blot. DMSO served as the negative control, not influencing the amount of cleaved PARP in the cell lines. However, BARD served as the positive control, facilitating the increase of cleaved PARP in HCT116 and DLD1 cell lines. DLD1 cells treated with TASIN-1 exhibited an increase in cleaved PARP, while under the same conditions HCT116 cells did not. HCT116 expresses wild type APC, while DLD1 expresses truncated APC. Additionally, caspase activity was increased in DLD1 cells treated with 2.5 μM TASIN-1.
Figure 15A:
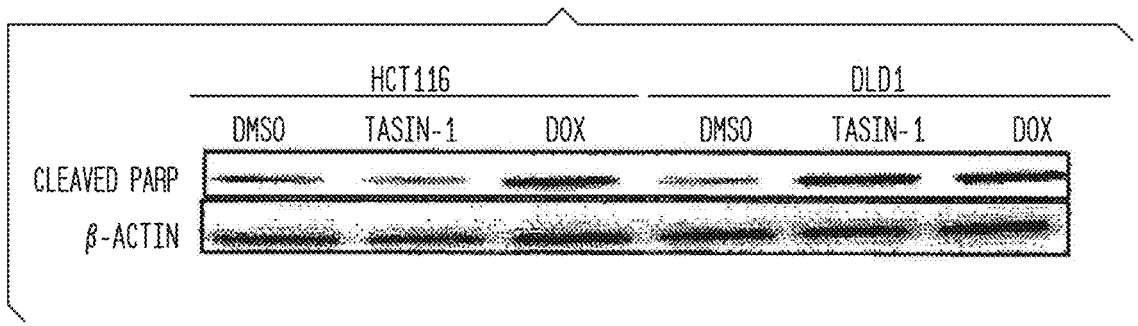
FIG. 15A-15G illustrates that TASIN-1 induces c-Jun N-terminal kinase (JNK)-dependent apoptosis in DLD1 but not in HCT116 cells. Incubation with TASIN-1 induces cleavage of PARP (a), cytochrome c release from mitochondria (b) and caspase 3 activation in DLD1 cells (c). Doxorubincin (DOX) was used as a positive control for apoptosis. β-actin was used as the loading control. The values in (c) represent fold induction of caspase3/7 activity normalized to DMSO treated cells. RLU: relative luciferase unit. (d) TASIN-1 treatment induces phosphorylation of JNK in DLD1 cells. (e)-(g) Cotreatment of TASIN-1 with SP600125 reverses TASIN-1's killing effects (e), inhibits phosphorylation of JNK, abolishes cleavage of PARP induced by TASIN-1 treatment (f) and reduces caspase3/7 activity (g). Data represent mean±s.d., n=3. Student's t-test, P<0.01, *P<0.001.
Figure 15B:
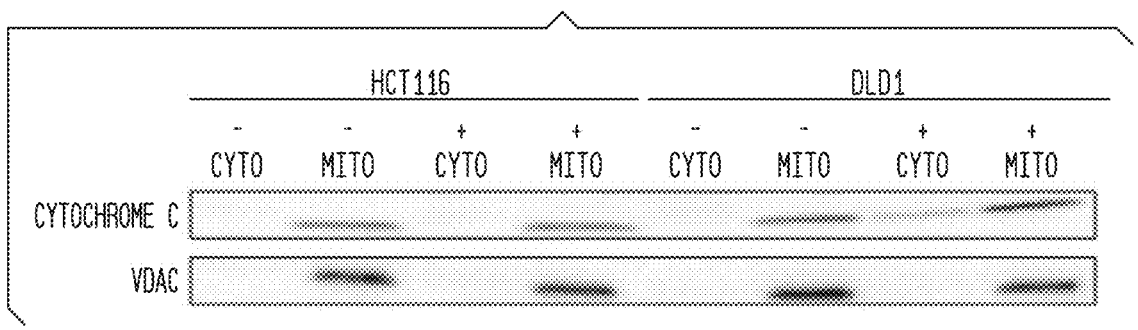
Figure 15C:
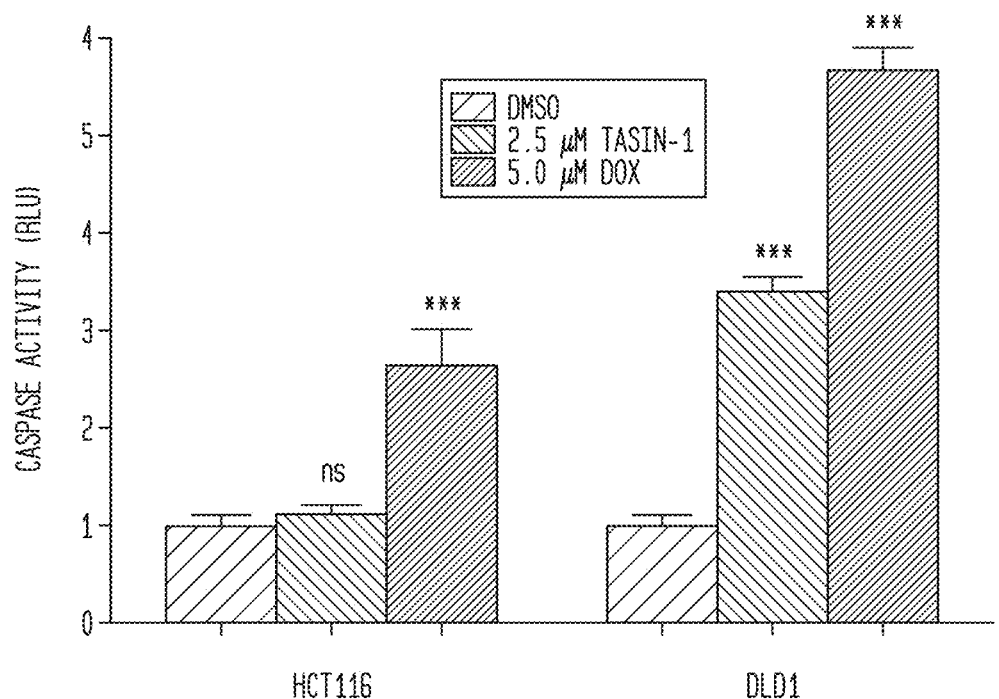
Figure 15D:
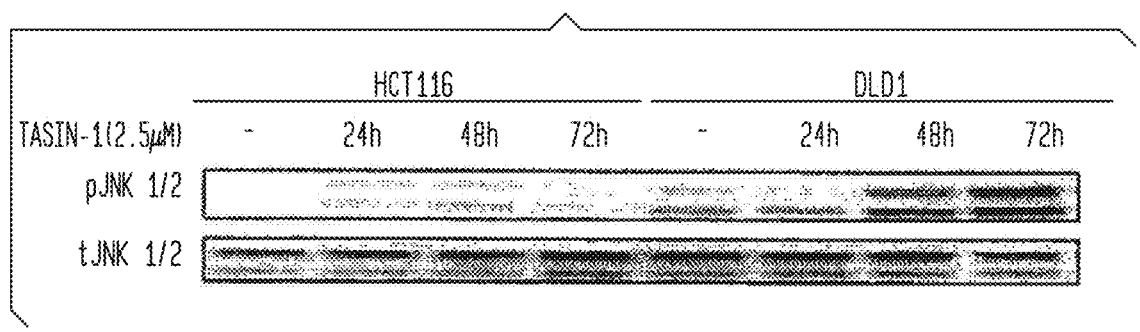
Figure 15E:
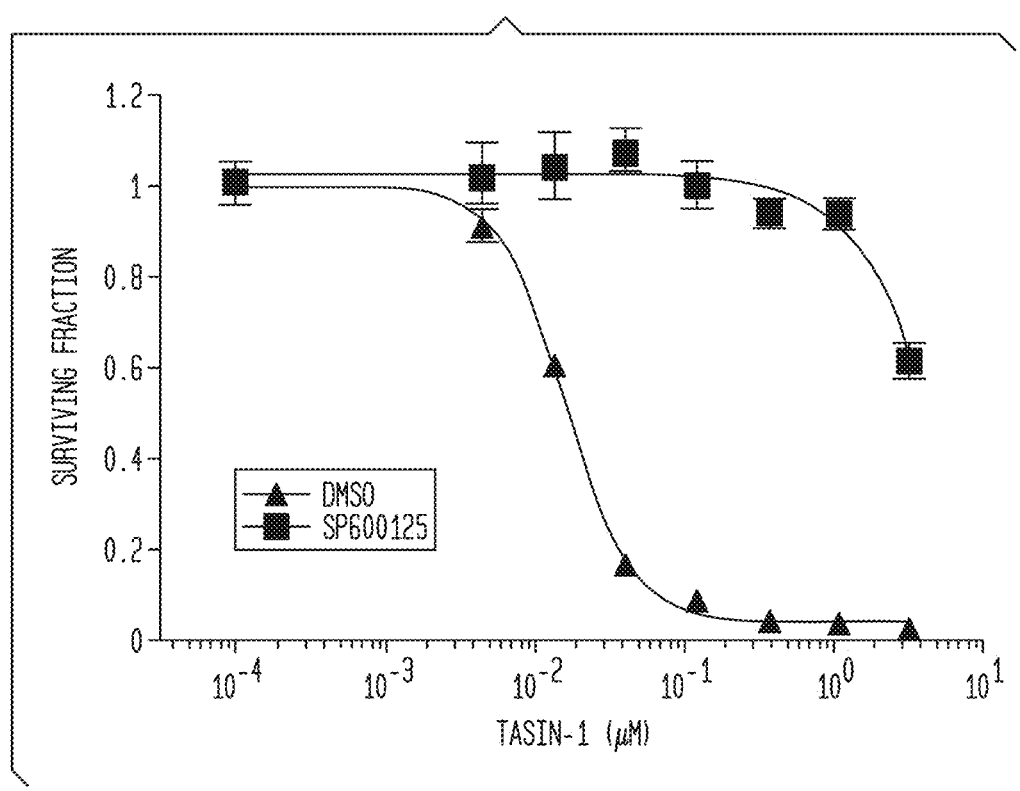
Figure 15F:
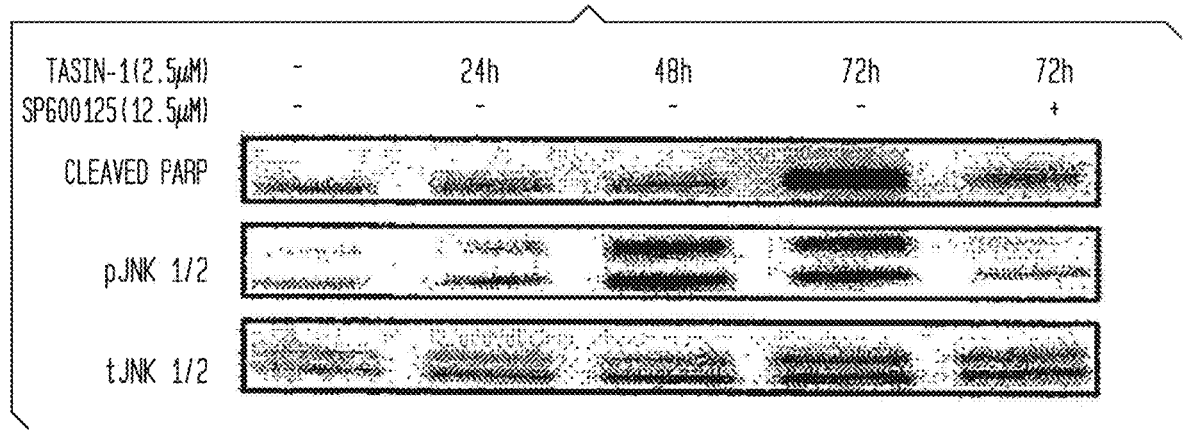
Figure 15G:
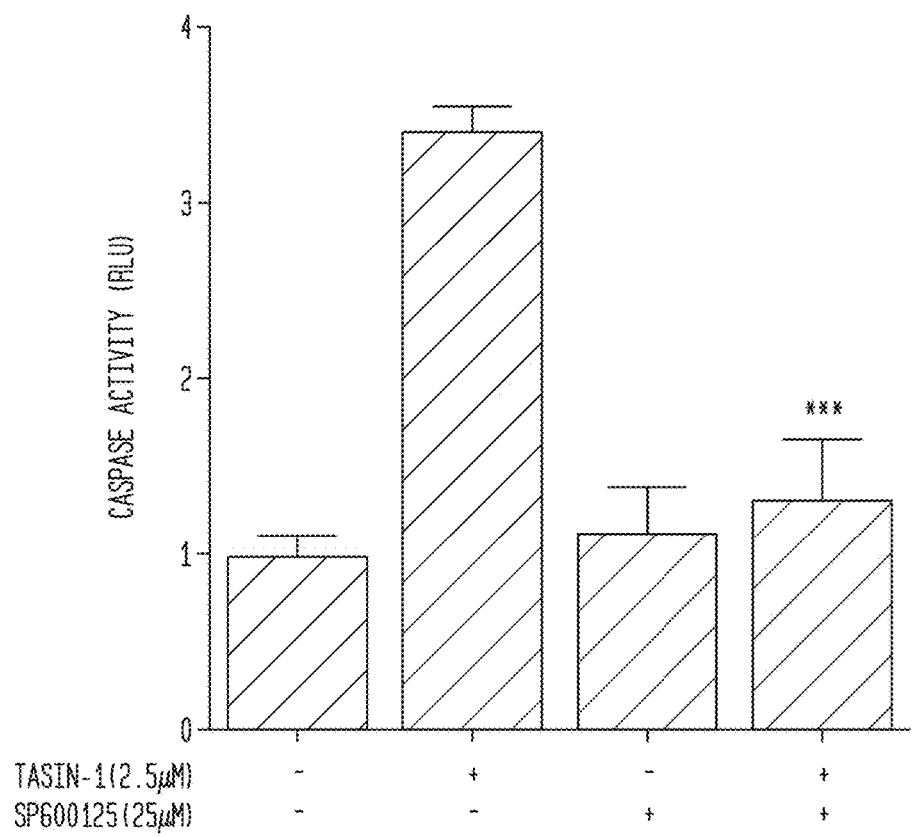
Figure 16:
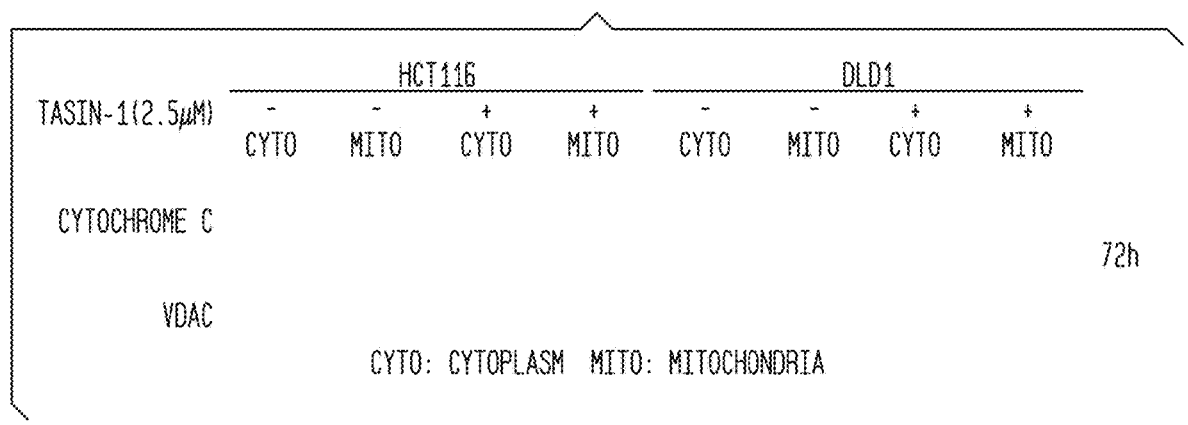
FIG. 16 shows that TASIN-1 induced cytochrome C release in DLD1 cells. Cyto: cytoplasm; mito: mitochondria. Voltage-dependent anion channel (VDAC), found on the mitochondrial outer membrane.

TASIN-1 caused poly (ADP ribose) polymerase 1 (PARP1) cleavage, cytochrome c release from mitochondria, and induced caspase 3/7 activity in DLD1 cells but not in HCT116 cells (FIGS. 12, 12' (a-c), 13), indicative of induction of apoptosis. Additionally, TASIN-1 treatment led to activation of JNK after 48 hours in DLD1 cells but not in HCT116 cells and this activation persisted for 72 hours (FIG. 12'(d)). Co-treatment with the JNK inhibitor SP600125 (Millipore) attenuated TASIN-1's effects and efficiently inhibited JNK activation and abolished cleavage of PARP1 as well as caspase 3/7 activation (FIG. 12' (e-g)). Collectively, these data demonstrate that TASIN-1 induces JNK-dependent apoptotic cell death in DLD1 cells.

Example 4. In Vivo Antitumor Activity of TASIN-1 in a Xenograft Mouse Model

Figure 19:
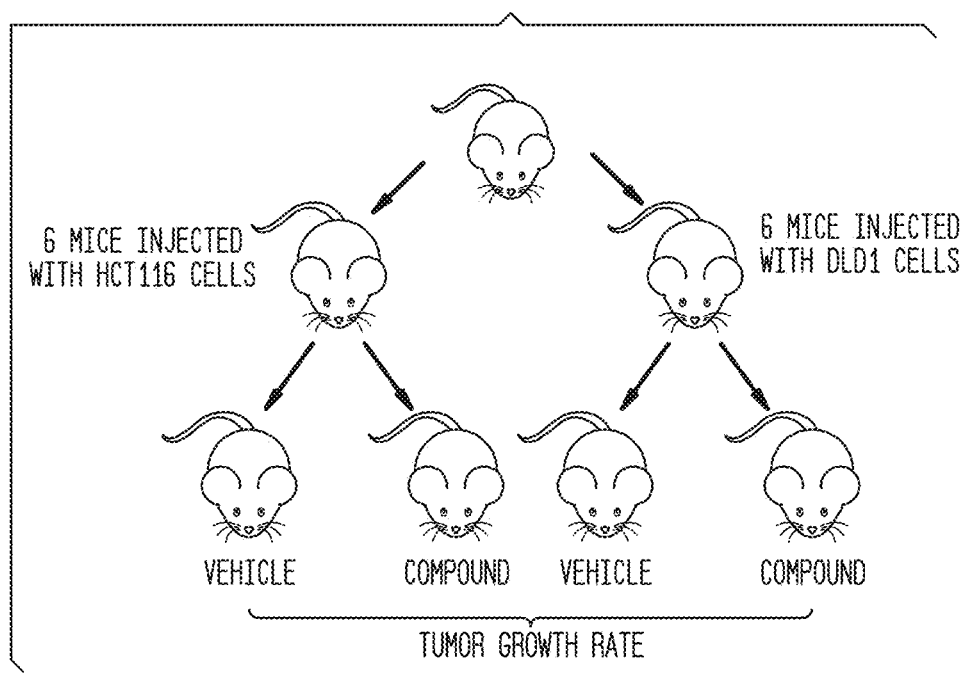
FIG. 19 illustrates the method by which the potency and selectivity of lead compounds was characterized in vivo.
Figure 20A:
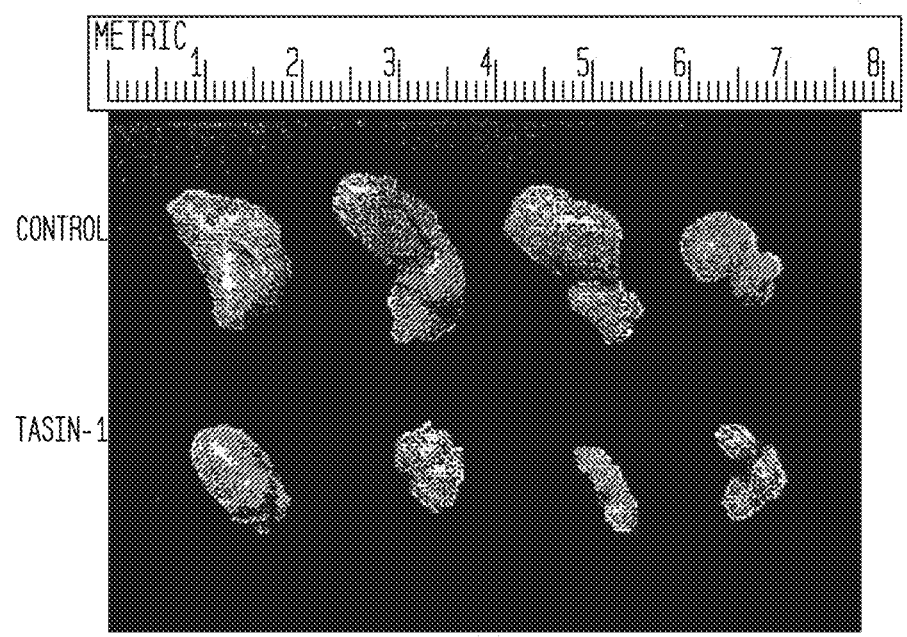
FIG. 20A-20C shows that TASIN-1 inhibits tumor growth in DLD1 xenografts. The dosing schedule was intraperitoneal over 18 days at 40 mg/kg, administered twice daily. (a) Tumor sizes of TASIN-1 treated DLD1 xenografts (below) are smaller than those of control mice (above). Scale bar, 10 mm. TASIN-1 significantly reduces tumor growth rate of DLD1 (b). Tasin-1 reduces tumor volume doubling time (c).
Figure 20B:
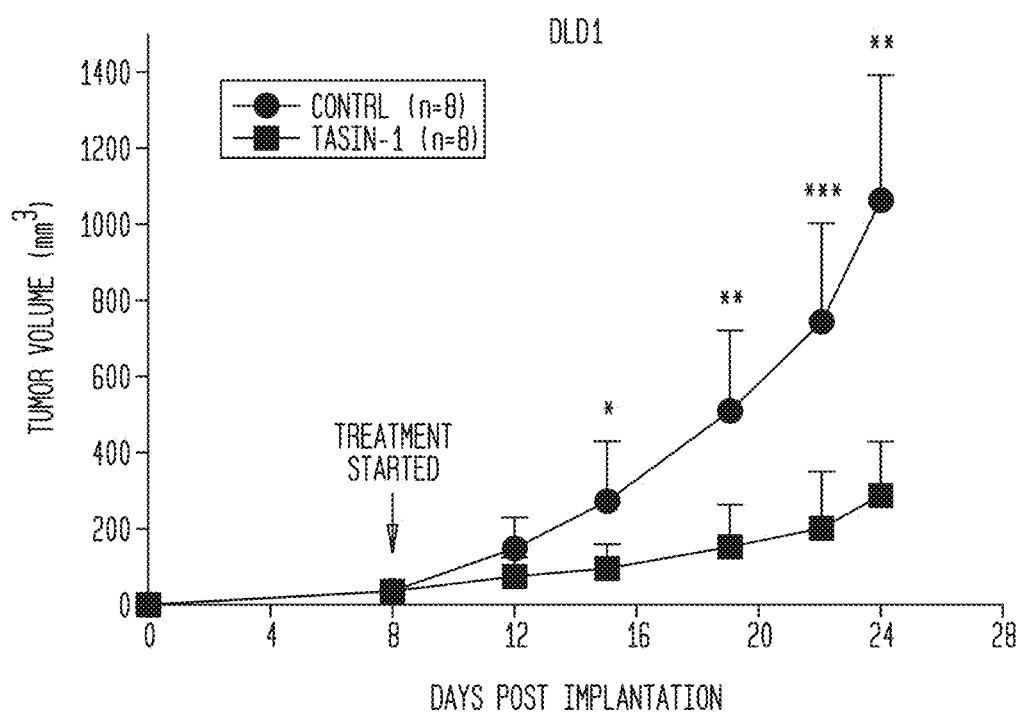
Figure 20C:
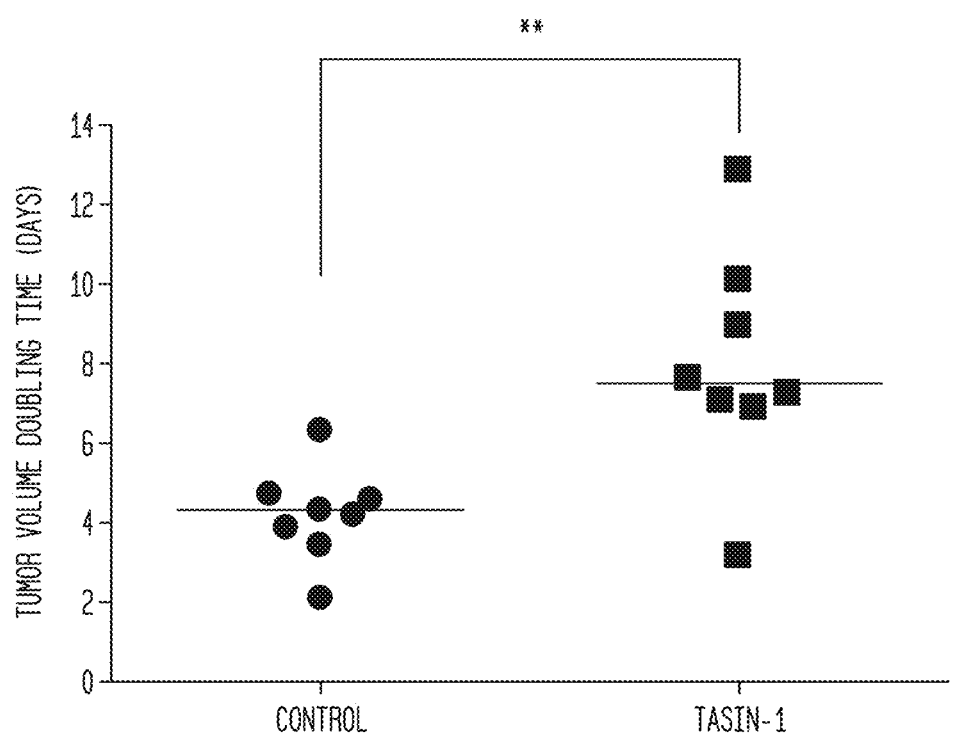
Figure 21A:
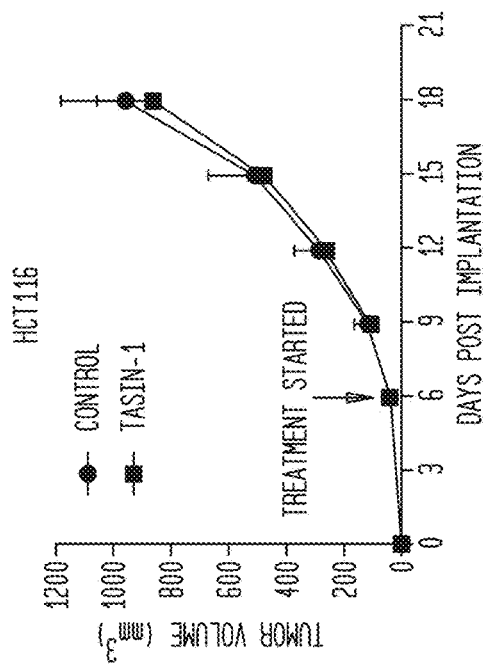
FIG. 21A-21E shows that TASIN-1 selectively inhibits tumor growth in xenografts with APC truncation (a-b) and reduces tumorigenicity in a genetic CRC mouse model (c-e). TASIN-1 significantly reduces tumor growth rate of HT29 (a) but not HCT116 xenografts (b). (a)-(b), data represent means±s.d. of 8 tumors. TASIN-1 treatment significantly reduces the number of benign (polyps) tumors (c) and decreases polyp size (d) in CPC;Apc mice. In (c), each dot represents one mouse. Mean is indicated by the solid black line. (e) TASIN-1 did not inhibit the growth of mice. In (d) and (e), data represent mean±s.d. of 8-10 mice. Student's t-test (a)-(c), (e) and multiple t test ((d), FDR=1%) were used. *P<0.05, P<0.01, *P<0.001.
Figure 21B:
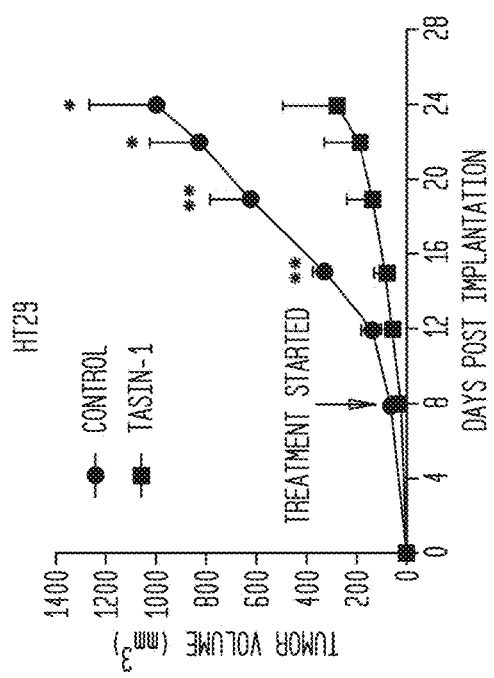
Figure 21C:
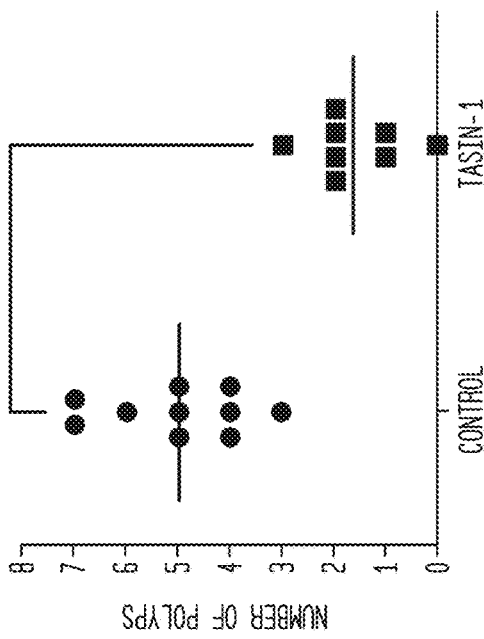
Figure 21D:
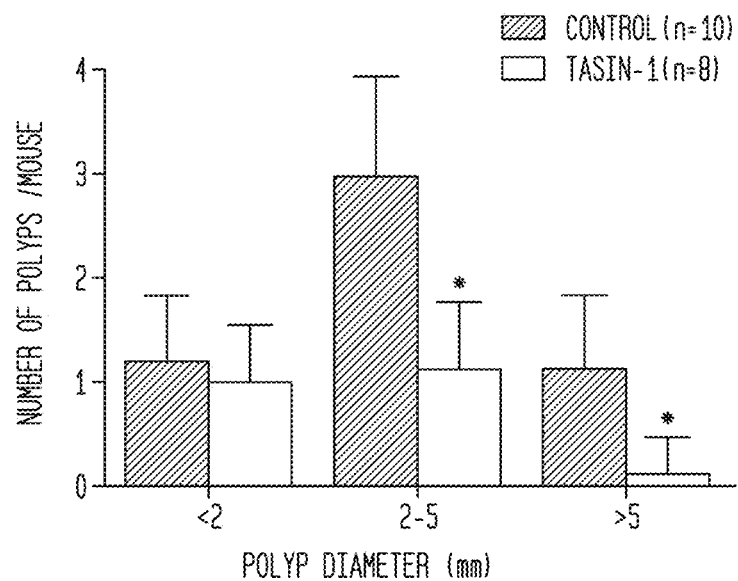
Figure 21E:
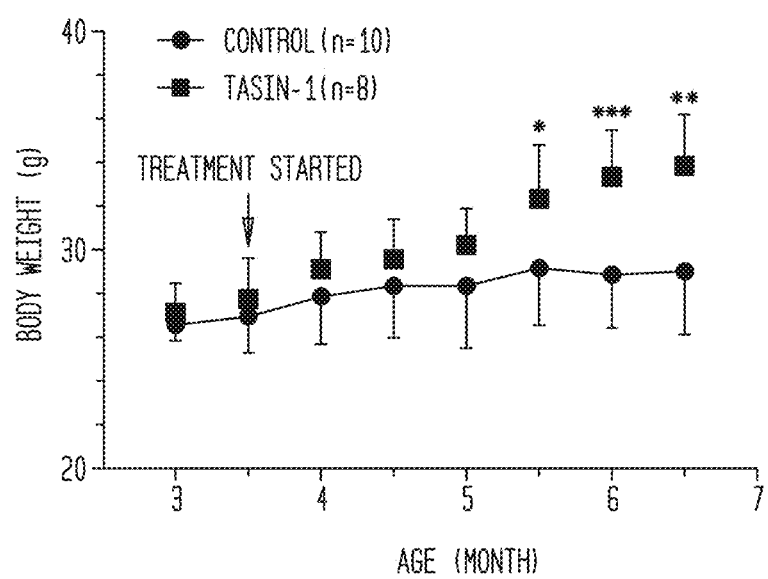
Figure 22:
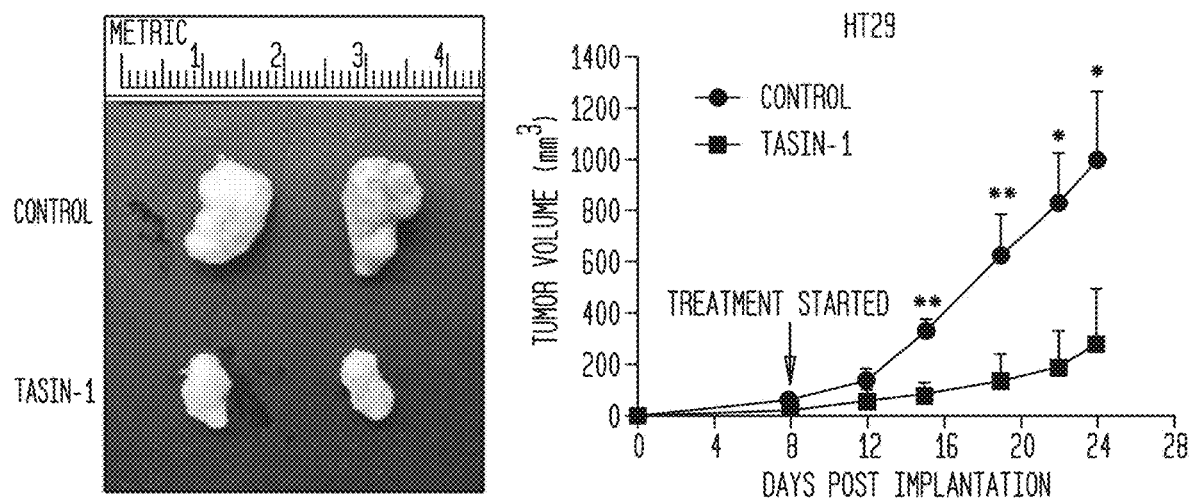
FIG. 22 shows that TASIN-1 inhibited tumor growth in HT29 xenografts. The dosing schedule was intraperitoneal over 18 days at 40 mg/kg, administered twice daily.
Figure 23:
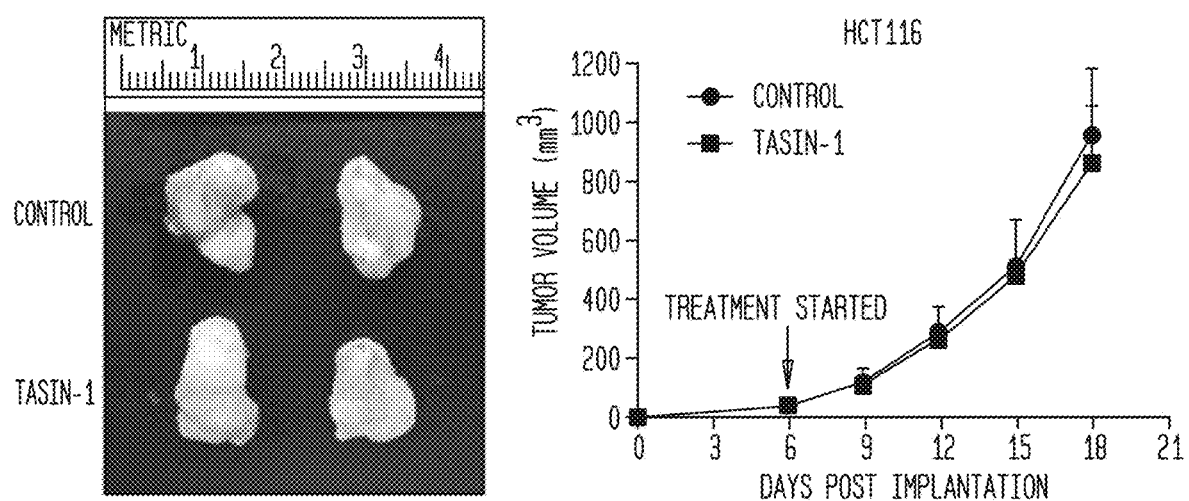
FIG. 23 shows that TASIN-1 does not inhibit tumor growth in HCT116 xenografts. The dosing schedule was intraperitoneal over 18 days at 40 mg/kg, administered twice daily. HCT116 has wild type APC. Thus, TASIN-1 maintains selectivity for truncated APC in vivo.
Figure 24A:
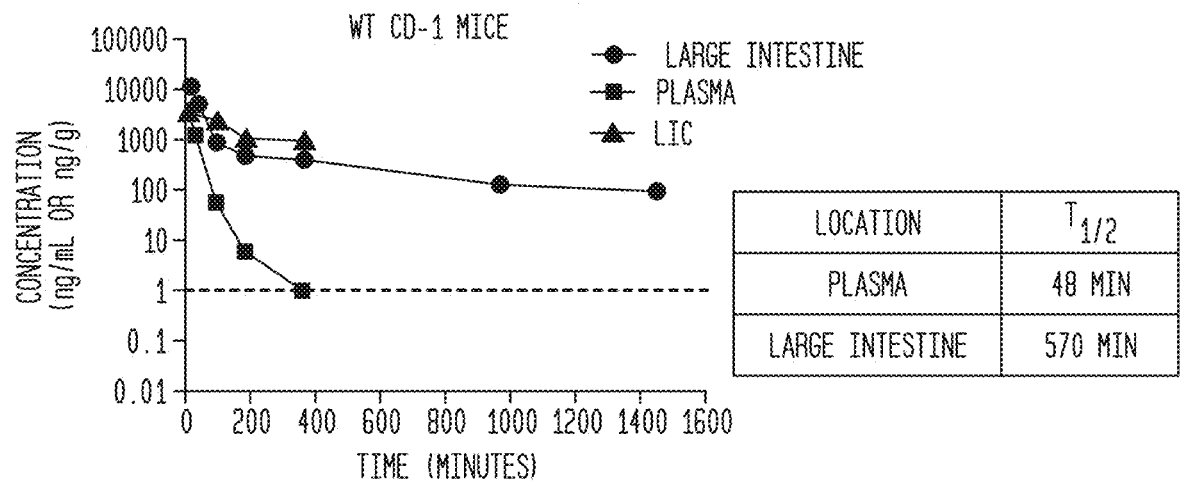
FIG. 24A-24C shows that TASIN-1 reduces tumorigenesis in a genetically engineered CRC mouse model. (a) TASIN-1 is mainly retained in large intestine tissue after i.p. injection. (b) Representative photographs of colons from control and TASIN-1 treated groups. (c) TASIN-1 suppresses expression of inflammatory gene set in vivo. RNA was extracted from tumor lysates of control and TASIN-1 treated group, cDNA synthesized and subjected to qPCR analysis. Data represent mean±s.d. of 5 mice. Student's t-test, *P<0.05, **P<0.01.
Figure 24B:
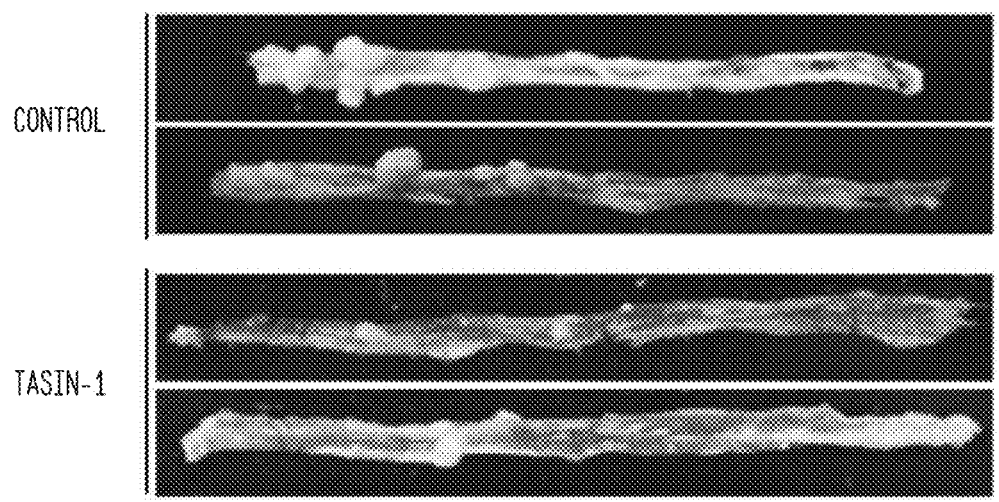
Figure 24C:
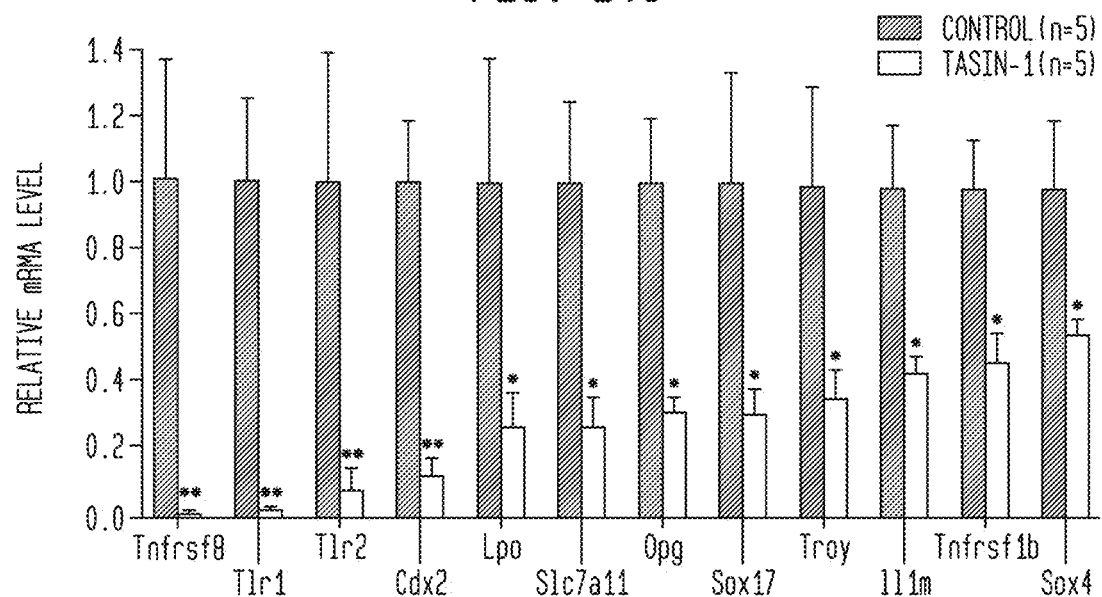
Figure 26:
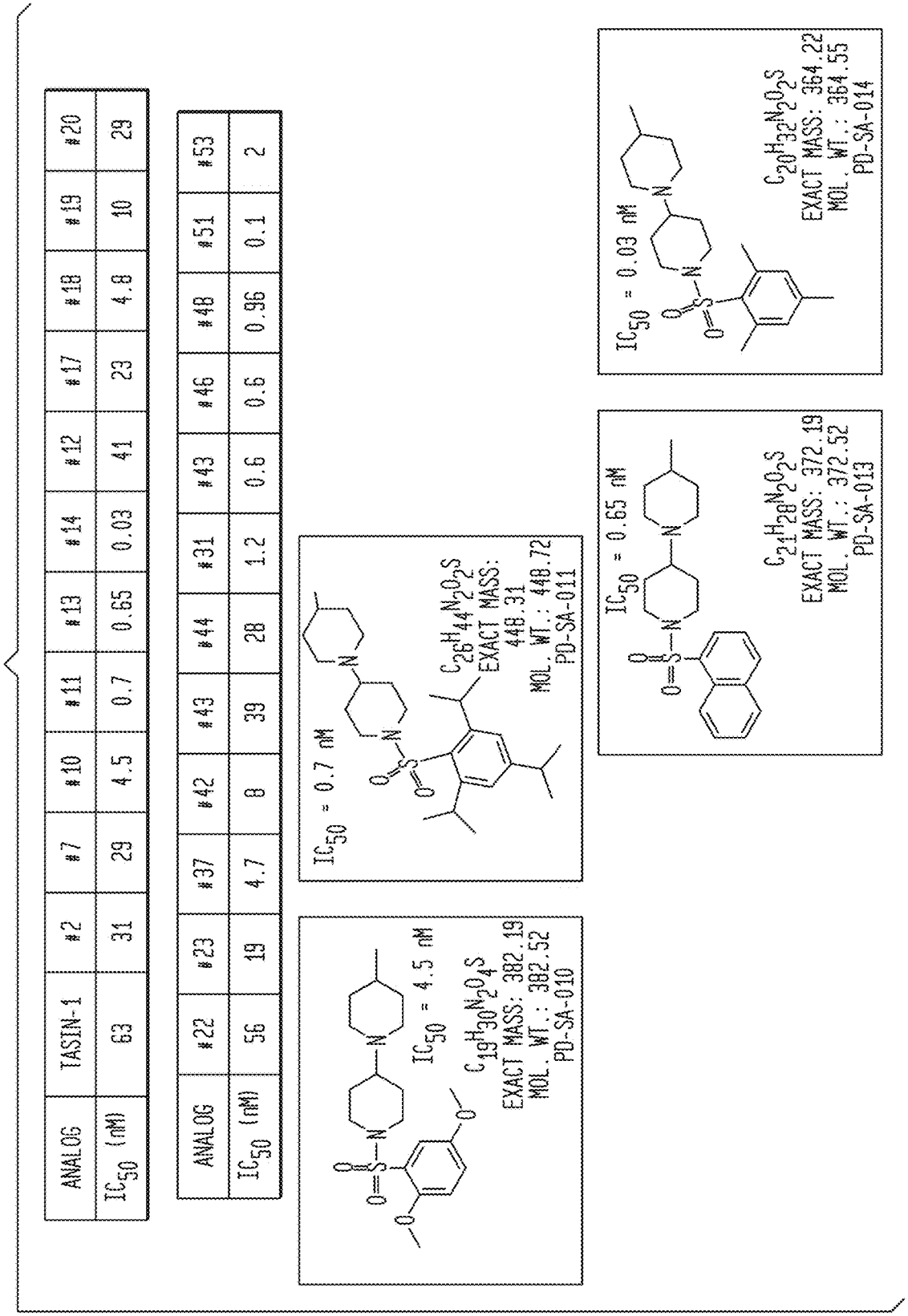
FIG. 26 shows structure-activity relationship (SAR) analysis to identify analogs of TASIN-1. Analogs were tested with different chemotypes. 101 analogues have been tested and 40 of these analogs show greater potency in DLD1 cells than TASIN-1.
Figure 27A:
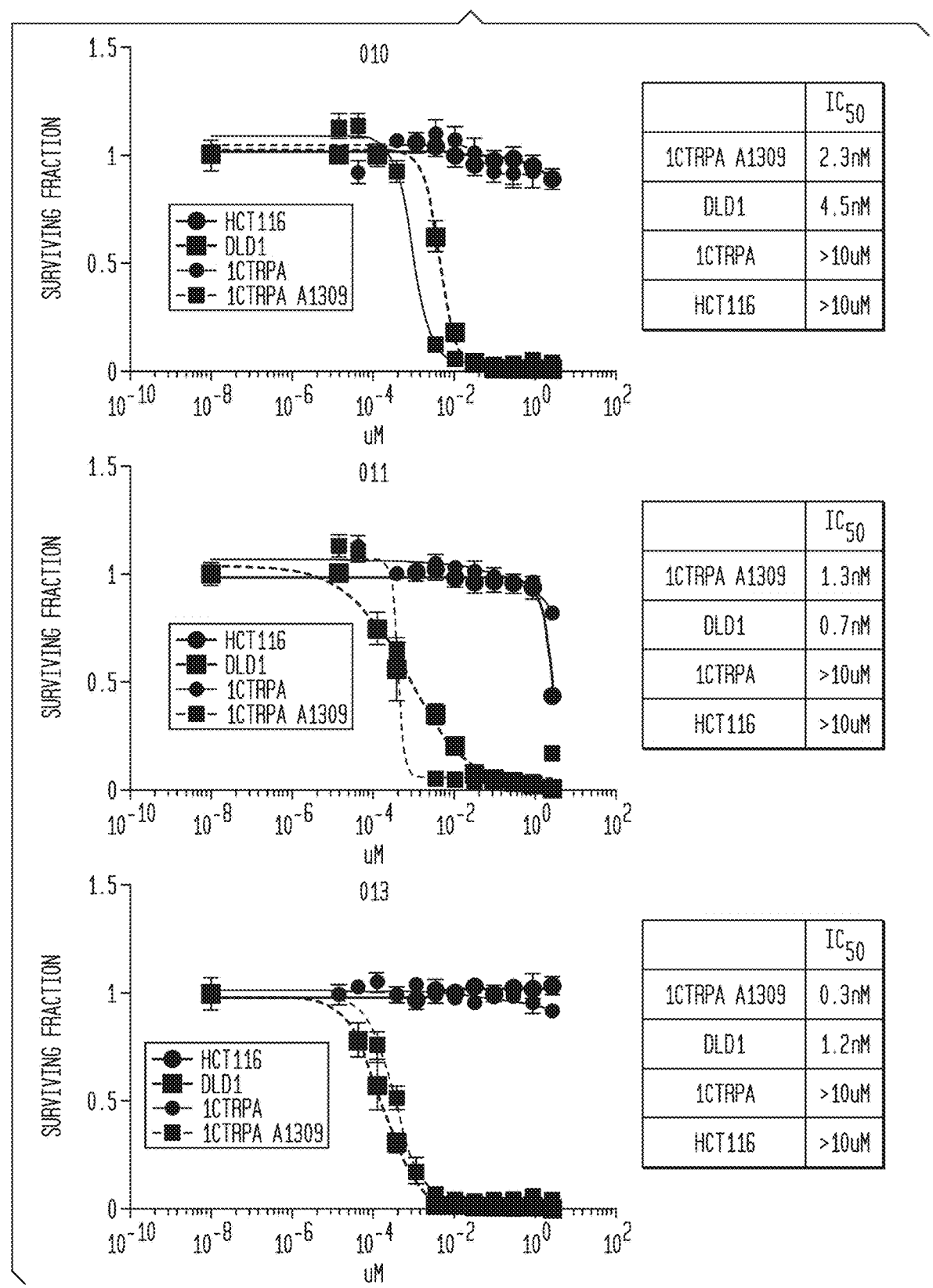
FIG. 27A-B shows that small molecule anti-cancer compounds PDSA-010, PDSA-011, PDSA-013 and PDSA-014 potently and selectively kill DLD1 and 1CTRPAA1309 cells (a-b).
Figure 27B:
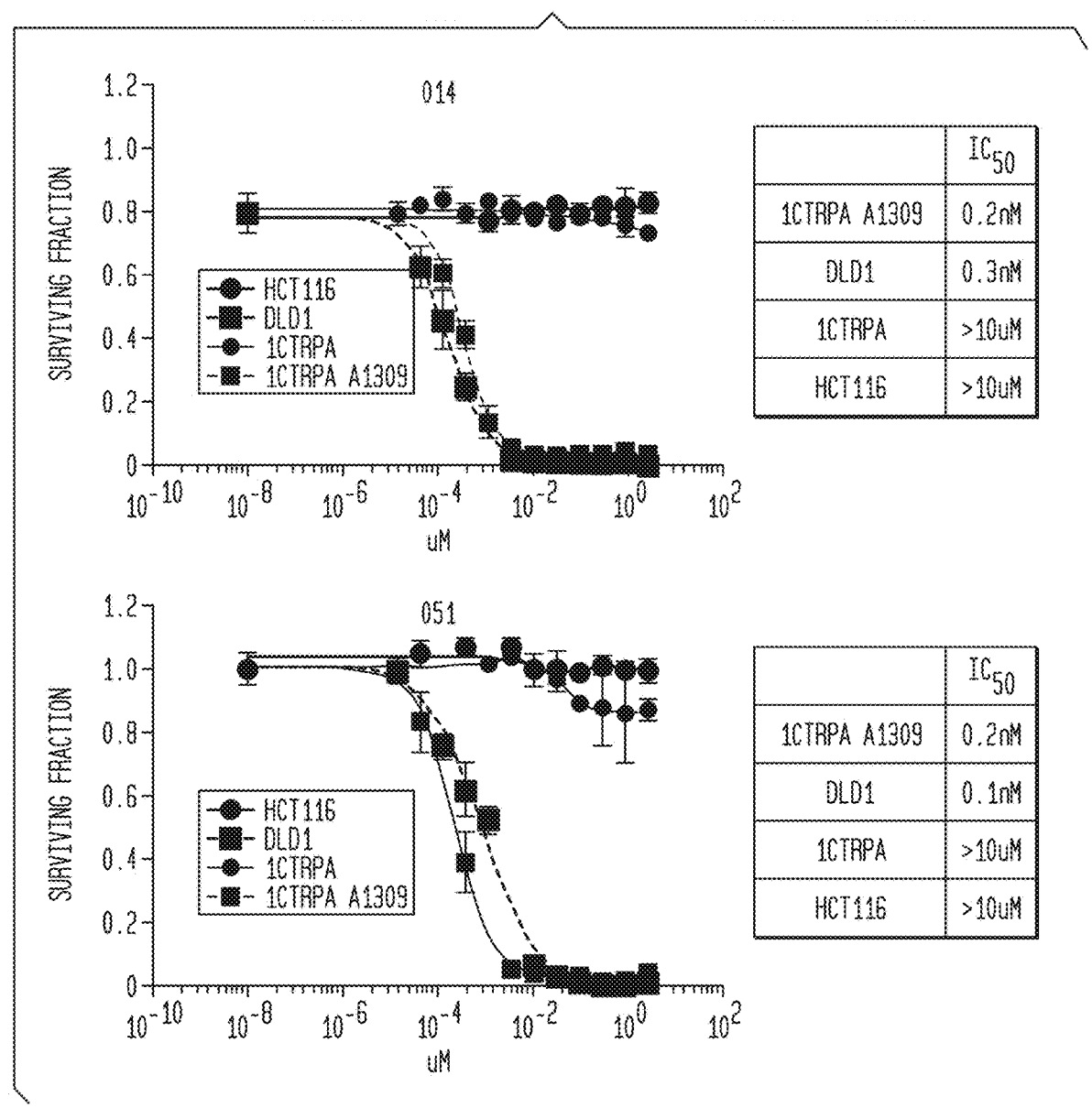
Figure 28:
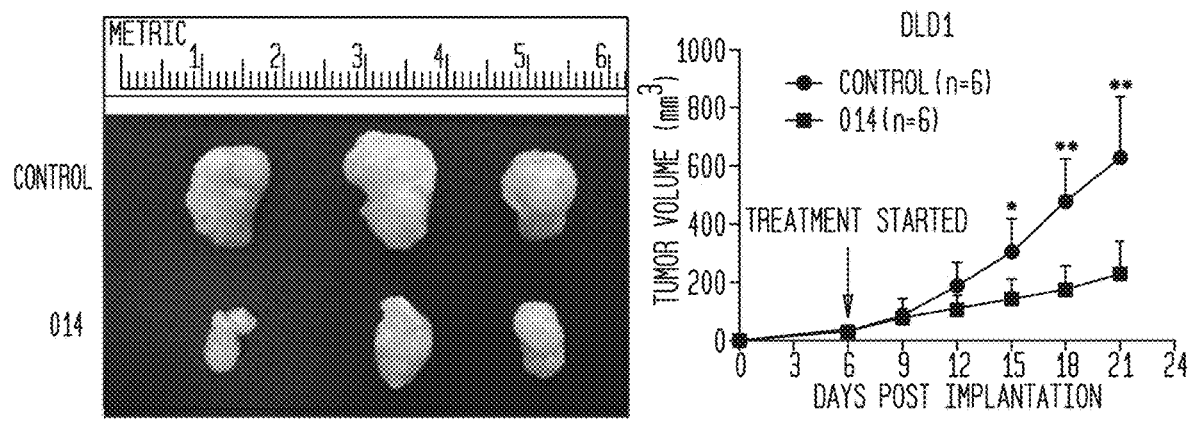
FIG. 28 shows that small molecule anti-cancer compound PDSA-014, administered by intraperitoneal injection at 10 mg/kg twice daily, inhibits tumor growth in DLD1 xenografts.
Figure 29:
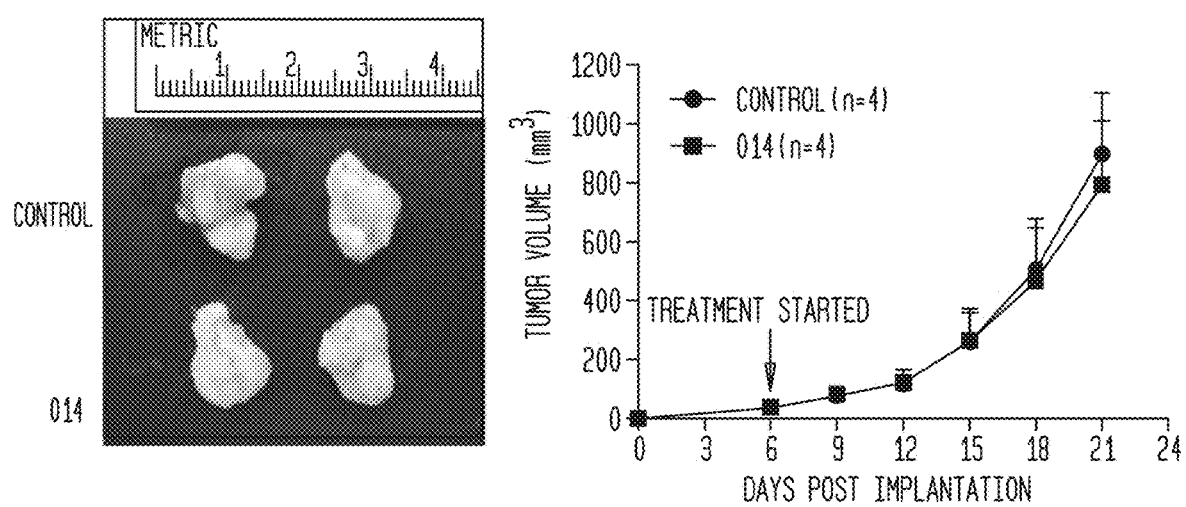
FIG. 29 shows that small molecule anti-cancer compound PDSA-014, administered by intraperitoneal injection at 10 mg/kg twice daily, does not inhibit tumor growth in HCT116 xenografts.
Figure 33A:
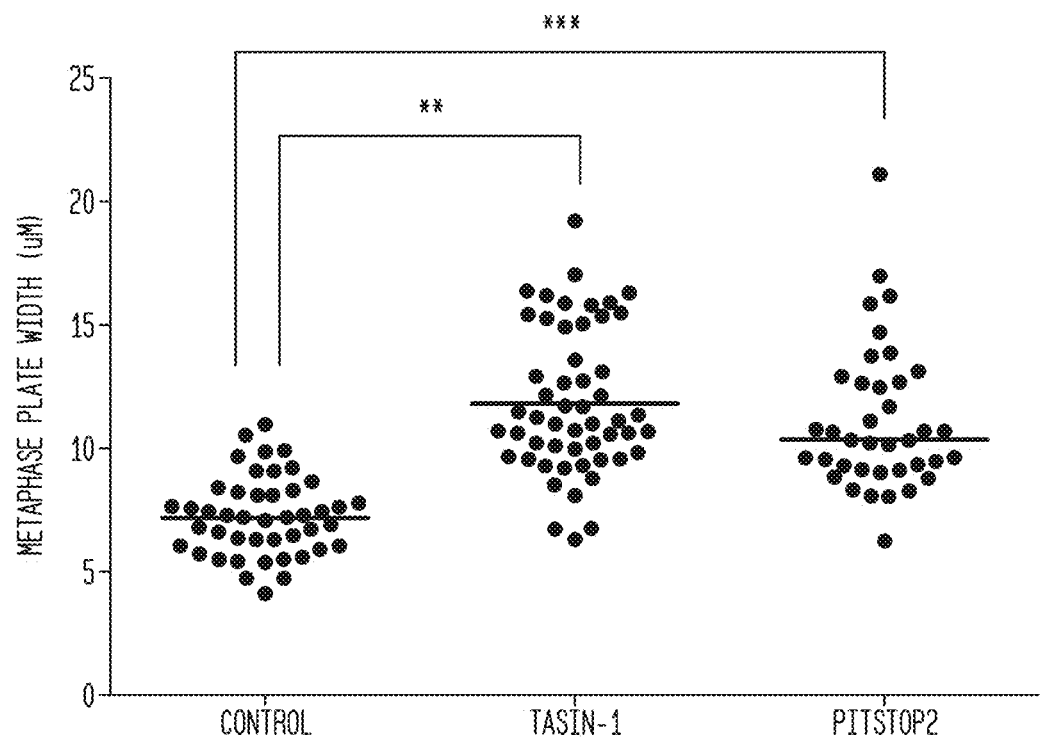
FIG. 33A-33D shows that TASIN-1 disrupts mitotic spindles, chromosome alignment and K-fiber organization during mitosis in DLD1 cells. (a) The width of the metaphase plate. (b) The ratio of spindle width/total cell width of metaphase cells. Pitstop2 is a positive control for spindle disruption. Each dot represents a cell. Mean is indicated by the solid black line. (c) Representative images for metaphase synchronized cells stained for α-tubulin (red), HURP (green), and DNA (DAPI, blue). The graph shows the percentage of TASIN-1 treated cells with abnormal HURP localization. Data represent mean±s.e.m. of 50 cells scored from 3 biological triplicates. Student's t-test, **P<0.001. (d)
Figure 33B:
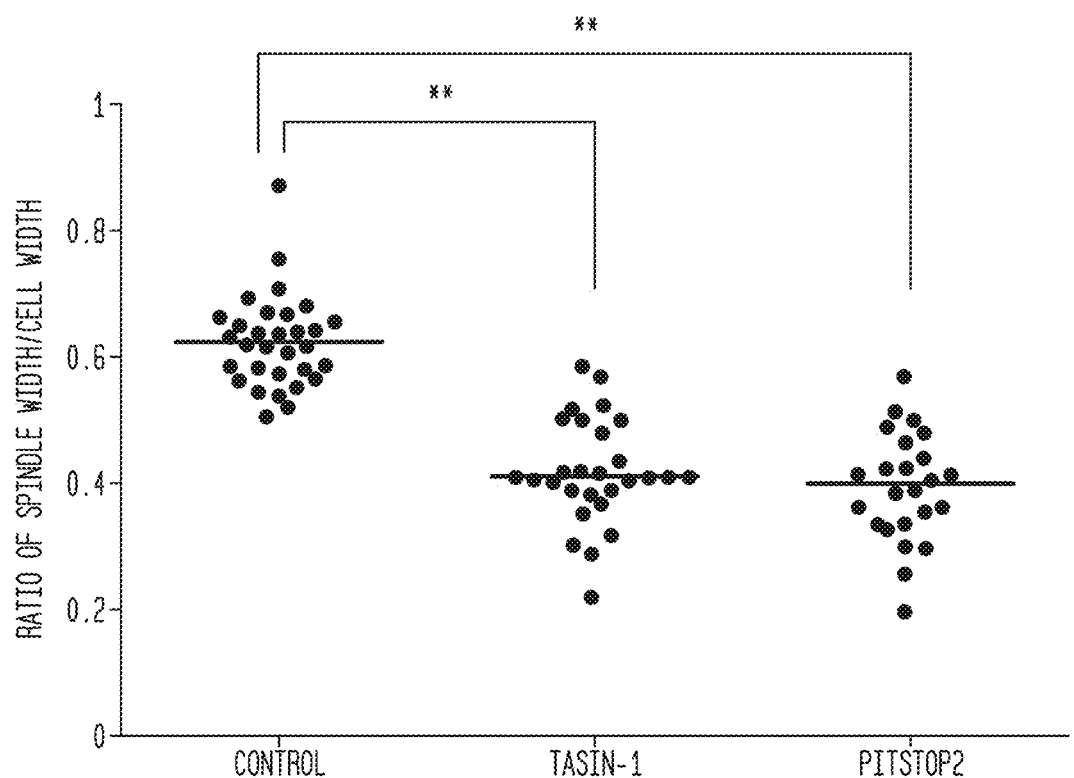
Figure 33C:
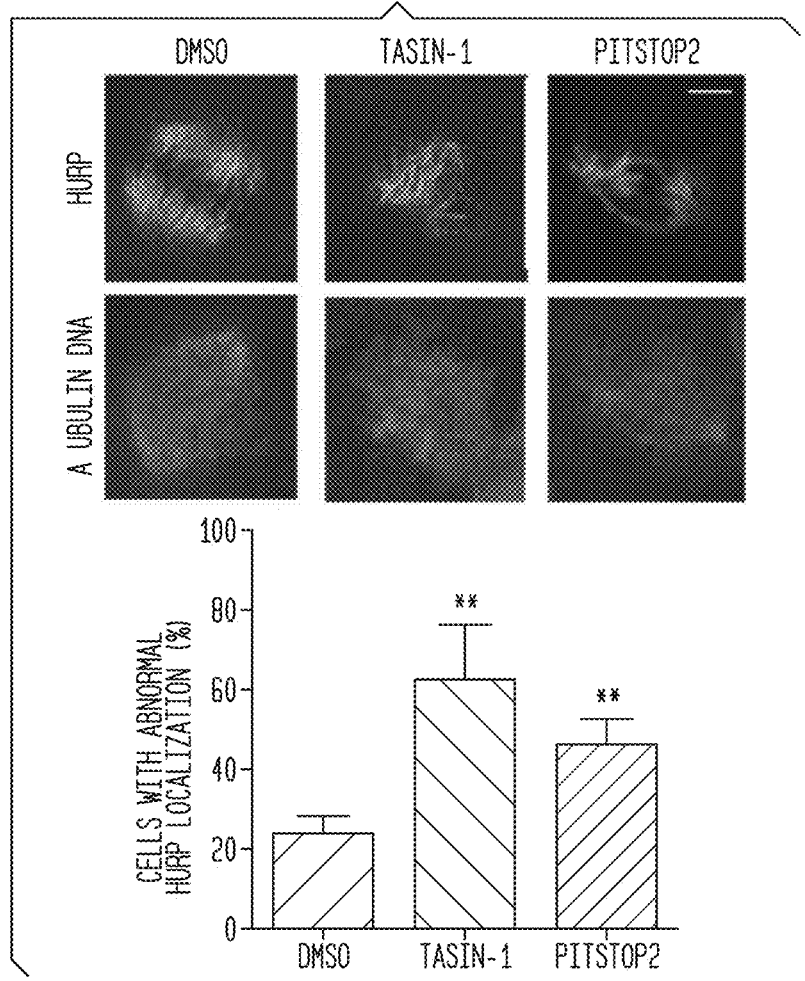
Figure 33D:
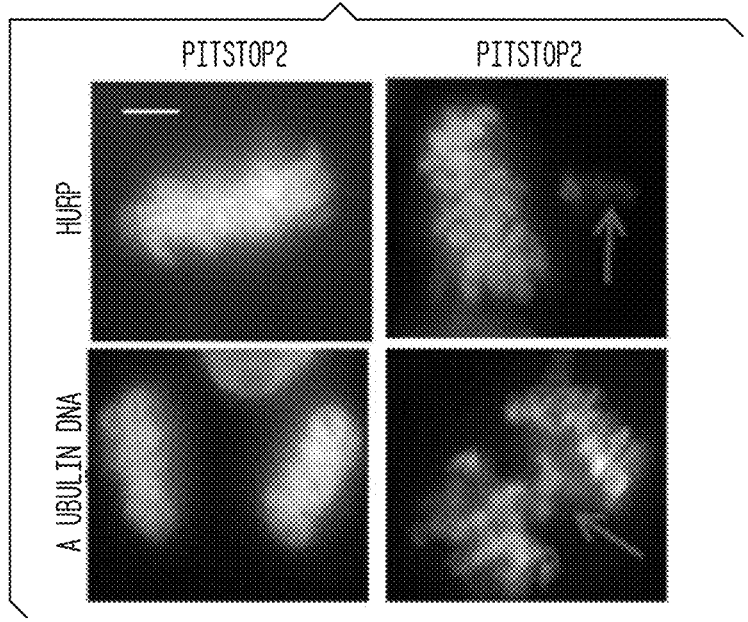

The in vivo antitumor activity of TASIN-1 was examined in a xenograft mouse model. Nude mice with established DLD1 tumors were injected intraperitoneally with either solvent (control) or 40 mg/kg of TASIN-1 twice daily for 18 days. TASIN-1 treatment reduced the size of tumor xenografts (FIGS. 17, 17') and reduced tumor growth rates (FIG. 17' (b)) compared with control mice. No overt toxicity and no statistically significant differences were observed in the body weights of mice between control group and TASIN-1 treated group (FIG. 20 (a)). Similar antitumor activity was observed in HT29 xenografts, which also harbors truncated APC and demonstrated a similar sensitivity as DLD1 in vitro (FIG. 17'(c)). However, TASIN-1 did not inhibit tumor growth in HCT116 (WT APC) xenografts (FIG. 19), demonstrating that TASIN-1 maintains selectivity in vivo. Immunohistochemistry analysis of excised tumors showed that TASIN-1 induced a significant increase in the apoptotic marker, cleaved caspase 3 in TASIN-1 treated DLD1 tumors compared with control tumors (FIG. 20 (b)). Induction of apoptosis was confirmed by detection of cleaved PARP1 in tumor lysates from control and TASIN-1 treated DLD1 xenografts (FIG. 20 (c)).

Example 5. Anti-tumor Effects of TASIN-1 in CPC;Apc Mice

Considering that TASIN-1 has a long retention time in mouse large intestine tissue (FIG. 19'), the antitumor effects in CPC;Apc mice, a genetically engineered mouse model that mainly develops colorectal tumors, were further tested. These mice carry a CDX2P-NLS Cre recombinase transgene and a loxP-targeted Apc allele that deletes exon 14, leading to a frame shift at codon 580 and a truncated APC protein (Hinoi, T. et al. Mouse model of colonic adenoma-carcinoma progression based on somatic Apc inactivation. *Cancer Res* 67, 9721-9730 (2007)). Mice ~110 days old were injected intraperitoneally with either solvent or 20 mg/kg/injection of TASIN-1 twice a week for 90 days. Weights were measured every 15 days over the treatment period. These studies were performed according to the guidelines of the UT Southwestern Institutional Animal Care and Use Committee.

Figure 1:
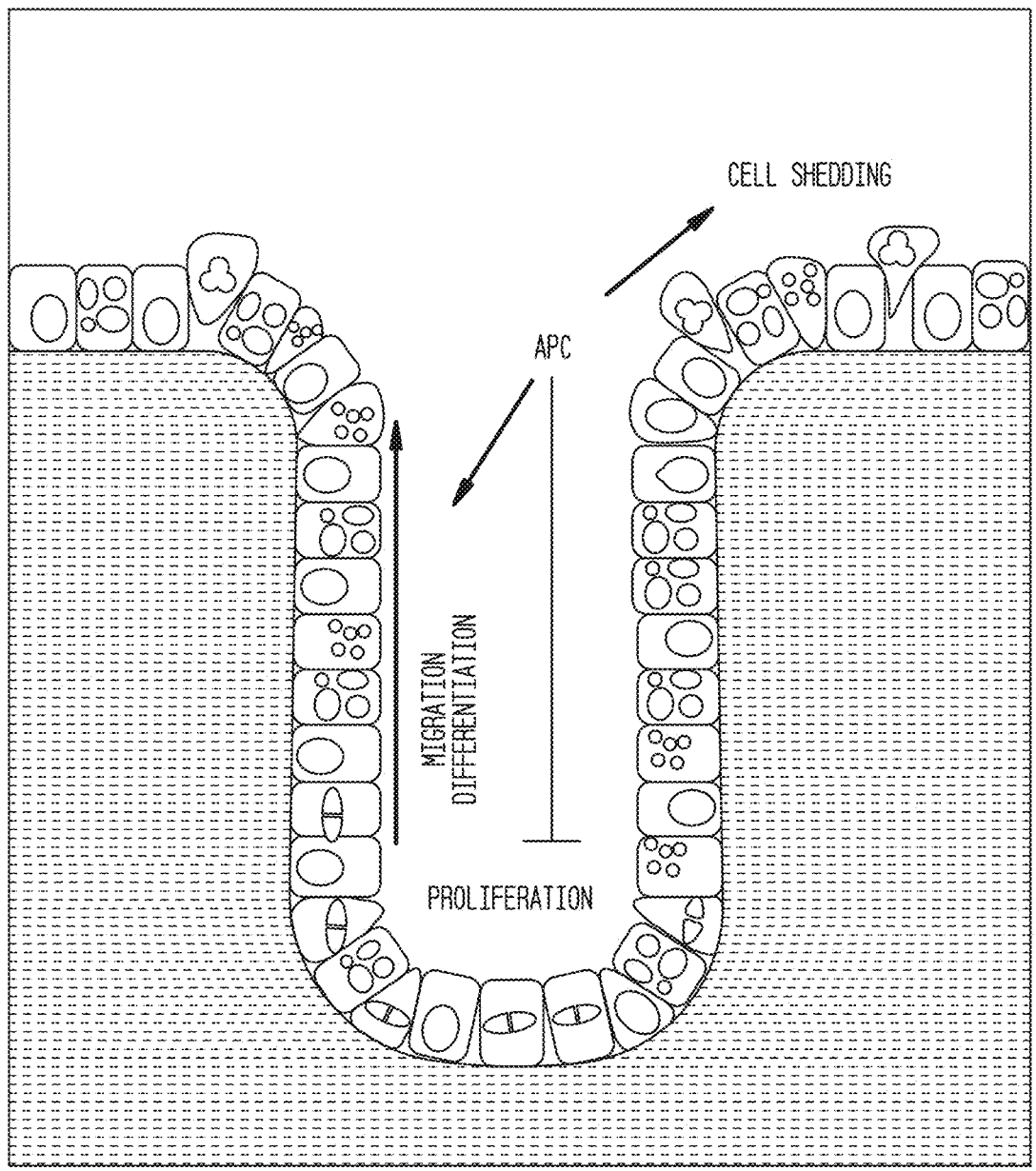
FIG. 1 is a diagram of a colonic crypt. The colonic crypts are composed of an epithelial layer of cells that include stem cells undergoing mitosis, columnar absorptive cells, mucin-producing goblet cells, and enteroendocrine cells. Cells differentiate and migrate to the luminal surface of the crypt where they are extruded into the lumen of the intestine by programmed cell death. It is believed that APC participates in all of these processes directly or indirectly by modulating transcription profiles within the intestinal epithelial cells (See Goss et al., Journal of Clinical Oncology, 2000; 18:1967-1979). APC influences Wnt signaling through beta-catenin/TCF. Full-length APC influences cell cycle control by arresting cells at G1/S through the retinoblastoma (Rb) pathway and localizing to mitotic spindles and centrosomes during the M phase. APC influences cell migration by stabilizing microtubules and activating cell division control protein 42 (cdc42). Lastly, full-length APC influences cellular differentiation and apoptosis.
Figure 2:
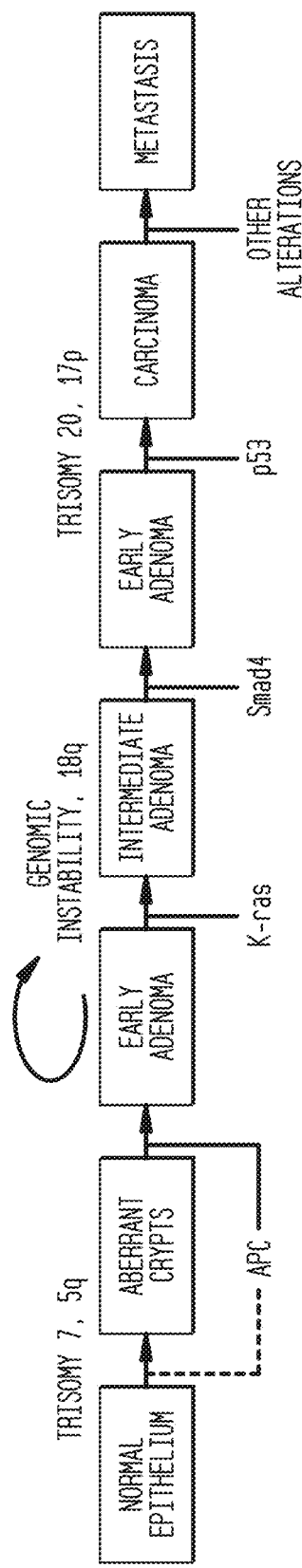
FIG. 2 illustrates possible genes involved in progression from normal colonic epithelium to colon cancer. APC mutation is believed to be a frequent and early event in colorectal cancer, since APC mutations are detected in more than 80% of colorectal tumors, and over 90% of APC mutations generate premature stop codons resulting in truncated gene products.
Figure 3:
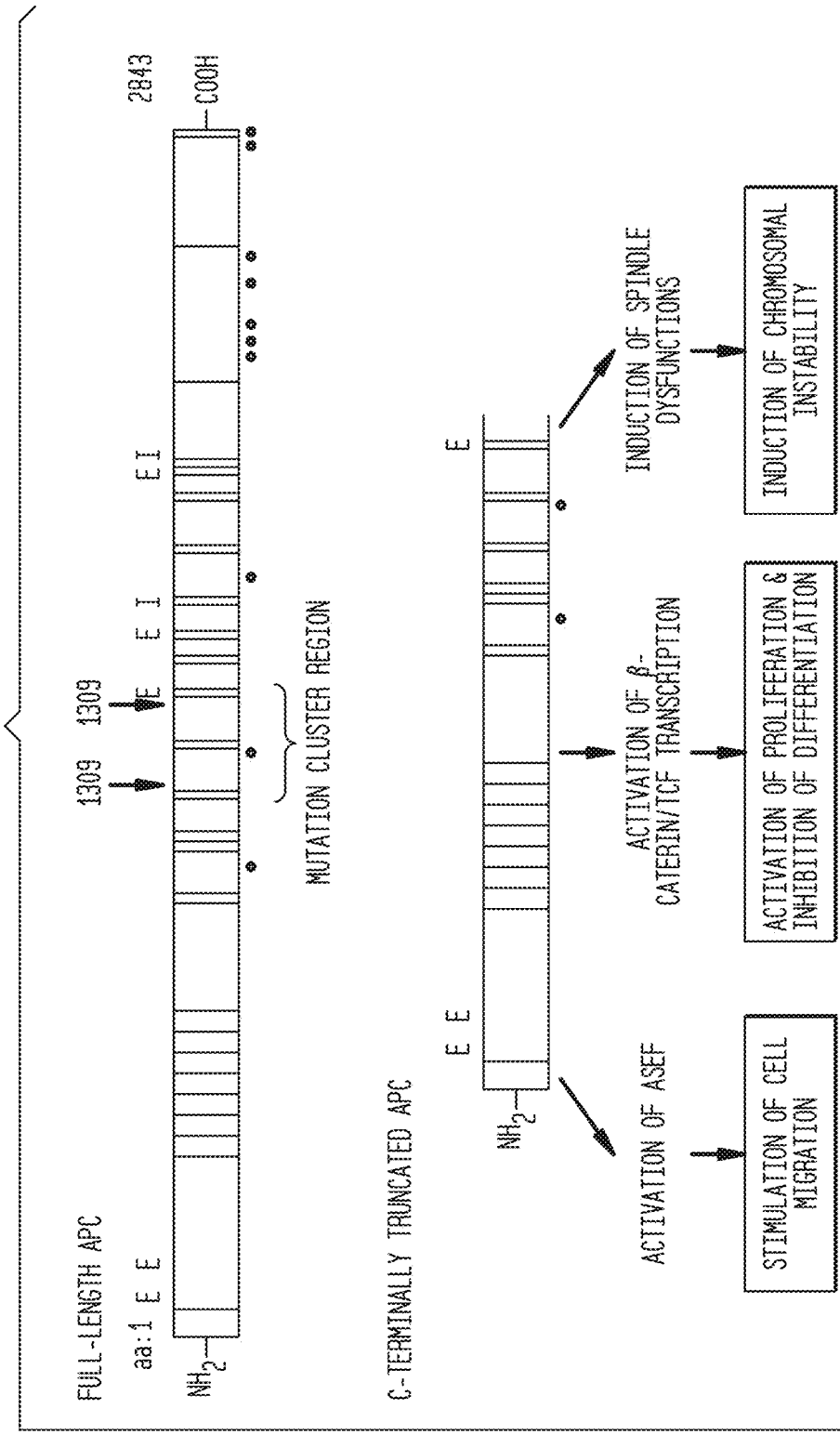
FIG. 3 shows the structure of full-length and truncated APC. Truncated APC lacks the binding domains for beta-catenin and microtubules but retains the binding domains for Asef, thus leading to activation of proliferation, induction of chromosomal instability and stimulation of cell migration. (See Fodde et al., Nat Rev Cancer, 1:55-67) Mutations A1309 and A1450 are most highly represented.
Figure 4A:
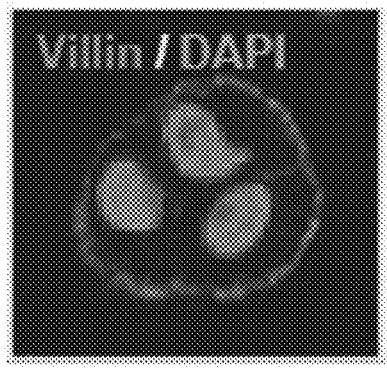
FIG. 4A-4D illustrates that immortalized human colonic epithelial cells (HCECs) are normal diploid and can differentiate. (A) Small self-organizing multicellular structures show evidence of polarized villin and general nuclear staining. (B) Small self-organizing multicellular structures (day 11) show evidence of zonula occludens-1 (ZO-1) and general nuclear staining. (C) Small self-organizing multicellular structures (day 11) show evidence of mucin [MUC]2, zonula occludens-1 (ZO-1) and general nuclear staining. (D) shows that hTERT CDK4 immortalized human colonic epithelial cells differentiated similarly to primary mouse intestinal cells. The hTERT CDK cells are 100% LGR-5 positive. LGR-5 is an accepted biomarker of colonic stem cells. (See Roig et al. Gastro, 2010; 138:1012-1021).
Figure 4B:
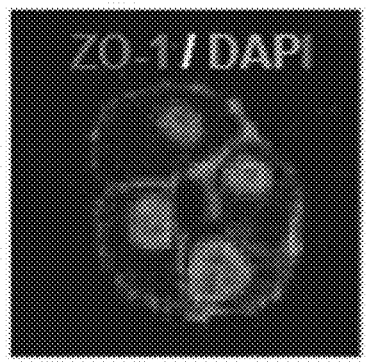
Figure 4C:
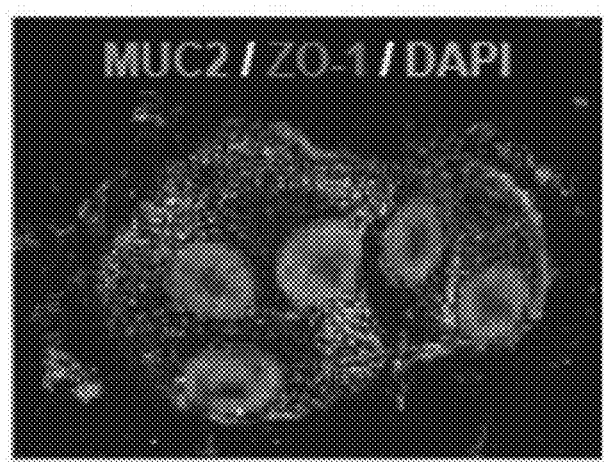
Figure 4D:
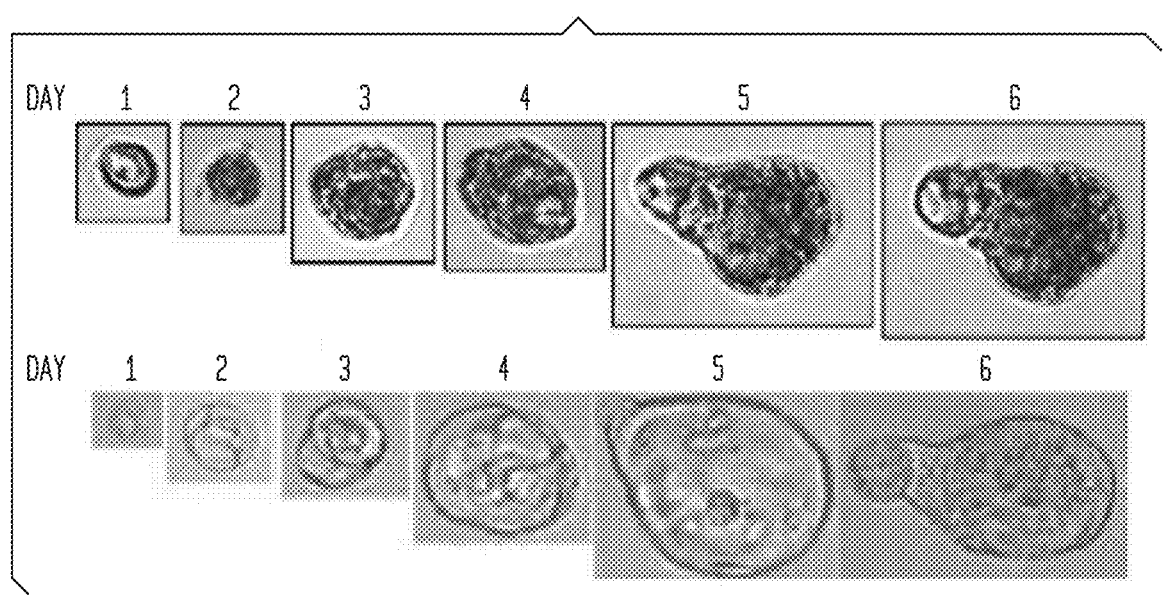
Figure 5A:
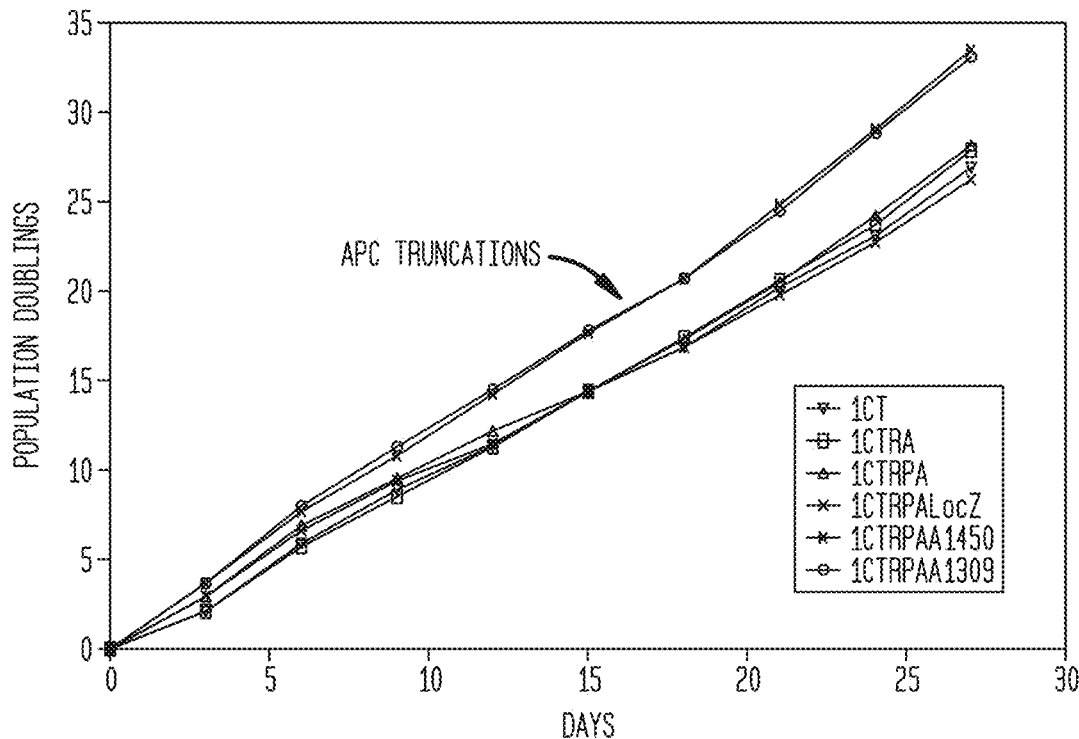
FIG. 5A-5D shows that APC truncations confer tumorigenic properties. The figures show the effect of APC truncations in population doubling time (A); matrigel invading cells (B); anchorage independent colony formation (C); and expression (D). The isogenic Human Colonic Epithelial Cells (HCECs) used were: HCECs immortalized with cyclin-dependent kinase 4 (CDK4) and human telomerase reverse transcriptase (hTERT) (1CT); HCECs with the genetic alterations CDK4, hTERT, Kirsten rat sarcoma viral oncogene homolog (Kras$^{v12}$), small hairpin RNA against APC (shAPC), (1CTRA); HCECs with the genetic alterations CDK4, hTERT, Kras$^{v12}$, small hairpin RNA against tumor protein p53 (shp53), shAPC (1CTRPA); 1CTRPA expressing LacZ (1CTRPA LacZ); 1CTRPA having a somatic mutation at codon 1450 (1CTRPA 1450); and 1CTRPA having a somatic mutation at codon 1309 (1CTRPA 1309). While a 90% loss of APC function does not increase tumorgenic properties, the isogenic cell line derivative containing a truncated APC does show the hallmarks of transformation. This indicates that truncated APC provides a gain of function representing an increase in cancer progression and may explain why a large fraction of patients with CRC retain a truncated APC protein.
Figure 5B:
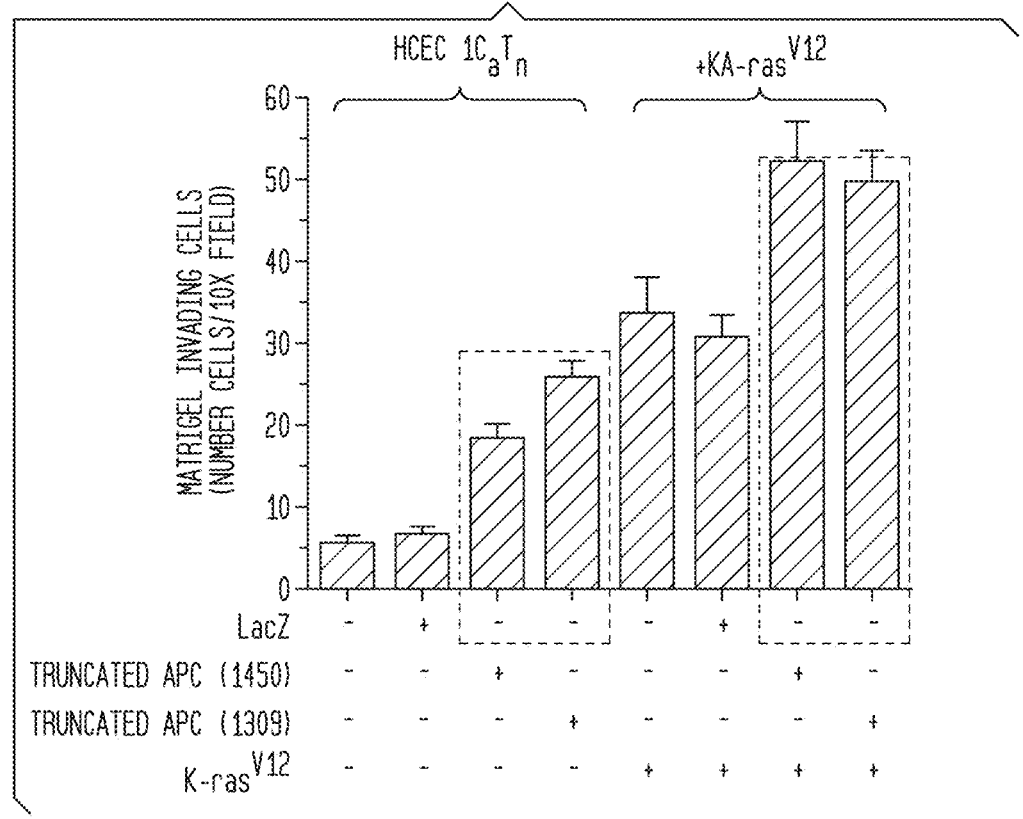
Figure 5C:
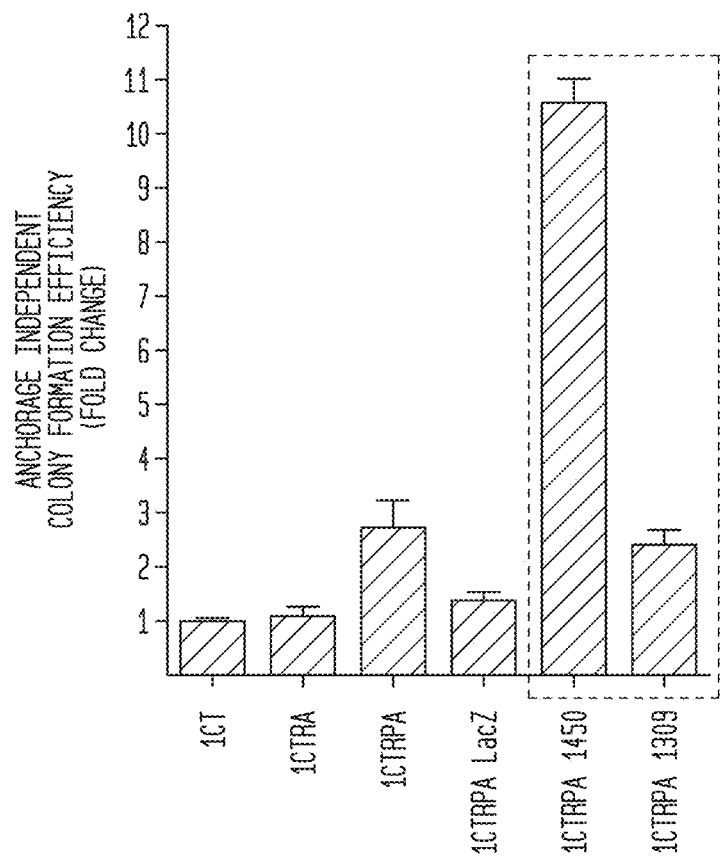
Figure 5D:
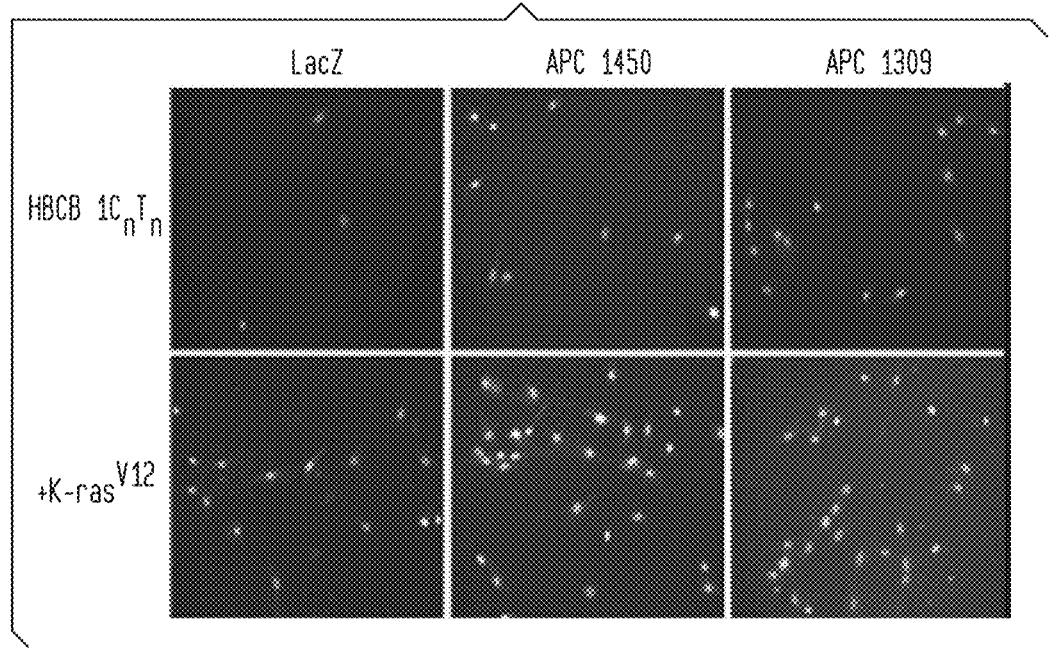
Figure 17:
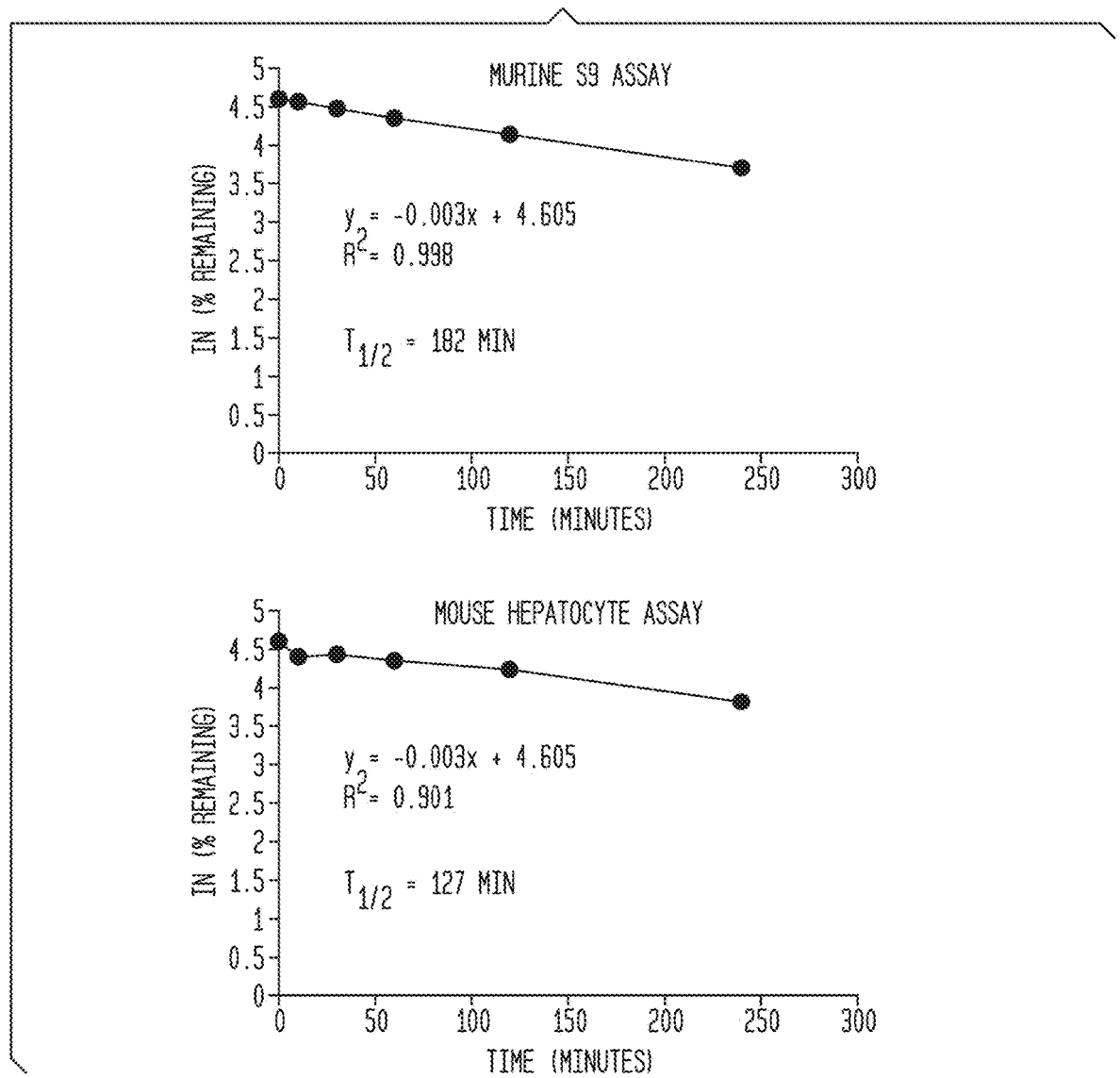
FIG. 17 shows metabolic stability of TASIN-1 in mouse S9 and hepatocyte assays.
Figure 18:
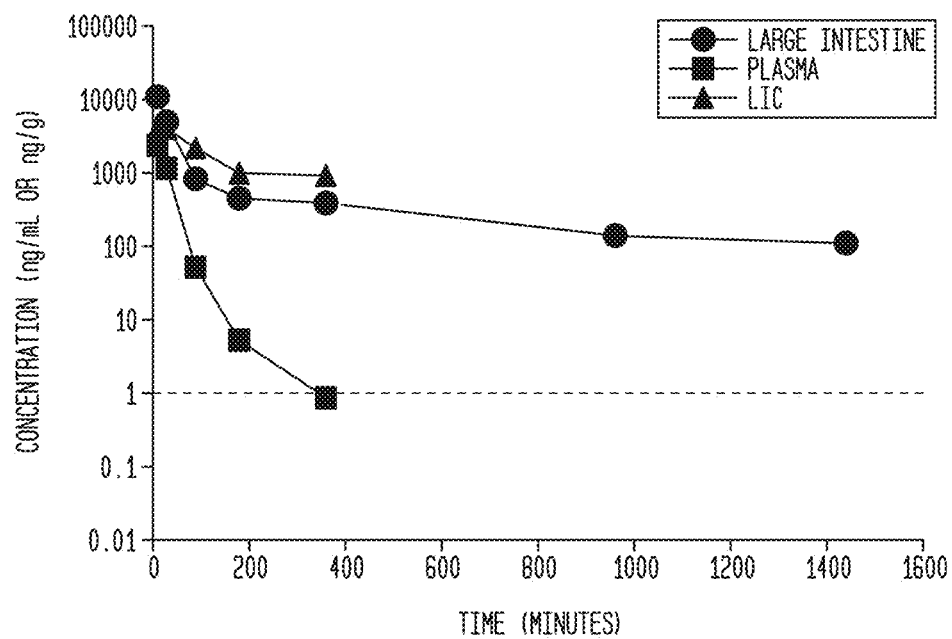
FIG. 18 shows that TASIN-1 is retained in the large intestine after being absorbed from the peritoneal space. LIC: large intestine content.

TASIN-1 treatment resulted in significant reduction in tumor formation in the colon of CPC;Apc mice (FIGS. 17', 19'). Benign tumors (polyps) that developed in TASIN-1 treated CPC;Apc mice were much smaller compared to the control group (FIG. 3f). Additionally, TASIN-1 treated mice with less tumor burden gained weight to a level similar to WT mice over the 90 days' treatment (FIG. 17'). Finally, TASIN-1 treated mice showed suppressed expression of a panel of inflammatory response genes (FIG. 19') and reduced staining for Ki67 and cyclin D1, accompanied by increased staining for cleaved caspase 3 in colon tumor sections. Taken together, these in vivo experiments show that TASIN-1 efficiently attenuates tumorigenesis in both human xenografts and genetically engineered CRC mouse models without noticeable toxicity.

\* \* \*

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A compound according to Formula I-h:

Ring-L-B     [Formula I-h], wherein the Ring is selected from the group consisting of

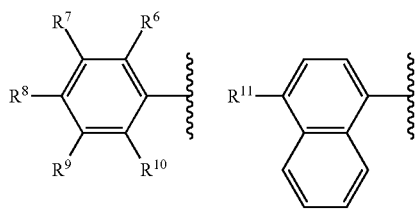

-continued

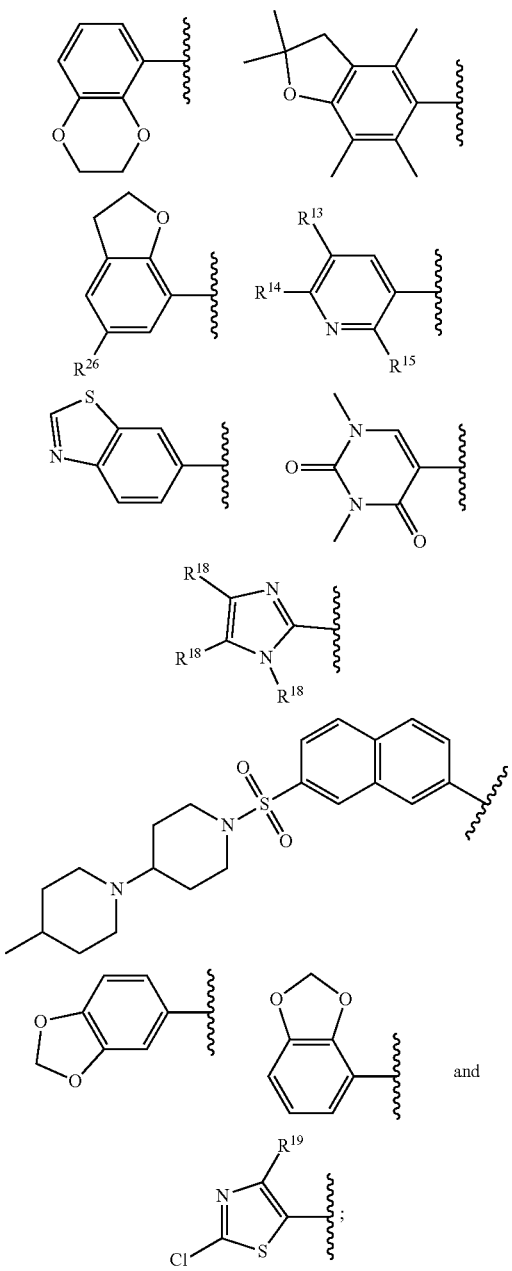

L is selected from the group consisting of —SO₂—, —CH₂—, and —CO—;
B is selected from the group consisting of

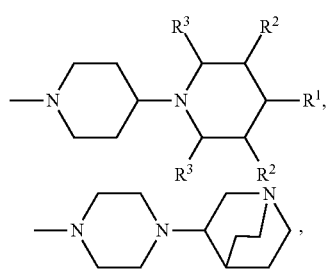

-continued $R^1$ is selected from the group consisting of $C_{1-3}$ alkyl optionally substituted with $R^{21}$, —CH₂COCH₂CH₂C≡CH, and —(CH₂)₀₋₁-phenyl optionally substituted with F;

each $R^2$ is independently selected from the group consisting of H and $C_{1-4}$ alkyl;

each $R^3$ is selected from the group consisting of H and $C_{1-3}$ alkyl optionally substituted with $R^{21}$;

$R^4$ is $C_{1-3}$ alkyl;

each $R^6$, $R^7$, $R^9$, and $R^{10}$ is independently selected from the group consisting of H, F, Cl, Br, $C_{1-4}$ alkyl, cyclopropyl, N₃, NH₂, CF₃, OCHF₂, OCF₃, $OC_{1-4}$ alkyl, benzoyl, phenoxy, naphthyl, —C≡C—$R^{24}$, $R^{25}$, —OCH₂C≡CH, CN, NO₂, —CO₂—$C_{1-4}$ alkyl, CO₂H, —NR¹⁸CO—($C_{1-4}$alkyl), —CON($C_{1-4}$ alkyl)₂, —SO₂NR¹⁸₂, —SO₂(pyrrolidin-N-yl), —N(CH₂phenyl)₂, —NH(CH₂phenyl), —N($C_{1-4}$alkyl)₂, —NH($C_{1-4}$alkyl), $R^{23}$, —N($C_{1-4}$alkyl)C(O)CH₃, —N($C_{1-4}$alkyl)C(O)CH₂CH₃, —CO($C_{1-4}$alkyl), —OC(O)NR¹⁸₂, —OC(O)(pyrrolidin-N-yl), and —NR¹⁸C(O)O—($C_{1-4}$alkyl);

$R^8$ is selected from the group consisting of H, CH₃, CH₂CH₃, propyl, isopropyl, n-butyl, cyclopropyl, Br, N₃, NH₂, —N($C_{1-4}$alkyl)₂, —NH($C_{1-4}$alkyl), OCHF₂, benzoyl, phenoxy, $R^{23}$, —N($C_{1-4}$alkyl)C(O)CH₃, —N($C_{1-4}$alkyl)C(O)CH₂CH₃, —NHC(O)CH₂CH₃, —CO($C_{1-4}$alkyl), —CO₂—($C_{1-4}$alkyl), —O($C_{1-4}$alkyl), —OC(O)NR¹⁸₂, —OC(O))pyrrolidin-N-yl), and —NR¹⁸C(O)O—($C_{1-4}$alkyl);

each $R^{21}$ is independently selected from the group consisting of H, CN, —C≡C—H, —C≡C—SiMe₃ and OR²²;

each $R^{22}$ is independently selected from the group consisting of H, —CH₂C≡CH and —CH₂C≡CSiMe₃;

$R^{23}$ is phenyl optionally substituted with one or more substituents selected from the group consisting of F, Cl, Br, $C_{1-4}$ alkyl, cyclopropyl, N₃, NH₂, CF₃, CH₂F, OCHF₂, OCF₃, $OC_{1-4}$ alkyl, benzoyl, phenoxy, —C≡C—$R^{24}$, $R^{25}$, —OCH₂C≡CH, NO₂, —CO₂—$C_{1-4}$ alkyl, CO₂H, —NR¹⁸CO—($C_{1-4}$alkyl), —CON($C_{1-4}$ alkyl)₂, —SO₂NR¹⁸₂, —SO₂(pyrrolidin-N-yl), —N(CH₂phenyl)₂, —NH(CH₂phenyl), —N($C_{1-4}$alkyl)₂, —NH($C_{1-4}$alkyl), —N($C_{1-4}$alkyl)C(O)CH₃, —N($C_{1-4}$alkyl)C(O)CH₂CH₃, —NHC(O)CH₂CH₃, —CO($C_{1-4}$alkyl), —OC(O)NR¹⁸₂, —OC(O)(pyrrolidin-N-yl), and —NR¹⁸C(O)O—($C_{1-4}$alkyl);

each $R^{24}$ is independently selected from the group consisting of $C_{1-4}$ alkyl and —(CH₂)₁₋₄OH;

$R^{11}$ is H, Cl or NHC(O)CH₃;

$R^{13}$ is H, Cl or Br;

$R^{14}$ and $R^{15}$ are independently H, F, Cl or Br;

each $R^{18}$ is independently H, methyl or ethyl, $R^{19}$ is CH₃ or cyclopropyl;

each $R^{25}$ is independently phenyl optionally substituted with F, Cl, methoxy or CF₃; and $R^{26}$ is H or Br.

2. The compound according to claim 1, wherein
$R^1$ is selected from the group consisting of $C_{1-3}$ alkyl optionally substituted with $R^{21}$ and —$CH_2$-phenyl optionally substituted with F;
each $R^2$ is independently selected from the group consisting of H and methyl;
each $R^3$ is H;
$R^4$ is $CH_3$;
each $R^6$, $R^7$, $R^9$, and $R^{10}$ is independently selected from the group consisting of H, F, Cl, Br, $C_{1-4}$ alkyl, $N_3$, $CF_3$, $OCHF_2$, $OCF_3$, $OCH_3$, —$OCH_2C\equiv CH$, and $R^{23}$;
$R^8$ is selected from the group consisting of H, $CH_3$, $CH_2CH_3$, Br, $OCHF_2$, benzoyl, $N_3$, and $R^{23}$;
each $R^{21}$ is independently selected from the group consisting of H, —$C\equiv C$—H, and $OR^{22}$;
each $R^{22}$ is independently selected from the group consisting of H and —$CH_2C\equiv CH$;
$R^{23}$ is phenyl optionally substituted with one or more substituents selected from the group consisting of F, Cl, $OCH_3$, $CF_3$, and $CH_3$;
$R^{11}$ is H or Cl;
$R^{13}$ is H, Cl or Br;
$R^{14}$ and $R^{15}$ are independently H, F, Cl or Br;
each $R^{18}$ is independently H, methyl or ethyl,
$R^{19}$ is $CH_3$ or cyclopropyl;
$R^{26}$ is H or Br.
3. The compound according to claim 2, wherein the compound is of Formula I-i:

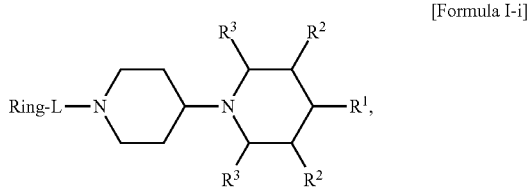

[Formula I-i]

wherein
L is $CH_2$ or CO;
the Ring is selected from the group consisting of

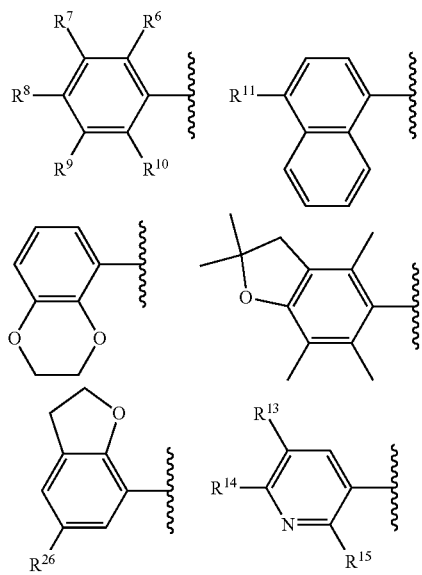

-continued

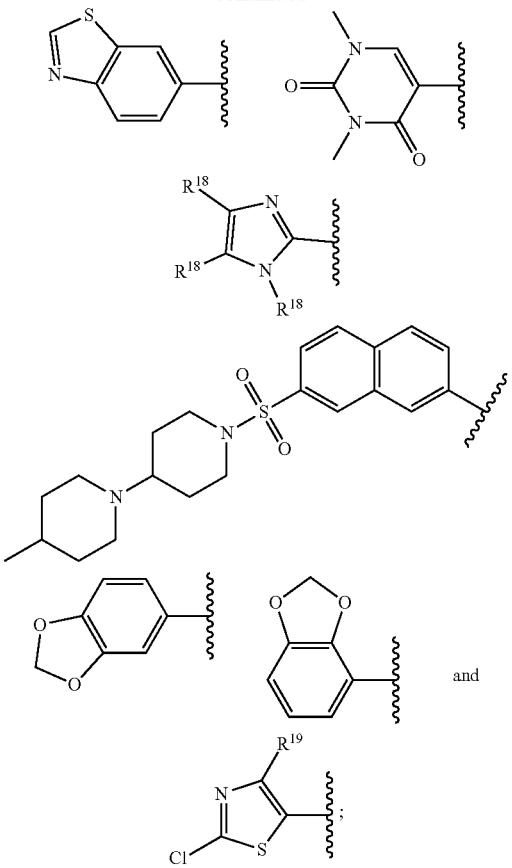

and $R^1$ is selected from the group consisting of $C_{1-3}$ alkyl optionally substituted with $R^{21}$ and —$CH_2$-phenyl optionally substituted with F;
each $R^2$ is independently selected from the group consisting of H and methyl;
each $R^3$ is H;
each $R^6$, $R^7$, $R^9$, and $R^{10}$ is independently selected from the group consisting of H, F, Cl, Br, $C_{1-4}$ alkyl, $N_3$, $CF_3$, $OCHF_2$, $OCF_3$, $OCH_3$, —$OCH_2C\equiv CH$, and $R^{23}$;
$R^8$ is selected from the group consisting of H, $CH_3$, $CH_2CH_3$, Br, $OCHF_2$, benzoyl, $N_3$, and $R^{23}$;
each $R^{21}$ is independently selected from the group consisting of H, —$C\equiv C$—H, and $OR^{22}$;
each $R^{22}$ is independently selected from the group consisting of H and —$CH_2C\equiv CH$;
$R^{23}$ is phenyl optionally substituted with one or more substituents selected from the group consisting of F, Cl, $OCH_3$, $CF_3$, and $CH_3$;
$R^{11}$ is H or Cl;
$R^{13}$ is H, Cl or Br;
$R^{14}$ and $R^{15}$ are independently H, F, Cl or Br;
each $R^{18}$ is independently H, methyl or ethyl,
$R^{19}$ is $CH_3$ or cyclopropyl;
$R^{26}$ is H or Br.
4. The compound according to claim 3, wherein the compound is of Formula I-j:

[Formula I-j]

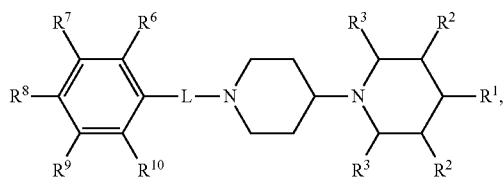

wherein
L is CH$_2$ or CO;
R$^1$ is selected from the group consisting of C$_{1-3}$ alkyl optionally substituted with R$^{21}$ and —CH$_2$-phenyl optionally substituted with F;
each R$^2$ is independently selected from the group consisting of H and methyl;
each R$^3$ is H;
each R$^6$, R$^7$, R$^9$, and R$^{10}$ is independently selected from the group consisting of H, F, Cl, Br, C$_{1-4}$ alkyl, N$_3$, CF$_3$, OCHF$_2$, OCF$_3$, OCH$_3$, —OCH$_2$C≡CH, and R$^{23}$;
R$^8$ is selected from the group consisting of H, CH$_3$, CH$_2$CH$_3$, Br, OCHF$_2$, benzoyl, N$_3$, and R$^{23}$;
each R$^{21}$ is independently selected from the group consisting of H, —C≡C—H, and OR$^{22}$;
each R$^{22}$ is independently selected from the group consisting of H and —CH$_2$C≡CH;
R$^{23}$ is phenyl optionally substituted with one or more substituents selected from the group consisting of F, Cl, OCH$_3$, CF$_3$, and CH$_3$.

5. The compound according to claim 2, wherein the compound is of Formula I-k:

[Formula I-k]

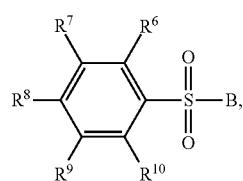

wherein
B is selected from the group consisting of:

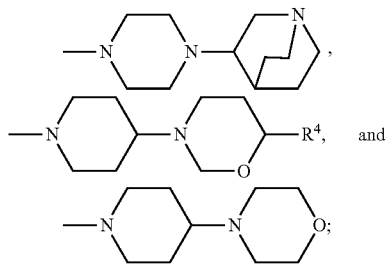

R$^4$ is CH$_3$;
each R$^6$, R$^7$, R$^9$, and R$^{10}$ is independently selected from the group consisting of H, F, Cl, Br, C$_{1-4}$ alkyl, N$_3$, CF$_3$, OCHF$_2$, OCF$_3$, OCH$_3$, —OCH$_2$C≡CH, and R$^{23}$;
R$^8$ is selected from the group consisting of H, CH$_3$, CH$_2$CH$_3$, Br, OCHF$_2$, benzoyl, N$_3$, and R$^{23}$;
R$^{23}$ is phenyl optionally substituted with one or more substituents selected from the group consisting of F, Cl, OCH$_3$, CF$_3$, and CH$_3$.

6. The compound according to claim 2, wherein the compound is of Formula I-l:

[Formula I-l]

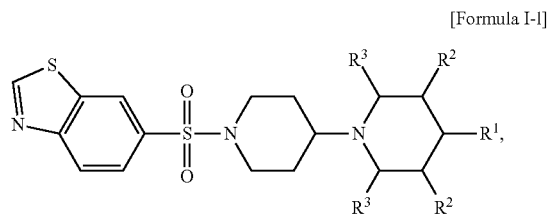

wherein
R$^1$ is selected from the group consisting of C$_{1-3}$ alkyl optionally substituted with R$^{21}$ and —CH$_2$-phenyl optionally substituted with F;
each R$^2$ is independently selected from the group consisting of H and methyl;
each R$^3$ is H;
each R$^{21}$ is independently selected from the group consisting of H, —C≡C—H, and OR$^{22}$;
each R$^{22}$ is independently selected from the group consisting of H and —CH$_2$C≡CH.

7. The compound according to claim 6, wherein
R$^1$ is selected from the group consisting of C$_{1-3}$ alkyl optionally substituted with R$^{21}$;
each R$^2$ is H;
each R$^3$ is H;
R$^{21}$ is selected from the group consisting of H and —C≡C—H.

8. A compound selected from the group consisting of:

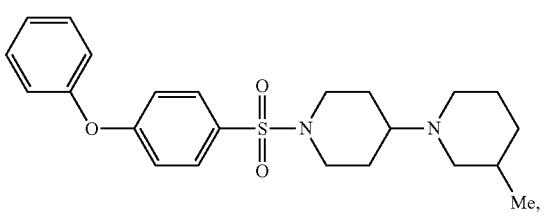

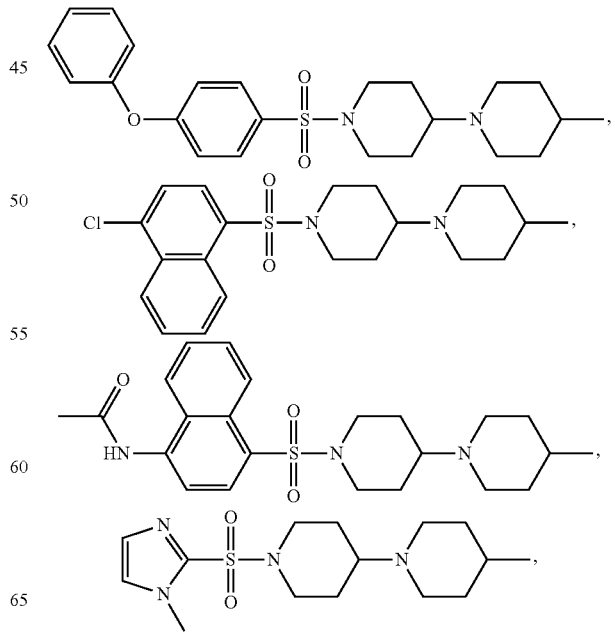

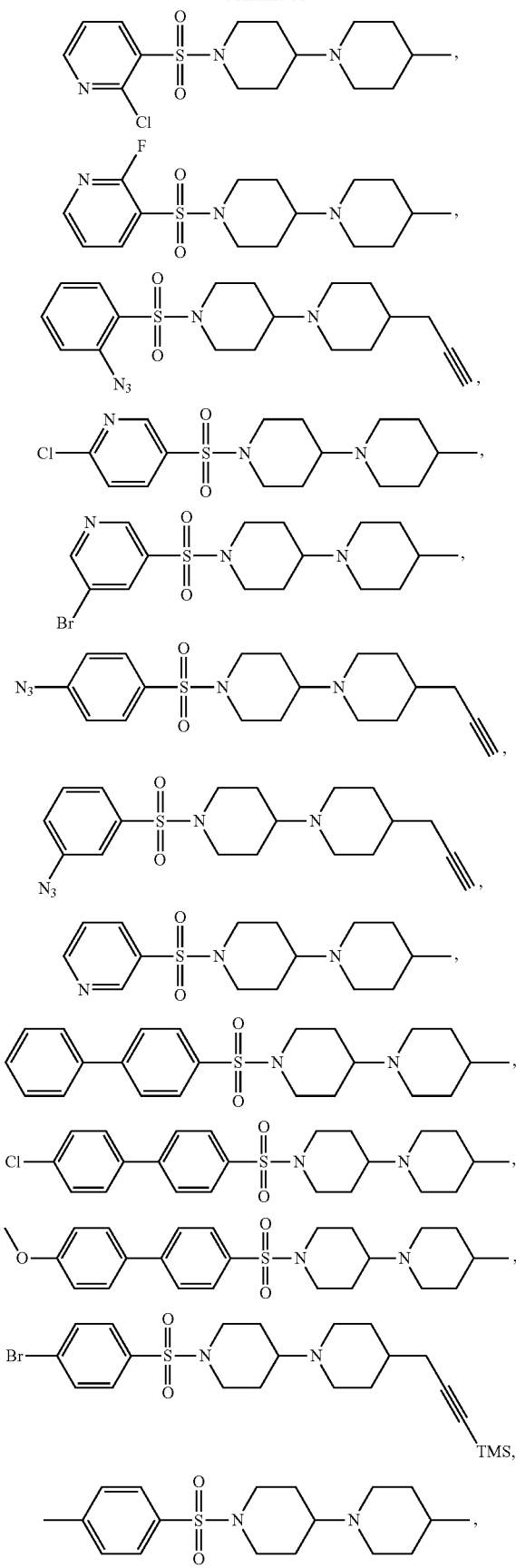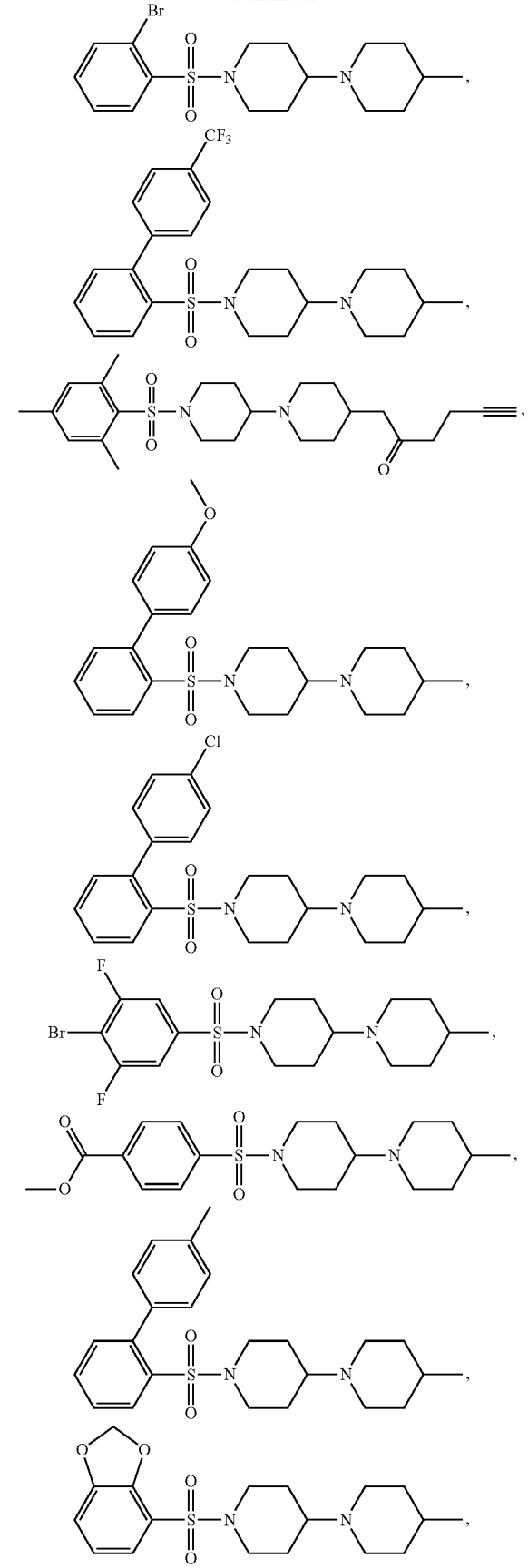

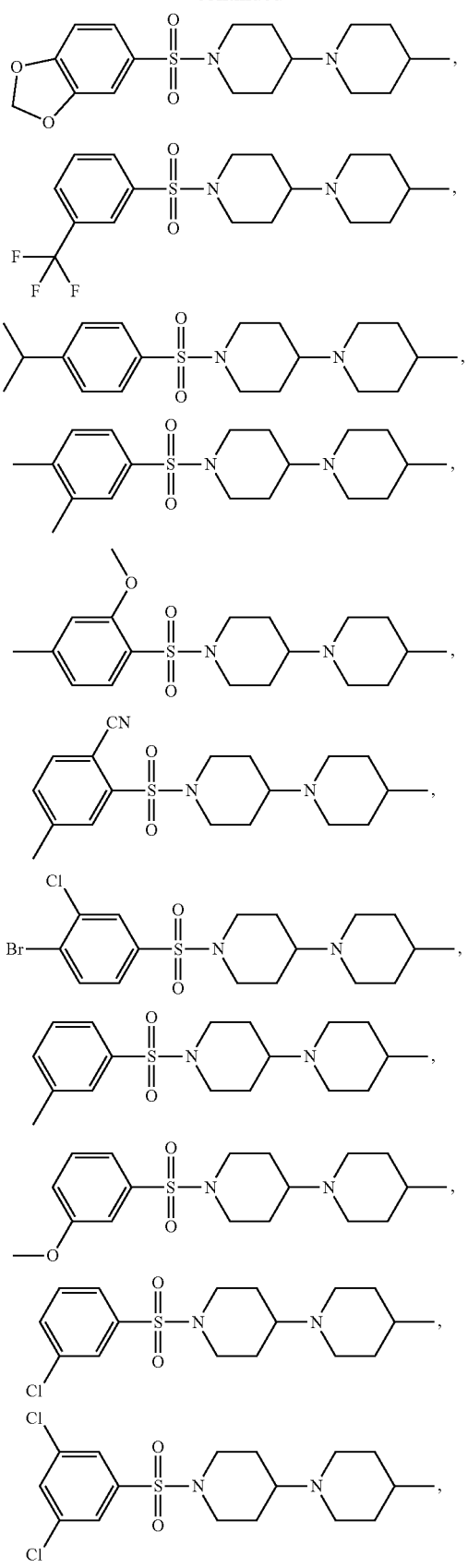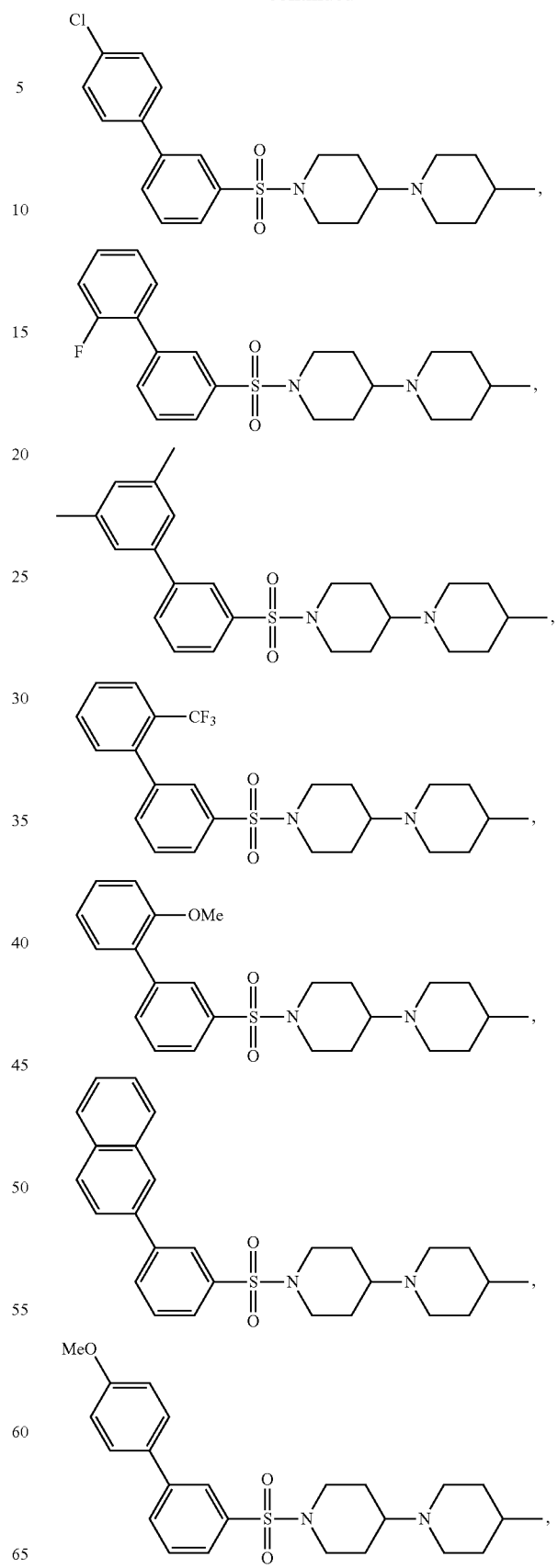

141

-continued

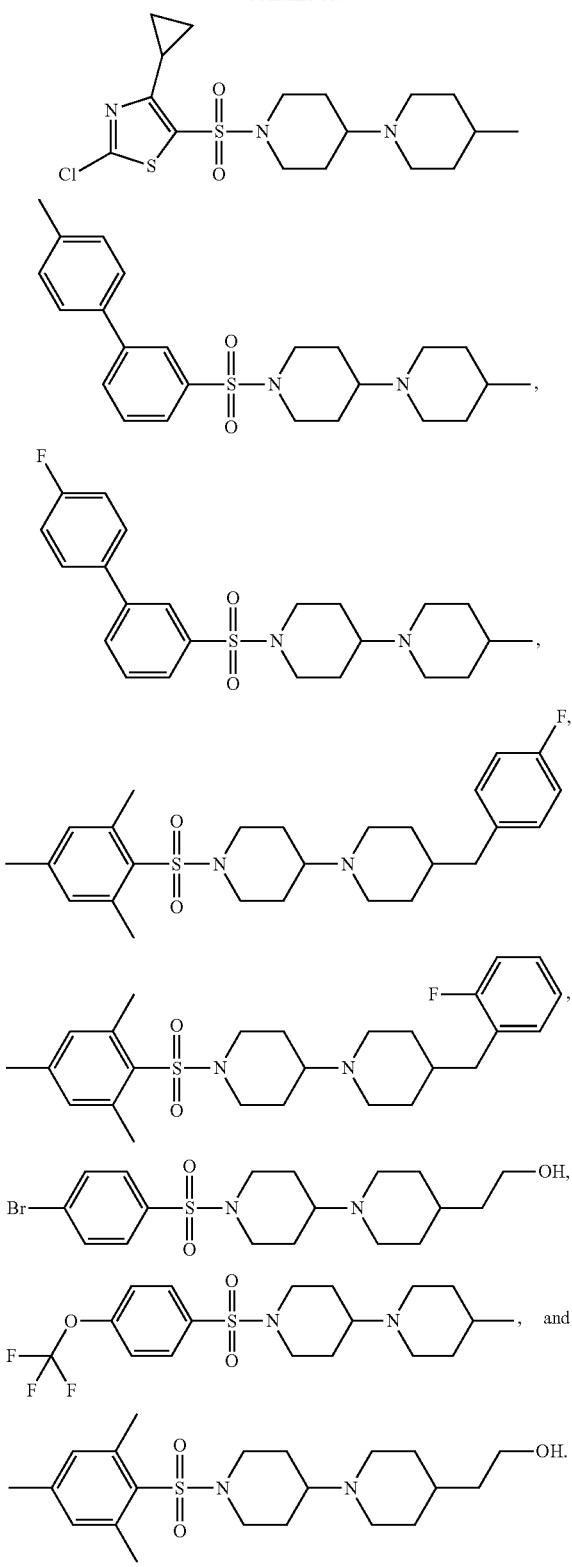

9. A compound selected from the group consisting of:

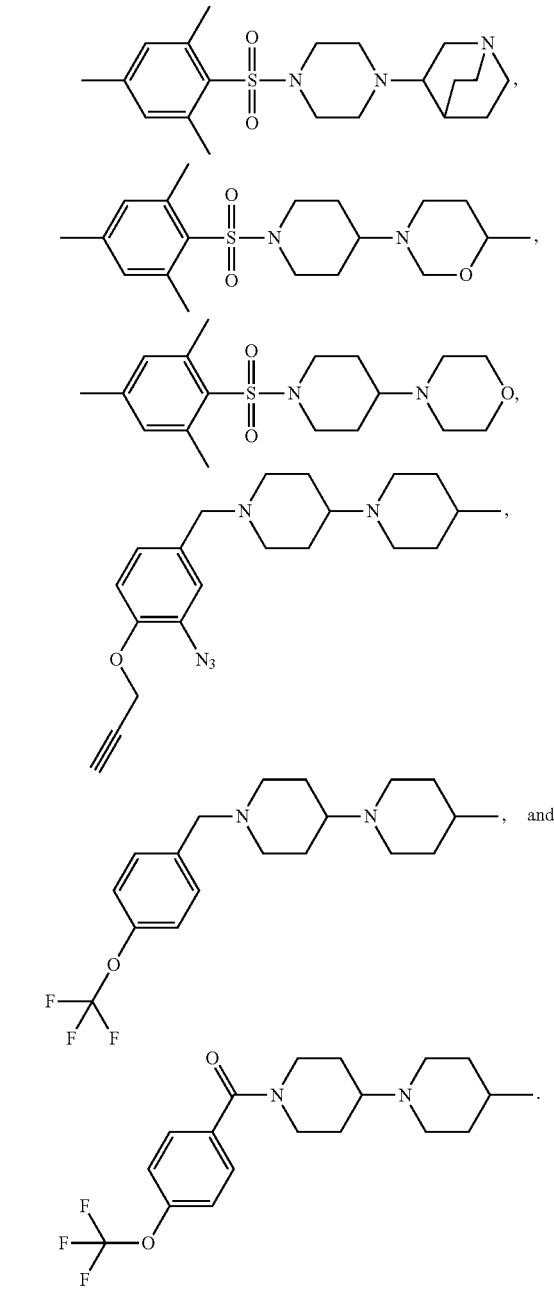

10. The compound according to claim 1, wherein the compound is in form of a pharmaceutical composition comprising a therapeutic amount of the compound and a pharmaceutically acceptable carrier.

11. The compound according to claim 10, wherein the therapeutic amount is effective to inhibit tumor growth, inhibit tumor proliferation, induce cell death or a combination thereof.

12. A stereoisomer, a diastereomer or an enantiomer of the compound according to claim 1.

13. A pharmaceutically acceptable salt or solvate of the compound according to claim 1.

14. The compound according to claim 1, wherein the compound is of Formula I-g:

Formula I-g

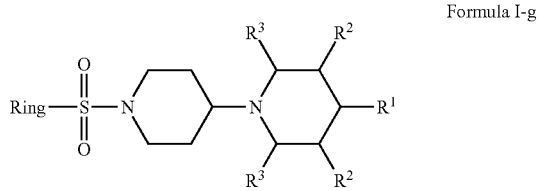

wherein
the Ring is selected from the group consisting of:

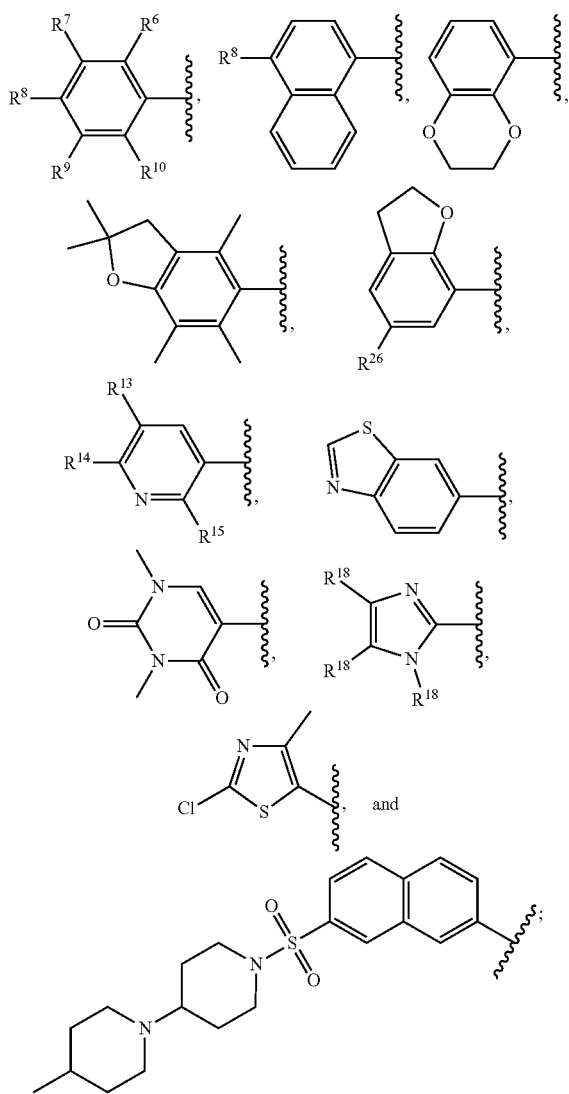

wherein $R^1$ is selected from the group consisting of $C_{1-3}$ alkyl optionally substituted with $R^{21}$ and —$(CH_2)_{0-1}$-phenyl;

each $R^2$ is independently selected from the group consisting of H and $C_{1-4}$ alkyl;

each $R^3$ is selected from the group consisting of H and $C_{1-3}$ alkyl optionally substituted with $R^{21}$;

each $R^6$, $R^7$, $R^9$, and $R^{10}$ is independently selected from the group consisting of H, F, Cl, Br, $C_{1-4}$ alkyl, cyclopropyl, $N_3$, $NH_2$, $CF_3$, $OCHF_2$, $OCF_3$, $OC_{1-4}$ alkyl, benzoyl, phenoxy, —C≡C—$R^{24}$, $R^{25}$, —$OCH_2C$≡CH, CN, $NO_2$, —$CO_2$—$C_{1-4}$ alkyl, $CO_2H$, —$NR^{18}CO$—($C_{1-4}$alkyl), —CON($C_{1-4}$ alkyl)$_2$, —$SO_2NR^{18}{}_2$, —$SO_2$(pyrrolidin-N-yl), —N($CH_2$phenyl)$_2$, —NH($CH_2$phenyl), —N($C_{1-4}$ alkyl)$_2$, —NH($C_{1-4}$alkyl), $R^{23}$, —N($C_{1-4}$alkyl)C(O)CH$_3$, —N($C_{1-4}$alkyl)C(O)CH$_2$CH$_3$, —CO($C_{1-4}$alkyl), —OC(O)NR$^{18}{}_2$, —OC(O)(pyrrolidin-N-yl), and —NR$^{18}$C(O)O—($C_{1-4}$alkyl);

$R^8$ is selected from the group consisting of H, propyl, isopropyl, n-butyl, cyclopropyl, Br, $N_3$, $NH_2$, —N($C_{1-4}$alkyl)$_2$, —NH($C_{1-4}$alkyl), $OCHF_2$, benzoyl, phenoxy, $R^{23}$, —N($C_{1-4}$alkyl)C(O)CH$_3$, —N($C_{1-4}$alkyl)C(O)CH$_2$CH$_3$, —NHC(O)CH$_2$CH$_3$, —CO($C_{1-4}$alkyl),—O($C_{2-4}$alkyl), —OC(O)NR$^{18}{}_2$, —OC(O)(pyrrolidin-N-yl), and —NR$^{18}$C(O)O—($C_{1-4}$alkyl);

each $R^{21}$ is independently selected from the group consisting of H, CN, —C≡CH, —C≡CSiMe$_3$, and OR$^{22}$;

each $R^{22}$ is independently selected from the group consisting of H, —CH$_2$C≡CH and —CH$_2$C≡CSiMe$_3$;

$R^{23}$ is phenyl optionally substituted with one or more substituents selected from the group consisting of F, Cl, Br, $C_{1-4}$ alkyl, cyclopropyl, $N_3$, $NH_2$, $CF_3$, $OCHF_2$, $OCF_3$, $OC_{1-4}$ alkyl, benzoyl, phenoxy, —C≡C—$R^{24}$, $R^{25}$, —OCH$_2$C≡CH, $NO_2$, —CO$_2$—$C_{1-4}$ alkyl, $CO_2H$,—NR$^{18}$CO—($C_{1-4}$alkyl), —CON($C_{1-4}$ alkyl)$_2$, —SO$_2$NR$^{18}{}_2$, —SO$_2$(pyrrolidin-N-yl),—N(CH$_2$phenyl)$_2$, —NH(CH$_2$phenyl), —N($C_{1-4}$alkyl)$_2$, —NH($C_{1-4}$alkyl), —N($C_{1-4}$alkyl)C(O)CH$_3$, —N($C_{1-4}$alkyl)C(O)CH$_2$CH$_3$, —NHC(O)CH$_2$CH$_3$, —CO($C_{1-4}$alkyl),—OC(O)NR$^{18}{}_2$, —OC(O)(pyrrolidin-N-yl), and —NR$^{18}$C(O)O—($C_{1-4}$alkyl);

each $R^{24}$ is independently selected from the group consisting of $C_{1-4}$ alkyl and —(CH$_2$)$_{1-4}$OH;

each $R^{25}$ is independently phenyl optionally substituted with F, Cl, methoxy or $CF_3$;

$R^{11}$ is H, Cl or NHC(O)CH$_3$;

$R^{13}$ is H, Cl or Br;

$R^{14}$ and $R^{15}$ are independently H, F, Cl or Br;

each $R^{18}$ is independently H, methyl or ethyl; and $R^{26}$ is H or Br.

15. The compound according to claim 14, wherein $R^1$ is selected from the group consisting of phenyl, —CH$_2$phenyl and $C_{1-3}$ alkyl optionally substituted with $R^{21}$;

each $R^2$ is independently selected from the group consisting of H and methyl;

each $R^3$ is selected from the group consisting of H and $C_{1-3}$ alkyl optionally substituted with $R^{21}$;

$R^6$, $R^7$, $R^9$, and $R^{10}$ are independently H, F, Cl, Br, $C_{1-4}$ alkyl, $N_3$, $NH_2$, $CF_3$, $OCHF_2$, $OCF_3$, methoxy, benzoyl, phenoxy, —C≡C—$R^{24}$, $R^{25}$, or —OCH$_2$C≡CH;

$R^8$ is selected from the group consisting of H, isopropyl, Br, $N_3$, $NH_2$, $OCHF_2$, benzoyl, phenoxy and $R^{23}$;

each $R^{21}$ is independently selected from the group consisting of H, CN,—C≡C—H,—C≡C—SiMe$_3$ and OR$^{22}$;

each $R^{22}$ is independently selected from the group consisting of H, —CH$_2$C≡CH and —CH$_2$C≡CSiMe$_3$;

$R^{23}$ is phenyl optionally substituted with F, Cl or methoxy;

each $R^{24}$ is independently selected from the group consisting of $C_{1-4}$ alkyl and —(CH$_2$)$_{1-4}$OH;

each $R^{25}$ is independently phenyl optionally substituted with F, Cl, methoxy or $CF_3$;

$R^{11}$ is H, Cl or NHC(O)CH$_3$;

$R^{13}$ is H, Cl or Br;

$R^{14}$ and $R^{15}$ are independently H, F, Cl or Br;

each $R^{18}$ is independently H, methyl or ethyl; and $R^{26}$ is H or Br.

16. The compound according to claim 15, wherein the Ring is

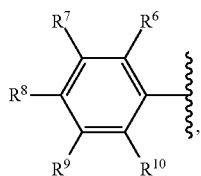

wherein
R¹ is selected from the group consisting of phenyl, —CH₂phenyl and $C_{1-3}$ alkyl optionally substituted with $R^{21}$;
each $R^2$ is independently selected from the group consisting of H and methyl;
each $R^3$ is selected from the group consisting of H and $C_{1-3}$ alkyl optionally substituted with $R^{21}$;
$R^6$, $R^7$, $R^9$, and $R^{10}$ are independently H, F, Cl, Br, $C_{1-4}$ alkyl, $N_3$, $NH_2$, $CF_3$, $OCHF_2$, $OCF_3$, methoxy, benzoyl, phenoxy, —C≡C—$R^{24}$, $R^{25}$, or —OCH₂C≡CH;
$R^8$ is selected from the group consisting of H, isopropyl, Br, $N_3$, $NH_2$, $OCHF_2$, benzoyl, phenoxy and $R^{23}$;
each $R^{21}$ is independently selected from the group consisting of H, CN, —C≡CH, —C≡CSiMe₃, and $OR^{22}$;
each $R^{22}$ is independently selected from the group consisting of H, —CH₂C≡CH and —CH₂C≡CSiMe₃;
$R^{23}$ is phenyl optionally substituted with F, Cl or methoxy;
each $R^{24}$ is independently selected from the group consisting of $C_{1-4}$ alkyl and —(CH₂)$_{1-4}$OH; and
each $R^{25}$ is independently phenyl optionally substituted with F, Cl, methoxy or $CF_3$.

17. The compound according to claim 14, wherein the compound is in form of a pharmaceutical composition comprising a therapeutic amount of the compound and a pharmaceutically acceptable carrier.

18. The compound according to claim 17, wherein the therapeutic amount is effective to inhibit tumor growth, inhibit tumor proliferation, induce cell death or a combination thereof.

19. The compound which is

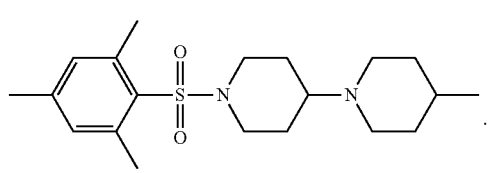

20. The compound which is

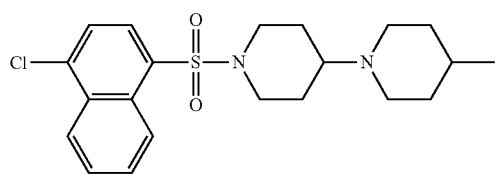

21. The compound which is

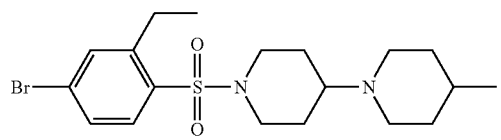 [SMILES: CCc1cc(Br)ccc1S(=O)(=O)N1CCC(N2CCC(C)CC2)CC1]

22. The compound which is

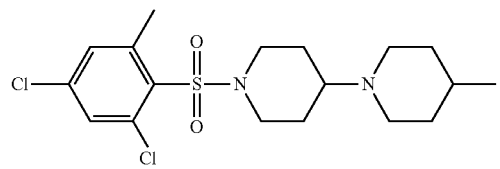

23. The compound which is

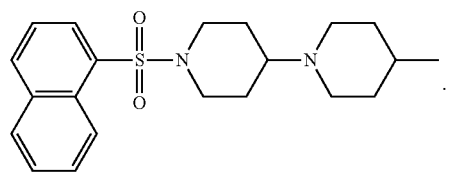 [SMILES: CC1CCN(C2CCN(S(=O)(=O)c3cccc4ccccc34)CC2)CC1]

24. The compound which is

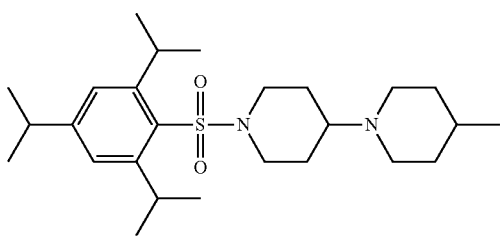

25. The compound which is

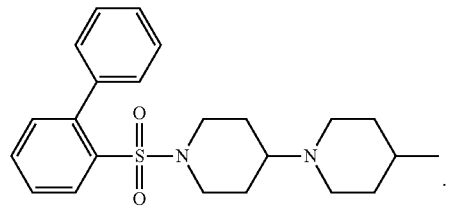 [SMILES: CC1CCN(C2CCN(S(=O)(=O)c3ccccc3-c3ccccc3)CC2)CC1]

26. The compound which is

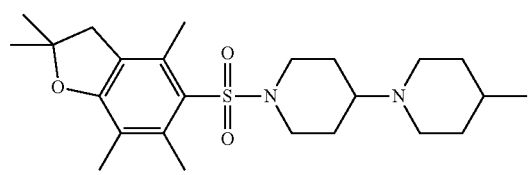

27. The compound which is

28. The compound which is
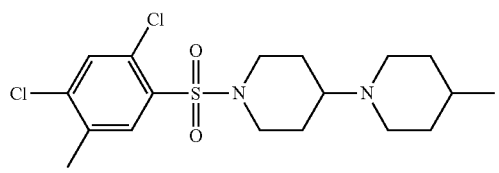
29. The compound which is
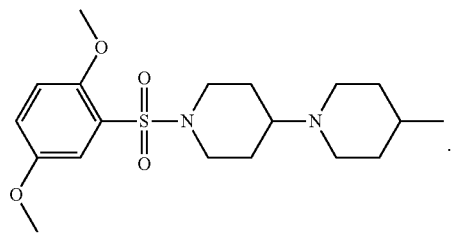
30. The compound which is
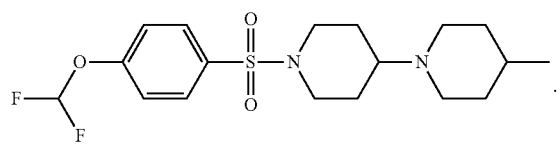 [SMILES: CC1CCN(C2CCN(S(=O)(=O)c3ccc(OC(F)F)cc3)CC2)CC1]
31. The compound which is
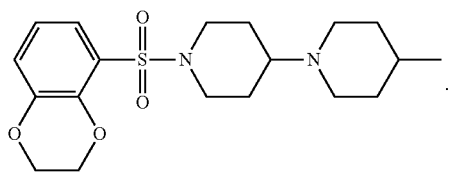
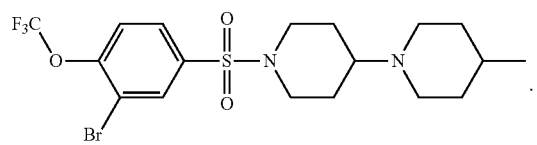 [SMILES: CC1CCN(C2CCN(S(=O)(=O)c3ccc(OC(F)(F)F)c(Br)c3)CC2)CC1]
* * * * *

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Il1rn forward primer

<400> SEQUENCE: 1
ttgtgccaag tctggagatg                                              20

```
<210> SEQ ID NO 2
<211> LENGTH: 20
<212> TYPE: DNA
<213> ORGANISM: Artificial Sequence
<220> FEATURE:
<223> OTHER INFORMATION: Il1rn reverse primer

<400> SEQUENCE: 2
ttctcagagc ggatgaaggt                                              20

<210> SEQ ID NO 3
<211> LENGTH: 19
<212> TYPE: DNA
<213> ORGANISM: Artificial Sequence
<220> FEATURE:
<223> OTHER INFORMATION: Lpo forward primer

<400> SEQUENCE: 3
tgaccttgct ccagactgc                                               19

<210> SEQ ID NO 4
<211> LENGTH: 20
<212> TYPE: DNA
<213> ORGANISM: Artificial Sequence
<220> FEATURE:
<223> OTHER INFORMATION: Lpo reverse primer

<400> SEQUENCE: 4
ttgacccaga ccttgacctc                                              20

<210> SEQ ID NO 5
<211> LENGTH: 20
<212> TYPE: DNA
<213> ORGANISM: Artificial Sequence
<220> FEATURE:
<223> OTHER INFORMATION: Opg forward primer

<400> SEQUENCE: 5
atgaacaagt ggctgtgctg                                              20

<210> SEQ ID NO 6
<211> LENGTH: 20
<212> TYPE: DNA
<213> ORGANISM: Artificial Sequence
<220> FEATURE:
<223> OTHER INFORMATION: Opg reverse primer

<400> SEQUENCE: 6
tcacacagga gctgatgacc                                              20

<210> SEQ ID NO 7
<211> LENGTH: 20
<212> TYPE: DNA
<213> ORGANISM: Artificial Sequence
<220> FEATURE:
<223> OTHER INFORMATION: Slc7a11 forward primer

<400> SEQUENCE: 7
tctggtctgc ctgtggagta                                              20

<210> SEQ ID NO 8
<211> LENGTH: 20
<212> TYPE: DNA
<213> ORGANISM: Artificial Sequence
<220> FEATURE:
```

<223> OTHER INFORMATION: Slc7a11 reverse primer

<400> SEQUENCE: 8
caaaggacca aagacctcca                                               20

<210> SEQ ID NO 9
<211> LENGTH: 20
<212> TYPE: DNA
<213> ORGANISM: Artificial Sequence
<220> FEATURE:
<223> OTHER INFORMATION: Sox4 forward primer

<400> SEQUENCE: 9
aattgcacca actcctcagc                                               20

<210> SEQ ID NO 10
<211> LENGTH: 20
<212> TYPE: DNA
<213> ORGANISM: Artificial Sequence
<220> FEATURE:
<223> OTHER INFORMATION: Sox4 reverse primer

<400> SEQUENCE: 10
tcgattgcag ttcacgagag                                               20

<210> SEQ ID NO 11
<211> LENGTH: 20
<212> TYPE: DNA
<213> ORGANISM: Artificial Sequence
<220> FEATURE:
<223> OTHER INFORMATION: Sox17 forward primer

<400> SEQUENCE: 11
tgaaatatgg cccactcaca                                               20

<210> SEQ ID NO 12
<211> LENGTH: 21
<212> TYPE: DNA
<213> ORGANISM: Artificial Sequence
<220> FEATURE:
<223> OTHER INFORMATION: Sox17 reverse primer

<400> SEQUENCE: 12
ctgtcttccc tgtcttggtt g                                             21

<210> SEQ ID NO 13
<211> LENGTH: 20
<212> TYPE: DNA
<213> ORGANISM: Artificial Sequence
<220> FEATURE:
<223> OTHER INFORMATION: Tlr1 forward primer

<400> SEQUENCE: 13
ggacctaccc ttgcaaacaa                                               20

<210> SEQ ID NO 14
<211> LENGTH: 20
<212> TYPE: DNA
<213> ORGANISM: Artificial Sequence
<220> FEATURE:
<223> OTHER INFORMATION: Tlr1 reverse primer

<400> SEQUENCE: 14
tatcaggacc ctcagcttgg                                               20

```
<210> SEQ ID NO 15
<211> LENGTH: 19
<212> TYPE: DNA
<213> ORGANISM: Artificial Sequence
<220> FEATURE:
<223> OTHER INFORMATION: Tlr2 forward primer

<400> SEQUENCE: 15
gagcatccga attgcatca                                                   19

<210> SEQ ID NO 16
<211> LENGTH: 20
<212> TYPE: DNA
<213> ORGANISM: Artificial Sequence
<220> FEATURE:
<223> OTHER INFORMATION: Tlr2 reverse primer

<400> SEQUENCE: 16
acagcgtttg ctgaagagga                                                  20

<210> SEQ ID NO 17
<211> LENGTH: 20
<212> TYPE: DNA
<213> ORGANISM: Artificial Sequence
<220> FEATURE:
<223> OTHER INFORMATION: Tnfrsf1b forward primer

<400> SEQUENCE: 17
gtcttcgaac tgcagctgtg                                                  20

<210> SEQ ID NO 18
<211> LENGTH: 20
<212> TYPE: DNA
<213> ORGANISM: Artificial Sequence
<220> FEATURE:
<223> OTHER INFORMATION: Tnfrsf1b reverse primer

<400> SEQUENCE: 18
tacccaggtt ccggtttgta                                                  20

<210> SEQ ID NO 19
<211> LENGTH: 20
<212> TYPE: DNA
<213> ORGANISM: Artificial Sequence
<220> FEATURE:
<223> OTHER INFORMATION: Tnfrsf8 forward primer

<400> SEQUENCE: 19
gagactcggg aagccaagat                                                  20

<210> SEQ ID NO 20
<211> LENGTH: 20
<212> TYPE: DNA
<213> ORGANISM: Artificial Sequence
<220> FEATURE:
<223> OTHER INFORMATION: Tnfrsf8 reverse primer

<400> SEQUENCE: 20
ggtggtcttg agtggtcgat                                                  20

<210> SEQ ID NO 21
<211> LENGTH: 20
<212> TYPE: DNA
<213> ORGANISM: Artificial Sequence
<220> FEATURE:
<223> OTHER INFORMATION: Troy forward primer
```

```
<400> SEQUENCE: 21
cgctgccatt ctcttcctac                                              20

<210> SEQ ID NO 22
<211> LENGTH: 20
<212> TYPE: DNA
<213> ORGANISM: Artificial Sequence
<220> FEATURE:
<223> OTHER INFORMATION: Troy reverse primer

<400> SEQUENCE: 22
tcgatccttg aattcctgct                                              20

<210> SEQ ID NO 23
<211> LENGTH: 21
<212> TYPE: DNA
<213> ORGANISM: Artificial Sequence
<220> FEATURE:
<223> OTHER INFORMATION: APC (B7) sense

<400> SEQUENCE: 23
taatgaacac tacagataga a                                            21

<210> SEQ ID NO 24
<211> LENGTH: 21
<212> TYPE: DNA
<213> ORGANISM: Artificial Sequence
<220> FEATURE:
<223> OTHER INFORMATION: APC (B7) antisense

<400> SEQUENCE: 24
ttctatctgt agtgttcatt a                                            21

<210> SEQ ID NO 25
<211> LENGTH: 21
<212> TYPE: DNA
<213> ORGANISM: Artificial Sequence
<220> FEATURE:
<223> OTHER INFORMATION: APC (G3) sense

<400> SEQUENCE: 25
cccagtttgt ttctcaagaa a                                            21

<210> SEQ ID NO 26
<211> LENGTH: 21
<212> TYPE: DNA
<213> ORGANISM: Artificial Sequence
<220> FEATURE:
<223> OTHER INFORMATION: APC (G3) antisense

<400> SEQUENCE: 26
tttcttgaga aacaaactgg g                                            21
```